US012241891B2

(12) United States Patent
Previte et al.

(10) Patent No.: US 12,241,891 B2
(45) Date of Patent: *Mar. 4, 2025

(54) MULTIVALENT BINDING COMPOSITION FOR NUCLEIC ACID ANALYSIS

(71) Applicant: Element Biosciences, Inc., San Diego, CA (US)

(72) Inventors: Michael Previte, San Diego, CA (US); Molly He, San Diego, CA (US); Junhua Zhao, San Diego, CA (US); Hui Zhen Mah, San Diego, CA (US); Chunhong Zhou, San Diego, CA (US); Sinan Arslan, San Diego, CA (US); Matthew Kellinger, San Diego, CA (US); Lorenzo Berti, San Diego, CA (US); Steve Xiangling Chen, San Diego, CA (US)

(73) Assignee: ELEMENT BIOSCIENCES, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/675,154

(22) Filed: Feb. 18, 2022

(65) Prior Publication Data

US 2022/0170919 A1 Jun. 2, 2022

Related U.S. Application Data

(63) Continuation of application No. 17/356,929, filed on Jun. 24, 2021, now Pat. No. 11,287,422, which is a continuation of application No. PCT/US2020/052305, filed on Sep. 23, 2020.

(60) Provisional application No. 62/904,623, filed on Sep. 23, 2019.

(51) Int. Cl.
*G01N 33/53* (2006.01)
*C12Q 1/68* (2018.01)
*C12Q 1/6874* (2018.01)
*G01N 33/58* (2006.01)

(52) U.S. Cl.
CPC ....... *G01N 33/5308* (2013.01); *C12Q 1/6874* (2013.01); *G01N 33/582* (2013.01)

(58) Field of Classification Search
CPC ............. G01N 33/5308; G01N 33/582; C12Q 1/6874; C12Q 1/6869
See application file for complete search history.

(56) References Cited

U.S. PATENT DOCUMENTS

| | | | |
|---|---|---|---|
| 3,950,649 A | 4/1976 | Yonekubo |
| 4,222,743 A | 9/1980 | Wang |
| 5,184,021 A | 2/1993 | Smith |
| 5,422,712 A | 6/1995 | Ogino |
| 5,512,131 A | 4/1996 | Kumar et al. |
| 5,558,991 A | 9/1996 | Trainor |
| 5,695,936 A | 12/1997 | Mandrand et al. |
| 6,287,766 B1 | 9/2001 | Nolan et al. |
| 6,440,748 B1 | 8/2002 | Katerkamp et al. |
| 6,482,590 B1 | 11/2002 | Ullman et al. |
| 6,548,607 B2 | 4/2003 | Halverson et al. |
| 6,664,079 B2 | 12/2003 | Ju et al. |
| 6,818,425 B2 | 11/2004 | Hjorleifsdottir et al. |
| 6,829,051 B2 | 12/2004 | Abe et al. |
| 6,833,246 B2 | 12/2004 | Balasubramanian |
| 7,030,383 B2 | 4/2006 | Babayoff et al. |
| 7,169,560 B2 | 1/2007 | Lapidus et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,264,934 B2 | 9/2007 | Fuller |
| 7,416,844 B2 | 8/2008 | Korlach et al. |
| 7,566,537 B2 | 7/2009 | Balasubramanian et al. |
| 7,755,841 B2 | 7/2010 | Christenson et al. |
| 7,960,116 B2 | 6/2011 | Eid et al. |
| 8,039,817 B2 | 10/2011 | Feng et al. |
| 8,120,002 B2 | 2/2012 | Van Dijk et al. |
| 8,133,672 B2 | 3/2012 | Bjornson et al. |
| 8,143,599 B2 | 3/2012 | Feng et al. |
| 8,242,463 B2 | 8/2012 | Feng et al. |
| 8,257,954 B2 | 9/2012 | Clark et al. |
| 8,278,630 B1 | 10/2012 | Feng et al. |
| 8,367,813 B2 | 2/2013 | Korlach |
| 8,399,196 B2 | 3/2013 | Hoser |

(Continued)

FOREIGN PATENT DOCUMENTS

| | | |
|---|---|---|
| EP | 3947731 A1 | 2/2022 |
| WO | WO-9001069 A1 | 2/1990 |

(Continued)

OTHER PUBLICATIONS

Gabbatiss: New form of DNA discovered inside living human cells. The Independent, accessed Apr. 28, 2018. (2018).

(Continued)

*Primary Examiner* — Jezia Riley

(74) *Attorney, Agent, or Firm* — WILSON SONSINI GOODRICH & ROSATI

(57) ABSTRACT

Multivalent binding compositions including a particle-nucleotide conjugate having a plurality of copies of a nucleotide attached to the particle are described. The multivalent binding compositions allow one to localize detectable signals to active regions of biochemical interaction, e.g., sites of protein-protein interaction, protein-nucleic acid interaction, nucleic acid hybridization, or enzymatic reaction, and can be used to identify sites of base incorporation in elongating nucleic acid chains during polymerase reactions and to provide improved base discrimination for sequencing and array based applications.

20 Claims, 32 Drawing Sheets

(56) References Cited

U.S. PATENT DOCUMENTS

| | | |
|---|---|---|
| 8,405,048 B2 | 3/2013 | Hayashi |
| 8,481,258 B2 | 7/2013 | Church et al. |
| 8,481,264 B2 | 7/2013 | Bjornson et al. |
| 8,530,164 B2 | 9/2013 | Patel et al. |
| 8,546,772 B2 | 10/2013 | Feng et al. |
| 8,580,539 B2 | 11/2013 | Korlach |
| 8,586,947 B1 | 11/2013 | Feng et al. |
| 8,592,148 B2 | 11/2013 | Williams et al. |
| 8,632,975 B2 | 1/2014 | Vander Horn et al. |
| 8,637,650 B2 | 1/2014 | Cherkasov et al. |
| 8,658,365 B2 | 2/2014 | Bjornson et al. |
| 8,698,102 B2 | 4/2014 | Feng et al. |
| 8,703,461 B2 | 4/2014 | Peris et al. |
| 8,715,932 B2 | 5/2014 | Su et al. |
| 8,741,566 B2 | 6/2014 | Winther et al. |
| 9,068,220 B2 | 6/2015 | Feng et al. |
| 9,255,258 B2 | 2/2016 | Vander Horn et al. |
| 9,273,349 B2 | 3/2016 | Nguyen et al. |
| 9,279,154 B2 | 3/2016 | Previte et al. |
| 9,365,898 B2 | 6/2016 | Feng et al. |
| 9,399,767 B2 | 7/2016 | Peris et al. |
| 9,546,398 B2 | 1/2017 | Peter et al. |
| 9,593,315 B2 | 3/2017 | Peris et al. |
| 9,605,310 B2 | 3/2017 | Balasubramanian et al. |
| 9,765,310 B2 | 9/2017 | Vander Horn et al. |
| 9,932,631 B1 | 4/2018 | Dambacher et al. |
| 9,951,385 B1 | 4/2018 | Vijayan et al. |
| 9,957,291 B2 | 5/2018 | Sebo et al. |
| 10,077,470 B2 | 9/2018 | Vijayan et al. |
| 10,233,490 B2 | 3/2019 | Stapleton et al. |
| 10,246,744 B2 | 4/2019 | Vijayan et al. |
| 10,253,352 B2 | 4/2019 | Nguyen et al. |
| 10,294,514 B2 | 5/2019 | Iyidogan et al. |
| 10,300,452 B2 | 5/2019 | Sun et al. |
| 10,301,622 B2 | 5/2019 | Mirkin et al. |
| 10,309,879 B2 | 6/2019 | Chen et al. |
| 10,336,991 B2 | 7/2019 | Peris et al. |
| 10,400,272 B1 | 9/2019 | Middleton et al. |
| 10,400,275 B2 | 9/2019 | Aurich-Costa |
| 10,415,029 B2 | 9/2019 | Dambacher et al. |
| 10,428,378 B2 | 10/2019 | Iyidogan et al. |
| 10,443,098 B2 | 10/2019 | Vijayan et al. |
| 10,501,796 B2 | 12/2019 | Buermann et al. |
| 10,519,496 B2 | 12/2019 | Balasubramanian et al. |
| 10,584,379 B2 | 3/2020 | Vijayan et al. |
| 10,597,643 B2 | 3/2020 | Iyidogan et al. |
| 10,655,176 B2 | 5/2020 | Stromberg et al. |
| 10,704,094 B1 | 7/2020 | Arslan et al. |
| 10,731,141 B2 | 8/2020 | Iyidogan |
| 10,768,173 B1 | 9/2020 | Arslan et al. |
| 10,787,573 B2 | 9/2020 | Zheng et al. |
| 10,876,148 B2 | 12/2020 | Zhou et al. |
| 10,919,033 B2 | 2/2021 | Ren et al. |
| 10,961,566 B2 | 3/2021 | Chee |
| 10,982,280 B2 | 4/2021 | Arslan et al. |
| 11,053,540 B1 | 7/2021 | Chen et al. |
| 11,060,138 B1 | 7/2021 | Chen et al. |
| 11,118,214 B2 | 9/2021 | Matthiesen et al. |
| 11,118,220 B2 | 9/2021 | Daugharthy et al. |
| 11,198,121 B1 | 12/2021 | Guo et al. |
| 11,200,446 B1 | 12/2021 | Zhou et al. |
| 11,220,707 B1 | 1/2022 | Arslan et al. |
| 11,236,388 B1 | 2/2022 | Arslan et al. |
| 11,261,489 B2 | 3/2022 | Chen et al. |
| 11,287,422 B2 | 3/2022 | Previte et al. |
| 11,339,433 B2 | 5/2022 | Chen et al. |
| 11,427,855 B1 | 8/2022 | Arslan et al. |
| 11,535,892 B1 | 12/2022 | Arslan et al. |
| 11,781,185 B2 | 10/2023 | Arslan et al. |
| 11,795,504 B2 | 10/2023 | Chen et al. |
| 2001/0031483 A1 | 10/2001 | Sorge et al. |
| 2002/0030811 A1 | 3/2002 | Schindler |
| 2002/0119455 A1 | 8/2002 | Chan |
| 2002/0139936 A1 | 10/2002 | Dumas |
| 2003/0152490 A1 | 8/2003 | Trulson et al. |
| 2005/0064435 A1 | 3/2005 | Su et al. |
| 2006/0286570 A1 | 12/2006 | Rowlen et al. |
| 2007/0009954 A1 | 1/2007 | Wang et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2008/0065609 A1 | 3/2008 | Jenkins et al. |
| 2008/0160580 A1 | 7/2008 | Adessi et al. |
| 2008/0219888 A1 | 9/2008 | Lawson et al. |
| 2009/0186343 A1 | 7/2009 | Wang et al. |
| 2009/0286691 A1 | 11/2009 | Kim et al. |
| 2010/0093992 A1 | 4/2010 | Cherkasov et al. |
| 2010/0137143 A1 | 6/2010 | Rothberg et al. |
| 2010/0233696 A1 | 9/2010 | Joseph et al. |
| 2010/0311144 A1 | 12/2010 | Peris et al. |
| 2010/0330570 A1 | 12/2010 | Vander Horn et al. |
| 2011/0039259 A1 | 2/2011 | Ju et al. |
| 2011/0111975 A1 | 5/2011 | Schneider et al. |
| 2011/0301044 A1 | 12/2011 | Feng et al. |
| 2012/0014977 A1 | 1/2012 | Furihata et al. |
| 2012/0165219 A1 | 6/2012 | Van Der Zaag et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0322666 A1 | 12/2012 | Pham et al. |
| 2013/0171631 A1 | 7/2013 | Becker et al. |
| 2013/0225623 A1 | 8/2013 | Buxbaum et al. |
| 2014/0113839 A1 | 4/2014 | Wu et al. |
| 2015/0362458 A1 | 12/2015 | Yanagawa et al. |
| 2016/0076023 A1 | 3/2016 | Quake et al. |
| 2016/0083786 A1 | 3/2016 | Liu et al. |
| 2016/0357173 A1 | 12/2016 | Foschini et al. |
| 2017/0145495 A1 | 5/2017 | Sebo et al. |
| 2017/0145496 A1 | 5/2017 | Sebo et al. |
| 2017/0159136 A1 | 6/2017 | Church et al. |
| 2017/0189444 A1 | 7/2017 | Ismagilov et al. |
| 2017/0191125 A1 | 7/2017 | Vijayan et al. |
| 2017/0362649 A1 | 12/2017 | Lieberman-Aiden et al. |
| 2017/0369857 A1 | 12/2017 | Vander Horn et al. |
| 2018/0023108 A1 | 1/2018 | Chen et al. |
| 2018/0080073 A1 | 3/2018 | Vijayan et al. |
| 2018/0187245 A1 | 7/2018 | Dambacher et al. |
| 2018/0195099 A1 | 7/2018 | Kranz et al. |
| 2018/0208983 A1 | 7/2018 | Dambacher et al. |
| 2018/0237847 A1 | 8/2018 | Culler et al. |
| 2018/0251825 A1 | 9/2018 | Stoeckius et al. |
| 2018/0280975 A1 | 10/2018 | Kilcoin et al. |
| 2018/0346507 A1 | 12/2018 | Sebo et al. |
| 2018/0360974 A1 | 12/2018 | Kwiatkowski et al. |
| 2019/0048404 A1 | 2/2019 | Dambacher |
| 2019/0119740 A1 | 4/2019 | Ahn et al. |
| 2019/0119742 A1 | 4/2019 | Zhang et al. |
| 2019/0241945 A1 | 8/2019 | Malyshev et al. |
| 2019/0276884 A1 | 9/2019 | Stapleton et al. |
| 2019/0338352 A1 | 11/2019 | Nemiroski et al. |
| 2019/0367974 A1 | 12/2019 | Fleischer et al. |
| 2020/0010885 A1 | 1/2020 | Malyshev et al. |
| 2020/0032317 A1 | 1/2020 | Rohrman et al. |
| 2020/0087637 A1 | 3/2020 | Iyidogan |
| 2020/0149095 A1 | 5/2020 | Arslan et al. |
| 2020/0179921 A1 | 6/2020 | Arslan et al. |
| 2020/0182866 A1 | 6/2020 | Arslan et al. |
| 2020/0347443 A1 | 11/2020 | Arslan et al. |
| 2020/0370113 A1 | 11/2020 | Kellinger et al. |
| 2021/0040534 A1 | 2/2021 | Zhou et al. |
| 2021/0072234 A1 | 3/2021 | Arslan et al. |
| 2021/0121882 A1 | 4/2021 | Guo et al. |
| 2021/0123098 A1 | 4/2021 | Previte et al. |
| 2021/0123911 A1 | 4/2021 | Arslan et al. |
| 2021/0139884 A1 | 5/2021 | Kellinger et al. |
| 2021/0139981 A1 | 5/2021 | Arslan et al. |
| 2021/0223161 A1 | 7/2021 | Chen et al. |
| 2021/0247389 A1 | 8/2021 | Arslan et al. |
| 2021/0269793 A1 | 9/2021 | Kellinger et al. |
| 2021/0318295 A1 | 10/2021 | Arslan et al. |
| 2021/0332416 A1 | 10/2021 | Chen et al. |
| 2021/0332430 A1 | 10/2021 | Arslan et al. |
| 2021/0333211 A1 | 10/2021 | Chen et al. |
| 2021/0373000 A1 | 12/2021 | Arslan et al. |

(56) References Cited

U.S. PATENT DOCUMENTS

| | | |
|---|---|---|
| 2021/0387184 A1 | 12/2021 | Guo et al. |
| 2022/0136047 A1 | 5/2022 | Chen et al. |
| 2022/0186310 A1 | 6/2022 | Arslan et al. |
| 2022/0251643 A1 | 8/2022 | Chen et al. |
| 2022/0251644 A1 | 8/2022 | Chen et al. |
| 2022/0267842 A1 | 8/2022 | Chen et al. |
| 2022/0275437 A1 | 9/2022 | Stapleton et al. |
| 2022/0290216 A1 | 9/2022 | Middleton et al. |
| 2022/0389408 A1 | 12/2022 | Ben-Yehezkel |
| 2023/0167434 A1 | 6/2023 | Kellinger et al. |
| 2023/0235392 A1 | 7/2023 | Arslan et al. |
| 2023/0295692 A1 | 9/2023 | Berti et al. |
| 2023/0296592 A1 | 9/2023 | Previte et al. |
| 2023/0296593 A1 | 9/2023 | Previte et al. |
| 2023/0323450 A1 | 10/2023 | Arslan et al. |
| 2024/0117428 A1 | 4/2024 | Previte et al. |
| 2024/0200133 A1 | 6/2024 | Ghorbani et al. |
| 2024/0201088 A1 | 6/2024 | Ghorbani et al. |
| 2024/0230631 A1 | 7/2024 | Arslan et al. |

FOREIGN PATENT DOCUMENTS

| | | |
|---|---|---|
| WO | WO-2005111240 A2 | 11/2005 |
| WO | WO-2006065266 A2 | 6/2006 |
| WO | WO-2006084132 A2 | 8/2006 |
| WO | WO-2007061425 A1 | 5/2007 |
| WO | WO-2008151127 A1 | 12/2008 |
| WO | WO-2009073201 A2 | 6/2009 |
| WO | WO-2010016937 A2 | 2/2010 |
| WO | WO-2012027625 A2 | 3/2012 |
| WO | WO-2013123258 A1 | 8/2013 |
| WO | WO-2014171898 A2 | 10/2014 |
| WO | WO-2015085268 A1 | 6/2015 |
| WO | WO-2017007774 A1 | 1/2017 |
| WO | WO-2017014762 A1 | 1/2017 |
| WO | WO-2017117235 A1 | 7/2017 |
| WO | WO-2018045109 A1 | 3/2018 |
| WO | WO-2019018366 A1 | 1/2019 |
| WO | WO-2019033062 A2 | 2/2019 |
| WO | WO-2019241305 A1 | 12/2019 |
| WO | WO-2020028194 A1 | 2/2020 |
| WO | WO-2020076976 A1 | 4/2020 |
| WO | WO-2020102594 A1 | 5/2020 |
| WO | WO-2020102766 A2 | 5/2020 |
| WO | WO-2020118255 A1 | 6/2020 |
| WO | WO-2020223695 A1 | 11/2020 |
| WO | WO-2020242901 A1 | 12/2020 |
| WO | WO-2020243017 A1 | 12/2020 |
| WO | WO-2021061841 A1 | 4/2021 |
| WO | WO-2021146597 A1 | 7/2021 |
| WO | WO-2021236792 A1 | 11/2021 |
| WO | WO-2021252671 A2 | 12/2021 |
| WO | WO-2022026891 A1 | 2/2022 |
| WO | WO-2022094332 A1 | 5/2022 |
| WO | WO-2022266470 A1 | 12/2022 |
| WO | WO-2023004014 A1 | 1/2023 |
| WO | WO-2022266462 A3 | 5/2023 |
| WO | WO-2023107719 A2 | 6/2023 |
| WO | WO-2023196924 A2 | 10/2023 |
| WO | WO-2023205707 A2 | 10/2023 |
| WO | WO-2024151556 A1 | 7/2024 |
| WO | WO-2024173403 A2 | 8/2024 |

OTHER PUBLICATIONS

Joyce et al.: Fingers-closing and other rapid conformational changes in DNA polymerase I (Klenow fragment) and their role in nucleotide selectivity. Biochemistry 47(23):6103-6116 doi:10.1021/bi7021848 (2008).
Kramer et al.: Spanning binding sites on allosteric proteins with polymer-linked ligand dimers. Nature 395(6703):710-713 doi:10.1038/27227 (1998).
Krishnamurthy et al.: Dependence of Effective Molarity on Linker Length for an Intramolecular Protein-Ligand System. J. Am. Chem. Soc. 129(5):1312-1320 DOI:10.1021/JA066780E (2007).
Pack et al.: Tetravalent miniantibodies with high avidity assembling in *Escherichia coli*. J Mol Biol. 246(1):28-34 doi:10.1006/jmbi.1994.0062 (1992).
Terry: 10 Best Genome Sequencing Companies by Revenue. List of the best genome sequencing companies by there[sic] revenue. BioSpace Online, pp. 1-6 [Retrieved online Jun. 16, 2022] URL:https://www.biospace.com/article/top-10-gene-sequencing-companies-by-revenue/ (2019).
U.S. Appl. No. 17/144,945 Non-Final Office Action dated Jun. 6, 2022.
Anderson et al., Fluorescent Structural DNA Nanoballs Functionalized with Phosphate-Linked Nucleotide Triphosphates. Nano Letters 10(3): 788-792 (2010).
Batra et al., Magnesium-induced assembly of a complete DNA polymerase catalytic complex.. Structure 14(4):757-766 (2006).
Bentley, D. R. Whole-genome re-sequencing. Curr Opin Genet Dev. Dec. 2006;16(6):545-52. Epub Oct. 18, 2006.
Bentley et al. Accurate whole human genome sequencing using reversible terminator chemistry. Nature 456(7218):53-59 (2008).
Berki et al., Advanced Fluorescent Polymer Probes for the Site-Specific Labeling of Proteins in Live Cells Using the HaloTag Technology. ACS Omega 4: 12841-12847 (2019).
Related U.S. Appl. No. 63/059,723.
Dubber et al., Solid Phase Synthesis and Multivalent Glycoconjugates on a DNA Synthesizer. Bioconjugate Chem 14: 239-246 (2003).
Duret et al., Labeling of native proteins with fluorescent RAFT polymer probes: Application to the detection of a cell surface protein using flow cytometry. Polym. Chem. 9: 1857-1868 (2018).
Eschenmoser et al., Chemical etiology of nucleic acid structure. Science. 284(5423):2118-2124 (1999).
Favier et al., Synthesis on N-acryloxysuccinimide copolymers by RAFT polymerization, as reactive building blocks with full control of composition and molecular weights. Polymer 45: 7821-7830 (2004).
Ferraro et al., Biocatalytic selective modifications of conventional nucleosides, carbocyclic nucleosides, and C-nucleosides. Chem Rev. 100(12):4319-4348 (2000).
Gebeyehu et al., Novel biotinylated nucleotide—analogs for labeling and colorimetric detection of DNA. Nucleic Acids Research 15(11): 4513-4534 (1987).
Heather et al. The Sequence of Sequencers: The History of Sequencing DNA. Genomics 107:1-8 (2016).
Joeng et al., Structure-activity relationships of beta-D-(2S,5R)- and alpha-D-(2S,5S)-1,3-oxathiolanyl nucleosides as potential anti-HIV agents. J Med Chem. 36(18):2627-2638 (1993).
Ju et al. Four-Color DNA Sequencing by Synthesis Using Cleavable Fluorescent Nucleotide Reversible Terminators. PNAS USA 103:19635-19640 (2006).
Ju et al. Supporting Text—Four-Color DNA Sequencing by Synthesis Using Cleavable Fluorescent Nucleotide Reversible Terminators. PNAS USA 103:19635-19640 (2006).
Kim et al., 1,3-dioxolanylpurine nucleosides (2R,4R) and (2R,4S) with selective anti-HIV-1 activity in human lymphocytes. J Med Chem. 36(1):30-37 (1993).
Lorenz, et al. Polymerase chain reaction: basic protocol plus troubleshooting and optimization strategies. Journal of visualized experiments: JoVE 63 (2012).
Mardis. Next-Generation DNA Sequencing Methods. Annu Rev Genomics Hum Genet 9:387-402 (2008).
Martinez et al., Acyclic nucleoside triphosphate analogs as terminators in biocatalytic DNA replication. Bioorganic & Medicinal Chemistry Letters 7(23): 3013-3016 (1997).
Martinez et al., An allylic/acyclic adenosine nucleoside triphosphate for termination of DNA synthesis by DNA template-dependent polymerases. Nucleic Acids Res 27(5):1271-1274 (1999).
PCT/US2020/034409 International Search Report and Written Opinion dated Aug. 3, 2020.
PCT/US2020/052305 International Search Report and Written Opinion dated Feb. 1, 2021.

(56) References Cited

OTHER PUBLICATIONS

Sah et al., Complete genome sequence of a 2019 novel coronavirus (SARS-COV-2) strain isolated in Nepal. Microbiol Resour Announc. 9(11):e00169-20 (2020).
Singer et al., UV Spectral Characteristics and Acidic Dissociation Constants of 280 Alkyl Bases, Nucleosides, and Nucleotides. Practical Handbook of Biochemistry and Molecular Biology. pp. 255-261 (2010).
Technology Spotlight: Illumina Sequencing (2010).
U.S. Appl. No. 17/144,945 Final Office Action dated Oct. 1, 2021.
U.S. Appl. No. 17/144,945 Non-Final Office Action dated Jun. 4, 2021.
U.S. Appl. No. 17/356,929 Final Office Action dated Nov. 22, 2021.
U.S. Appl. No. 17/356,929 Non-Final Office Action dated Jul. 27, 2021.
U.S. Appl. No. 16/579,794 Non-Final Office Action dated Jan. 30, 2020.
Zhang, et al. Reconstruction of DNA sequencing by hybridization. Bioinformatics. Jan. 2003;19(1):14-21.
Chen, et al., Expansion Microscopy. Science, Jan. 30, 2015; vol. 347, Issue 6221: 543-549.
Goransson et al.: A single molecule array for digital targeted molecular analyses. Nucleic Acids Res. 37(1):e7:1-9 doi:10.1093/nar/gkn921 (2009).

Spacer:

Linkers:

11 atom Linker:

16 atom Linker:

23 atom Linker:

N3 Linker:

Linker 1:

Linker 2:

Linker 3:

Linker 4:

Linker 5:

Chemical Formula: $C_{30}H_{31}N_5O_8$
Exact Mass: 589.22
Molecular Weight: 589.61

Linker 6:

Molecular Weight: 352.35

Linker 7:

Molecular Weight: 449.42

Linker 8:

Molecular Weight: 518.57

Linker 9:

Molecular Weight: 615.64

MULTIVALENT BINDING COMPOSITION FOR NUCLEIC ACID ANALYSIS

CROSS-REFERENCE

This application is a continuation of U.S. patent application Ser. No. 17/356,929, filed Jun. 24, 2021, which is a continuation of International Patent Application No. PCT/US2020/052305, filed on Sep. 23, 2020, which claims the benefit of U.S. Provisional Application No. 62/904,623, filed on Sep. 23, 2019, each of which is incorporated by reference in its entirety.

BACKGROUND

Emerging methods of diagnosis for cancers, infectious diseases, dysbiosis, and other disease and conditions rely on next generation sequencing (NGS) methods to provide high resolution genetic and genomic data, enabling robust and personalized diagnosis, treatment planning, and eventually cures for diseases that were not previously tractable. While powerful, NGS methods are still limited by the methods available to provide nucleic acid samples to the instruments that carry out the actual sequencing. For example, identifying the precise nature of the mutations present in a particular tumor requires isolation of tumor tissue, isolation of nucleic acids, and multiple steps in the preparation of samples for particular sequencing methods, prior to the engagement of the instrument to obtain actual sequence data. Additionally, deconvolution and processing of sequence data in a way that allows the correlation of particular sequences with particular cells or tissues is complicated by the nature of NGS technologies, which often require pooling of samples, during which spatial and cellular identity information is lost.

Various methods have been proposed to address this problem of the loss of cellular addressability in NGS methods, toward the goal of providing molecular diagnostics with higher spatial or tissue resolution. For example, some approaches rely on separation of cells, followed by applying unique barcodes to the nucleic acids from each individual cell, and then bulk sequencing, using the unique barcodes to identify the sequences associated with each individual cell after the sequencing run is complete. This can be achieved, for example, by exposing individual cells to lysis and hybridization mixtures within an isolated environment such as a bead or emulsion. These methods may further require enrichment or processing of the target cell subpopulation, such as by cell sorting for circulating cells, or by tissue harvesting followed by dissociation and protease treatment for solid tumor cells.

While such methods can obtain cellularly addressable information, they face severe limitations, such as difficulties in processing solid tissues, and throughput rates limited by the ability to isolate, tag, and prepare nucleic acids for sequencing. Likewise, there are limitations associated with the need to transfer prepared libraries to separate instruments, systems, or locations in order to carry out sequencing steps. This provides a practical limitation on sequencing throughput of approximately 50,000 cells per sequencing run, which, given the vastly larger number of cells present in a diagnostically relevant sample of a tissue, secretion, excretion, or exudate, or a microbiome sample, places strict limits on the sensitivity and utility of these assays. A level of addressability may be achieved simply by physically isolating samples and performing isolations, library preparation, and sequencing reactions in a known sequence. However, this process is labor intensive and time consuming, making it impractical as a means of screening large numbers of patients or as a means of deploying systematic screening methods.

Accordingly, there is a need for compositions and methods that can increase the accuracy and throughput of cellularly addressable sequencing methods, as well as cellularly or spatially addressable sequencing methods that obviate the aforementioned limitations of existing technologies.

SUMMARY

Aspects disclosed herein provide methods for analyzing a target nucleic acid sequence, the method comprising: (a) providing a plurality of primed nucleic acid molecules; (b) contacting said plurality of primed nucleic acid molecules with a detectable polymer-nucleotide conjugate under conditions suitable to form a binding complex between a nucleotide moiety of said detectable polymer-nucleotide conjugate and a nucleotide of a primed nucleic acid molecule of said plurality of primed nucleic acid molecules; (c) detecting said binding complex; and (d) performing (b) to (c) for nucleotides in said primed nucleic acid molecule, thereby identifying a sequence of said primed nucleic acid molecule. In some embodiments, performing (b) to (d) is performed in less than or equal to about 60 minutes. In some embodiments, performing (b) to (d) is performed in less than or equal to about 30 minutes. In some embodiments, the detectable polymer-nucleotide conjugate comprises a plurality of detectable polymer-nucleotide conjugates, wherein each of the plurality of detectable polymer-nucleotide conjugate comprise a different type of nucleotide moiety. In some embodiments, said plurality of nucleic acid molecules is coupled to an interior surface of a flow cell. In some embodiments, said interior surface of said flow cell comprises one or more hydrophilic polymer layers. In some embodiments, said one or more hydrophilic polymer layers comprises a polymer comprising polyethylene glycol (PEG). In some embodiments, said one or more hydrophilic polymer layers comprises a branched polymer.

Aspects disclosed herein provide methods for analyzing a biological sample comprising: (a) detecting a multivalent binding complex formed in a presence of a biological sample or derivative thereof between a target nucleic acid sequence of a target nucleic acid molecule or derivative thereof and a detectable polymer-nucleotide conjugate; and (b) determining an origin of said target nucleic acid sequence in said biological sample or derivative thereof. In some embodiments, determining in (b) is performed at least in part by analyzing a relative three-dimensional relationship between said target nucleic acid sequence and a point of reference of said biological sample or derivative thereof. In some embodiments, methods further comprise contacting said biological sample or derivative thereof with said detectable polymer-nucleotide conjugate in said presence of the biological sample. In some embodiments, methods further comprise coupling at least a portion of said target nucleic acid sequence to a capture oligonucleotide molecule coupled to a surface of a substrate. In some embodiments, said surface has a water contact angle of less than or equal to 45 degrees. In some embodiments, coupling comprises hybridizing in a presence of a hybridization buffer comprising: (i) a first polar aprotic solvent having a dielectric constant that is no greater than 40 and having a polarity index of 4-9; and (ii) a second polar aprotic solvent having a dielectric constant that is less than or equal to 115. In some embodiments, methods further comprise immobilizing said biological sample or derivative thereof on said surface in a manner that is sufficient to fix said relative three-dimensional relationship. In some embodiments, methods further comprise amplifying said target nucleic acid sequence on said surface of said substrate, optionally, using rolling circle amplification. In some embodiments, an image of said surface in said presence of said biological sample or derivative thereof exhibits a contrast-to-noise ratio of greater than or equal to about 5 as measured by: (a) contacting said surface with a fluorescently labeled nucleotide molecule comprising a nucleic acid sequence that is complementary to at least a portion of a capture oligonucleotide immobilized to said surface; and (b) following (a), imaging said surface using an inverted microscope and a camera under non-signal saturating conditions while said surface is immersed in a buffer. In some embodiments, methods further comprise performing a nucleotide binding reaction between a nucleotide moiety coupled to said polymer-nucleotide conjugate and said target nucleic acid molecule or derivative thereof. In some embodiments, said target nucleic acid molecule or derivative thereof is a deoxyribonucleic acid (DNA) molecule. In some embodiments, said biological sample or derivative thereof comprises a fluid biological sample. In some embodiments, said origin is a cancerous tissue.

Aspects disclosed herein provide methods for identifying at least a portion of a sub-cellular component within a cell or tissue in situ, the method comprising: (a) detecting a signal from a multivalent binding complex between said sub-cellular component or derivative thereof and a detectable polymer-nucleotide conjugate; and (b) processing at least said signal detected in (a) to identify said at least said portion of said sub-cellular component or derivative thereof. In some embodiments, said sub-cellular component or derivative thereof is a nucleic acid. In some embodiments, said nucleic acid is DNA. In some embodiments, methods further comprise: (c) immobilizing said cell or said tissue on a surface of a substrate. In some embodiments, methods further comprise: (d) coupling at least a portion of said sub-cellular component to a capture molecule coupled to a said surface. In some embodiments, methods further comprise: (e) permeabilizing said tissue or lysing said cell prior to detecting in (a). In some embodiments, said surface has a water contact angle of less than or equal to 45 degrees. In some embodiments, coupling in (d) comprises hybridizing said capture molecule with said at least said portion of said sub-cellular component in a presence of a hybridization buffer comprising: (i) a first polar aprotic solvent having a dielectric constant that is no greater than 40 and having a polarity index of 4-9; and (ii) a second polar aprotic solvent having a dielectric constant that is less than or equal to 115. In some embodiments, an image of said surface exhibits a contrast-to-noise ratio of greater than or equal to about 5 as measured by: (a) contacting said surface with a fluorescently labeled nucleotide molecule comprising a nucleic acid sequence that is complementary to at least a portion of a capture oligonucleotide immobilized to said surface; and (b) following (a), imaging said surface using an inverted microscope and a camera under non-signal saturating conditions while said surface is immersed in a buffer. In some embodiments, detecting said signal from said multivalent binding complex in (a) comprises performing a nucleotide binding reaction between a nucleotide moiety coupled to said polymer-nucleotide conjugate and said sub-cellular component or derivative thereof. In some embodiments, said tissue is from a tumor.

Aspects disclosed herein provide systems for analyzing a biological sample comprising: a substrate comprising a surface having coupled thereto a polymer layer suitable to immobilize said biological sample to said surface, wherein: said biological sample or derivative thereof comprises a target nucleic acid molecule or derivative thereof; said polymer layer is configured to couple with (i) said biological sample or derivative thereof, or (ii) said target nucleic acid molecule or derivative thereof, said target nucleic acid molecule or derivative thereof is configured to couple with a nucleotide moiety comprising a detectable label; and an image of said surface exhibits a contrast-to-noise ratio of greater than or equal to about 5 when said image of said surface is obtained using an inverted microscope and a camera under non-signal saturating conditions while said surface is immersed in a buffer and wherein said detectable label is a fluorescent dye. In some embodiments, said polymer layer is hydrophilic. In some embodiments, systems further comprise a fixing agent that fixes said biological sample to said surface when said biological sample is contacted with said fixing agent while adjacent to said surface. In some embodiments, said fixing agent comprises formaldehyde or glutaraldehyde. In some embodiments, said target nucleic acid molecule is a concatemer. In some embodiments, said target nucleic acid molecule comprises a universal sequence region comprising a spatial barcode sequence or a sample barcode sequence configured to retain an origin of said target nucleic acid molecule in said biological sample. In some embodiments, an image of said surface exhibits a contrast-to-noise ratio of greater than or equal to about 10 when said image of said surface is obtained. In some embodiments, said substrate is a flow cell device comprising a first flow channel and, optionally, a second flow channel. In some embodiments, said substrate is a planar substrate that is reflective, transparent, or translucent. In some embodiments, said flow cell device is a capillary flow cell device.

Aspects disclosed herein provide systems for analyzing nucleic acid sequence information in a biological sample or derivative thereof, the system comprising: one or more computer processors programed to: (a) detect a signal from a multivalent binding complex formed in a presence of said biological sample or derivative thereof between a target nucleic acid sequence of a target nucleic acid molecule or derivative thereof and a detectable polymer-nucleotide conjugate, wherein said signal is indicative of an identity of a nucleotide in said target nucleic acid sequence; and (b) determine an origin of said target nucleic acid sequence in said biological sample. In some embodiments, said one or more computer processors is programmed to determine said origin of said target nucleic acid sequence in (b) by analyzing a relative three-dimensional relationship between said target nucleic acid molecule or derivative thereof and said biological sample or derivative thereof. In some embodiments, said system further comprises a database configured to store three-dimensional data related to said origin of said target nucleic acid sequence. In some embodiments, said database is further configured to store sequencing data comprising said identity of said nucleotide in said target nucleic acid sequence. In some embodiments, (b) is performed by associating said sequencing data and said three-dimensional data. In some embodiments, said one or more computer processors is programed to identify said target nucleic acid sequence in less than 60 minutes by repeating (a) to (b). In some embodiments, said one or more computer processors is programed to perform (a) to (b) with an accuracy of base-calling that is characterized by a Q-score of greater than 25 for at least 80% of nucleotides identified. In some embodiments, said detectable polymer-nucleotide conjugate comprises: (a) a polymer core; and (b) two or more nucleotide moieties attached to said polymer core, wherein said polymer-nucleotide conjugate is configured to form a multivalent binding complex between said two or more nucleotide moieties and said target nucleic acid molecule or derivative thereof. In some embodiments, said one or more nucleotide moieties comprises a nucleotide, a nucleotide analog, a nucleoside, or a nucleoside analog. In some embodiments, said polymer core comprises a polymer that has a star, comb, cross-linked, bottle brush, or dendrimer configuration. In some embodiments, said polymer core comprises a branched polyethylene glycol (PEG) molecule. In some embodiments, systems further comprise an optical imaging system comprising a field-of-view (FOV) greater than 1.0 mm$^2$.

Aspects disclosed herein provide kits comprising: (a) a detectable polymer-nucleotide conjugate comprising: (i) a polymer core; and (ii) (ii) two or more nucleotide moieties attached to said polymer core; and (b) instructions for identifying at least a portion of a sub-cellular component within a cell or tissue in situ by contacting said detectable polymer-nucleotide conjugate with said sub-cellular component under conditions sufficient to form a multivalent binding complex between said two or more nucleotide moieties and said sub-cellular component. In some embodiments, kits comprise 4 types of said detectable polymer-nucleotide conjugate, wherein each of said 4 types has a different nucleotide moiety attached thereto.

Aspects disclosed herein comprise kits comprising: (a) a substrate comprising a surface having coupled thereto a polymer layer suitable to immobilize a biological sample or derivative thereof to said surface; and (b) instructions for determining a target nucleic acid sequence and an origin of said target nucleic acid sequence in said biological sample or derivative on said surface. In some embodiments, kits further comprise: (a) a hybridization buffer comprising: (i) a first polar aprotic solvent having a dielectric constant that is no greater than 40 and having a polarity index of 4-9; and (ii) a second polar aprotic solvent having a dielectric constant that is less than or equal to 115; and (b) instructions for hybridizing at least a portion of said target nucleic acid sequence to at least a portion of a capture oligonucleotide coupled to said surface.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 shows an enlarged section of the support having an array of features each having a circular shape and labeled for spatial identification on the support (see the right schematic). Each feature comprises a plurality of immobilized capture oligonucleotides and circularization oligonucleotides.

FIG. 8A: illustration of imaging front and rear interior surfaces of a flow cell. FIG. 8B: illustration of imaging front and rear exterior surfaces of a substrate.

FIG. 9A: top isometric view. FIG. 9B: bottom isometric view.

FIG. 10A: top view. FIG. 10B: side view.

FIG. 11A: first surface. FIG. 11B: second surface.

FIG. 12A: first surface. FIG. 12B: second surface.

FIG. 13A: first surface. FIG. 15B: second surface.

FIG. 14A: plot of the Strehl ratios for imaging a second flow cell surface through a first flow cell surface as a function of the thickness of the intervening fluid layer (fluid channel height) for different objective lens and/or optical system numerical apertures. FIG. 14B: plot of the Strehl ratio as a function of numerical aperture for imaging a second flow cell surface through a first flow cell surface and an intervening layer of water having a thickness of 0.1 mm.

DETAILED DESCRIPTION

Provided herein are spatially addressable and cellularly addressable sequencing methods and systems, as well as compositions, devices, and kits useful for performing the methods and systems described herein. The methods and systems described herein may utilize a polymer-nucleotide conjugate in a nucleotide binding reaction in situ. The nucleotide binding reaction may be performed on a hydrophilic surface, which provide a number of advantages described herein. Hybridization buffers that comprise polar and aprotic solvents in combination with a pH buffer are also provided herein. Also provided are optical systems useful for spatially resolving sequencing data. In some embodiments, the optical systems described herein have a field of view that is greater than 1.0 mm$^2$.

Figure 7:
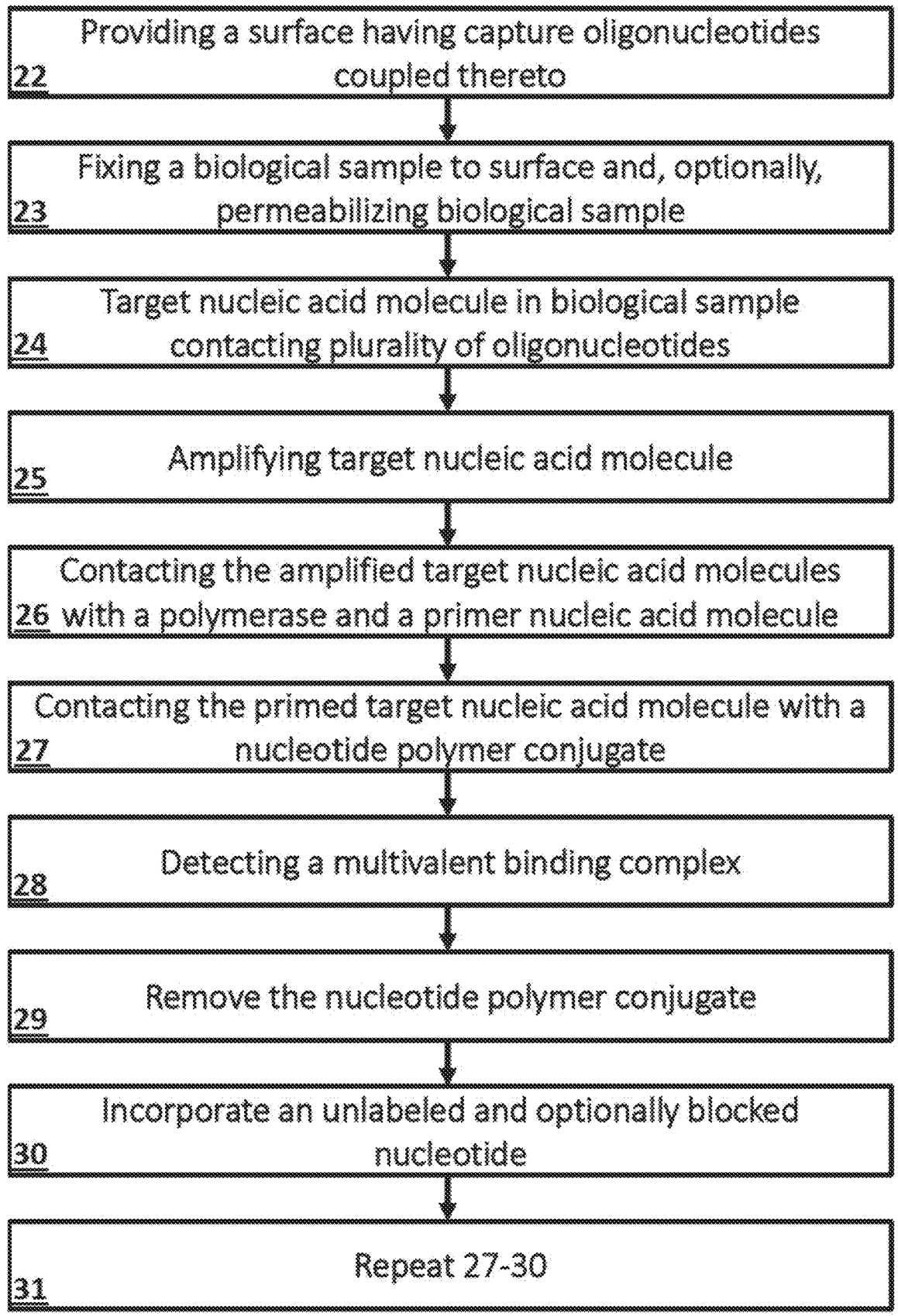
FIG. 7 shows a work flow according to an embodiment of the present disclosure.

As shown in FIG. 7, methods described herein comprise, in some embodiments: (a) providing a surface (e.g., low non-specific binding surface) having a plurality of capture oligonucleotides coupled thereto (22); fixing a biological sample containing a target nucleic acid molecule to the surface, and optionally permeabilizing the biological sample (23); (c) contacting the plurality of capture oligonucleotides with the target nucleic acid molecule under conditions sufficient to allow hybridization of at least a portion of the plurality of capture oligonucleotides to the target nucleic acid molecule (24); (d) amplifying the target nucleic acid molecule to produce amplified target nucleic acid molecules or derivatives thereof (25); (e) contacting the amplified target nucleic acid molecules or derivatives thereof with one or more polymerases and one or more primer nucleic acid molecules having a primer sequence that is complementary to one or more regions of the amplified target nucleic acid molecules or derivatives thereof, to produce primed target nucleic acid molecules or derivatives thereof (26); (f) contacting the primed target nucleic acid molecules or derivatives thereof with a polymer-nucleotide conjugate comprising two or more nucleotide moieties coupled to a polymer (e.g., PEG) core that is labeled with a detectable label (e.g., fluorophore) (27); (g) detecting a multivalent binding complex formed between the primed target nucleic acid molecules or derivatives thereof and the polymer-nucleotide conjugate (28); (h) wash the surface with a buffer sufficient to remove the polymer-nucleotide conjugate from the primed target nucleic acid molecule or derivative thereof (29); (i) incorporate a nucleotide that does not contain a detectable label and which optionally comprises a blocking group (e.g., azidomethyl) that blocks incorporation of a second nucleotide at an N+1 position on the primed target nucleic acid molecule or derivative thereof (30); and (j) optionally, repeat steps (f)-(j) (31).

Existing methods of spatially addressable sequence identification (also referred to herein as spatial transcriptomic technology) suffer from low sensitivity, non-specificity and inaccurate spatial location of the transcripts of interest. In contrast, the methods, systems, compositions and kits described herein overcome these challenges, for example, by leveraging low non-specific binding surfaces, high efficiency hybridization buffers, methods to prepare nanoballs with high copy number, and multivalent molecules.

The low non-specific binding and improved signal of the instant disclosure provide significantly improved contrast-to-noise (CNR) ratios, as compared with existing methodologies. The CNR is at least partially improved by utilizing highly compact foci of reaction (e.g., highly compact nucleic acid clusters with high copy number), highly efficient surface hybridization (allowing precise localization of nucleic acid capture), and very low background, while enabling highly efficient capture, amplification, and clustering of target nucleic acids. When a biological sample (e.g., tissue, cellular suspension) is coupled to the substrate, the sequencing reaction can be performed in the presence of the biological sample. Analysis of the sequencing reaction can be performed in a manner that provides cellular addressability and/or spatial addressability, such that sequence data may be linked to the tissue, cell type, physiological location, or spatial location from which it was derived.

The high efficiency hybridization buffers described herein promote high stringency (e.g., specificity), speed, and efficacy of nucleic acid hybridization reactions and increases the efficiency of the subsequent amplification and sequencing steps. The high efficiency hybridization buffers can significantly shorten nucleic acid hybridization times, and decreases sample input requirements. The high efficiency hybridization buffers can be used for nucleic acid annealing workflows at isothermal conditions which eliminates requirement of a cooling step for annealing. The high efficiency hybridization buffers provide precise localization of nucleic acid capture on a surface for accurate spatial localization of nucleic acids (e.g., transcripts) that originate from a cell or tissue.

The rolling circle amplification methods described herein includes a two-stage method that employs non-catalytic and then catalytic divalent cations to synchronize the rolling circle amplification events on a surface and generate concatemers. The rolling circle amplification reaction can be followed by a relaxant condition and a flexing amplification reaction which generates new concatemers from the existing concatemers. Together, these amplification methods generate highly compact nanoballs containing high copy number of the target sequence which improves sequencing signal intensity.

The nucleic acid analysis methods described herein may have higher throughput than existing methods, allowing the analysis of 50,000, 100,000, 150,000, 250,000, 500,000, 750,000, 1,000,000 or more cells per run, enabling vastly higher diagnostic sensitivity by allowing the detection of, in principal, mutations in as few as one cell per million. A further advantage of the nucleic acid methods disclosed herein is that the reactions required may be carried out at a single temperature (e.g., isothermal conditions), such as, for example, 20° C., 25° C., 30° C., 35° C., 37° C., 40° C., 42° C., 50° C., 60° C., 65° C., 70° C., or 72° C. or more, or within a range defined by any two of the foregoing.

The multivalent molecules used during the sequencing reaction offer many advantages that are not provided by free nucleotides. The multivalent molecules comprise a core attached to multiple arms with each arm tethered to a nucleotide. The multivalent molecules increase the local concentration of nucleotides in proximity of a polymerase/template binding site. The multivalent molecules also exhibit increased persistence time in formation of a stable ternary complex with a polymerase and nucleic acid template. Thus, a labeled multivalent molecule provides shorter imaging time and increase signal intensity during a sequencing reaction.

Cellular and spatial resolution of sequencing data generating using the methods and systems described herein are achieved by the imaging methods and systems described herein, which provide increased optical resolution and improved image quality for genomics applications.

Disclosed herein are optical component and system designs for high-performance fluorescence imaging methods and systems that may provide any one or more of: larger fields-of-view, improved optical resolution (including high performance optical resolution), improved contrast, improved image quality, faster transitions between image capture when repositioning the sample plane to capture a series of images (e.g., of different fields-of-view), improved imaging system duty cycle, and higher throughput image acquisition and analysis.

In some instances, improvements in imaging performance, e.g., for dual-side (flow cell) imaging applications comprising the use of thick flow cell walls (e.g., wall (or coverslip) thickness >700 μm) and fluid channels (e.g., fluid channel height or thickness of 50-200 μm) may be achieved using novel objective lens designs that correct for optical aberration introduced by imaging surfaces on the opposite side of thick coverslips and/or fluid channels from the objective.

In some instances, improvements in imaging performance, e.g., for dual-side (flow cell) imaging applications comprising the use of thick flow cell walls (e.g., wall (or coverslip) thickness >700 μm) and fluid channels (e.g., fluid channel height or thickness of 50-200 μm) may be achieved even when using commercially-available, off-the-shelf objectives by using a novel tube lens design that, unlike the tube lens in a conventional microscope that simply forms an image at the intermediate image plane, corrects for the optical aberrations induced by the thick flow cell walls and/or intervening fluid layer in combination with the objective.

In some instances, improvements in imaging performance, e.g., for multichannel (e.g., two-color or four-color) imaging applications, may be achieved by using multiple tube lenses, one for each imaging channel, where each tube lens design has been optimized for the specific wavelength range used in that imaging channel.

In some instances, improvements in imaging performance, e.g., for dual-side (flow cell) imaging applications, may be achieved by using an electro-optical phase plate in combination with an objective lens to compensate for the optical aberrations induced by the layer of fluid separating the upper (near) and lower (far) interior surfaces of a flow cell. In some instances, this design approach may also compensate for vibrations introduced by, e.g., a motion-actuated compensator that is moved in or out of the optical path depending on which surface of the flow cell is being imaged.

Further advantageous features of the disclosed imaging optics designs may include the position and orientation of one or more excitation light sources and one or more detection optical paths with respect to the objective lens and to a dichroic filter that receives the excitation beam. The excitation beam may also be linearly-polarized and the orientation of the linear polarization may be such that s-polarized light is incident on the dichroic reflective surface of the dichroic filter. Such features may potentially improve excitation beam filtering and/or reduce wave front error introduced into the emission light beam due to, e.g., surface deformation of dichroic filters.

Although discussed herein primarily in the context of fluorescence imaging (including, e.g., fluorescence microscopy imaging, fluorescence confocal imaging, two-photon fluorescence, and the like), it will be understood by those of skill in the art that many of the disclosed optical design approaches and features are applicable to other imaging modes, e.g., bright-field imaging, dark-field imaging, phase contrast imaging, and the like.

In addition to the optical components and imaging system designs disclosed herein, flow cell devices and systems for performing a variety of genomic analysis methods, including cellularly-addressable nucleic acid sequencing, are disclosed that may comprise various combinations of the disclosed optical, mechanical, fluidic, thermal, electrical, and computing modules or sub-systems. The advantages conferred by the disclosed flow cell devices, cartridges, and analysis systems include, but are not limited to: (i) reduced device and system manufacturing complexity and cost, (ii) significantly lower consumable costs (e.g., as compared to those for currently available nucleic acid sequencing systems), (iii) compatibility with typical flow cell surface functionalization methods, (iv) flexible flow control when combined with microfluidic components, e.g., syringe pumps and diaphragm valves, etc., and (v) flexible system throughput.

In some instances, the disclosed capillary flow-cell devices and capillary flow cell cartridges may be constructed from off-the-shelf, disposable, single lumen (e.g., single fluid flow channel) or multi-lumen capillaries that may also comprise fluidic adaptors, cartridge chassis, one or more integrated fluid flow control components, or any combination thereof. In some instances, the disclosed flow cell-based systems that may comprise one or more capillary flow cell devices (or microfluidic chips), one or more capillary flow cell cartridges (or microfluidic cartridges), fluid flow controller modules, temperature control modules, imaging modules, or any combination thereof. The design features of some disclosed capillary flow cell devices, cartridges, and systems include, but are not limited to, (i) unitary flow channel construction, (ii) sealed, reliable, and repetitive switching between reagent flows that can be implemented with a simple load/unload mechanism such that fluidic interfaces between the system and capillaries are reliably sealed, thereby facilitating capillary replacement and system reuse, and enabling precise control of reaction conditions such as reagent concentration, pH, and temperature, (iii) replaceable single fluid flow channel devices or capillary flow cell cartridges comprising multiple flow channels that can be used interchangeably to provide flexible system throughput, and (iv) compatibility with a wide variety of detection methods such as fluorescence imaging.

Although the disclosed capillary flow cell and microfluidic devices and systems are described primarily in the context of their use for nucleic acid sequencing applications, various aspects of the disclosed devices and systems may be applied not only to nucleic acid sequencing but also to any other type of chemical analysis, biochemical analysis, nucleic acid analysis, cell analysis, or tissue analysis application. It shall be understood that different aspects of the disclosed methods, devices, and systems can be appreciated individually, collectively, or in combination with each other.

Embodiments described herein provide significant advantages for the diagnosis of cancers, including both circulating and solid tumors, the analysis of biopsy samples, e.g., for the diagnosis of genetic disorders, the analysis of microbiome samples, e.g., for the diagnosis of disorders linked to dysbiosis in microbial flora, for the diagnosis of disorders accompanying a secretion or exudate, or for the assessment of general health or disease risk, where such risk may be assessed with respect to the presence or identity of particular genetic sequences in a particular cell, tissue, or location. For example, it may be useful to use high resolution cellularly addressable sequencing techniques to identify the presence of low levels of circulating tumor cells for the diagnosis of blood cancers or early metastases.

In some embodiments, cells in a tissue or individual cells may be exposed to a surface under conditions optimized for binding (capturing) of target nucleic acids by, for example, inclusion of high densities of poly-T or poly-dT oligonucleotides for the capture of RNA transcripts followed by reverse transcription, or inclusion of random-sequence capture oligonucleotides for hybridization to genomic, circulating, or organellar DNA. In some embodiments, this capture process may be followed by one or more library preparation steps, such as appending at least one adaptor to the captured nucleic acid where the adaptor can include an index sequence, barcode sequence and/or a Unique Molecular Identifier (UMI). The adaptor appending step can be conducted by ligation (e.g., blunt end ligation) or by use of "splint" oligonucleotides. These library preparation steps may result in or may further include circularization of the captured nucleic acids. In some embodiments, a circularized nucleic acid molecule, may be amplified such as by Rolling Circle Amplification (RCA), yielding a large multicopy nucleic acid molecule (e.g., concatemer) comprising multiple tandem repeat sequences of the target sequence. In some embodiments, said large multicopy nucleic acid may form a condensed state, such as by the use of buffer conditions favoring compact DNA states, surfaces having high densities of capture oligonucleotides, the use of bivalent or bispecific oligonucleotides that bridge two or more sites within a large multicopy nucleic acid ("clustering oligonucleotides" or "clustering oligos"), or by any combination of the foregoing, or by any method as is or becomes known in the art to produce compact clusters comprising large multicopy nucleic acids.

In some embodiments, the surface used to capture nucleic acids from the tissue or cells may be composed to retain nucleic acids with high activity while simultaneously maintaining a low level of binding for unwanted proteins, lipids, carbohydrates, or other components of cell debris. Thus, the surfaces contemplated herein are capable of binding to the nucleic acids from cells in a tissue, or from a single cell, that is/are lysed in contact with or in proximity to the surface. Further, the surfaces do not retain cell debris, nor do they show significant nonspecific binding of added proteins such as nucleic acid polymerases, or other molecules, moieties, particles, or items such as dye molecules or fluorophores.

In some embodiments, cell lysis (and optionally nucleic acid fragmentation) are carried out in contact with or in proximity to the surface such that a significant amount, such as a representative quantity, or substantially all, of the DNA, RNA, or other target nucleic acids released from the cell or tissue sample will be captured by the surface. The surface may be composed such that cells can be flowed over the surface in order to reach capture sites on said surface. Alternatively, a capture surface may be composed such that a tissue (e.g., tissue section) can be placed in contact or in fluid communication with the surface, where reagents may then be flowed over the tissue in such a manner as to facilitate the capture in situ of nucleic acids from the tissue, such that the nucleic acids from one cell or region of the tissue will be captured in the same location and orientation relative to the nucleic acids from other cells or regions of the tissue, as the nucleic acids were oriented or located within the intact tissue.

In some embodiments, the capturing, adaptor-appending, circularizing, amplifying, and clustering of the target nucleic acids can be carried out while attached to, or in close proximity to, the surface. Alternatively, one or more of the foregoing preparatory steps may be carried out in free solution, or while attached to beads.

Spatially resolved binding of a cell-specific nucleic acid complement such as, for example, a cellular genome or a cellular transcriptome, followed by adaptor-appending, circularizing, amplifying, and clustering then enables the use of sequencing technologies, such as avidity based sequencing methods such as those described in U.S. Application Nos. 62/897,172 and Ser. No. 16/579,794, which are hereby incorporated by reference in their entireties; and as described elsewhere herein. Enablement of cellularly or tissue addressable sequencing is further provided by advances in low-binding surfaces, as disclosed in U.S. patent application Ser. No. 16/363,842, hybridization methods as disclosed in U.S. patent application Ser. No. 16/543,351, and library preparation methods as disclosed in U.S. Application Nos. 62/767,943 and related published International Application No. WO 2020/102766, the contents of which are hereby expressly incorporated by reference for all purposes. Thus, in some embodiments, sequence data can be obtained in a manner that maps spatially to the cell or tissue from which the genomic or transcriptomic nucleic acids were obtained. In some embodiments, the sequence data can be obtained with a substantially one-to-one correspondence with the cellular location of the origin of the sample. In some embodiments, the sequence data can be obtained with other than a one-to-one spatial correspondence with the cellular locations within the original sample, but with substantially the same locations relative to other cells or sources of genetic, genomic, or transcriptomic samples within the tissue.

Figure 1:
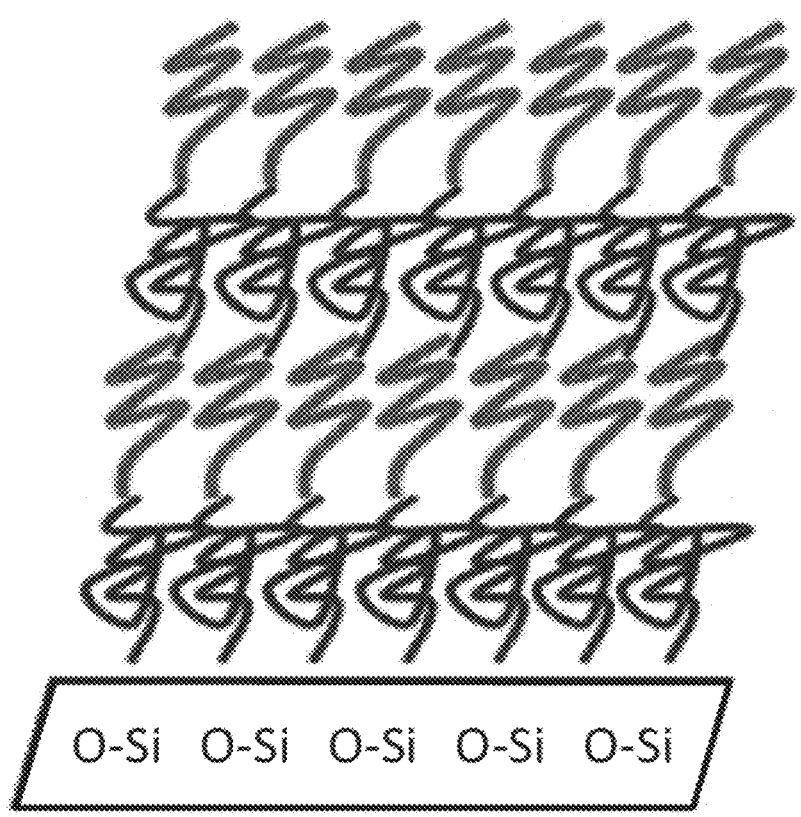
FIG. 1 is a schematic illustration of one embodiment of the low binding support comprising a glass substrate and alternating layers of hydrophilic coatings which are covalently or non-covalently adhered to the glass, and which further comprises chemically-reactive functional groups that serve as attachment sites for oligonucleotide primers (e.g., capture oligonucleotides and circularization oligonucleotides) according to an embodiment of the present disclosure. In an alternative embodiment, the support can be made of any material such as glass, plastic or a polymer material.

Solid Support Surfaces. Provided herein solid supports comprising surfaces (e.g., low non-specific binding). In some instances, the solid support comprises a surface that is not hydrophilic. In some instances, the solid support comprises a surface that is hydrophilic. In general, the disclosed supports may comprise a substrate (or support structure), one or more layers of a covalently or non-covalently attached low-binding, chemical modification layers, e.g., silane layers, polymer films, and one or more covalently or non-covalently attached primer sequences that may be used for tethering single-stranded template oligonucleotides to the support surface (FIG. 1). In some instances, the formulation of the surface, e.g., the chemical composition of one or more layers, the coupling chemistry used to cross-link the one or more layers to the support surface and/or to each other, and the total number of layers, may be varied such that non-specific binding of proteins, nucleic acid molecules, and other hybridization and amplification reaction components to the support surface is minimized or reduced relative to a comparable monolayer. Often, the formulation of the surface may be varied such that non-specific hybridization on the support surface is minimized or reduced relative to a comparable monolayer. The formulation of the surface may be varied such that non-specific amplification on the support surface is minimized or reduced relative to a comparable monolayer. The formulation of the surface may be varied such that specific amplification rates and/or yields on the support surface are maximized. Amplification levels suitable for detection are achieved in no more than 2, 3, 4, 5, 6, 7, 8, 9, 10, 15, 20, 25, 30, or more than 30 amplification cycles in some cases disclosed herein.

Examples of materials from which the substrate or support structure may be fabricated include, but are not limited to, glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The substrate or support structure may be rendered in any of a variety of geometries and dimensions known to those of skill in the art, and may comprise any of a variety of materials known to those of skill in the art. For example, in some instances the substrate or support structure may be locally planar (e.g., comprising a microscope slide or the surface of a microscope slide). Globally, the substrate or support structure may be cylindrical (e.g., comprising a capillary or the interior surface of a capillary), spherical (e.g., comprising the outer surface of a non-porous bead), or irregular (e.g., comprising the outer surface of an irregularly-shaped, non-porous bead or particle). In some instances, the surface of the substrate or support structure used for nucleic acid hybridization and amplification may be a solid, non-porous surface. In some instances, the surface of the substrate or support structure used for nucleic acid hybridization and amplification may be porous, such that the coatings described herein penetrate the porous surface, and nucleic acid hybridization and amplification reactions performed thereon may occur within the pores.

The substrate or support structure that comprises the one or more chemically-modified layers, e.g., layers of a low non-specific binding polymer, may be independent or integrated into another structure or assembly. For example, in some instances, the substrate or support structure may comprise one or more surfaces within an integrated or assembled microfluidic flow cell. The substrate or support structure may comprise one or more surfaces within a microplate format, e.g., the bottom surface of the wells in a microplate. As noted above, in some preferred embodiments, the substrate or support structure comprises the interior surface (such as the lumen surface) of a capillary. In alternate preferred embodiments the substrate or support structure comprises the interior surface (such as the lumen surface) of a capillary etched into a planar chip.

The chemical modification layers may be applied uniformly across the surface of the substrate or support structure. Alternately, the surface of the substrate or support structure may be non-uniformly distributed or patterned, such that the chemical modification layers are confined to one or more discrete regions of the substrate. For example, the substrate surface may be patterned using photolithographic techniques to create an ordered array or random pattern of chemically-modified regions on the surface. Alternately or in combination, the substrate surface may be patterned using, e.g., contact printing and/or ink-jet printing techniques. In some instances, an ordered array or random pattern of chemically-modified discrete regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions, or any intermediate number spanned by the range herein.

In order to achieve low non-specific binding surfaces (also referred to herein as "low binding" or "passivated" surfaces), hydrophilic polymers may be non-specifically adsorbed or covalently grafted to the substrate or support surface. Typically, passivation is performed utilizing poly (ethylene glycol) (PEG, also known as polyethylene oxide (PEO) or polyoxyethylene), poly(vinyl alcohol) (PVA), poly(vinyl pyridine), poly(vinyl pyrrolidone) (PVP), poly (acrylic acid) (PAA), polyacrylamide, poly(N-isopropylacrylamide) (PNIPAM), poly(methyl methacrylate) (PMA), poly(2-hydroxyethyl methacrylate) (PHEMA), poly(oligo (ethylene glycol) methyl ether methacrylate) (POEGMA), polyglutamic acid (PGA), poly-lysine, poly-glucoside, streptavidin, dextran, or other hydrophilic polymers with different molecular weights and end groups that are linked to a surface using, for example, silane chemistry. The end groups distal from the surface can include, but are not limited to, biotin, methoxy ether, carboxylate, amine, NHS ester, maleimide, and bis-silane. In some instances, two or more layers of a hydrophilic polymer, e.g., a linear polymer, branched polymer, or multi-branched polymer, may be deposited on the surface. In some instances, two or more layers may be covalently coupled to each other or internally cross-linked to improve the stability of the resulting surface. In some instances, oligonucleotide primers with different base sequences and base modifications (or other biomolecules, e.g., enzymes or antibodies) may be tethered to the resulting surface layer at various surface densities. In some instances, for example, both surface functional group density and oligonucleotide concentration may be varied to target a certain primer density range. Additionally, primer density can be controlled by diluting oligonucleotide with other molecules that carry the same functional group. For example, amine-labeled oligonucleotide can be diluted with amine-labeled polyethylene glycol in a reaction with an NHS-ester coated surface to reduce the final primer density. Primers with different lengths of linker between the hybridization region and the surface attachment functional group can also be applied to control surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure the primer density, fluorescently-labeled primers may be tethered to the surface and a fluorescence reading then compared with that for a dye solution of known concentration.

In some embodiments, the hydrophilic polymer can be a cross linked polymer. In some embodiments, the cross-linked polymer can include one type of polymer cross linked with another type of polymer. Examples of the crossed-linked polymer can include poly(ethylene glycol) cross-linked with another polymer selected from polyethylene oxide (PEO) or polyoxyethylene), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, dextran, or other hydrophilic polymers. In some embodiments, the cross-linked polymer can be a poly(ethylene glycol) cross-linked with polyacrylamide.

As a result of the surface passivation techniques disclosed herein, proteins, nucleic acids, and other biomolecules do not "stick" to the substrates, that is, they exhibit low nonspecific binding (NSB). Examples are shown below using standard monolayer surface preparations with varying glass preparation conditions. Hydrophilic surface that have been passivated to achieve ultra-low NSB for proteins and nucleic acids require novel reaction conditions to improve primer deposition reaction efficiencies, hybridization performance, and induce effective amplification. All of these processes require oligonucleotide attachment and subsequent protein binding and delivery to a low binding surface. As described below, the combination of a new primer surface conjugation formulation (Cy3 oligonucleotide graft titration) and resulting ultra-low non-specific background (NSB functional tests performed using red and green fluorescent dyes) yielded results that demonstrate the viability of the disclosed approaches. Some surfaces disclosed herein exhibit a ratio of specific (e.g., hybridization to a tethered primer or probe) to nonspecific binding (e.g., Brer) of a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein. Some surfaces disclosed herein exhibit a ratio of specific to nonspecific fluorescence signal (e.g., for specifically-hybridized to nonspecifically bound labeled oligonucleotides, or for specifically-amplified to nonspecifically-bound ($B_{inter}$) or non-specifically amplified ($B_{intra}$) labeled oligonucleotides or a combination thereof ($B_{inter}+B_{intra}$)) for a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein.

In order to scale primer surface density and add additional dimensionality to hydrophilic or amphoteric surfaces, substrates comprising multi-layer coatings of PEG and other hydrophilic polymers have been developed. By using hydrophilic and amphoteric surface layering approaches that include, but are not limited to, the polymer/co-polymer materials described below, it is possible to increase primer loading density on the surface significantly. Traditional PEG coating approaches use monolayer primer deposition, which have been generally reported for single molecule applications, but do not yield high copy numbers for nucleic acid amplification applications. As described herein "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, poly acrylamide, polyester, dextran, poly-lysine, and copolymers of poly-lysine and PEG. In some instances, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some instances, high primer density materials may be constructed in solution and subsequently layered onto the surface in multiple steps.

The attachment chemistry used to graft a first chemically-modified layer to a support surface will generally be dependent on both the material from which the support is fabricated and the chemical nature of the layer. In some instances, the first layer may be covalently attached to the support surface. In some instances, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques known to those of skill in the art may be used to clean or treat the support surface. For example, glass or silicon surfaces may be acid-washed using a Piranha solution (a mixture of sulfuric acid (H2SO4) and hydrogen peroxide (H2O2)) and/or cleaned using an oxygen plasma treatment method.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding support surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (i.e., comprising a free amino functional group), maleimide-PEG silane, biotin-PEG silane, and the like.

Any of a variety of molecules known to those of skill in the art including, but not limited to, amino acids, peptides, nucleotides, oligonucleotides, other monomers or polymers, or combinations thereof may be used in creating the one or more chemically-modified layers on the support surface, where the choice of components used may be varied to alter one or more properties of the support surface, e.g., the surface density of functional groups and/or tethered oligonucleotide primers, the hydrophilicity/hydrophobicity of the support surface, or the three three-dimensional nature (i.e., "thickness") of the support surface. Examples of preferred polymers that may be used to create one or more layers of low non-specific binding material in any of the disclosed support surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the support surface and/or to cross-link the layers to each other include, but are not limited to, biotin-streptavidin interactions (or variations thereof), his tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

One or more layers of a multi-layered surface may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some instances, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branches. Molecules often exhibit a 'power of 2' number of branches, such as 2, 4, 8, 16, 32, 64, or 128 branches.

Exemplary PEG multilayers include PEG (8,16,8) (8 arm, 16 arm, 8 arm)? on PEG-amine-APTES. Similar concentrations were observed for 3-layer multi-arm PEG (8 arm, 16 arm, 8 arm) and (8 arm, 64 arm, 8 arm) on PEG-amine-APTES exposed to 8 uM primer, and 3-layer multi-arm PEG (8 arm, 8 arm, 8 arm) using star-shape PEG-amine to replace 16 arm and 64 arm PEG multilayers having comparable first, second and third PEG layers are also contemplated.

Linear, branched, or multi-branched polymers used to create one or more layers of any of the multi-layered surfaces disclosed herein may have a molecular weight of at least 500, at least 1,000, at least 1,500, at least 2,000, at least 2,500, at least 3,000, at least 3,500, at least 4,000, at least 4,500, at least 5,000, at least 7,500, at least 10,000, at least 12,500, at least 15,000, at least 17,500, at least 20,000, at least 25,000, at least 30,000, at least 35,000, at least 40,000, at least 45,000, or at least 50,000 Daltons. In some instances, the linear, branched, or multi-branched polymers used to create one or more layers of any of the multi-layered surfaces disclosed herein may have a molecular weight of at most 50,000, at most 45,000, at most 40,000, at most 35,000, at most 30,000, at most 25,000, at most 20,000, at most 17,500, at most 15,000, at most 12,500, at most 10,000, at most 7,500, at most 5,000, at most 4,500, at most 4,000, at most 3,500, at most 3,000, at most 2,500, at most 2,000, at most 1,500, at most 1,000, or at most 500 Daltons. Any of the lower and upper values described in this paragraph may be combined to form a range included within the present disclosure, for example, in some instances the molecular weight of linear, branched, or multi-branched polymers used to create one or more layers of any of the multi-layered surfaces disclosed herein may range from about 1,500 to about 20,000 Daltons. Those of skill in the art will recognize that the molecular weight of linear, branched, or multi-branched polymers used to create one or more layers of any of the multi-layered surfaces disclosed herein may have any value within this range, e.g., about 1,260 Daltons.

In some instances, e.g., wherein at least one layer of a multi-layered surface comprises a branched polymer, the number of covalent bonds between a branched polymer molecule of the layer being deposited and molecules of the previous layer may range from about one covalent linkage per molecule and about 32 covalent linkages per molecule. In some instances, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32, or more than 32 covalent linkages per molecule. In some instances, the number of covalent bonds between a branched polymer molecule of the new layer and molecules of the previous layer may be at most 32, at most 30, at most 28, at most 26, at most 24, at most 22, at most 20, at most 18, at most 16, at most 14, at most 12, at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of covalent bonds between a branched polymer molecule of the new layer and molecules of the previous layer may range from about 4 to about 16. Those of skill in the art will recognize that the number of covalent bonds between a branched polymer molecule of the new layer and molecules of the previous layer may have any value within this range, e.g., about 11 in some instances, or an average number of about 4.6 in other instances.

Any reactive functional groups that remain following the coupling of a material layer to the support surface may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

The number of layers of low non-specific binding material, e.g., a hydrophilic polymer material, deposited on the surface of the disclosed low binding supports may range from 1 to about 10. In some instances, the number of layers is at least 1, at least 2, at least 3, at least 4, at least 5, at least 6, at least 7, at least 8, at least 9, or at least 10. In some instances, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of layers may range from about 2 to about 4. In some instances, all of the layers may comprise the same material. In some instances, each layer may comprise a different material. In some instances, the plurality of layers may comprise a plurality of materials. In some instances at least one layer may comprise a branched polymer. In some instance, all of the layers may comprise a branched polymer.

One or more layers of low non-specific binding material may in some cases be deposited on and/or conjugated to the substrate surface using a polar protic solvent, a polar aprotic solvent, a nonpolar solvent, or any combination thereof. In some instances the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some instances, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, or any percentage spanned or adjacent to the range herein, with the balance made up of water or an aqueous buffer solution. In some instances, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, or any percentage spanned or adjacent to the range herein, with the balance made up of an organic solvent. The pH of the solvent mixture used may be less than 5, 5, 5, 5, 6, 6, 6.5, 7, 7.5, 8, 8.5, 9, 9.5, 10, or greater than 10, or any value spanned or adjacent to the range described herein.

In some instances, one or more layers of low non-specific binding material may be deposited on and/or conjugated to the substrate surface using a mixture of organic solvents, wherein the dielectric constant of at least once component is less than 40 and constitutes at least 50% of the total mixture by volume. In some instances, the dielectric constant of the at least one component may be less than 10, less than 20, less than 30, less than 40. In some instances, the at least one component constitutes at least 20%, at least 30%, at least 40%, at least 50%, at least 50%, at least 60%, at least 70%, or at least 80% of the total mixture by volume.

As noted, the low non-specific binding supports of the present disclosure exhibit reduced non-specific binding of proteins, nucleic acids, and other components of the hybridization and/or amplification formulation used for solid-phase nucleic acid amplification. The degree of non-specific binding exhibited by a given support surface may be assessed either qualitatively or quantitatively. For example, in some instances, exposure of the surface to fluorescent dyes (e.g., Cy3, Cy5, etc.), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some instances, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under conditions where fluorescence signal is linearly related (or related in a predictable manner) to the number of fluorophores on the support surface (e.g., under conditions where signal saturation and/or self-quenching of the fluorophore is not an issue) and suitable calibration standards are used. In some instances, other techniques known to those of skill in the art, for example, radioisotope labeling and counting methods may be used for quantitative assessment of the degree to which non-specific binding is exhibited by the different support surface formulations of the present disclosure.

Some surfaces disclosed herein exhibit a ratio of specific to non-specific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. Some surfaces disclosed herein exhibit a ratio of specific to non-specific fluorescence of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

As noted, in some instances, the degree of non-specific binding exhibited by the disclosed low non-specific binding supports may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some instances, the label may comprise a fluorescent label. In some instances, the label may comprise a radioisotope. In some instances, the label may comprise any other detectable label known to one of skill in the art. In some instances, the degree of non-specific binding exhibited by a given support surface formulation may thus be assessed in terms of the number of non-specifically bound protein molecules (or other molecules) per unit area. In some instances, the low non-specific binding supports of the present disclosure may exhibit non-specific protein binding (or non-specific binding of other specified molecules, e.g., Cy3 dye) of less than 0.001 molecule per µm2, less than 0.01 molecule per µm2, less than 0.1 molecule per µm2, less than 0.25 molecule per µm2, less than 0.5 molecule per µm2, less than 1 molecule per µm2, less than 10 molecules per µm2, less than 100 molecules per µm2, or less than 1,000 molecules per µm2. Those of skill in the art will realize that a given support surface of the present disclosure may exhibit non-specific binding falling anywhere within this range, for example, of less than 86 molecules per µm2. For example, some modified surfaces disclosed herein exhibit non-specific protein binding of less than 0.5 molecule/um2 following contact with a 1 uM solution of Cy3 labeled streptavidin (GE Amersham) in phosphate buffered saline (PBS) buffer for 15 minutes, followed by 3 rinses with deionized water. Some modified surfaces disclosed herein exhibit non-specific binding of Cy3 dye molecules of less than 0.25 molecules per um2. In independent non-specific binding assays, 1 uM labeled Cy3 SA (ThermoFisher), 1 uM Cy5 SA dye (ThermoFisher), 10 uM Aminoallyl-dUTP-ATTO-647N (Jena Biosciences), 10 uM Aminoallyl-dUTP-ATTO-Rho11 (Jena Biosciences), 10 uM Aminoallyl-dUTP-ATTO-Rho11 (Jena Biosciences), 10 uM 7-Propargylamino-7-deaza-dGTP-Cy5 (Jena Biosciences, and 10 uM 7-Propargylamino-7-deaza-dGTP-Cy3 (Jena Biosciences) were incubated on the low binding substrates at 37° C. for 15 minutes in a 384 well plate format. Each well was rinsed 2-3× with 50 ul deionized RNase/DNase Free water and 2-3× with 25 mM ACES buffer pH 7.4. The 384 well plates were imaged on a GE Typhoon (GE Healthcare Lifesciences, Pittsburgh, PA) instrument using the Cy3, AF555, or Cy5 filter sets (according to dye test performed) as specified by the manufacturer at a PMT gain setting of 800 and resolution of 50-100 µm. For higher resolution imaging, images were collected on an Olympus IX83 microscope (Olympus Corp., Center Valley, PA) with a total internal reflectance fluorescence (TIRF) objective (20×, 0.75 NA or 100λ, 1.5 NA, Olympus), an sCMOS Andor camera (Zyla 4.2), and excitation wavelengths of 532 nm or 635 nm. Dichroic mirrors were purchased from Semrock (IDEX Health & Science, LLC, Rochester, New York.), e.g., 405, 488, 532, or 633 nm dichroic reflectors/beamsplitters, and band pass filters were chosen as 532 LP or 645 LP concordant with the appropriate excitation wavelength. Some modified surfaces disclosed herein exhibit non-specific binding of dye molecules of less than 0.25 molecules per µm2.

In some instances, the surfaces disclosed herein exhibit a ratio of specific to non-specific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. In some instances, the surfaces disclosed herein exhibit a ratio of specific to non-specific fluorescence signals for a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

The low-background surfaces consistent with the disclosure herein may exhibit specific dye attachment (e.g., Cy3 attachment) to non-specific dye adsorption (e.g., Cy3 dye adsorption) ratios of at least 3:1, 4:1, 5:1, 6:1, 7:1, 8:1, 9:1, 10:1, 15:1, 20:1, 30:1, 40:1, 50:1, or more than 50 specific dye molecules attached per molecule non-specifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 3:1, 4:1, 5:1, 6:1, 7:1, 8:1, 9:1, 10:1, 15:1, 20:1, 30:1, 40:1, 50:1, or more than 50:1.

In some instances, the degree of hydrophilicity (or "wettability" with aqueous solutions) of the disclosed support surfaces may be assessed, for example, through the measurement of water contact angles in which a small droplet of water is placed on the surface and its angle of contact with the surface is measured using, e.g., an optical tensiometer. In some instances, a static contact angle may be determined. In some instances, an advancing or receding contact angle may be determined. In some instances, the water contact angle for the hydrophilic, low-binding support surfaced disclosed herein may range from about 0 degrees to about 50 degrees. In some instances, the water contact angle for the hydrophilic, low-binding support surfaced disclosed herein may no more than 50 degrees, 45 degrees, 40 degrees, 35 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than any value within this range, e.g., no more than 40 degrees. Those of skill in the art will realize that a given hydrophilic, low-binding support surface of the present disclosure may exhibit a water contact angle having a value of anywhere within this range, e.g., about 27 degrees.

In some instances, the hydrophilic surfaces disclosed herein facilitate reduced wash times for bioassays, often due to reduced non-specific binding of biomolecules to the low-binding surfaces. In some instances, adequate wash steps may be performed in less than 60, 50, 40, 30, 20, 15, 10, or less than 10 seconds. For example, in some instances adequate wash steps may be performed in less than 30 seconds.

Some low-binding surfaces of the present disclosure exhibit significant improvement in stability or durability to prolonged exposure to solvents and elevated temperatures, or to repeated cycles of solvent exposure or changes in temperature. For example, in some instances, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some instances, the degree of change in the fluorescence used to assess the quality of the surface may be less than 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents and/or elevated temperatures (or any combination of these percentages as measured over these time periods). In some instances, the degree of change in the fluorescence used to assess the quality of the surface may be less than 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes and/or changes in temperature (or any combination of these percentages as measured over this range of cycles).

In some instances, the surfaces disclosed herein may exhibit a high ratio of specific signal to non-specific signal or other background. For example, when used for nucleic acid amplification, some surfaces may exhibit an amplification signal that is at least 3, 4, 5, 6, 7, 8, 9, 10, 15, 20, 30, 40, 50, 75, 100, or greater than 100 fold greater than a signal of an adjacent unpopulated region of the surface. Similarly, some surfaces exhibit an amplification signal that is at least 3, 4, 5, 6, 7, 8, 9, 10, 15, 20, 30, 40, 50, 75, 100, or greater than 100 fold greater than a signal of an adjacent amplified nucleic acid population region of the surface.

Fluorescence excitation energies vary among particular fluorophores and protocols, and may range in excitation wavelength from less than 400 nm to over 800 nm, consistent with fluorophore selection or other parameters of use of a surface disclosed herein.

Accordingly, low non-specific binding surfaces as disclosed herein exhibit low background fluorescence signals or high contrast to noise (CNR) ratios relative to known surfaces in the art. For example, in some instances, the background fluorescence of the surface at a location that is spatially distinct or removed from a labeled feature on the surface (e.g., a labeled spot, cluster, discrete region, subsection, or subset of the surface) comprising a hybridized cluster of nucleic acid molecules, or a clonally-amplified cluster of nucleic acid molecules produced by, e.g., 20 cycles of nucleic acid amplification via thermocycling, may be no more than 20×, 10×, 5×, 2×, 1×, 0.5×, 0.1×, or less than 0.1× greater than the background fluorescence measured at that same location prior to performing said hybridization or said 20 cycles of nucleic acid amplification.

In some instances, fluorescence images of the disclosed low background surfaces when used in nucleic acid hybridization or amplification applications to create clusters of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

In general, at least one layer of the one or more layers of low non-specific binding material may comprise functional groups for covalently or non-covalently attaching oligonucleotide molecules, e.g., adapter or primer sequences, or the at least one layer may already comprise covalently or non-covalently attached oligonucleotide adapter or primer sequences at the time that it is deposited on the support surface. In some instances, the oligonucleotides tethered to the polymer molecules of at least one third layer may be distributed at a plurality of depths throughout the layer.

In some instances, the oligonucleotide adapter or primer molecules are covalently coupled to the polymer in solution, e.g., prior to coupling or depositing the polymer on the surface. In some instances, the oligonucleotide adapter or primer molecules are covalently coupled to the polymer after it has been coupled to or deposited on the surface. In some instances, at least one hydrophilic polymer layer comprises a plurality of covalently-attached oligonucleotide adapter or primer molecules. In some instances, at least two, at least three, at least four, or at least five layers of hydrophilic polymer comprise a plurality of covalently-attached adapter or primer molecules.

In some instances, the oligonucleotide adapter or primer molecules may be coupled to the one or more layers of hydrophilic polymer using any of a variety of suitable conjugation chemistries known to those of skill in the art. For example, the oligonucleotide adapter or primer sequences may comprise moieties that are reactive with amine groups, carboxyl groups, thiol groups, and the like. Examples of suitable amine-reactive conjugation chemistries that may be used include, but are not limited to, reactions involving isothiocyanate, isocyanate, acyl azide, NHS ester, sulfonyl chloride, aldehyde, glyoxal, epoxide, oxirane, carbonate, aryl halide, imidoester, carbodiimide, anhydride, and fluorophenyl ester groups. Examples of suitable carboxyl-reactive conjugation chemistries include, but are not limited to, reactions involving carbodiimide compounds, e.g., water soluble EDC (1-ethyl-3-(3-dimethylaminopropyl)carbodiimide•HCL). Examples of suitable sulfydryl-reactive conjugation chemistries include maleimides, haloacetyls and pyridyl disulfides.

One or more types of oligonucleotide molecules may be attached or tethered to the support surface. In some instances, the one or more types of oligonucleotide adapters or primers may comprise spacer sequences, adapter sequences for hybridization to adapter-ligated template library nucleic acid sequences, forward amplification primers, reverse amplification primers, sequencing primers, and/or molecular barcoding sequences, or any combination thereof. In some instances, 1 primer or adapter sequence may be tethered to at least one layer of the surface. In some instances, at least 2, 3, 4, 5, 6, 7, 8, 9, 10, or more than 10 different primer or adapter sequences may be tethered to at least one layer of the surface.

The tethered oligonucleotide adapter and/or primer sequences may range in length from about 10 nucleotides to about 100 nucleotides. In some instances, the tethered oligonucleotide adapter and/or primer sequences may be at least 10, at least 20, at least 30, at least 40, at least 50, at least 60, at least 70, at least 80, at least 90, or at least 100 nucleotides in length. In some instances, the tethered oligonucleotide adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some instances the length of the tethered oligonucleotide adapter and/or primer sequences may range from about 20 nucleotides to about 80 nucleotides. Those of skill in the art will recognize that the length of the tethered oligonucleotide adapter and/or primer sequences may have any value within this range, e.g., about 24 nucleotides.

In some instances, the tethered adapter or primer sequences may comprise modifications designed to facilitate the specificity and efficiency of nucleic acid amplification as performed on the low-binding supports. For example, in some instances the primer may comprise polymerase stop points such that the stretch of primer sequence between the surface conjugation point and the modification site is always in single-stranded form and functions as a loading site for 5' to 3' helicases in some helicase-dependent isothermal amplification methods. Other examples of primer modifications that may be used to create polymerase stop points include, but are not limited to, an insertion of a PEG chain into the backbone of the primer between two nucleotides towards the 5' end, insertion of an abasic nucleotide (i.e., a nucleotide that has neither a purine nor a pyrimidine base), or a lesion site which can be bypassed by the helicase.

As will be discussed further in the examples below, it may be desirable to vary the surface density of tethered oligonucleotide adapters or primers on the support surface and/or the spacing of the tethered adapters or primers away from the support surface (e.g., by varying the length of a linker molecule used to tether the adaptors or primers to the surface) in order to "tune" the support for optimal performance when using a given amplification method. As noted below, adjusting the surface density of tethered oligonucleotide adapters or primers may impact the level of specific and/or non-specific amplification observed on the support in a manner that varies according to the amplification method selected. In some instances, the surface density of tethered oligonucleotide adapters or primers may be varied by adjusting the ratio of molecular components used to create the support surface. For example, in the case that an oligonucleotide primer—PEG conjugate is used to create the final layer of a low-binding support, the ratio of the oligonucleotide primer—PEG conjugate to a non-conjugated PEG molecule may be varied. The resulting surface density of tethered primer molecules may then be estimated or measured using any of a variety of techniques known to those of skill in the art. Examples include, but are not limited to, the use of radioisotope labeling and counting methods, covalent coupling of a cleavable molecule that comprises an optically-detectable tag (e.g., a fluorescent tag) that may be cleaved from a support surface of defined area, collected in a fixed volume of an appropriate solvent, and then quantified by comparison of fluorescence signals to that for a calibration solution of known optical tag concentration, or using fluorescence imaging techniques provided that care has been taken with the labeling reaction conditions and image acquisition settings to ensure that the fluorescence signals are linearly related to the number of fluorophores on the surface (e.g., that there is no significant self-quenching of the fluorophores on the surface).

In some instances, the resultant surface density of oligonucleotide adapters or primers on the low binding support surfaces of the present disclosure may range from about 100 primer molecules per µm2 to about 1,000,000 primer molecules per µm2. In some instances, the surface density of oligonucleotide adapters or primers may be at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 5,500, at least 6,000, at least 6,500, at least 7,000, at least 7,500, at least 8,000, at least 8,500, at least 9,000, at least 9,500, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 molecules per µm2. In some instances, the surface density of oligonucleotide adapters or primers may be at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,500, at most 9,000, at most 8,500, at most 8,000, at most 7,500, at most 7,000, at most 6,500, at most 6,000, at most 5,500, at most 5,000, at most 4,500, at most 4,000, at most 3,500, at most 3,000, at most 2,500, at most 2,000, at most 1,500, at most 1,000, at most 900, at most 800, at most 700, at most 600, at most 500, at most 400, at most 300, at most 200, or at most 100 molecules per µm2. Any of the lower and upper values described in this paragraph may be combined to form a range included within the present disclosure, for example, in some instances the surface density of adapters or primers may range from about 10,000 molecules per µm2 to about 100,000 molecules per µm2. Those of skill in the art will recognize that the surface density of adapter or primer molecules may have any value within this range, e.g., about 3,800 molecules per µm2 in some instances, or about 455,000 molecules per µm2 in other instances. In some instances, as will be discussed further below, the surface density of template library nucleic acid sequences (e.g., sample DNA molecules) initially hybridized to adapter or primer sequences on the support surface may be less than or equal to that indicated for the surface density of tethered oligonucleotide primers. In some instances, as will also be discussed further below, the surface density of clonally-amplified template library nucleic acid sequences hybridized to adapter or primer sequences on the support surface may span the same range or a different range as that indicated for the surface density of tethered oligonucleotide adapters or primers.

Local surface densities of adapter or primer molecules as listed above do not preclude variation in density across a surface, such that a surface may comprise a region having an oligo density of, for example, 500,000/um2, while also comprising at least a second region having a substantially different local density.

Figure 2:
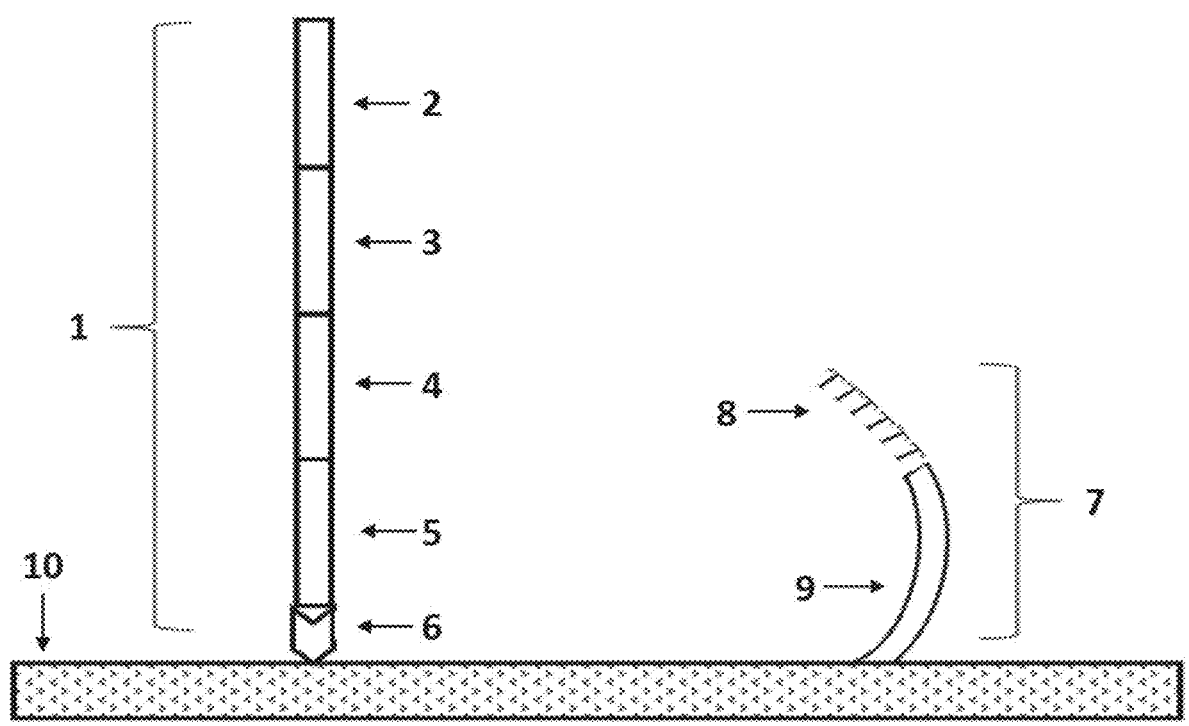
FIG. 2 is a schematic showing a support comprising a capture oligonucleotide and a circularization oligonucleotide immobilized thereon according to an embodiment of the present disclosure. In some embodiments, the support comprises a plurality of capture oligonucleotides and a plurality of circularization oligonucleotides immobilized thereon.

Solid Supports for Capturing and Analyzing DNA. In some embodiments, the surface has bound thereto a plurality of oligonucleotides for the capture of target nucleic acids, such as DNA molecules (e.g., capture oligonucleotides; (1)), as shown in FIG. 2. In some embodiments, the capture oligonucleotides each comprise single-stranded oligonucleotides. The capture oligonucleotides can be immobilized to the passivated surface by their 5' ends, or an internal portion of the capture oligonucleotides can be immobilized to the passivated surface. The capture oligonucleotides can each include an extendible 3' end. As shown in FIG. 2, the capture oligonucleotides can each include a cleavable region (6) which can be located near the end that is immobilized to the passivated surface. For example, the capture oligonucleotides can each include a cleavable region near the 5' end. The cleavable region can be cleaved with an enzyme, a chemical compound, light or heat. In some embodiments, the capture oligonucleotides each comprise a target capture region (2) and a universal sequence region (3, 4, 5). In some embodiments, the target capture region of the capture oligonucleotides comprise a sequence that can hybridize to at least a portion of the target nucleic acid. The target capture region may comprise, for example, a random nucleotide sequence or a target-specific sequence that corresponds to a known sequence of the target nucleic acid. In some embodiments, the universal sequence region comprises a sample barcode sequence (3) that can be used to distinguish target nucleic acids from different sample sources in a multiplex assay. In some embodiments, the universal sequence region comprises a spatial barcode sequence (4) which conveys positional information of the capture oligonucleotide on the support which in turn conveys positional information of the cell within the tissue sample or of a single cell. In some embodiments, the sample barcode sequence (3) can be upstream or downstream of the spatial barcode sequence (4). In some embodiments, the universal sequence region of the capture oligonucleotides comprise a circularization anchor region (5) that hybridizes to a portion of a second type of oligonucleotide that promotes circularization of the captured nucleic acid (7). In some embodiments, the universal sequence region of the capture oligonucleotides comprise at least one sequence that binds/hybridizes to a universal primer sequence such as a sequencing primer sequence and/or an amplification primer sequence. In some embodiments, the circularization anchor region (5) includes any one or any combination of two or more of the sequencing primer sequence, the amplification primer sequence, the sample barcode sequence and/or the spatial barcode sequence. In some embodiments, the circularization anchor region (5) comprises a separate sequence that hybridizes with a portion of the second type of oligonucleotide that promotes circularization of the captured nucleic acid. In some embodiments, the universal sequence region comprises a cleavable region which is cleavable with an enzyme, a chemical compound, light or heat.

Still referring to FIG. 2, in some embodiments, the surface has bound thereto a plurality of a second type of oligonucleotide (e.g., circularization oligonucleotides (7)) that promote circularization of the captured target nucleic acids. In some embodiments, the circularization oligonucleotides each comprise single-stranded oligonucleotides. The circularization oligonucleotides can be immobilized to the passivated surface by their 5' ends, or an internal portion of the circularization oligonucleotides can be immobilized to the passivated surface. The circularization oligonucleotides can each include an extendible 3' end. The circularization oligonucleotides each comprise a homopolymer region (8) and a universal sequence region (9), as shown in FIG. 2. The homopolymer region can be selected from a group consisting of poly-T tail, poly-dT tail, poly-A tail, poly-dA tail, poly-C tail, poly-dC tail, poly-G tail and poly-dG tail. The homopolymer region can be located at or near the 3' end of the circularization oligonucleotides. In some embodiments, the universal sequence region of the circularization oligonucleotides hybridizes to the circularization anchor region of the capture oligonucleotides. In some embodiments, the universal sequence region of the circularization oligonucleotides comprise at least one sequence that binds/hybridizes to a universal primer sequence such as a sequencing primer sequence of the capture oligonucleotides. In some embodiments, the universal sequence region of the circularization oligonucleotides comprise at least one sequence that binds/hybridizes to a universal primer sequence such as an amplification primer sequence of the capture oligonucleotides. In some embodiments, the universal sequence region of the circularization oligonucleotides comprise at least one sequence that binds/hybridizes to the sample barcode sequence and/or the spatial barcode sequence of the capture oligonucleotides. In some embodiments, the circularization oligonucleotides comprise a separate sequence that binds/hybridizes with a portion of the circularization anchor region of the capture oligonucleotides (e.g., a circularization anchor binding sequence).

In some embodiments, the capture oligonucleotides (FIG. 2, 1) and the circularization oligonucleotides (FIG. 2, 7) can be immobilized on the passivated surface prior to contacting the passivated surface with the target nucleic acid molecules for the target molecule capturing steps. In an alternative embodiment, the capture oligonucleotides is immobilized on the passivated surface prior to contacting the passivated surface with the target nucleic acid molecules for the target molecule capturing steps, and subsequently the plurality of circularization oligonucleotides (e.g., in soluble form) can be provided in solution and flowed onto the passivated surface to immobilize the circularization oligonucleotides.

In some embodiments, said circularization oligo may be the same as, may comprise, or may be comprised within, said capture oligo. In some embodiments, said circularization oligo may comprise a separate molecule.

Figure 3:
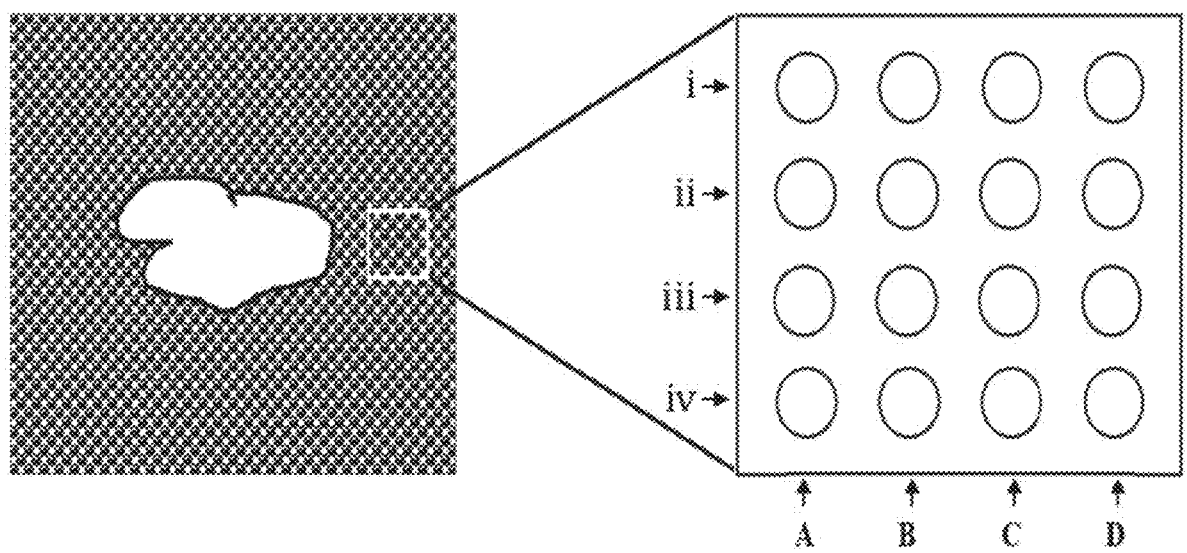
FIG. 3 is a schematic showing a support comprising a plurality of capture oligonucleotides and circularization oligonucleotides immobilized thereon and a biological sample (e.g., a tissue sample) placed on the support (see the left schematic), according to an embodiment of the present disclosure.

The present disclosure provides a low-binding support having a coating where the coating provides a low non-specific binding surface to proteins, carbohydrates, lipids, cell debris, or solution borne dye molecules. In some embodiments, a tissue sample or cells or a single cell can be place on the surface of the support (FIG. 3, left). In some embodiments, the low non-specific binding surface comprises a plurality of regions (e.g., features) located at different pre-determined locations on the support (FIG. 3, right). The different features on the support can be placed at non-overlapping positions or at overlapping positions on the support. The features can be configured to have any shape, for example circular, ovular, square, rectangular, or polygonal. The features can be arranged in a grid pattern having rows and columns, or can be arranged in a row or a column. In some embodiments, any given feature contains a plurality of capture oligonucleotides and a plurality of circularization oligonucleotides immobilized to the coating. The plurality of features includes at least a first and second feature.

In some embodiments, the first feature comprises a plurality of first capture oligonucleotides having a first target capture region, a first spatial barcode sequence, a first sample barcode sequence and a first cleavable region, and the first feature comprises a plurality of first circularization oligonucleotides having a first circularization anchor binding sequence, a first amplification primer binding sequence and a first sequencing primer binding sequence. In some embodiments, the first capture oligonucleotides also include a first amplification primer binding sequence and/or a first amplification primer binding sequence. In some embodiments, the first circularization oligonucleotides also include a sequence that can bind/hybridize to the first spatial barcode sequence and/or a sequence that can bind to the first sample barcode sequence.

In some embodiments, the second feature comprises a plurality of second capture oligonucleotides having a second target capture region, a second spatial barcode sequence, a second sample barcode sequence and a second cleavable region, and the second feature comprises a plurality of second circularization oligonucleotides having a second circularization anchor binding sequence, a second amplification primer binding sequence and a second sequencing primer binding sequence. In some embodiments, the second capture oligonucleotides also include a second amplification primer binding sequence and/or a second amplification primer binding sequence. In some embodiments, the second circularization oligonucleotides also include a sequence that can bind/hybridize to the second spatial barcode sequence and/or a sequence that can bind to the second sample barcode sequence.

In some embodiments, the sequence of the first target capture region in the first feature is the same or different from the sequence of the second target capture region in the second feature. In some embodiments, the first spatial barcode sequence in the first feature differs from the second spatial barcode sequence in the second feature. In some embodiments, the first sample barcode sequence in the first feature is the same or different as the second sample barcode sequence in the second feature. The first amplification primer binding sequence in the first feature can be the same as the second amplification primer binding sequence in the second feature. The first sequencing primer binding sequence in the first feature can be the same as the second sequence primer binding sequence in the second feature. The first cleavable region in the first feature can be cleavable with the same or different conditions (e.g., the same enzyme, chemical compound, light or heat) as the second cleavable region in the second feature.

In some embodiments, the low non-specific binding coating comprises a plurality of regions (e.g., features) where the features are attached with a plurality of capture and circularization oligonucleotides that are attached to the coating. In some embodiments, a first feature is attached with a first plurality of capture oligonucleotides and a first plurality of circularization oligonucleotides, and a second feature is attached with a second plurality of capture oligonucleotides and a second plurality of circularization oligonucleotides, wherein the first and second capture oligonucleotides and the first and second circularization oligonucleotides are in fluid communication with each other so that the capture and circularization oligonucleotides can react with reagents (e.g., enzymes including polymerases, polymer-nucleotide conjugates, nucleotides and/or divalent cations) in a massively parallel manner.

In some embodiments, the cleavable region of the capture oligonucleotides are cleavable with an enzyme. In some embodiments, the cleavable region as shown in FIG. 2 (6) comprises at least one uracil base, or a poly-uracil sequence, which is cleavable with a uracil DNA glycosylase (UDG) enzyme or a DNA glycosylase-lyase Endonuclease VIII (e.g., commercially-available enzyme USER™). In some embodiments, the cleavable site comprises at least one 8-koxoguanine (8-oxoG) which is cleavable with a DNA-formamidopyrimidine glycosylase enzyme (Fpg). In some embodiments, the cleavable region comprises an abasic site which is cleavable with an endonuclease IV or endonuclease VIII. In some embodiments, the cleavable region which is cleavable with an enzyme comprises a nucleotide sequence which is recognized and cleaved with a restriction endonuclease enzyme which cleaves double-stranded or single-stranded nucleic acid strands (e.g., DNA). In some embodiments, the enzyme-cleavable region comprises a glycosidic linkage which is cleavable with an amylase enzyme, or a peptide linkage which is cleavable with a protease.

As shown in FIG. 2, in some embodiments, the cleavable region (6) of the capture oligonucleotides is cleavable with a chemical compound comprise a labile chemical bond, for example including but not limited to ester linkages, a thiol linkage, a vicinal diol linkage, a sulfone linkage, a silyl ether linkage, an abasic or apurinic/apyrimidinic (AP) site. The ester linkages can be cleavable with an acid, base, or hydroxylamine. The thiol linkage can be a disulfide linkage which is cleavable with glutathione or a reducing agent. The vincinal diol linkage can be cleavable with sodium periodate. The sulfonate linkage can be cleavable with a base. The silyl ether linkage can be cleavable with an acid. The abasic or apurinic/apyrimidinic (AP) site can be cleavable with an alkali or an AP endonuclease enzyme.

In some embodiments, the cleavable region (6) of the capture oligonucleotides is cleavable with light comprises a photo-cleavable moiety which can be cleaved with exposure to light, UV light or a laser. The photo-cleavable moiety can be cleaved by exposure to any wavelength of light. The photo-cleavable moiety comprises 3-amino-3-(2-nitrophenyl)propionic acid (ANP), dicoumarin, 6-bromo-7-alkixycoumarin-4-ylmethoxycarbonyl, phenacyl ester derivatives, or 8-quinolinyl benzenesulfonate. The photo-cleavable moiety comprises a bimane-based linker, a bis-arylhydrazone based linker, or an ortho-nitrobenzyl (ONB) linker. In some embodiments, the cleavable region (6) of the capture oligonucleotides is cleavable with exposure to heat comprise a Diels-Alder linker.

Figure 4:
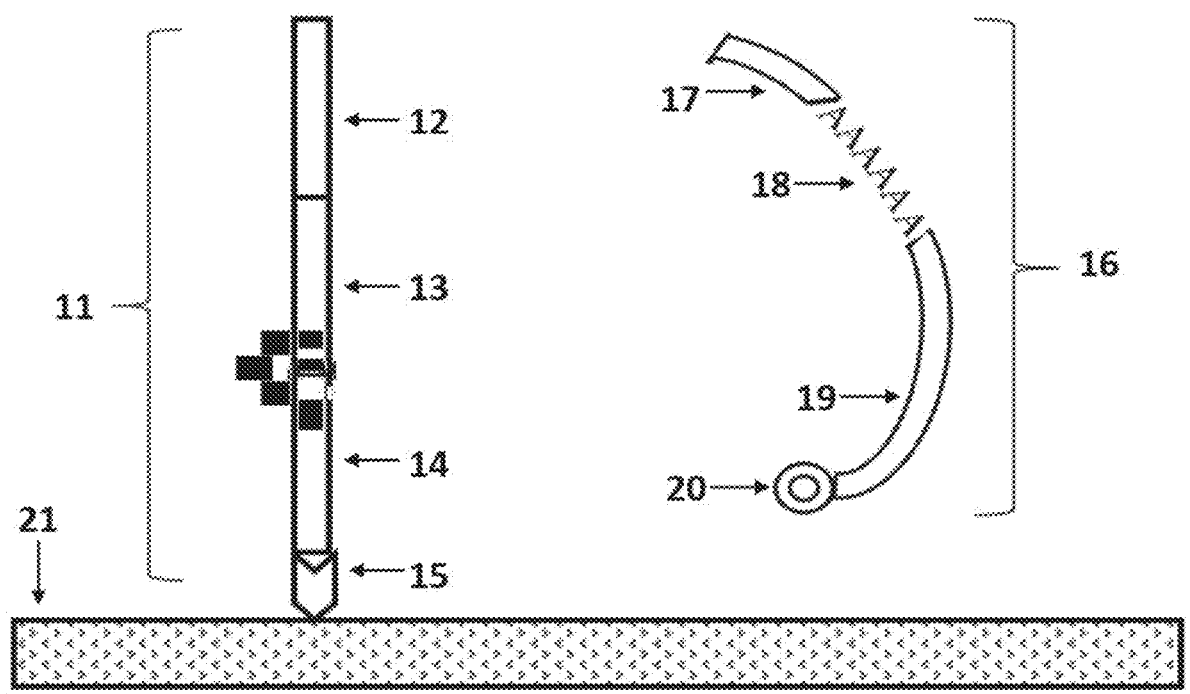
FIG. 4 is a schematic showing a support comprising a capture oligonucleotide immobilized thereon, and a soluble circularization oligonucleotide, according to an embodiment of the present disclosure. In some embodiments, the support comprises a plurality of capture oligonucleotides immobilized thereon.

Supports for Capturing and Analyzing RNA. Provided herein in FIG. 4 are supports (11) comprising a plurality of immobilized oligonucleotides. The support can be used to capture and analyze target nucleic acids, for example RNA molecules. In some embodiments, the support comprises a passivated surface (e.g., coating or layer) (FIG. 1) which is disclosed elsewhere herein, such that the surface provides low or no binding to proteins, carbohydrates, lipids, cell debris, or solution borne dye molecules. In some embodiments, the surface has bound thereto a plurality of oligonucleotides for the capture of target nucleic acids (e.g., capture oligonucleotides; FIG. 4 (11)). In some embodiments, the capture oligonucleotides each comprise single-stranded oligonucleotides. The capture oligonucleotides can be immobilized to the passivated surface by their 5' ends, or an internal portion of the capture oligonucleotides can be immobilized to the passivated surface. The capture oligonucleotides can each include an extendible 3' end. As shown in FIG. 4, the capture oligonucleotides can each include a cleavable region (15) which can be located near the end that is immobilized to the passivated surface. For example, the capture oligonucleotides can each include a cleavable region near the 5' end. The cleavable region can be cleaved with an enzyme, a chemical compound, light or heat. In some embodiments, the capture oligonucleotides each comprise a target capture region (12) and a universal sequence region (13, 14). In some embodiments, the target capture region of the capture oligonucleotides comprise a sequence that can hybridize to at least a portion of the target nucleic acid. The target capture region may comprise, for example, a homopolymer sequence (e.g., poly-T or poly-dT), a random nucleotide sequence, or a target-specific sequence that corresponds to a known sequence of the target nucleic acid. In some embodiments, the universal sequence region comprises a sample barcode sequence (13) that can be used to distinguish target nucleic acids from different sample sources in a multiplex assay. In some embodiments, the universal sequence region comprises a spatial barcode sequence (14) which conveys positional information of the capture oligonucleotide on the support which in turn conveys positional information of the cell within the tissue sample or of a single cell. In some embodiments, the sample barcode sequence (13) can be upstream or downstream of the spatial barcode sequence (14). In some embodiments, the universal sequence region of the capture oligonucleotides comprise at least one sequence that binds/hybridizes to a universal primer sequence such as a sequencing primer sequence and/or an amplification primer sequence. In some embodiments, the capture oligonucleotide comprises a cleavable region (15) which is cleavable with an enzyme, a chemical compound, light or heat.

Still referring to FIG. 4, in some embodiments, provided herein are a plurality of a second type of oligonucleotide (e.g., circularization oligonucleotides; 16) in soluble form or immobilized to the surface (e.g., coating). The circularization oligonucleotides can promote circularization of the captured target nucleic acids. In some embodiments, the circularization oligonucleotides each comprise single-stranded oligonucleotides. The circularization oligonucleotides can be in soluble form, or can be immobilized to the passivated surface by their 5' ends or an internal portion of the circularization oligonucleotides can be immobilized to the passivated surface. The circularization oligonucleotides can each include an extendible 3' end. The circularization oligonucleotides each comprise an adaptor binding region (17). In some embodiments, the adaptor binding region includes a sequencing primer binding region. In some embodiments, the adaptor binding region include an amplification primer binding region. In some embodiments, the circularization oligonucleotides each comprise a homopolymer region (FIG. 4 (19)). The homopolymer region can be selected from a group consisting of poly-T, poly-dT, poly-A, poly-dA, poly-C, poly-dC, poly-G and poly-dG. In some embodiments, the circularization oligonucleotides each comprise an anchor region (19) and an anchor moiety (20).

In some embodiments, the capture oligonucleotides (FIG. 4 (11)) and the circularization oligonucleotides (FIG. 4 (16)) can be immobilized on the passivated surface prior to contacting the passivated surface with the target nucleic acid molecules (e.g., RNA) for the target molecule capturing steps. In an alternative embodiment, the capture oligonucleotides is immobilized on the passivated surface prior to contacting the passivated surface with the target nucleic acid molecules for the target molecule capturing steps, and subsequently the plurality of circularization oligonucleotides (e.g., in soluble form) can be provided in solution and flowed onto the passivated surface to immobilize the circularization oligonucleotides.

In some embodiments, said circularization oligo may be the same as, may comprise, or may be comprised within, said capture oligo. In some embodiments, said circularization oligo may comprise a separate molecule.

In some embodiments, the cleavable region (FIG. 4 (15)) of the capture oligonucleotides are cleavable with an enzyme. In some embodiments, the cleavable region comprises at least one uracil base, or a poly-uracil sequence, which is cleavable with a uracil RNA glycosylase (UDG) enzyme or a RNA glycosylase-lyase Endonuclease VIII (e.g., commercially-available enzyme USER™). In some embodiments, the cleavable site comprises at least one 8-koxoguanine (8-oxoG) which is cleavable with a RNA-formamidopyrimidine glycosylase enzyme (Fpg). In some embodiments, the cleavable region comprises an abasic site which is cleavable with an endonuclease IV or endonuclease VIII. In some embodiments, the cleavable region which is cleavable with an enzyme comprises a nucleotide sequence which is recognized and cleaved with a restriction endonuclease enzyme which cleaves double-stranded or single-stranded nucleic acid strands (e.g., RNA). In some embodiments, the enzyme-cleavable region comprises a glycosidic linkage which is cleavable with an amylase enzyme, or a peptide linkage which is cleavable with a protease.

In some embodiments, the cleavable region (FIG. 4 (15)) of the capture oligonucleotides is cleavable with a chemical compound comprise a labile chemical bond, for example including but not limited to ester linkages, a thiol linkage, a vicinal diol linkage, a sulfone linkage, a silyl ether linkage, an abasic or apurinic/apyrimidinic (AP) site. The ester linkages can be cleavable with an acid, base, or hydroxylamine. The thiol linkage can be a disulfide linkage which is cleavable with glutathione or a reducing agent. The vincinal diol linkage can be cleavable with sodium periodate. The sulfonate linkage can be cleavable with a base. The silyl ether linkage can be cleavable with an acid. The abasic or apurinic/apyrimidinic (AP) site can be cleavable with an alkali or an AP endonuclease enzyme.

In some embodiments, the cleavable region (FIG. 4 (15)) of the capture oligonucleotides is cleavable with light comprises a photo-cleavable moiety which can be cleaved with exposure to light, UV light or a laser. The photo-cleavable moiety can be cleaved by exposure to any wavelength of light. The photo-cleavable moiety comprises 3-amino-3-(2-nitrophenyl)propionic acid (ANP), dicoumarin, 6-bromo-7-alkixycoumarin-4-ylmethoxycarbonyl, phenacyl ester derivatives, or 8-quinolinyl benzenesulfonate. The photo-cleavable moiety comprises a bimane-based linker, a bis-arylhydrazone based linker, or an ortho-nitrobenzyl (ONB) linker. In some embodiments, the cleavable region (FIG. 4 (15)) of the capture oligonucleotides is cleavable with exposure to heat comprise a Diels-Alder linker.

Fixation of Biological Sample to Surfaces. Provided herein are solid supports (e.g., low non-specific binding supports) further comprising a biological sample adjacent thereto. In some embodiments, the biological sample comprises a single cell, a plurality of cells, a tissue, an organ, an organism, or section of these biological samples. In some embodiments, the biological sample is derived from eukaryotes (such as animals, plants, fungi, protista), archaebacteria, or eubacteria. The biological sample may be derived from prokaryotic or eukaryotic cells, such as adherent or non-adherent eukaryotic cells. The biological sample may be derived from a primary or immortalized cell line from a rodent, porcine, feline, canine, bovine, equine, primate, or human cell lines.

The biological sample may be a solid sample, such as a tissue biopsy. The biological sample may be a fluid sample, such as blood or a component of blood (e.g., serum or plasma). In some embodiments, the biological sample is obtained from skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, micropiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. A biological sample may be a cell-free sample.

The biological sample may comprise cells. The cells described herein may be white blood cells, red blood cells, platelets, epithelial cells, endothelial cells, neurons, glial cells, astrocytes, fibroblasts, skeletal muscle cells, smooth muscle cells, gametes, or cells from the heart, lungs, brain, liver, kidney, spleen, pancreas, thymus, bladder, stomach, colon, or small intestine. The cells may be normal or healthy cells. Alternately or in combination, the cells may be diseased cells, such as cancerous cells, or from pathogenic cells that are infecting a host. In some embodiments, the cell belongs to a subset of cells, such as immune cell (e.g., T cells, cytotoxic (killer) T cells, helper T cells, alpha beta T cells, gamma delta T cells, T cell progenitors, B cells, B-cell progenitors, lymphoid stem cells, myeloid progenitor cells, lymphocytes, granulocytes, Natural Killer cells, plasma cells, memory cells, neutrophils, eosinophils, basophils, mast cells, monocytes, dendritic cells, and/or macrophages, or any combination thereof), undifferentiated human stem cells, human stem cells that have been induced to differentiate, or rare cells (e.g., circulating tumor cells (CTCs), circulating epithelial cells, circulating endothelial cells, circulating endometrial cells, bone marrow cells, progenitor cells, foam cells, mesenchymal cells, or trophoblasts). Other cells are contemplated and consistent with the disclosure herein.

The biological sample can be extracted (e.g., biopsied) from an organism, or obtained from a cell culture grown in liquid or in a culture dish. The biological sample comprises a sample that is fresh, frozen, fresh frozen, or archived (e.g., formalin-fixed paraffin-embedded; FFPE). The biological sample can be embedded in a wax, resin, epoxy or agar. The biological sample can be fixed, for example in any one or any combination of two or more of acetone, ethanol, methanol, formaldehyde, paraformaldehyde-Triton or glutaraldehyde. The biological sample can be sectioned or non-sectioned. The biological sample can be stained, de-stained or non-stained.

In some embodiments, the biological sample can be permeabilized after being fixed to the surface described herein to permit the nucleic acids within the sample, including the target nucleic acid molecule, to migrate from the cell(s) to the plurality of capture oligonucleotides that are immobilized to the surface. Permeabilization may allow an agent (such as a phospho-selective antibody, a nucleic acid conjugated antibody, a nucleic acid probe, a primer, etc.) to enter into a cell and reach a concentration within the cell that is greater than that which would normally penetrate into the cell in the absence of such permeabilizing treatment. In some embodiments, cells may be permeabilized in the presence of at least about 60%, 70%, 80%, 90%, or more methanol (or ethanol) and incubated on ice for a period of time. The period of time for incubation can be at least about 10, 15, 20, 25, 30, 35, 40, 50, 60 or more minutes.

The biological sample can be permeabilized by contacting the biological sample with one or more permeabilizing agents, including organic solvents, detergents, cross-linking agents and/or enzymes. In some embodiments, the organic solvents comprise acetone, ethanol, and methanol. In some embodiments, the detergents comprise saponin, Triton X-100, Tween-20, or sodium dodecyl sulfate (SDS), or N-lauroylsarcosine sodium salt solution. In some embodiments, the cross-linking agent comprises paraformaldehyde. In some embodiments, the enzyme comprises trypsin, pepsin or protease (e.g. proteinase K). In some embodiments, the target nucleic acid molecule from the biological sample is hybridized (captured) on the capture oligonucleotides immobilized on the support in a manner that preserves spatial location information of the target nucleic acid molecule in the biological sample.

The biological sample can be utilized to generate a three-dimensional polymer matrix comprising the cellular and sub-cellular components (e.g., nucleic acid molecules) of the biological sample. The three-dimensional polymer matrix can be coupled to the surface described herein, covalently or non-covalently. In some embodiments, the three-dimensional polymer matrix is porous and comprises polymerized or cross-linked sub-cellular components, including the target nucleic acid molecules. A polymer matrix may be formed within a biological sample (e.g., a cell or tissue) by flowing one or more polymer precursors (e.g., monomers, such as, for example, ethylene oxide for polyethene glycol) into the biological sample and subjecting the one or more polymer precursors to polymerization or cross-linking. Prior to, during, or subsequent to formation of the polymer matrix, positions of moieties (e.g., DNA, RNA, protein) within the biological sample may be fixed, using for example, a fixation agent (e.g., formaldehyde). A porous matrix may be made according to various methods. For example, a polyacrylamide gel matrix can be polymerized with biotinylated DNA molecules and acrydite-modified streptavidin monomers, using a suitable acrylamide:bis-acrylamide ratio to control the cross-linking density. Additional control over the molecular sieve size and density can be achieved by adding additional cross-linkers such as functionalized polyethylene glycols. Enablement for fixing biological sample to a surface, as well as generating a polymer matrix within a biological sample, is provided in PCT/US2019/055434, which is hereby incorporated by reference in its entirety.

The biological sample comprises target nucleic acid molecule(s) that, in some cases, are analyzed using the systems, methods and compositions described herein. In some embodiments, the target nucleic acids comprise naturally-occurring nucleic acids, recombinant nucleic acids and/or synthesized nucleic acids. The target nucleic acid includes linear and/or circular forms. In some embodiments, the target nucleic acid may be DNA. In some embodiments, the target nucleic acid may be genomic DNA. In some embodiments, the target nucleic acid may be viral DNA. In some embodiments, the target nucleic acid may be cell free DNA (cfDNA). In some embodiments, the DNA is genomic DNA, methylated or un-methylated DNA, and/or organellar DNA. The DNA can be fragmented and/or unfragmented. In some embodiments, the target nucleic acid molecule(s) comprise RNA, including poly-A RNA and/or non-poly-a RNA. The RNA comprises coding and/or non-coding RNA. The RNA comprises tRNA, rRNA, small nuclear RNA (snRNA), small nucleolar RNA (snoRNA), microRNA (miRNA), small interfering RNA (siRNA), piwi-interacting RNA (piRNA), antisense RNA, non-coding RNA and/or protein-encoding RNA.

The target nucleic acids of the instant disclosure have a fixed three-dimensional relationship with the biological sample after the biological sample is coupled to the surface. This fixed three-dimensional relationship, at least partially, enables the identification of spatial and cellular origin within the biological sample following nucleic acid identification using the systems and methods described herein.

Target Nucleic Acid Capture and Preparation. Provided herein are methods of hybridizing the target nucleic acid to the capture oligonucleotides coupled to the surface (e.g., low non-specific binding surface) in the presence of the biological sample. In some cases, hybridization buffer formulations described which, in combination with the disclosed low-binding supports, provide for improved hybridization rates, hybridization specificity (or stringency), and hybridization efficiency (or yield). As used herein, hybridization specificity is a measure of the ability of tethered adapter sequences, primer sequences, or oligonucleotide sequences in general to correctly hybridize only to completely complementary sequences, while hybridization efficiency is a measure of the percentage of total available tethered adapter sequences, primer sequences, or oligonucleotide sequences in general that are hybridized to complementary sequences.

Improved hybridization specificity and/or efficiency may be achieved through optimization of the hybridization buffer formulation used with the disclosed low-binding surfaces, and will be discussed in more detail in the examples below. Examples of hybridization buffer components that may be adjusted to achieve improved performance include, but are not limited to, buffer type, organic solvent mixtures, buffer pH, buffer viscosity, detergents and zwitterionic components, ionic strength (including adjustment of both monovalent and divalent ion concentrations), antioxidants and reducing agents, carbohydrates, BSA, polyethylene glycol, dextran sulfate, betaine, other additives, and the like.

By way of non-limiting example, suitable buffers for use in formulating a hybridization buffer may include, but are not limited to, phosphate buffered saline (PBS), succinate, citrate, histidine, acetate, Tris, TAPS, MOPS, PIPES, HEPES, MES, and the like. The choice of appropriate buffer will generally be dependent on the target pH of the hybridization buffer solution. In general, the desired pH of the buffer solution will range from about pH 4 to about pH 8.4. In some embodiments, the buffer pH may be at least 4.0, at least 4.5, at least 5.0, at least 5.5, at least 6.0, at least 6.2, at least 6.4, at least 6.6, at least 6.8, at least 7.0, at least 7.2, at least 7.4, at least 7.6, at least 7.8, at least 8.0, at least 8.2, or at least 8.4. In some embodiments, the buffer pH may be at most 8.4, at most 8.2, at most 8.0, at most 7.8, at most 7.6, at most 7.4, at most 7.2, at most 7.0, at most 6.8, at most 6.6, at most 6.4, at most 6.2, at most 6.0, at most 5.5, at most 5.0, at most 4.5, or at most 4.0. Any of the lower and upper values described in this paragraph may be combined to form a range included within the present disclosure, for example, in some instances, the desired pH may range from about 6.4 to about 7.2. Those of skill in the art will recognize that the buffer pH may have any value within this range, for example, about 7.25.

Suitable detergents for use in hybridization buffer formulation include, but are not limited to, zitterionic detergents (e.g., 1-Dodecanoyl-sn-glycero-3-phosphocholine, 3-(4-tert-Butyl-1-pyridinio)-1-propanesulfonate, 3-(N,N-Dimethylmyristylammonio)propanesulfonate, 3-(N,NDimethylmyristylammonio) propanesulfonate, ASB-C80, C7BzO, CHAPS, CHAPS hydrate, CHAPSO, DDMAB, Dimethylethylammoniumpropane sulfonate, N,N-Dimethyldodecylamine Noxide, N-Dodecyl-N,N-dimethyl-3-ammonio-1-propanesulfonate, or N-Dodecyl-N,N-dimethyl-3-ammonio-1-propanesulfonate) and anionic, cationic, and non-ionic detergents. Examples of nonionic detergents include poly(oxyethylene) ethers and related polymers (e.g. Brij®, TWEEN®, TRITON®, TRITON X-100 and IGEPAL® CA-630), bile salts, and glycosidic detergents.

The use of the disclosed low non-specific binding supports either alone or in combination with optimized buffer formulations may yield relative hybridization rates that range from about 2× to about 20× faster than that for a conventional hybridization protocol. In some instances, the relative hybridization rate may be at least 2×, at least 3×, at least 4×, at least 5×, at least 6×, at least 7×, at least 8×, at least 9×, at least 10×, at least 12×, at least 14×, at least 16×, at least 18×, at least 20×, at least 25×, at least 30×, or at least 40× that for a conventional hybridization protocol.

The use of the disclosed low non-specific binding supports alone or in combination with optimized buffer formulations may yield total hybridization reaction times (i.e., the time required to reach 90%, 95%, 98%, or 99% completion of the hybridization reaction) of less than 60 minutes, 50 minutes, 40 minutes, 30 minutes, 20 minutes, 15 minutes, 10 minutes, or 5 minutes for any of these completion metrics.

The use of the disclosed low non-specific binding supports alone or in combination with optimized buffer formulations may yield improved hybridization specificity compared to that for a conventional hybridization protocol. In some embodiments, the hybridization specificity that may be achieved is better than 1 base mismatch in 10 hybridization events, 1 base mismatch in 20 hybridization events, 1 base mismatch in 30 hybridization events, 1 base mismatch in 40 hybridization events, 1 base mismatch in 50 hybridization events, 1 base mismatch in 75 hybridization events, 1 base mismatch in 100 hybridization events, 1 base mismatch in 200 hybridization events, 1 base mismatch in 300 hybridization events, 1 base mismatch in 400 hybridization events, 1 base mismatch in 500 hybridization events, 1 base mismatch in 600 hybridization events, 1 base mismatch in 700 hybridization events, 1 base mismatch in 800 hybridization events, 1 base mismatch in 900 hybridization events, 1 base mismatch in 1,000 hybridization events, 1 base mismatch in 2,000 hybridization events, 1 base mismatch in 3,000 hybridization events, 1 base mismatch in 4,000 hybridization events, 1 base mismatch in 5,000 hybridization events, 1 base mismatch in 6,000 hybridization events, 1 base mismatch in 7,000 hybridization events, 1 base mismatch in 8,000 hybridization events, 1 base mismatch in 9,000 hybridization events, or 1 base mismatch in 10,000 hybridization events.

In some instances, the use of the disclosed low non-specific binding supports alone or in combination with optimized buffer formulations may yield improved hybridization efficiency (e.g., the fraction of available oligonucleotide primers on the support surface that are successfully hybridized with target oligonucleotide sequences) compared to that for a conventional hybridization protocol. In some instances, the hybridization efficiency that may be achieved is better than 50%, 60%, 70%, 80%, 85%, 90%, 95%, 98%, or 99% for any of the input target oligonucleotide concentrations specified below and in any of the hybridization reaction times specified above. In some instances, e.g., wherein the hybridization efficiency is less than 100%, the resulting surface density of target nucleic acid sequences hybridized to the support surface may be less than the surface density of oligonucleotide adapter or primer sequences on the surface.

In some instances, use of the disclosed low non-specific binding supports for nucleic acid hybridization (or amplification) applications using conventional hybridization (or amplification) protocols, or optimized hybridization (or amplification) protocols may lead to a reduced requirement for the input concentration of target (or sample) nucleic acid molecules contacted with the support surface. For example, in some instances, the target (or sample) nucleic acid molecules may be contacted with the support surface at a concentration ranging from about 10 pM to about 1 µM (i.e., prior to annealing or amplification). In some instances, the target (or sample) nucleic acid molecules may be administered at a concentration of at least 10 pM, at least 20 pM, at least 30 pM, at least 40 pM, at least 50 pM, at least 100 pM, at least 200 pM, at least 300 pM, at least 400 pM, at least 500 pM, at least 600 pM, at least 700 pM, at least 800 pM, at least 900 pM, at least 1 nM, at least 10 nM, at least 20 nM, at least 30 nM, at least 40 nM, at least 50 nM, at least 60 nM, at least 70 nM, at least 80 nM, at least 90 nM, at least 100 nM, at least 200 nM, at least 300 nM, at least 400 nM, at least 500 nM, at least 600 nM, at least 700 nM, at least 800 nM, at least 900 nM, or at least 1 μM. In some instances, the target (or sample) nucleic acid molecules may be administered at a concentration of at most 1 μM, at most 900 nM, at most 800 nm, at most 700 nM, at most 600 nM, at most 500 nM, at most 400 nM, at most 300 nM, at most 200 nM, at most 100 nM, at most 90 nM, at most 80 nM, at most 70 nM, at most 60 nM, at most 50 nM, at most 40 nM, at most 30 nM, at most 20 nM, at most 10 nM, at most 1 nM, at most 900 pM, at most 800 pM, at most 700 pM, at most 600 pM, at most 500 pM, at most 400 pM, at most 300 pM, at most 200 pM, at most 100 pM, at most 90 pM, at most 80 pM, at most 70 pM, at most 60 pM, at most 50 pM, at most 40 pM, at most 30 pM, at most 20 pM, or at most 10 pM. Any of the lower and upper values described in this paragraph may be combined to form a range included within the present disclosure, for example, in some instances the target (or sample) nucleic acid molecules may be administered at a concentration ranging from about 90 pM to about 200 nM. Those of skill in the art will recognize that the target (or sample) nucleic acid molecules may be administered at a concentration having any value within this range, e.g., about 855 nM.

In another example, a volume of the biological sample that may be contacted with the surface may be reduced relative to a comparable biological sample analyzed using a comparable surface using standard hybridization reagents. In some embodiments, a fluid sample comprising the target (or sample) nucleic acid molecules may be in a range of sample volumes that is about 5 μl to about 900 μl. In some instances, the range of sample volumes is about 5 μl to about 800 μl. In some instances, the range of sample volumes is about 5 μl to about 700 μl. In some instances, the range of sample volumes is about 5 μl to about 600 μl. In some instances, the range of sample volumes is about 5 μl to about 500 μl. In some instances, the range of sample volumes is about 5 μl to about 400 μl. In some instances, the range of sample volumes is about 5 μl to about 300 μl. In some instances, the range of sample volumes is about 5 μl to about 200 μl. In some instances, the range of sample volumes is about 5 μl to about 150 μl. In some instances, the range of sample volumes is 5 μl to about 100 μl. In some instances, the range of sample volumes is about 5 μl to about 90 μl. In some instances, the range of sample volumes is about 5 μl to about 85 μl. In some instances, the range of sample volumes is about 5 μl to about 80 μl. In some instances, the range of sample volumes is about 5 μl to about 75 μl. In some instances, the range of sample volumes is about 5 μl to about 70 μl. In some instances, the range of sample volumes is about 5 μl to about 65 μl. In some instances, the range of sample volumes is about 5 μl to about 60 μl. In some instances, the range of sample volumes is about 5 μl to about 55 μl. In some instances, the range of sample volumes is about 5 μl to about 50 μl. In some instances, the range of sample volumes is about 15 μl to about 150 μl. In some instances, the range of sample volumes is about 15 μl to about 120 μl. In some instances, the range of sample volumes is 15 μl to about 100 μl. In some instances, the range of sample volumes is about 15 μl to about 90 μl. In some instances, the range of sample volumes is about 15 μl to about 85 μl. In some instances, the range of sample volumes is about 15 μl to about 80 μl. In some instances, the range of sample volumes is about 15 μl to about 75 μl. In some instances, the range of sample volumes is about 15 μl to about 70 μl. In some instances, the range of sample volumes is about 15 μl to about 65 μl. In some instances, the range of sample volumes is about 15 μl to about 60 μl. In some instances, the range of sample volumes is about 15 μl to about 55 μl. In some instances, the range of sample volumes is about 15 μl to about 50 μl.

In some instances, the use of the disclosed low non-specific binding supports alone or in combination with optimized hybridization buffer formulations may result in a surface density of hybridized target (or sample) oligonucleotide molecules (i.e., prior to performing any subsequent solid-phase or clonal amplification reaction) ranging from about from about 0.0001 target oligonucleotide molecules per μm2 to about 1,000,000 target oligonucleotide molecules per μm2. In some instances, the surface density of hybridized target oligonucleotide molecules may be at least 0.0001, at least 0.0005, at least 0.001, at least 0.005, at least 0.01, at least 0.05, at least 0.1, at least 0.5, at least 1, at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 5,500, at least 6,000, at least 6,500, at least 7,000, at least 7,500, at least 8,000, at least 8,500, at least 9,000, at least 9,500, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 molecules per μm2. In some instances, the surface density of hybridized target oligonucleotide molecules may be at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,500, at most 9,000, at most 8,500, at most 8,000, at most 7,500, at most 7,000, at most 6,500, at most 6,000, at most 5,500, at most 5,000, at most 4,500, at most 4,000, at most 3,500, at most 3,000, at most 2,500, at most 2,000, at most 1,500, at most 1,000, at most 900, at most 800, at most 700, at most 600, at most 500, at most 400, at most 300, at most 200, at most 100, at most 90, at most 80, at most 70, at most 60, at most 50, at most 40, at most 30, at most 20, at most 10, at most 5, at most 1, at most 0.5, at most 0.1, at most 0.05, at most 0.01, at most 0.005, at most 0.001, at most 0.0005, or at most 0.0001 molecules per μm2. Any of the lower and upper values described in this paragraph may be combined to form a range included within the present disclosure, for example, in some instances the surface density of hybridized target oligonucleotide molecules may range from about 3,000 molecules per µm2 to about 20,000 molecules per µm2. Those of skill in the art will recognize that the surface density of hybridized target oligonucleotide molecules may have any value within this range, e.g., about 2,700 molecules per µm2.

Stated differently, in some instances the use of the disclosed low non-specific binding supports alone or in combination with optimized hybridization buffer formulations may result in a surface density of hybridized target (or sample) oligonucleotide molecules (i.e., prior to performing any subsequent solid-phase or clonal amplification reaction) ranging from about 100 hybridized target oligonucleotide molecules per mm2 to about 1×107 oligonucleotide molecules per mm2 or from about 100 hybridized target oligonucleotide molecules per mm2 to about 1×1012 hybridized target oligonucleotide molecules per mm2. In some instances, the surface density of hybridized target oligonucleotide molecules may be at least 100, at least 500, at least 1,000, at least 4,000, at least 5,000, at least 6,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least 1×107, at least 5×107, at least 1×108, at least 5×108, at least 1×109, at least 5×109, at least 1×1010, at least 5×1010, at least 1×1011, at least 5×1011, or at least 1×1012 molecules per mm2. In some instances, the surface density of hybridized target oligonucleotide molecules may be at most 1×1012, at most 5×1011, at most 1×1011, at most 5×1010, at most 1×1010, at most 5×109, at most 1×109, at most 5×108, at most 1×108, at most 5×107, at most 1×107, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per mm2. Any of the lower and upper values described in this paragraph may be combined to form a range included within the present disclosure, for example, in some instances the surface density of hybridized target oligonucleotide molecules may range from about 5,000 molecules per mm2 to about 50,000 molecules per mm2. Those of skill in the art will recognize that the surface density of hybridized target oligonucleotide molecules may have any value within this range, e.g., about 50,700 molecules per mm2.

In some instances, the target (or sample) oligonucleotide molecules (or nucleic acid molecules) hybridized to the oligonucleotide adapter or primer molecules attached to the low-binding support surface may range in length from about 0.02 kilobases (kb) to about 20 kb or from about 0.1 kilobases (kb) to about 20 kb. In some instances, the target oligonucleotide molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 0.6 kb in length, at least 0.7 kb in length, at least 0.8 kb in length, at least 0.9 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, at least 20 kb in length, at least 30 kb in length, or at least 40 kb in length, or any intermediate value spanned by the range described herein, e.g., at least 0.85 kb in length.

In some instances, the target (or sample) oligonucleotide molecules (or nucleic acid molecules) may comprise single-stranded or double-stranded, multimeric nucleic acid molecules further comprising repeats of a regularly occurring monomer unit. In some instances, the single-stranded or double-stranded, multimeric nucleic acid molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, at least 30 kb in length, or at least 40 kb in length, or any intermediate value spanned by the range described herein, e.g., about 2.45 kb in length.

In some instances, the target (or sample) oligonucleotide molecules (or nucleic acid molecules) may comprise single-stranded or double-stranded multimeric nucleic acid molecules comprising from about 2 to about 100 copies of a regularly repeating monomer unit. In some instances, the number of copies of the regularly repeating monomer unit may be at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. In some instances, the number of copies of the regularly repeating monomer unit may be at most 100, at most 95, at most 90, at most 85, at most 80, at most 75, at most 70, at most 65, at most 60, at most 55, at most 50, at most 45, at most 40, at most 35, at most 30, at most 25, at most 20, at most 15, at most 10, at most 5, at most 4, at most 3, or at most 2. Any of the lower and upper values described in this paragraph may be combined to form a range included within the present disclosure, for example, in some instances the number of copies of the regularly repeating monomer unit may range from about 4 to about 60. Those of skill in the art will recognize that the number of copies of the regularly repeating monomer unit may have any value within this range, e.g., about 17. Thus, in some instances, the surface density of hybridized target sequences in terms of the number of copies of a target sequence per unit area of the support surface may exceed the surface density of oligonucleotide primers even if the hybridization efficiency is less than 100%.

As used herein, the phrase "nucleic acid surface amplification" (NASA) is used interchangeably with the phrase "solid-phase nucleic acid amplification" (or simply "solid-phase amplification"). In some aspects of the present disclosure, nucleic acid amplification formulations are described which, in combination with the disclosed low-binding supports, provide for improved amplification rates, amplification specificity, and amplification efficiency. As used herein, specific amplification refers to amplification of template library oligonucleotide strands that have been tethered to the solid support either covalently or non-covalently. As used herein, non-specific amplification refers to amplification of primer-dimers or other non-template nucleic acids. As used herein, amplification efficiency is a measure of the percentage of tethered oligonucleotides on the support surface that are successfully amplified during a given amplification cycle or amplification reaction. Nucleic acid amplification performed on surfaces disclosed herein may obtain amplification efficiencies of at least 50%, 60%, 70%, 80%, 90%, 95%, or greater than 95%, such as 98% or 99%.

Any of a variety of thermal cycling or isothermal nucleic acid amplification schemes may be used with the disclosed low-binding supports. Examples of nucleic acid amplification methods that may be utilized with the disclosed low non-specific binding supports include, but are not limited to, polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, or single-stranded binding (SSB) protein-dependent amplification.

In some embodiments, a rolling circle amplification reaction comprises: (1) forming a trapped nucleotide-polymerase complexes by contacting a plurality of immobilized covalently closed circular nucleic acid molecules with (i) a first plurality of polymerases having strand displacement activity; (ii) a plurality of nucleotides (e.g., one type of nucleotide or, a mixture of dATP, dGTP, dCTP and dTTP); (iii) a non-catalytic divalent cation that mediates nucleotide binding but not nucleotide incorporation (e.g., strontium or barium), and optionally (iv) a plurality of amplification primers if the covalently closed circular molecules lack a primer. The rolling circle amplification reaction further comprises: (4) conducting a nucleotide polymerization reaction by contacting the trapped nucleotide-polymerase complex with (i) at least one divalent cation that mediates nucleotide binding and mediates nucleotide incorporation (e.g., magnesium and/or manganese), and (ii) a second plurality of nucleotides (e.g., a mixture of dATP, dGTP, dCTP and dTTP), under a condition suitable for conducting an isothermal rolling circle amplification reaction to generate a plurality of immobilized concatemers.

In some embodiments, the rolling circle amplification reaction further comprises a plurality of compaction oligonucleotides that can hybridize to portions of the concatemer to collapse the concatemer into a more compact shape and size. the compaction oligonucleotide is a single-stranded nucleic acid molecule having two identical sequences separated by a short linker sequence, where the two identical sequences are reverse-complementary to a portion of the concatemer. The compaction oligonucleotide can be any length, for example 20-100 nucleotides. The two identical sequence regions hybridize to the concatemer to pull together distal portions of the concatemer causing compaction of the concatemer. In some embodiments, the compaction oligonucleotide is resistant to 3' exonuclease degradation and/or single-stranded endonuclease degradation. In some embodiments, the compaction oligonucleotide comprises any one or any combination of two or more of: 3' terminal end phosphorylation; at least two 3' terminal end nucleotides having a phosphorothioate bond therebetween; at least one 3' terminal end nucleotide having a 2'-O-methyl moiety; and/or at least one 3' terminal nucleotide having a 2' fluoro base.

In some embodiments, in the trapped nucleotide-polymerase mixture of step (c), the first plurality of polymerases having strand displacement activity comprise phi29 DNA polymerase, large fragment of Bst DNA polymerase, large fragment of Bsu DNA polymerase, and Bca (exo-) DNA polymerase, Klenow fragment of E. coli DNA polymerase, T5 polymerase, M-MuLV reverse transcriptase, HIV viral reverse transcriptase, or Deep Vent DNA polymerase. The phi29 DNA polymerase can be wild type phi29 DNA polymerase (e.g., MagniPhi from Expedeon), or variant EquiPhi29 DNA polymerase (e.g., from Thermo Fisher Scientific), or chimeric QualiPhi DNA polymerase (e.g., from 4basebio).

In some embodiments, in the amplification primers comprise single-stranded nucleic acid primers having a length of about 5-25 nucleotides. In some embodiments, the amplification primers are resistant to 3' exonuclease degradation and/or single-stranded endonuclease degradation. In some embodiments, the amplification primers comprise any one or any combination of two or more of: 3' terminal end phosphorylation; at least two 3' terminal end nucleotides having a phosphorothioate bond therebetween; at least one 3' terminal end nucleotide having a 2'-O-methyl moiety; and/or at least one 3' terminal nucleotide having a 2' fluoro base.

In some embodiments, the rolling circle amplification reaction further comprises at least one accessory protein or enzyme, including helicase, single-stranded binding (SSB) protein, or recombinase (e.g., T4 uvsX) and/or recombinase accessory factor (e.g., T4 uvsY or T4 gp32).

In some embodiments, the isothermal rolling circle amplification reaction can be conducted at a temperature of about 30, 31, 32, 33, 34, 35, 36, 37, 38, 39 or 40° C.

In some embodiments, the concatemer can contain at least 2, 10, 100, 200, 500, 1000, 2000, 3000, 4000, 5000, 6000, 7000, 8000, 9000, 10,000, or more copies of the repeat units.

The rolling circle amplification method can be followed by a multiple displacement amplification reaction which employs random-sequence primers. The multiple displacement amplification reaction comprises: (1) forming a multiple displacement amplification (MDA) reaction mixture by contacting the plurality of immobilized concatemers with (i) a second plurality of polymerases having strand displacement activity, and (ii) a plurality of soluble amplification primers wherein individual amplification primers in the plurality are exonuclease-resistant and have a 3' extendible end and comprise a random sequence that can hybridize to a portion of the single-stranded circular nucleic acid templates, (iii) a second plurality of nucleotides (e.g., a mixture of dATP, dGTP, dCTP and dTTP), and (iv) at least one divalent cation that mediates nucleotide binding and mediates nucleotide incorporation (e.g., magnesium and/or manganese); and (2) conducting an isothermal multiple displacement amplification (MDA) reaction to generate a plurality of immobilized branched concatemers.

In some embodiments, in the multiple displacement amplification (MDA) reaction mixture, the second plurality of polymerases having strand displacement activity comprises phi29 DNA polymerase, large fragment of Bst DNA polymerase, large fragment of Bsu DNA polymerase, and Bca (exo-) DNA polymerase, Klenow fragment of E. coli DNA polymerase, T5 polymerase, M-MuLV reverse transcriptase, HIV viral reverse transcriptase, or Deep Vent DNA polymerase. The phi29 DNA polymerase can be wild type phi29 DNA polymerase (e.g., MagniPhi from Expedeon), or variant EquiPhi29 DNA polymerase (e.g., from Thermo Fisher Scientific), or chimeric QualiPhi DNA polymerase (e.g., from 4basebio).

In some embodiments, in the multiple displacement amplification (MDA) reaction mixture, the plurality of amplification primers comprise single-stranded nucleic acid primers having a length of about 5-25 nucleotides. In some embodiments, the plurality of soluble amplification primers comprise non-protected single-stranded nucleic acid primers. In some embodiments, the plurality of soluble amplification primers comprise protected single-stranded nucleic acid primers that are resistant to 3' exonuclease degradation and/or single-stranded endonuclease degradation. In some embodiments, the plurality of soluble amplification primers comprise any one or any combination of two or more of: 3' terminal end phosphorylation; at least two 3' terminal end nucleotides having a phosphorothioate bond therebetween; at least one 3' terminal end nucleotide having a 2'-O-methyl moiety; and/or at least one 3' terminal nucleotide having a 2' fluoro base. In some embodiments, the plurality of soluble amplification primers comprise a population of primers having the same length, for example a length of 6 or 9 nucleotides. In some embodiments, the plurality of soluble amplification primers comprise a population of primers having a mixture of different lengths, for example a mixture comprising 6-mer and 9-mer primers. In some embodiments, the plurality of soluble amplification primers comprise a mixture of primers having random sequences including up to $4^6$ different sequences (e.g., for the 6-mers) or $4^9$ different sequences (e.g., for the 9-mers).

In some embodiments, the multiple displacement amplification (MDA) reaction mixture can further comprise at least one accessory protein or enzyme, including helicase, single-stranded binding (SSB) protein, or recombinase (e.g., T4 uvsX) and/or recombinase accessory factor (e.g., T4 uvsY or T4 gp32).

In some embodiments, the isothermal multiple displacement amplification (MDA) reaction can be conducted at a temperature of about 30, 31, 32, 33, 34, 35, 36, 37, 38, 39, 40, 41, 42, 43, 44 or 45° C.

The rolling circle amplification method can be followed by a multiple displacement amplification reaction which employs a primase-polymerase enzyme. The multiple displacement amplification reaction comprises: (1) forming a multiple displacement amplification (MDA) reaction mixture by contacting the plurality of immobilized concatemers with (i) a second plurality of polymerases having strand displacement activity, (ii) a plurality of DNA primase-polymerase enzymes, (iii) a second plurality of nucleotides (e.g., a mixture of dATP, dGTP, dCTP and dTTP), and (iv) at least one divalent cation that mediates nucleotide binding and mediates nucleotide incorporation (e.g., magnesium and/or manganese), and (2) conducting an isothermal multiple displacement amplification (MDA) reaction to generate a plurality of immobilized branched concatemers. In some embodiments, the multiple displacement amplification reaction is conducted without added amplification primers (e.g., a primerless reaction).

In some embodiments, in the multiple displacement amplification (MDA) reaction mixture, the second plurality of polymerases having strand displacement activity comprises phi29 DNA polymerase, large fragment of Bst DNA polymerase, large fragment of Bsu DNA polymerase, and Bca (exo-) DNA polymerase, Klenow fragment of *E. coli* DNA polymerase, T5 polymerase, M-MuLV reverse transcriptase, HIV viral reverse transcriptase, or Deep Vent DNA polymerase. The phi29 DNA polymerase can be wild type phi29 DNA polymerase (e.g., MagniPhi from Expedeon), or variant EquiPhi29 DNA polymerase (e.g., from Thermo Fisher Scientific), or chimeric QualiPhi DNA polymerase (e.g., from 4basebio).

In some embodiments, the plurality of DNA primase-polymerase enzymes comprise an enzyme from *Thermus thermophilus* HB27 (e.g., Tth PrimPol enzyme).

In some embodiments, the multiple displacement amplification (MDA) reaction mixture further comprises at least one accessory protein or enzyme, including helicase, single-stranded binding (SSB) protein, or recombinase (e.g., T4 uvsX) and/or recombinase accessory factor (e.g., T4 uvsY or T4 gp32).

In some embodiments, the isothermal multiple displacement amplification (MDA) reaction can be conducted at a temperature of about 30, 31, 32, 33, 34, 35, 36, 37, 38, 39, 40, 41, 42, 43, 44 or 45° C.

Another embodiment of the two stage amplification methods includes exposing the concatemer to nucleic acid relaxing agents (first stage) and then conducting a flexing amplification reaction during the second stage. Without wishing to be bound by theory, it is postulated that the nucleic acid relaxing agent(s) can disrupt hydrogen bonding (e.g., denaturation) in the plurality of immobilized nucleic acid concatemers which causes the structure of the nucleic acid concatemers to relax and increases the number of new duplex formations between the immobilized surface capture primers and portions of the nucleic acid concatemers, thereby increasing the opportunity to generate new concatemers from the duplexed immobilized surface capture primers. The new concatemers can be generated during the flexing amplification reaction. The inclusion of the relaxing agents can cause nucleic acid denaturation without use of denaturation temperatures or denaturation chemicals.

In some embodiments, the amplification method comprises: (1) conducting an on-support rolling circle amplification to generate a plurality of single-stranded concatemers, (2) forming a relaxant reaction mixture, (3) forming a flexing amplification reaction mixture, (4) conducting a flexing amplification reaction on the support (e.g., with no added soluble primers) to generate a plurality of double-stranded concatemers, (5) washing, and (6) repeating steps (2)-(5) at least once.

In some embodiments, the relaxant reaction mixture of step (2) can be formed with at least one nucleic acid relaxing agent that can disrupt hydrogen bonding in the immobilized nucleic acid concatemers. Exemplary relaxing agents include nucleic acid denaturants, chaotropic compounds, amide compounds, aprotic compounds, primary alcohols and ethylene glycol derivatives. Chaotropic compounds comprise urea, guanidine hydrochloride or guanidine thiocyanate. Amide compounds comprise formamide, acetamide or NN-dimethylformamide (DMF). Aprotic compounds comprise acetonitrile, DMSO (dimethyl sulfoxide), 1,4-dioxane or tetrahydrofuran. Primary alcohols comprise 1-propanol, ethanol or methanol. Ethylene glycol derivatives comprise 1,3-propanediol, ethylene glycol, glycerol, 1,2-dimethyoxyethane or 2-methoxyethanol. Other relaxing agents include sodium iodide, potassium iodide and polyamines In some embodiments, the relaxant reaction mixture comprises any one or a combination of two or more of a group selected from urea, guanidine hydrochloride, guanidine thiocyanate, formamide, acetamide, NN-dimethylformamide (DMF), acetonitrile, DMSO (dimethyl sulfoxide), 1,4-dioxane, tetrahydrofuran, 1-propanol, ethanol, methanol, 1,3- propanediol, ethylene glycol, glycerol, 1,2-dimethyoxyethane, 2-methoxyethanol, sodium iodide, potassium iodide and/or polyamines.

In some embodiments, the relaxant reaction mixture comprises formamide and SSC. In some embodiments, the relaxant reaction mixture comprises acetonitrile, formamide and SSC. In some embodiments, the relaxant reaction mixture comprises acetonitrile, formamide and MES (2-(4-morpholino)-ethane sulfonic acid). In some embodiments, the relaxant reaction mixture comprises acetonitrile, formamide, guanidium hydrochloride and HEPES (4-(2-hydroxyethyl)-1-piperazineethanesulfonic acid). In some embodiments, the relaxant reaction mixture comprises acetonitrile, formamide, urea and HEPES. In some embodiments, the SSC in the relaxant reaction mixture can be 1×, 2×, 3× or 4×.

In some embodiments, in the forming the relaxant reaction mixture of step (2), the temperature ramp-up condition can be conducted from about 20° C. to about 70° C., the relaxant incubation condition can be conducted at a temperature of about 40-70° C., and the temperature ramp-down condition can be conducted from about 70° C. to about 20° C. A skilled artisan will recognize that the temperature ramp-up, relaxant incubation temperature, and temperature ramp-down conditions can be modified.

In some embodiments, in the flexing amplification reaction mixture of step (3), the second plurality of polymerases having strand displacement activity comprises large fragment of Bst DNA polymerase (e.g., exonuclease minus), phi29 DNA polymerase, large fragment of Bsu DNA polymerase, and Bca (exo-) DNA polymerase, Klenow fragment of E. coli DNA polymerase, T5 polymerase, M-MuLV reverse transcriptase, HIV viral reverse transcriptase, or Deep Vent DNA polymerase. The phi29 DNA polymerase can be wild type phi29 DNA polymerase (e.g., MagniPhi from Expedeon), or variant EquiPhi29 DNA polymerase (e.g., from Thermo Fisher Scientific), or chimeric QualiPhi DNA polymerase (e.g., from 4basebio).

In some embodiments, in the flexing amplification reaction mixture of step (2), the concentration (e.g., total concentration) of the third plurality of nucleotides can promote a nucleotide polymerization reaction. For example, the concentration (e.g., total concentration) of the third plurality of nucleotides is about 0.1-10 mM.

In some embodiments, the third plurality of nucleotides in the flexing amplification reaction mixture of step (2) comprise a mixture of two or more nucleotides selected from a group consisting of dATP, dGTP, dCTP and dTTP.

In some embodiments, in the flexing amplification reaction mixture of step (2), the at least one divalent cation that mediates nucleotide binding and mediates nucleotide polymerization comprises a catalytic divalent cation. In some embodiments, the catalytic divalent cation comprises magnesium and/or manganese. The concentration of the catalytic divalent cation in the amplification reaction mixture can be about 1-20 mM.

In some embodiments, the flexing amplification reaction mixture of step (2) can include at least one accessory protein or enzyme, including helicase, single-stranded binding (SSB) protein, or recombinase (e.g., T4 uvsX) and/or recombinase accessory factor (e.g., T4 uvsY or T4 gp32). In some embodiments, these accessory proteins can be omitted.

In some embodiments, in the flexing amplification reaction of step (4), the temperature ramp-up condition can be conducted from about 20° C. to about 90° C. In some embodiments, in the flexing amplification reaction of step (4), the temperature ramp-up condition can be conducted for about 5-15 seconds, or about 15-30 seconds, or about 30-45 seconds, or about 45-60 seconds, or longer. In some embodiments, in the flexing amplification reaction of step (4), the amplification incubation condition can be about 50, 51, 52, 53, 54, 55, 56, 57, 58, 59, 60, 61, 62, 63, 64, 65, 66, 67, 68, 69 or 70° C., or at a higher temperature. In some embodiments, in the flexing amplification reaction of step (4), the amplification incubation condition can be conducted for about 30-45 seconds, or about 45-60 seconds, or about 60-75 seconds, or about 75-90 seconds, or longer. In some embodiments, in the flexing amplification reaction of step (4), the temperature ramp-down condition can be conducted from about 90° C. to about 20° C.

In some embodiments, in the flexing amplification reaction of step (4), the temperature ramp-down condition can be conducted for about 5-15 seconds, or about 15-30 seconds, or about 30-45 seconds, or about 45-60 seconds, or longer. In some embodiments, in the washing of step (5), the wash buffer comprises 1×SSC, or 1×SSC with cobalt hexamine. In some embodiments, steps (2)-(5) can be repeated at least once, or repeated up to 10 times, or repeated up to 15 times, or repeated up to 20 times, or repeated up to 30 times or more.

Often, improvements in amplification rate, amplification specificity, and amplification efficiency may be achieved using the disclosed low non-specific binding supports alone or in combination with formulations of the amplification reaction components. In addition to inclusion of nucleotides, one or more polymerases, helicases, single-stranded binding proteins, etc. (or any combination thereof), the amplification reaction mixture may be adjusted in a variety of ways to achieve improved performance including, but are not limited to, choice of buffer type, buffer pH, organic solvent mixtures, buffer viscosity, detergents and zwitterionic components, ionic strength (including adjustment of both monovalent and divalent ion concentrations), antioxidants and reducing agents, carbohydrates, BSA, polyethylene glycol, dextran sulfate, betaine, other additives, and the like.

The use of the disclosed low non-specific binding supports alone or in combination with optimized amplification reaction formulations may yield increased amplification rates compared to those obtained using conventional supports and amplification protocols. In some instances, the relative amplification rates that may be achieved may be at least 2×, at least 3×, at least 4×, at least 5×, at least 6×, at least 7×, at least 8×, at least 9×, at least 10×, at least 12×, at least 14×, at least 16×, at least 18×, or at least 20× that for use of conventional supports and amplification protocols for any of the amplification methods described above.

In some instances, the use of the disclosed low non-specific binding supports alone or in combination with optimized buffer formulations may yield total amplification reaction times (i.e., the time required to reach 90%, 95%, 98%, or 99% completion of the amplification reaction) of less than 180 mins, 120 mins, 90 min, 60 minutes, 50 minutes, 40 minutes, 30 minutes, 20 minutes, 15 minutes, 10 minutes, 5 minutes, 3 minutes, 1 minute, 50 s, 40s, 30s, 20s, or 10s for any of these completion metrics.

Some low-binding support surfaces disclosed herein exhibit a ratio of specific binding to nonspecific binding of a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein. Some surfaces disclosed herein exhibit a ratio of specific to nonspecific fluorescence signal for a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein.

In some instances, the use of the disclosed low non-specific binding supports alone or in combination with optimized amplification buffer formulations may enable faster amplification reaction times (i.e., the times required to reach 90%, 95%, 98%, or 99% completion of the amplification reaction) of no more than 60 minutes, 50 minutes, 40 minutes, 30 minutes, 20 minutes, or 10 minutes. Similarly, use of the disclosed low non-specific binding supports alone or in combination with optimized buffer formulations may enable amplification reactions to be completed in some cases in no more than 2, 3, 4, 5, 6, 7, 8, 9, 10, 15, or no more than 30 cycles.

In some instances, the use of the disclosed low non-specific binding supports alone or in combination with optimized amplification reaction formulations may yield increased specific amplification and/or decreased non-specific amplification compared to that obtained using conventional supports and amplification protocols. In some instances, the resulting ratio of specific amplification-to-non-specific amplification that may be achieved is at least 4:1 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1,000:1.

In some instances, the use of the low non-specific binding supports alone or in combination with optimized amplification reaction formulations may yield increased amplification efficiency compared to that obtained using conventional supports and amplification protocols. In some instances, the amplification efficiency that may be achieved is better than 50%, 60%, 70% 80%, 85%, 90%, 95%, 98%, or 99% in any of the amplification reaction times specified above.

In some instances, the clonally-amplified target (or sample) oligonucleotide molecules (or nucleic acid molecules) hybridized to the oligonucleotide adapter or primer molecules attached to the low-binding support surface may range in length from about 0.02 kilobases (kb) to about 20 kb or from about 0.1 kilobases (kb) to about 20 kb. In some instances, the clonally-amplified target oligonucleotide molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, or any intermediate value spanned by the range described herein, e.g., at least 0.85 kb in length.

In some instances, the clonally-amplified target (or sample) oligonucleotide molecules (or nucleic acid molecules) may comprise single-stranded or double-stranded, multimeric nucleic acid molecules further comprising repeats of a regularly occurring monomer unit. In some instances, the clonally-amplified single-stranded or double-stranded, multimeric nucleic acid molecules may be at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, or any intermediate value spanned by the range described herein, e.g., about 2.45 kb in length.

In some instances, the clonally-amplified target (or sample) oligonucleotide molecules (or nucleic acid molecules) may comprise single-stranded or double-stranded multimeric nucleic acid molecules comprising from about 2 to about 100 copies of a regularly repeating monomer unit. In some instances, the number of copies of the regularly repeating monomer unit may be at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. In some instances, the number of copies of the regularly repeating monomer unit may be at most 100, at most 95, at most 90, at most 85, at most 80, at most 75, at most 70, at most 65, at most 60, at most 55, at most 50, at most 45, at most 40, at most 35, at most 30, at most 25, at most 20, at most 15, at most 10, at most 5, at most 4, at most 3, or at most 2. Any of the lower and upper values described in this paragraph may be combined to form a range included within the present disclosure, for example, in some instances the number of copies of the regularly repeating monomer unit may range from about 4 to about 60. Those of skill in the art will recognize that the number of copies of the regularly repeating monomer unit may have any value within this range, e.g., about 12. Thus, in some instances, the surface density of clonally-amplified target sequences in terms of the number of copies of a target sequence per unit area of the support surface may exceed the surface density of oligonucleotide primers even if the hybridization and/or amplification efficiencies are less than 100%.

In some instances, the use of the disclosed low non-specific binding supports alone or in combination with optimized amplification reaction formulations may yield increased clonal copy number compared to that obtained using conventional supports and amplification protocols. In some instances, e.g., wherein the clonally-amplified target (or sample) oligonucleotide molecules comprise concatenated, multimeric repeats of a monomeric target sequence, the clonal copy number may be substantially smaller than compared to that obtained using conventional supports and amplification protocols. Thus, in some instances, the clonal copy number may range from about 1 molecule to about 100,000 molecules (e.g., target sequence molecules) per amplified colony. In some instances, the clonal copy number may be at least 1, at least 5, at least 10, at least 50, at least 100, at least 500, at least 1,000, at least 2,000, at least 3,000, at least 4,000, at least 5,000, at least 6,000, at least 7,000, at least 8,000, at least 9,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, or at least 100,000 molecules per amplified colony. In some instances, the clonal copy number may be at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,000, at most 8,000, at most 7,000, at most 6,000, at most 5,000, at most 4,000, at most 3,000, at most 2,000, at most 1,000, at most 500, at most 100, at most 50, at most 10, at most 5, or at most 1 molecule per amplified colony. Any of the lower and upper values described in this paragraph may be combined to form a range included within the present disclosure, for example, in some instances the clonal copy number may range from about 2,000 molecules to about 9,000 molecules. Those of skill in the art will recognize that the clonal copy number may have any value within this range, e.g., about 2,220 molecules in some instances, or about 2 molecules in others.

As noted above, in some instances the amplified target (or sample) oligonucleotide molecules (or nucleic acid molecules) may comprise concatenated, multimeric repeats of a monomeric target sequence. In some instances, the amplified target (or sample) oligonucleotide molecules (or nucleic acid molecules) may comprise a plurality of molecules each of which comprises a single monomeric target sequence. Thus, the use of the disclosed low non-specific binding supports alone or in combination with optimized amplification reaction formulations may result in a surface density of target sequence copies that ranges from about 100 target sequence copies per mm2 to about 1×1012 target sequence copies per mm2. In some instances, the surface density of target sequence copies may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least 1×107, at least 5×107, at least 1×108, at least 5×108, at least 1×109, at least 5×109, at least 1×1010, at least 5×1010, at least 1×1011, at least 5×1011, or at least 1×1012 of clonally amplified target sequence molecules per mm2. In some instances, the surface density of target sequence copies may be at most 1×1012, at most 5×1011, at most 1×1011, at most 5×1010, at most 1×1010, at most 5×109, at most 1×109, at most 5×108, at most 1×108, at most 5×107, at most 1×107, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 target sequence copies per mm2. Any of the lower and upper values described in this paragraph may be combined to form a range included within the present disclosure, for example, in some instances the surface density of target sequence copies may range from about 1,000 target sequence copies per mm2 to about 65,000 target sequence copies mm2. Those of skill in the art will recognize that the surface density of target sequence copies may have any value within this range, e.g., about 49,600 target sequence copies per mm2.

In some instances, the use of the disclosed low non-specific binding supports alone or in combination with optimized amplification buffer formulations may result in a surface density of clonally-amplified target (or sample) oligonucleotide molecules (or clusters) ranging from about from about 100 molecules per mm2 to about 1×1012 colonies per mm2. In some instances, the surface density of clonally-amplified molecules may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least 1×107, at least 5×107, at least 1×108, at least 5×108, at least 1×109, at least 5×109, at least 1×1010, at least 5×1010, at least 1×1011, at least 5×1011, or at least 1×1012 molecules per mm2. In some instances, the surface density of clonally-amplified molecules may be at most 1×1012, at most 5×1011, at most 1×1011, at most 5×1010, at most 1×1010, at most 5×109, at most 1×109, at most 5×108, at most 1×108, at most 5×107, at most 1×107, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per mm2. Any of the lower and upper values described in this paragraph may be combined to form a range included within the present disclosure, for example, in some instances the surface density of clonally-amplified molecules may range from about 5,000 molecules per mm2 to about 50,000 molecules per mm2. Those of skill in the art will recognize that the surface density of clonally-amplified colonies may have any value within this range, e.g., about 48,800 molecules per mm2.

In some instances, the use of the disclosed low non-specific binding supports alone or in combination with optimized amplification buffer formulations may result in a surface density of clonally-amplified target (or sample) oligonucleotide molecules (or clusters) ranging from about from about 100 molecules per mm2 to about 1×1012 colonies per mm2. In some instances, the surface density of clonally-amplified molecules may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least 1×107, at least 5×107, at least 1×108, at least 5×108, at least 1×109, at least 5×109, at least 1×1010, at least 5×1010, at least 1×1011, at least 5×1011, or at least 1×1012 molecules per mm2. In some instances, the surface density of clonally-amplified molecules may be at most $1\times10^{12}$, at most $5\times10^{11}$, at most $1\times10^{11}$, at most $5\times10^{10}$, at most $1\times10^{10}$, at most $5\times10^9$, at most $1\times10^9$, at most $5\times10^8$, at most $1\times10^8$, at most $5\times10^7$, at most $1\times10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per mm2. Any of the lower and upper values described in this paragraph may be combined to form a range included within the present disclosure, for example, in some instances the surface density of clonally-amplified molecules may range from about 5,000 molecules per mm2 to about 50,000 molecules per mm2. Those of skill in the art will recognize that the surface density of clonally-amplified colonies may have any value within this range, e.g., about 48,800 molecules per mm2.

In some instances, the use of the disclosed low non-specific binding supports alone or in combination with optimized amplification buffer formulations may result in a surface density of clonally-amplified target (or sample) oligonucleotide colonies (or clusters) ranging from about from about 100 colonies per mm2 to about $1\times10^{12}$ colonies per mm2. In some instances, the surface density of clonally-amplified colonies may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1\times10^7$, at least $5\times10^7$, at least $1\times10^8$, at least $5\times10^8$, at least $1\times10^9$, at least $5\times10^9$, at least $1\times10^{10}$, at least $5\times10^{10}$, at least $1\times10^{11}$, at least $5\times10^{11}$, or at least $1\times10^{12}$ colonies per mm2. In some instances, the surface density of clonally-amplified colonies may be at most $1\times10^{12}$, at most $5\times10^{11}$, at most $1\times10^{11}$, at most $5\times10^{10}$, at most $1\times10^{10}$, at most $5\times10^9$, at most $1\times10^9$, at most $5\times10^8$, at most $1\times10^8$, at most $5\times10^7$, at most $1\times10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 colonies per mm2. Any of the lower and upper values described in this paragraph may be combined to form a range included within the present disclosure, for example, in some instances the surface density of clonally-amplified colonies may range from about 5,000 colonies per mm2 to about 50,000 colonies per mm2. Those of skill in the art will recognize that the surface density of clonally-amplified colonies may have any value within this range, e.g., about 48,800 colonies per mm2.

In some cases the use of the disclosed low non-specific binding supports alone or in combination with optimized amplification reaction formulations may yield signal from the amplified and labeled nucleic acid populations (e.g., a fluorescence signal) that has a coefficient of variance of no greater than 50%, such as 50%, 40%, 30%, 20%, 15%, 10%, 5%, or less than 5%.

In some cases, the support surfaces and methods as disclosed herein allow amplification at elevated extension temperatures, such as at 15° C., 20° C., 25° C., 30° C., 40° C., or greater, or for example at about 21° C. or 23° C.

In some cases, the use of the support surfaces and methods as disclosed herein enable simplified amplification reactions. For example, in some cases amplification reactions are performed using no more than 1, 2, 3, 4, or 5 discrete reagents.

In some cases, the use of the support surfaces and methods as disclosed herein enable the use of simplified temperature profiles during amplification, such that reactions are executed at temperatures ranging from a low temperature of 15° C., 20° C., 25° C., 30° C., or 40° C., to a high temperature of 40° C., 45° C., 50° C., 60° C., 65° C., 70° C., 75° C., 80° C., or greater than 80° C., for example, such as a range of 20° C. to 65° C.

Amplification reactions are also improved such that lower amounts of template (e.g., target or sample molecules) are sufficient to lead to discernable signals on a surface, such as 1 pM, 2 pM, 5 pM, 10 pM, 15 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, 900 pM, 1,000 pM, 2,000 pM, 3,000 pM, 4,000 pM, 5,000 pM, 6,000 pM, 7,000 pM, 8,000 pM, 9,000 pM, 10,000 pM or greater than 10,000 pM of a sample, such as 500 nM. In exemplary embodiments, inputs of about 100 pM are sufficient to generate signals for reliable signal determination.

The disclosed solid-phase nucleic acid amplification reaction formulations and low non-specific binding supports may be used in any of a variety of nucleic acid analysis applications, e.g., nucleic acid base discrimination, nucleic acid base classification, nucleic acid base calling, nucleic acid detection applications, nucleic acid sequencing applications, and nucleic acid-based (genetic and genomic) diagnostic applications. In many of these applications, fluorescence imaging techniques may be used to monitor hybridization, amplification, and/or sequencing reactions performed on the low-binding supports.

Fluorescence imaging may be performed using any of a variety of fluorophores, fluorescence imaging techniques, and fluorescence imaging instruments known to those of skill in the art. Examples of suitable fluorescence dyes that may be used (e.g., by conjugation to nucleotides, oligonucleotides, or proteins) include, but are not limited to, fluorescein, rhodamine, coumarin, cyanine, and derivatives thereof, including the cyanine derivatives Cyanine dye-3 (Cy3), Cyanine dye-5 (Cy5), Cyanine dye-7 (Cy7), etc. Examples of fluorescence imaging techniques that may be used include, but are not limited to, fluorescence microscopy imaging, fluorescence confocal imaging, two-photon fluorescence, and the like. Examples of fluorescence imaging instruments that may be used include, but are not limited to, fluorescence microscopes equipped with an image sensor or camera, confocal fluorescence microscopes, two-photon fluorescence microscopes, or custom instruments that comprise a suitable selection of light sources, lenses, mirrors, prisms, dichroic reflectors, apertures, and image sensors or cameras, etc. A non-limiting example of a fluorescence microscope equipped for acquiring images of the disclosed low-binding support surfaces and clonally-amplified colonies (or clusters) of target nucleic acid sequences hybridized thereon is the Olympus IX83 inverted fluorescence microscope equipped with) 20×, 0.75 NA, a 532 nm light source, a bandpass and dichroic mirror filter set optimized for 532 nm long-pass excitation and Cy3 fluorescence emission filter, a Semrock 532 nm dichroic reflector, and a camera (Andor sCMOS, Zyla 4.2) where the excitation light intensity is adjusted to avoid signal saturation. Often, the support surface may be immersed in a buffer (e.g., 25 mM ACES, pH 7.4 buffer) while the image is acquired.

In some instances, the performance of nucleic acid hybridization and/or amplification reactions using the disclosed reaction formulations and low non-specific binding supports may be assessed using fluorescence imaging techniques, where the contrast-to-noise ratio (CNR) of the images provides a key metric in assessing amplification specificity and non-specific binding on the support. CNR is commonly defined as: CNR=(Signal−Background)/Noise. The background term is commonly taken to be the signal measured for the interstitial regions surrounding a particular feature (diffraction limited spot, DLS) in a specified region of interest (ROI). While signal-to-noise ratio (SNR) is often considered to be a benchmark of overall signal quality, it can be shown that improved CNR can provide a significant advantage over SNR as a benchmark for signal quality in applications that require rapid image capture (e.g., sequencing applications for which cycle times must be minimized), as shown in the example below. The surfaces of the instant disclosure are also provided in co-pending International Application Serial No. PCT/US2019/061556, which is hereby incorporated by reference in its entirety.

In most ensemble-based sequencing approaches, the background term is typically measured as the signal associated with 'interstitial' regions. In addition to "interstitial" background ($B_{inter}$), "intrastitial" background ($B_{intra}$) exists within the region occupied by an amplified DNA colony. The combination of these two background signals dictates the achievable CNR, and subsequently directly impacts the optical instrument requirements, architecture costs, reagent costs, run-times, cost/genome, and ultimately the accuracy and data quality for cyclic array-based sequencing applications. The $B_{inter}$ background signal arises from a variety of sources; a few examples include auto-fluorescence from consumable flow cells, non-specific adsorption of detection molecules that yield spurious fluorescence signals that may obscure the signal from the ROI, the presence of non-specific DNA amplification products (e.g., those arising from primer dimers). In typical next generation sequencing (NGS) applications, this background signal in the current field-of-view (FOV) is averaged over time and subtracted. The signal arising from individual DNA colonies (i.e., (S)—$B_{inter}$ in the FOV) yields a discernable feature that can be classified. In some instances, the intrastitial background ($B_{intra}$) can contribute a confounding fluorescence signal that is not specific to the target of interest, but is present in the same ROI thus making it far more difficult to average and subtract.

As will be demonstrated in the examples below, the implementation of nucleic acid amplification on the low-binding substrates of the present disclosure may decrease the $B_{inter}$ background signal by reducing non-specific binding, may lead to improvements in specific nucleic acid amplification, and may lead to a decrease in non-specific amplification that can impact the background signal arising from both the interstitial and intrastitial regions. In some instances, the disclosed low-binding support surfaces, optionally used in combination with the disclosed hybridization and/or amplification reaction formulations, may lead to improvements in CNR by a factor of 2, 5, 10, 100, or 1000-fold over those achieved using conventional supports and hybridization, amplification, and/or sequencing protocols. Although described here in the context of using fluorescence imaging as the read-out or detection mode, the same principles apply to the use of the disclosed low non-specific binding supports and nucleic acid hybridization and amplification formulations for other detection modes as well, including both optical and non-optical detection modes.

The disclosed low-binding supports, optionally used in combination with the disclosed hybridization and/or amplification protocols, yield solid-phase reactions that exhibit. (i) negligible non-specific binding of protein and other reaction components (thus minimizing substrate background), (ii) negligible non-specific nucleic acid amplification product, and (iii) provide tunable nucleic acid amplification reactions.

Methods for Capturing and Analyzing DNA. The present disclosure provides methods for analyzing nucleic acids in a manner that is cellularly or spatially addressable, the method comprising: (a) providing a support comprising a low non-specific binding coating to which a plurality of capture oligonucleotides and a plurality of circularization oligonucleotides are immobilized (e.g., FIG. 2), wherein the plurality of capture oligonucleotides comprise (i) a target capture region that hybridizes to at least a portion of a target nucleic acid molecule, (ii) a universal sequence region comprising a spatial barcode sequence, (iii) a circularization anchor sequence, and (iv) a cleavable region, wherein the plurality of circularization oligonucleotides comprise (i) a homopolymer region, (ii) a universal sequence region comprising a sequencing primer binding sequence and (iii) a circularization anchor binding sequence, and wherein the low non-specific binding coating comprises at least one hydrophilic polymer coating having a water contact angle of no more than 45 degrees.

In some embodiments, the low non-specific binding coating in step (a) exhibits low background fluorescence signals or high contrast to noise (CNR) ratios relative to known surfaces in the art. In some embodiments, the low non-specific binding coating exhibits a level of non-specific Cy3 dye absorption of less than about 0.25 molecules/$\mu m^2$, where no more than 5% of the target nucleic acid is associated with the surface coating without hybridizing to an immobilized capture oligonucleotide. In some embodiments, a fluorescence image of the surface coating having a plurality of clonally-amplified clusters of nucleic acid exhibits a contrast-to-noise ratio (CNR) of at least 20, or at least 50, or higher contrast-to-noise ratios (CNR), when using a fluorescence imaging system under non-signal saturating conditions.

In some embodiments, the immobilized capture oligonucleotide in step (a) can include any combination of: (i) a target capture region that hybridizes to at least a portion of a target nucleic acid molecule, (ii) a universal sequence region comprising a spatial barcode sequence, (iii) a circularization anchor sequence that binds a portion of the circularization oligonucleotide, and/or (iv) a cleavable region.

In some embodiments, the target capture region of the immobilized capture oligonucleotides in step (a) comprise a target-specific sequence or a random sequence.

In some embodiments, the immobilized circularization oligonucleotides in step (a) can include any combination of: (i) a homopolymer region, (ii) a universal sequence region comprising a sequencing primer binding sequence and/or (iii) a circularization anchor binding sequence that binds the circularization anchor sequence of the capture oligonucleotide.

The method for analyzing nucleic acids further comprises the step: (b) contacting the low non-specific binding coating with a cellular biological sample in the presence of a high efficiency hybridization buffer under a condition suitable to promote migration of the target nucleic acid molecule from the cellular biological sample to one of the immobilized capture oligonucleotides thereby forming an immobilized target nucleic acid duplex, wherein the target nucleic acid molecule is immobilized to the low non-specific binding coating in a manner that preserves spatial location information of the target nucleic acid molecule in the cellular biological sample, wherein the target nucleic acid comprises DNA or RNA (e.g., FIG. 7).

In some embodiments, the cellular biological sample in step (b) comprises a cellular biological sample that is fresh, frozen, fresh frozen, or archived (e.g., formalin-fixed paraffin-embedded; FFPE).

In some embodiments, the cellular biological sample in step (b) is subjected to a permeabilizing reaction to promote migration of the cellular nucleic acid molecules (e.g., DNA and/or RNA), including the target nucleic acid molecule, from the cellular biological sample to one of the immobilized capture oligonucleotides.

In some embodiments, the high efficiency high efficiency hybridization buffer of step (b) comprises: (i) a first polar aprotic solvent having a dielectric constant that is no greater than 40 and having a polarity index of 4-9; (ii) a second polar aprotic solvent having a dielectric constant that is no greater than 115 and is present in the high efficiency high efficiency hybridization buffer formulation in an amount effective to denature double-stranded nucleic acids; (iii) a pH buffer system that maintains the pH of the high efficiency high efficiency hybridization buffer formulation in a range of about 4-8; and (iv) a crowding agent in an amount sufficient to enhance or facilitate molecular crowding.

In some embodiments, the high efficiency high efficiency hybridization buffer of step (b) comprises: (i) the first polar aprotic solvent comprises acetonitrile at 25-50% by volume of the high efficiency high efficiency hybridization buffer; (ii) the second polar aprotic solvent comprises formamide at 5-10% by volume of the high efficiency high efficiency hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the high efficiency high efficiency hybridization buffer. In some embodiments, the high efficiency hybridization buffer further comprises betaine.

In some embodiments, the high efficiency high efficiency hybridization buffer of step (b) promotes high stringency (e.g., specificity), speed, and efficacy of nucleic acid hybridization reactions and increases the efficiency of the subsequent amplification and sequencing steps. In some embodiments, the high efficiency hybridization buffer significantly shortens nucleic acid hybridization times, and decreases sample input requirements. Nucleic acid annealing can be performed at isothermal conditions and eliminate the cooling step for annealing.

The method for analyzing nucleic acids further comprises the step: (c) conducting a primer extension reaction on the immobilized nucleic acid duplex using the hybridized target nucleic acid molecule as a template thereby forming an immobilized target extension product. In some embodiments, the primer extension reaction comprises contacting the immobilized nucleic acid duplex with a plurality of nucleotides and a polymerase. In some embodiments, the polymerase comprises an E. coli DNA polymerase I, Klenow fragment of E. coli DNA polymerase I, T7 DNA polymerase, or T4 DNA polymerase.

In some embodiments, the primer extension reaction of step (c) can be a reverse transcription reaction which comprises (i) a reverse transcriptase enzyme, (ii) a plurality of nucleotides, and (iii) a plurality of reverse transcriptase primers. In some embodiments, the reverse transcription reaction of step (a) comprises a plurality of nucleotides and an enzyme having reverse transcription activity, including reverse transcriptase enzymes from AMV (avian myeloblastosis virus), M-MLV (moloney murine leukemia virus), or HIV (human immunodeficiency virus). In some embodiments, the reverse transcriptase can be a commercially-available enzyme, including MultiScribe™, ThermoScript™, or ArrayScript™. In some embodiments, the reverse transcriptase enzyme comprises Superscript I, II, III, or IV enzymes. In some embodiments, the reverse transcription reaction can include an RNase inhibitor.

Figure 27:
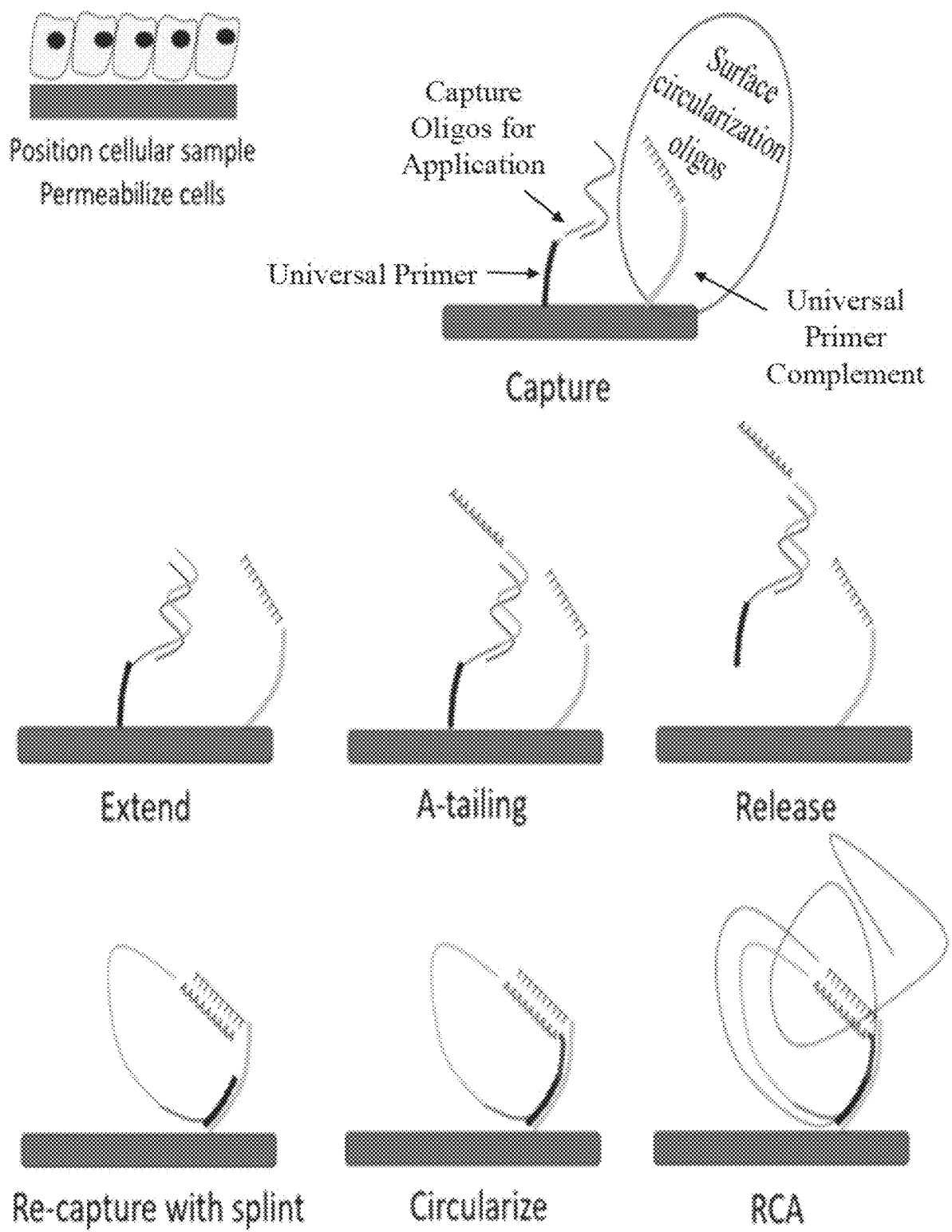
FIG. 27 is a schematic showing a support having immobilized thereon a capture oligonucleotide and circularization oligonucleotide, and an exemplary method for capturing nucleic acids from a cellular biological sample which is positioned on the support, according to various embodiments described herein.

The method for analyzing nucleic acids further comprises the step: (d) conducting a non-template tailing reaction on the immobilized target extension product under conditions suitable for appending a homopolymer tail to the immobilized target extension product thereby forming an immobilized tailed target extension product (e.g., FIG. 27). In some embodiments, the non-template tailing reaction comprises contacting the immobilized target extension product with a plurality of nucleotides and a polymerase where the polymerase is a Taq polymerase, Tfi DNA polymerase, 3' exonuclease minus-large (Klenow) fragment, or 3' exonuclease minus-T4 polymerase.

The method for analyzing nucleic acids further comprises the step: (e) cleaving the immobilized tailed target extension product to release the immobilized tailed target extension product from the low binding coating thereby forming a soluble tailed target extension product. In some embodiments, the cleavable region can be cleaved with an enzyme, a chemical compound, light or heat.

The method for analyzing nucleic acids further comprises the step: (f) binding the soluble tailed target extension product to one of the immobilized circularization oligonucleotides under a condition suitable to hybridize the appended homopolymer tail of the soluble tailed target extension product to the homopolymer region of the immobilized circularization oligonucleotide, and suitable to hybridize the circularization anchor sequence of the soluble tailed target extension product to the circularization anchor binding sequence of the immobilized circularization oligonucleotide thereby forming an open circular target extension product with a gap and/or nick, such that the immobilized circularization oligonucleotide serves as a splint molecule to promote circularization of the soluble tailed target extension product (e.g., FIG. 27).

The method for analyzing nucleic acids further comprises the step: (g) closing the gap (if present) by conducting a gap-filling primer extension reaction and closing the nick (if present) by conducting a ligation reaction on the open circular target extension product thereby forming a covalently closed circular target extension product which is hybridized to the immobilized circularization oligonucleotide, wherein the immobilized circularization oligonucleotide includes a homopolymer region with a 3' extendible end (e.g., FIG. 27).

In some embodiments, the forming the covalently closed circular target extension product of step (g) comprises a polymerase-mediated gap-filling reaction, an enzymatic ligation reaction, or a polymerase-mediated gap-filling reaction and enzymatic ligation reaction. In some embodiments, the polymerase-mediate gap-filling reaction comprises contacting the open circular target molecule with a DNA polymerase and a plurality of nucleotides, where the DNA polymerase comprises E. coli DNA polymerase I, Klenow fragment of E. coli DNA polymerase I, T7 DNA polymerase, or T4 DNA polymerase. In some embodiments, the enzymatic ligation reaction comprises use of a ligase enzyme, including a T3, T4, T7 or Taq DNA ligase enzyme. In some embodiments, the forming the covalently closed circular target molecule comprises contacting the open circular target molecule with a CircLigase or CircLigase II enzyme.

The method for analyzing nucleic acids further comprises the step: (h) conducting a rolling circle amplification reaction using the 3' extendible end of the homopolymer region of the immobilized circularization oligonucleotide under a condition suitable to form an immobilized nucleic acid concatemer molecule having tandem repeat regions comprising the sequencing primer binding sequence, the target sequence, and the spatial barcode sequence (e.g., FIG. 27).

In some embodiments, the rolling circle amplification reaction of step (h) comprises contacting the covalently closed circularized padlock probes (e.g., circularized nucleic acid template molecule(s)) with an amplification primer, a DNA polymerase, a plurality of nucleotides, and at least one catalytic divalent cation, under a condition suitable for generating at least one nucleic acid concatemer, wherein the at least one catalytic divalent cation comprises magnesium or manganese.

In some embodiments, the rolling circle amplification reaction of step (h) comprises: (1) contacting the covalently closed circularized padlock probes (e.g., circularized nucleic acid template molecule(s)) with an amplification primer, a DNA polymerase, a plurality of nucleotides, and at least one non-catalytic divalent cation that does not promote polymerase-catalyzed nucleotide incorporation into the amplification primer, wherein the non-catalytic divalent cation comprises strontium or barium; and (2) contacting the covalently closed circularized padlock probes with at least one catalytic divalent cation, under a condition suitable for generating at least one nucleic acid concatemer, wherein the at least one catalytic divalent cation comprises magnesium or manganese.

In some embodiments, the rolling circle amplification reaction of step (h) is conducted at a constant temperature (e.g., isothermal) ranging from room temperature to about 50° C., or from room temperature to about 65° C.

In some embodiments, the rolling circle amplification reaction of step (h) can be conducted in the presence of a plurality of compaction oligonucleotides which compacts the size and/or shape of the immobilized concatemer to form an immobilized compact nanoball.

In some embodiments, the rolling circle amplification reaction of step (h) comprises a DNA polymerase having a strand displacing activity which is selected from a group consisting of phi29 DNA polymerase, large fragment of Bst DNA polymerase, large fragment of Bsu DNA polymerase, and Bca (exo-) DNA polymerase, Klenow fragment of E. coli DNA polymerase, T5 polymerase, M-MuLV reverse transcriptase, HIV viral reverse transcriptase, or Deep Vent DNA polymerase. In some embodiments, the phi29 DNA polymerase can be wild type phi29 DNA polymerase (e.g., MagniPhi from Expedeon), or variant EquiPhi29 DNA polymerase (e.g., from Thermo Fisher Scientific), and chimeric QualiPhi DNA polymerase (e.g., from 4basebio).

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with at least one amplification primer comprising a random sequence, a DNA polymerase having strand displacement activity, a plurality of nucleotides, and a catalytic divalent cation comprising magnesium or manganese.

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with a DNA primase-polymerase enzyme, a DNA polymerase having strand displacement activity, a plurality of nucleotides, and a catalytic divalent cation comprising magnesium or manganese. In some embodiments, a DNA primase-polymerase comprises an enzyme having activities of a DNA polymerase and an RNA primase. A DNA primase-polymerase enzyme can utilize deoxyribonucleotide triphosphates to synthesize a DNA primer on a single-stranded DNA template in a template-sequence dependent manner, and can extend the primer strand via nucleotide polymerization (e.g., primer extension), in the presence of a catalytic divalent cation (e.g., magnesium and/or manganese). The DNA primase-polymerase include enzymes that are members of DnaG-like primases (e.g., bacteria) and AEP-like primases (Archaea and Eukaryotes). An exemplary DNA primase-polymerase enzyme is Tth PrimPol from *Thermus thermophilus* HB27.

In one embodiment, the rolling circle amplification reaction can be followed by a flexing amplification reaction instead of a multiple displacement amplification (MDA) reaction. In some embodiments, the flexing amplification reaction comprises: (a) forming a nucleic acid relaxant reaction mixture by contacting the nucleic acid concatemer with one or a combination of two or more compounds selected from a group consisting of formamide, acetonitrile, ethanol, guanidine hydrochloride, urea, potassium iodide and/or polyamines, to generate a relaxed nucleic acid concatemer, wherein the forming a nucleic acid relaxant reaction mixture is conducted with a temperature ramp-up, a relaxant incubation temperature, and a temperature ramp-down; (b) washing the relaxed concatemer; (c) forming a flexing amplification reaction mixture by contacting the relaxed concatemer with a strand-displacing DNA polymerase, a plurality of nucleotides, a catalytic divalent cation, (in the absence of added amplification primers), to generate double-stranded concatemers, wherein the forming a flexing amplification reaction mixture is conducted with a temperature ramp-up, a flexing incubation temperature, and a temperature ramp-down; (d) washing the double-stranded concatemer; and (e) repeating steps (a)-(d) at least once.

Methods of Capturing and Analyzing RNA. Provided herein are methods for analyzing nucleic acids (e.g., RNA), comprising: (a) providing a support comprising a low non-specific binding coating to which a plurality of capture oligonucleotides are immobilized (e.g., FIGS. 4 and 28), wherein the plurality of capture oligonucleotides comprise (i) a target capture region that hybridizes to at least a portion of a target nucleic acid molecule, (ii) a universal sequence region comprising a spatial barcode sequence and optionally a sample barcode sequence, and (iii) a cleavable region, wherein low non-specific binding coating comprises at least one hydrophilic polymer coating having a water contact angle of no more than 45 degrees. In some embodiments, the target capture region comprises a homopolymer region having a poly-T sequence.

In some embodiments, the low non-specific binding coating in step (a) exhibits low background fluorescence signals or high contrast to noise (CNR) ratios relative to known surfaces in the art. In some embodiments, the low non-specific binding coating exhibits a level of non-specific Cy3 dye absorption of less than about 0.25 molecules/µm², where no more than 5% of the target nucleic acid is associated with the surface coating without hybridizing to an immobilized capture oligonucleotide. In some embodiments, a fluorescence image of the surface coating having a plurality of clonally-amplified clusters of nucleic acid exhibits a contrast-to-noise ratio (CNR) of at least 20, or at least 50, or higher contrast-to-noise ratios (CNR), when using a fluorescence imaging system under non-signal saturating conditions.

The method for analyzing nucleic acids further comprises the step: (b) contacting the low non-specific binding coating with a cellular biological sample in the presence of a high efficiency hybridization buffer under a condition suitable to promote migration of the target nucleic acid molecule from the cellular biological sample to one of the immobilized capture oligonucleotides thereby forming an immobilized target nucleic acid duplex, wherein the target nucleic acid molecule is immobilized to the low non-specific binding coating in a manner that preserves spatial location information of the target nucleic acid molecule in the cellular biological sample, wherein the target nucleic acid comprises a poly-A RNA molecule. In some embodiments, the target capture region having a poly-T sequence can hybridize to poly-A RNA (e.g., FIG. 28).

In some embodiments, the cellular biological sample in step (b) comprises a cellular biological sample that is fresh, frozen, fresh frozen, or archived (e.g., formalin-fixed paraffin-embedded; FFPE).

In some embodiments, the cellular biological sample in step (b) is subjected to a permeabilizing reaction to promote migration of the cellular nucleic acid molecules (e.g., DNA and/or RNA), including the target nucleic acid molecule, from the cellular biological sample to one of the immobilized capture oligonucleotides.

In some embodiments, the high efficiency high efficiency hybridization buffer of step (b) comprises: (i) a first polar aprotic solvent having a dielectric constant that is no greater than 40 and having a polarity index of 4-9; (ii) a second polar aprotic solvent having a dielectric constant that is no greater than 115 and is present in the high efficiency high efficiency hybridization buffer formulation in an amount effective to denature double-stranded nucleic acids; (iii) a pH buffer system that maintains the pH of the high efficiency high efficiency hybridization buffer formulation in a range of about 4-8; and (iv) a crowding agent in an amount sufficient to enhance or facilitate molecular crowding.

In some embodiments, the high efficiency high efficiency hybridization buffer of step (b) comprises: (i) the first polar aprotic solvent comprises acetonitrile at 25-50% by volume of the high efficiency high efficiency hybridization buffer; (ii) the second polar aprotic solvent comprises formamide at 5-10% by volume of the high efficiency high efficiency hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the high efficiency high efficiency hybridization buffer. In some embodiments, the high efficiency hybridization buffer further comprises betaine.

In some embodiments, the high efficiency high efficiency hybridization buffer of step (b) promotes high stringency (e.g., specificity), speed, and efficacy of nucleic acid hybridization reactions and increases the efficiency of the subsequent amplification and sequencing steps. In some embodiments, the high efficiency hybridization buffer significantly shortens nucleic acid hybridization times, and decreases sample input requirements. Nucleic acid annealing can be performed at isothermal conditions and eliminate the cooling step for annealing.

The method for analyzing nucleic acids further comprises the step: (c) conducting a reverse transcription reaction on the immobilized nucleic acid duplex using the hybridized target nucleic acid molecule as a template thereby forming an immobilized target extension product (e.g., cDNA) (e.g., FIG. 28).

In some embodiments, the reverse transcription reaction of step (c) comprises (i) a reverse transcriptase enzyme, (ii) a plurality of nucleotides, and (iii) a plurality of reverse transcriptase primers. In some embodiments, the reverse transcription reaction of step (a) comprises a plurality of nucleotides and an enzyme having reverse transcription activity, including reverse transcriptase enzymes from AMV (avian myeloblastosis virus), M-MLV (moloney murine leukemia virus), or HIV (human immunodeficiency virus). In some embodiments, the reverse transcriptase can be a commercially-available enzyme, including MultiScribe™, ThermoScript™, or ArrayScript™. In some embodiments, the reverse transcriptase enzyme comprises Superscript I, II, III, or IV enzymes. In some embodiments, the reverse transcription reaction can include an RNase inhibitor.

Figure 28:
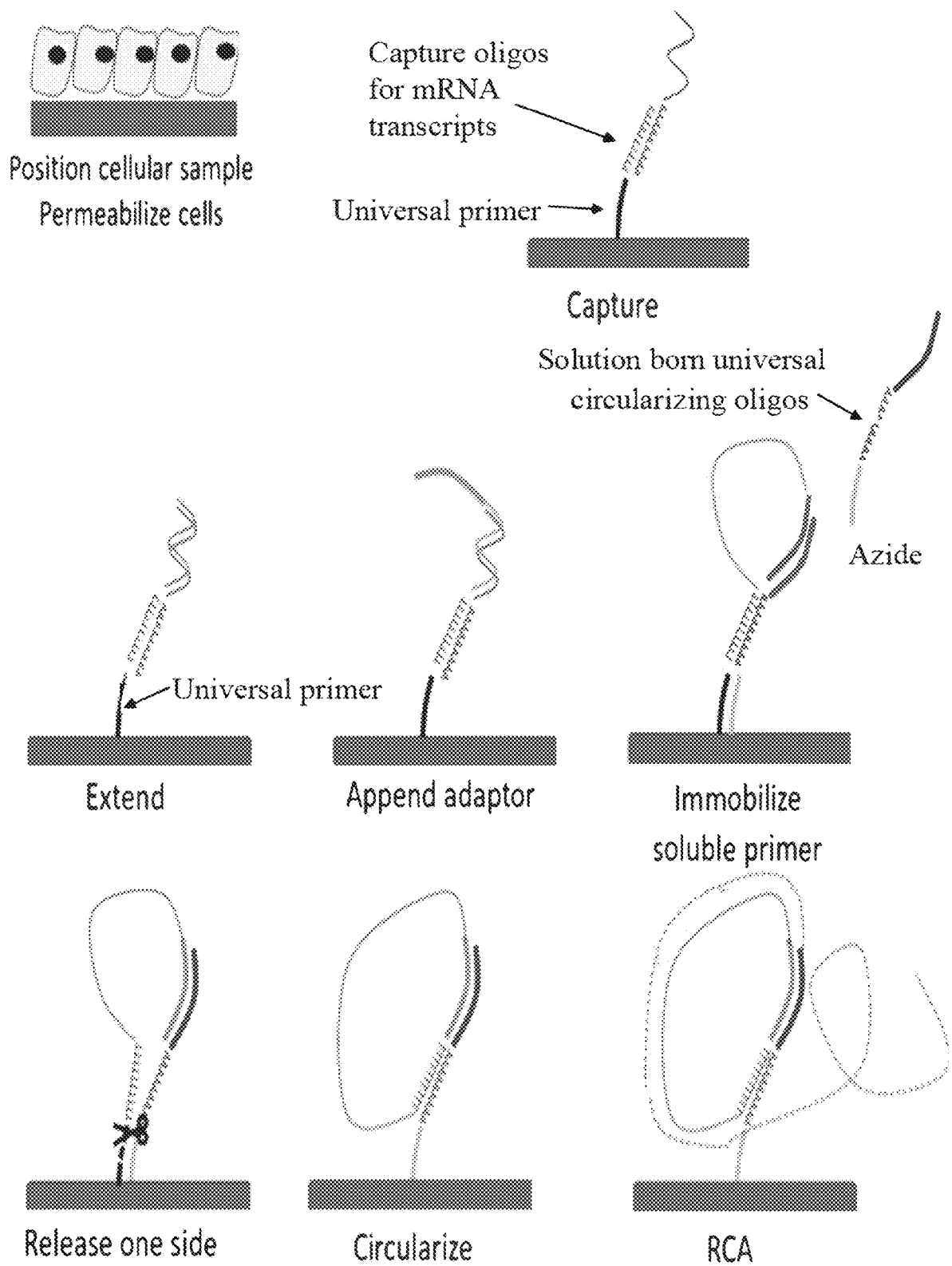
FIG. 28 is a schematic showing a support having immobilized thereon a capture oligonucleotide, and an exemplary method for capturing nucleic acids from a cellular biological sample which is positioned on the support where the method includes use of a soluble circularization oligonucleotide, according to various embodiments described herein.

In some embodiments, the method for analyzing nucleic acids (e.g., RNA) further comprises: (d) appending a nucleic acid adaptor to the non-immobilized end of the immobilized target extension product thereby generating an adaptor-appended immobilized double-stranded target extension product (FIG. 28). The nucleic acid adaptor can be single-stranded or double-stranded. The nucleic acid adaptor can be appended using an RNA ligase or DNA ligase. Single-stranded adaptors can be appended to the 3' end of one strand of the immobilized target extension product using T4 RNA ligase, KOD ligase, Circligase, or SplintR ligase. Double-stranded adaptors can be appended to the non-immobilized end of the immobilized target extension product using T4 DNA ligase, Tth DNA ligase, Taq DNA ligase, *Thermococcus* sp. (strain 9 degrees N) DNA ligase, Ampligase, or SplintR ligase. The adaptor-appended immobilized double-stranded target extension product comprises the immobilized capture oligonucleotide (extended via reverse transcription and appended with an adaptor) which is hybridized to the target nucleic acid molecule. In some embodiments the adaptor-appended immobilized double-stranded target extension product is subjected to a condition that dissociates/removes or degrades the target nucleic acid molecule so that the adaptor-appended immobilized single-stranded target extension product remains attached to the surface.

The method for analyzing nucleic acid may further comprises the step: (e) contacting the adaptor-appended immobilized single-stranded target extension product with plurality of soluble circularization oligonucleotides to form a target-circularization duplex, wherein the soluble circularization oligonucleotides each comprise (i) an adaptor binding region, (ii) a homopolymer region (iii) an anchor region, and (iv) an anchor moiety, wherein the homopolymer region comprises a poly-T sequence that can hybridize to the poly-A region of the target nucleic acid molecule, wherein the contacting is conducted under a condition suitable to immobilize at least one of the soluble circularization oligonucleotides to the low non-specific binding coating in close proximity to the adaptor-appended immobilized single-stranded target extension product (e.g., FIG. 28).

In some embodiments, the adaptor binding region includes a sequencing primer binding region. In some embodiments, the adaptor binding region include an amplification primer binding region. In some embodiments, the homopolymer region comprises a polynucleotide sequence selected from a group consisting of poly-T, poly-dT, poly-A, poly-dA, poly-C, poly-dC, poly-G and poly-dG. In some embodiments, the homopolymer region comprises a poly-T or poly-dT sequence. In some embodiments, the anchor moiety can attach to the surface thereby generating an immobilized circularization oligonucleotide. The adaptor binding region of the immobilized circularization oligonucleotide can hybridize to the appended adaptor sequence of the adaptor-appended immobilized single-stranded target extension product. The homopolymer region of the immobilized circularization oligonucleotide can hybridize to the homopolymer region (e.g., poly-A) of the adaptor-appended immobilized single-stranded target extension product.

The method for analyzing nucleic acids may further comprises the step: (f) cleaving the cleavable region of the target-circularization duplex to release the immobilized end from the low non-specific binding coating to generate a released target extension product, wherein the appended adaptor region of the released target extension product remains hybridized to the adaptor-binding region of the immobilized circularization oligonucleotide, and homopolymer region of the released target extension product can re-hybridize with the homopolymer region of the immobilized circularization oligonucleotide thereby forming an open circular target-circularization duplex with a gap and/or a nick, such that the immobilized circularization oligonucleotide serves as a splint molecule to promote circularization of the released target extension product (e.g., FIG. 28). In some embodiments, the cleavable region can be cleaved with an enzyme, a chemical compound, light or heat. In some embodiments, the appended adaptor region of the released target extension product remains hybridized to the adaptor-appended immobilized single-stranded target extension product. In some embodiments, the homopolymer region of the released target extension product can re-hybridize with the homopolymer region of the immobilized circularization oligonucleotide thereby forming an open circularized adaptor-appended target extension product with a gap or a nick. The immobilized circularization oligonucleotide can serve as a splint molecule to promote circularization of the released target extension product, as the homopolymer region and the adaptor binding region of the immobilized circularization oligonucleotide can hybridize to the ends of the released target extension product.

The method for analyzing nucleic acids may further comprises the step: (g) closing the gap (if present) by conducting a gap-filling primer extension reaction and closing the nick (if present) by conducting a ligation reaction on the open circular target-circularization duplex thereby forming a covalently closed circular target extension product which is hybridized to the immobilized circularization oligonucleotide, wherein the immobilized circularization oligonucleotide includes an adaptor-binding region with a 3' extendible end (e.g., FIG. 28).

In some embodiments, the forming the covalently closed circular target extension product of step (g) comprises a polymerase-mediated gap-filling reaction, an enzymatic ligation reaction, or a polymerase-mediated gap-filling reaction and enzymatic ligation reaction. In some embodiments, the polymerase-mediate gap-filling reaction comprises contacting the open circular target molecule with a DNA polymerase and a plurality of nucleotides, where the DNA polymerase comprises E. coli DNA polymerase I, Klenow fragment of E. coli DNA polymerase I, T7 DNA polymerase, or T4 DNA polymerase. In some embodiments, the enzymatic ligation reaction comprises use of a ligase enzyme, including a T3, T4, T7 or Taq DNA ligase enzyme. In some embodiments, the forming the covalently closed circular target molecule comprises contacting the open circular target molecule with a CircLigase or CircLigase II enzyme.

The method for analyzing nucleic acids may further comprises the step: (h) conducting a rolling circle amplification reaction by extending the 3' extendible end of the adaptor binding region of the immobilized circularization oligonucleotide under a condition suitable to form an immobilized nucleic acid concatemer molecule having tandem repeat regions comprising the sequencing primer binding sequence, the target sequence, and the spatial barcode sequence (e.g., FIG. 28).

In some embodiments, the rolling circle amplification reaction of step (h) comprises contacting the covalently closed circularized padlock probes (e.g., circularized nucleic acid template molecule(s)) with an amplification primer, a DNA polymerase, a plurality of nucleotides, and at least one catalytic divalent cation, under a condition suitable for generating at least one nucleic acid concatemer, wherein the at least one catalytic divalent cation comprises magnesium or manganese.

In some embodiments, the rolling circle amplification reaction of step (h) comprises: (1) contacting the covalently closed circularized padlock probes (e.g., circularized nucleic acid template molecule(s)) with an amplification primer, a DNA polymerase, a plurality of nucleotides, and at least one non-catalytic divalent cation that does not promote polymerase-catalyzed nucleotide incorporation into the amplification primer, wherein the non-catalytic divalent cation comprises strontium or barium; and (2) contacting the covalently closed circularized padlock probes with at least one catalytic divalent cation, under a condition suitable for generating at least one nucleic acid concatemer, wherein the at least one catalytic divalent cation comprises magnesium or manganese.

In some embodiments, the rolling circle amplification reaction of step (h) is conducted at a constant temperature (e.g., isothermal) ranging from room temperature to about 50° C., or from room temperature to about 65° C.

In some embodiments, the rolling circle amplification reaction of step (h) can be conducted in the presence of a plurality of compaction oligonucleotides which compacts the size and/or shape of the immobilized concatemer to form an immobilized compact nanoball.

In some embodiments, the rolling circle amplification reaction of step (h) comprises a DNA polymerase having a strand displacing activity which is selected from a group consisting of phi29 DNA polymerase, large fragment of Bst DNA polymerase, large fragment of Bsu DNA polymerase, and Bca (exo-) DNA polymerase, Klenow fragment of *E. coli* DNA polymerase, T5 polymerase, M-MuLV reverse transcriptase, HIV viral reverse transcriptase, or Deep Vent DNA polymerase. In some embodiments, the phi29 DNA polymerase can be wild type phi29 DNA polymerase (e.g., MagniPhi from Expedeon), or variant EquiPhi29 DNA polymerase (e.g., from Thermo Fisher Scientific), and chimeric QualiPhi DNA polymerase (e.g., from 4basebio).

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with at least one amplification primer comprising a random sequence, a DNA polymerase having strand displacement activity, a plurality of nucleotides, and a catalytic divalent cation comprising magnesium or manganese.

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with a DNA primase-polymerase enzyme, a DNA polymerase having strand displacement activity, a plurality of nucleotides, and a catalytic divalent cation comprising magnesium or manganese. In some embodiments, a DNA primase-polymerase comprises an enzyme having activities of a DNA polymerase and an RNA primase. A DNA primase-polymerase enzyme can utilize deoxyribonucleotide triphosphates to synthesize a DNA primer on a single-stranded DNA template in a template-sequence dependent manner, and can extend the primer strand via nucleotide polymerization (e.g., primer extension), in the presence of a catalytic divalent cation (e.g., magnesium and/or manganese). The DNA primase-polymerase include enzymes that are members of DnaG-like primases (e.g., bacteria) and AEP-like primases (Archaea and Eukaryotes). An exemplary DNA primase-polymerase enzyme is Tth PrimPol from *Thermus thermophilus* HB27.

In some embodiment, the rolling circle amplification reaction can be followed by a flexing amplification reaction instead of a multiple displacement amplification (MDA) reaction. In some embodiments, the flexing amplification reaction comprises: (a) forming a nucleic acid relaxant reaction mixture by contacting the nucleic acid concatemer with one or a combination of two or more compounds selected from a group consisting of formamide, acetonitrile, ethanol, guanidine hydrochloride, urea, potassium iodide and/or polyamines, to generate a relaxed nucleic acid concatemer, wherein the forming a nucleic acid relaxant reaction mixture is conducted with a temperature ramp-up, a relaxant incubation temperature, and a temperature ramp-down; (b) washing the relaxed concatemer; (c) forming a flexing amplification reaction mixture by contacting the relaxed concatemer with a strand-displacing DNA polymerase, a plurality of nucleotides, a catalytic divalent cation, (in the absence of added amplification primers), to generate double-stranded concatemers, wherein the forming a flexing amplification reaction mixture is conducted with a temperature ramp-up, a flexing incubation temperature, and a temperature ramp-down; (d) washing the double-stranded concatemer; and (e) repeating steps (a)-(d) at least once.

Methods and Compositions for Nucleic Acid Determination. Provided herein are methods for analyzing nucleic acid comprising determining the sequence of the target nucleic acid (e.g., immobilized concatemer) referred to herein. The sequencing may be targeted sequencing. The sequencing may be whole genome sequencing. Whole genome sequencing may comprise massive parallel sequencing ("next generation sequencing" or "second generation sequencing"). In some embodiments, the sequencing is performed by ligation. In some embodiments, the sequencing comprises the sequential monitoring of incorporation of labeled nucleotides in growing polynucleotide molecule. Sequencing may be performed by massively parallel array sequencing or single molecule sequencing.

The method for analyzing nucleic acids further comprises the step: (i) sequencing at least a portion of the immobilized nucleic acid concatemer, including sequencing the target sequence and the spatial barcode sequence, to determine the spatial location of the target nucleic acid in the cellular biological sample.

In some embodiments, the sequencing of step (i) comprises sequencing at least a portion of the nucleic acid concatemers using an optical imaging system comprising a field-of-view (FOV) greater than 1.0 mm$^2$.

In some embodiments, the sequencing of step (i) includes placing the cellular biological sample in a flow cell having walls (e.g., top or first wall, and bottom or second wall) and a gap in-between, where the gap can be filled with a fluid, where the flow cell is positioned in a fluorescence optical imaging system. The cellular biological sample has a thickness that may require using the imaging system to focus separately on the first and second surfaces of the flow cell, when using a traditional imaging system. For improved imaging of the sequencing reaction of the nucleic acids from the cellular biological sample, the flow cell can be positioned in a high performance fluorescence imaging system, which comprises two or more tube lenses which are designed to provide optimal imaging performance for the first and second surfaces of the flow cell at two or more fluorescence wavelengths. In some embodiments, the high-performance imaging system further comprises a focusing mechanism configured to refocus the optical system between acquiring images of the first and second surfaces of the flow cell. In some embodiments, the high performance imaging system is configured to image two or more fields-of-view on at least one of the first flow cell surface or the second flow cell surface.

In some embodiments, the sequencing of step (i) comprises: contacting the plurality of nucleic acid concatemers with a plurality of sequencing primers, a plurality of polymerases, and a plurality of multivalent molecules, wherein each of the multivalent molecules comprise two or more duplicates of a nucleotide moiety that are connected to a core via a linker.

In some embodiments, the multivalent molecule comprises multiple nucleotides that are bound to a particle (or core) such as a polymer, a branched polymer, a dendrimer, a micelle, a liposome, a microparticle, a nanoparticle, a quantum dot, or other suitable particle known in the art.

In some embodiments, the multivalent molecule comprises: (a) a core, and (b) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms. In some embodiments, the spacer is attached to the linker. In some embodiments, the linker is attached to the nucleotide unit. In some embodiments, the nucleotide unit comprises a base, sugar and at least one phosphate group, and wherein the linker is attached to the nucleotide unit through the base. In some embodiments, the linker comprises an aliphatic chain or an oligo ethylene glycol chain where both linker chains having 2-6 subunits and optionally the linker includes an aromatic moiety.

In some embodiments, the multivalent molecule comprises a core attached to multiple nucleotide arms, and wherein the multiple nucleotide arms have the same type of nucleotide unit which is selected from a group consisting of dATP, dGTP, dCTP, dTTP and dUTP.

In some embodiments, the multivalent molecule further comprises a plurality of multivalent molecules which includes a mixture of multivalent molecules having two or more different types of nucleotides selected from a group consisting of dATP, dGTP, dCTP, dTTP and dUTP.

In some embodiments, the multivalent molecule comprises a core attached to multiple nucleotide arms, and wherein individual nucleotide arms comprise a nucleotide unit having a chain terminating moiety (e.g., blocking moiety) at the sugar 2' position, at the sugar 3' position, or at the sugar 2' and 3' position.

In some embodiments, the chain terminating moiety comprise an azide, azido or azidomethyl group. In some embodiments, the chain terminating moiety is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, the chain terminating moiety is cleavable/removable from the nucleotide unit.

In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, the multivalent molecule comprises a core attached to multiple nucleotide arms, wherein the core is labeled with detectable reporter moiety. In some embodiments, the detectable reporter moiety comprises a fluorophore.

In some embodiments, the core of the multivalent molecule comprises an avidin-like moiety and the core attachment moiety comprises biotin.

In some embodiments, the sequencing of step (i) comprises. (1) contacting the plurality of nucleic acid concatemers with (i) a plurality of polymerases, (ii) at least one multivalent molecule comprising two or more duplicates of a nucleotide moiety that are connected to a core via a linker, and (iii) a plurality of sequencing primers that hybridize with a portion of the concatemers, under a condition suitable for binding at least one polymerase and at least one sequencing primer to a portion of one of the nucleic acid concatemer molecules, and suitable for binding at least one of the nucleotide moieties of the multivalent molecule to the 3' end of the sequencing primer at a position that is opposite a complementary nucleotide in the concatemer molecule wherein the bound nucleotide moiety does not incorporate into the sequencing primer; (2) detecting and identifying the bound nucleotide moiety of the multivalent molecule thereby determining the sequence of the concatemer molecule; (3) optionally repeating steps (1) and (2) at least once; (4) contacting the concatemer molecule with (i) a plurality of polymerases, and (ii) a plurality of nucleotides, under a condition suitable binding at least one polymerase to at least a portion of the concatemer molecule and suitable for binding at least one of the nucleotides from the plurality to the 3' ends of the hybridized sequencing primers at a position that is opposite a complementary nucleotide in the concatemer molecule wherein the bound nucleotides incorporate into the hybridized sequencing primers; (5) optionally detecting the incorporated nucleotides; (6) optionally identifying the incorporation nucleotides thereby determining or confirming the sequence of the concatemer; and (7) repeating steps (1)-(6) at least once.

In some embodiments, the sequencing of step (i) comprises: (1) contacting the plurality of immobilized concatemers with a plurality of sequencing primers that hybridize with the sequencing primer binding sequence, a plurality of polymerases, and a plurality of nucleotides, under a condition suitable for binding at least one polymerase and at least one sequencing primer to a portion of the immobilized concatemer, and suitable for binding at least one of the nucleotides to the 3' end of the sequencing primer at a position that is opposite a complementary nucleotide in the immobilized concatemer wherein the bound nucleotide incorporates into the 3' end of the sequencing primer; (2) detecting and identifying the incorporated nucleotide thereby determining the sequence of the immobilized concatemer molecule; and (3) optionally repeating steps (1) and (2) at least once. In some embodiments, at least one of the nucleotides in the plurality of nucleotides comprises a chain terminating moiety at the sugar 2' or 3' position. In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

The sequencing method can include contacting a target nucleic acid or multiple target nucleic acids, comprising multiple linked or unlinked copies of a target sequence, with the multivalent binding compositions described herein. Contacting said target nucleic acid, or multiple target nucleic acids comprising multiple linked or unlinked copies of a target sequence, with one or more polymer-nucleotide conjugates may provide a substantially increased local concentration of the correct nucleotide being interrogated in a given sequencing cycle, thus suppressing signals from improper incorporations or phased nucleic acid chains (i.e., those elongating nucleic acid chains which have had one or more skipped cycles).

Provided herein are methods of obtaining nucleic acid sequence information comprising contacting a target nucleic acid, or multiple target nucleic acids, with one or more polymer-nucleotide conjugates. In some embodiments, the target nucleic acid or multiple target nucleic acids comprise multiple linked or unlinked copies of a target sequence. In some embodiments, the method results in a reduction in the error rate of sequencing as indicated by reduction in the misidentification of bases, the reporting of nonexistent bases, or the failure to report correct bases. In some embodiments, said reduction in the error orate of sequencing may comprise a reduction of 5%, 10%, 15%, 20% 25%, 50%, 75%, 100%, 150%, 200%, or more compared to the error rate observed using monovalent ligands, including free nucleotides, labeled free nucleotides, protein or peptide bound nucleotides, or labeled protein or peptide bound nucleotides. In some embodiments, the method results in an increase in average read length of 5%, 10%, 15%, 20% 25%, 50%, 75%, 100%, 150%, 200%, 300%, or more compared to the average read length observed using monovalent ligands, including free nucleotides, labeled free nucleotides, protein or peptide bound nucleotides, or labeled protein or peptide bound nucleotides. In some embodiments, the method results in an increase in average read length of 10, 20, 25, 30, 50, 75, 100, 125, 150, 200, 250, 300, 350, 400, 500 nucleotides, or more compared to the average read length observed using monovalent ligands, including free nucleotides, labeled free nucleotides, protein or peptide bound nucleotides, or labeled protein or peptide bound nucleotides.

The use of the polymer-nucleotide conjugates for sequencing can shortens the total time of a sequencing reaction or sequencing run. The sequencing reaction cycle comprising the contacting, detecting, and incorporating steps is performed in a total time ranging from about 5 minutes to about 60 minutes. In some embodiments, the sequencing reaction cycle is performed in at least 5 minutes, at least 10 minutes, at least 20 minutes, at least 30 minutes, at least 40 minutes, at least 50 minutes, or at least 60 minutes. In some embodiments, the sequencing reaction cycle is performed in at most 60 minutes, at most 50 minutes, at most 40 minutes, at most 30 minutes, at most 20 minutes, at most 10 minutes, or at most 5 minutes. Any of the lower and upper values described in this paragraph may be combined to form a range included within the present disclosure, for example, in some embodiments the sequencing reaction cycle may be performed in a total time ranging from about 10 minutes to about 30 minutes. Those of skill in the art will recognize that the sequencing cycle time may have any value within this range, e.g., about 16 minutes.

The use of the polymer-nucleotide conjugates for sequencing provides an more accuracy base readout. The disclosed compositions and methods for nucleic acid sequencing will provide an average Q-score for base-calling accuracy over a sequencing run that ranges from about 20 to about 50. In some embodiments, the average Q-score is at least 20, at least 25, at least 30, at least 35, at least 40, at least 45, or at least 50. Those of skill in the art will recognize that the average Q-score may have any value within this range, e.g., about 32. In some embodiments, the disclosed compositions and methods for nucleic acid sequencing will provide a Q-score of greater than 30 for at least 50%, at least 60%, at least 70%, at least 80%, at least 85%, at least 90°/%, at least 95%, at least 98%, or at least 99% of the terminal (or N+1) nucleotides identified. In some embodiments, the disclosed compositions and methods for nucleic acid sequencing will provide a Q-score of greater than 35 for at least 50%, at least 60%, at least 70%, at least 80%, at least 85%, at least 90%, at least 95%, at least 98%, or at least 99% of the terminal (or N+1) nucleotides identified. In some embodiments, the disclosed compositions and methods for nucleic acid sequencing will provide a Q-score of greater than 40 for at least 50%, at least 60%, at least 70%, at least 80%, at least 85%, at least 90%, at least 95%, at least 98%, or at least 99% of the terminal (or N+1) nucleotides identified. In some embodiments, the disclosed compositions and methods for nucleic acid sequencing will provide a Q-score of greater than 45 for at least 50%, at least 60%, at least 70%, at least 80%, at least 85%, at least 90%, at least 95%, at least 98%, or at least 99% of the terminal (or N+1) nucleotides identified. In some embodiments, the disclosed compositions and methods for nucleic acid sequencing will provide a Q-score of greater than 50 for at least 50%, at least 60%, at least 70%, at least 80%, at least 85%, at least 90%, at least 95%, at least 98%, or at least 99% of the terminal (or N+1) nucleotides identified.

The present disclosure relates to polymer-nucleotide conjugates each having a plurality of nucleotides conjugated to a particle or core (e.g., a polymer, branched polymer, dendrimer, or equivalent structure). Contacting the polymer-nucleotide conjugate with a polymerase and a primed target nucleic acid may result in the formation of a ternary complex which may be detected and in turn achieve a more accurate determination of the bases of the target nucleic acid.

When the polymer-nucleotide conjugate is used in replacement of single unconjugated or untethered nucleotide to form a complex with the polymerase and the target nucleic acid, the local concentration of the nucleotide is increased many fold, which in turn enhances the signal intensity, particularly the correct signal versus mismatch. The polymer-nucleotide conjugate described herein can include at least one polymer-nucleotide conjugate for interacting with the target nucleic acid. The multivalent composition can also include two, three, or four different polymer-nucleotide conjugate s, each having a different nucleotide conjugated to the particle.

In a polymer-nucleotide conjugate having a polymer-nucleotide conjugate form or a core-nucleotide conjugate form, multiple copies of the same nucleotide may be covalently bound to or noncovalently bound to the particle. Examples of the particle can include a branched polymer; a dendrimer; a cross linked polymer particle such as an agarose, polyacrylamide, acrylate, methacrylate, cyanoacrylate, methyl methacrylate particle; a glass particle; a ceramic particle; a metal particle; a quantum dot; a liposome; an emulsion particle, or any other particle (e.g., nanoparticles, microparticles, or the like) known in the art. In a preferred embodiment, the particle is a branched polymer.

The nucleotide can be linked to the particle or core through a linker, and the nucleotide can be attached to one end or location of a polymer. The nucleotide can be conjugated to the particle through the base or the 5' end of the nucleotide. In some polymer-nucleotide conjugates, one nucleotide attached to one end or location of a polymer. In some polymer-nucleotide conjugate, multiple nucleotides are attached to one end or location of a polymer. The conjugated nucleotide is sterically accessible to one or more proteins, one or more enzymes, and nucleotide binding moieties. In some embodiments, a nucleotide may be provided separately from a nucleotide binding moiety such as a polymerase. In some embodiments, the linker does not comprise a photo emitting or photo absorbing group.

The particle or core can also have a binding moiety. In some embodiments, particles or cores may self-associate without the use of a separate interaction moiety. In some embodiments, particles or cores may self-associate due to buffer conditions or salt conditions, e.g., as in the case of calcium-mediated interactions of hydroxyapatite particles, lipid or polymer mediated interactions of micelles or liposomes, or salt-mediated aggregation of metallic (such as iron or gold) nanoparticles.

The polymer-nucleotide conjugates can have one or more labels (e.g., detectable reporter moieties). Examples of the labels include but are not limited to fluorophores, spin labels, metals or metal ions, colorimetric labels, nanoparticles, PET labels, radioactive labels, or other such label as may render said composition detectable by such methods as are known in the art of the detection of macromolecules or molecular interactions. The label may be attached to the nucleotide (e.g. by attachment to the base or the 5' phosphate moiety of a nucleotide), to the particle itself (e.g., to the PEG subunits) or to the core (e.g., to the streptavidin core), to an end of the polymer, to a central moiety, or to any other location within said polymer-nucleotide conjugate which would be recognized by one of skill in the art to be sufficient to render said composition, such as a particle, detectable by such methods as are known in the art or described elsewhere herein. In some embodiments, one or more labels are provided so as to correspond to or differentiate a particular polymer-nucleotide conjugate.

One example of the polymer-nucleotide conjugate (e.g., polymer-nucleotide conjugate) is a polymer-nucleotide conjugate. Examples of the branched polymer include polyethylene glycol (PEG), polypropylene glycol, polyvinyl alcohol, polylactic acid, polyglycolic acid, polyglycine, polyvinyl acetate, a dextran, or other such polymers. In one embodiment, the polymer is a PEG. In another embodiment, the polymer can have PEG branches.

Suitable polymers may be characterized by a repeating unit having a functional group suitable for derivatization such as an amine, a hydroxyl, a carbonyl, or an allyl group. The polymer can also have one or more pre-derivatized substituents such that one or more particular subunits comprise a site of derivatization or a branch site, whether or not other subunits include the same site, substituent, or moiety. A pre-derivatized substituent may comprise or may further comprise, for example, a nucleotide, a nucleoside, a nucleotide analog, a label such as a fluorescent label, radioactive label, or spin label, an interaction moiety, an additional polymer moiety, or the like, or any combination of the foregoing.

In the polymer-nucleotide conjugate (e.g., polymer-nucleotide conjugate), the polymer can have a plurality of branches. The branched polymer can have various configurations, including but are not limited to stellate ("starburst") forms, aggregated stellate ("helter skelter") forms, bottle brush, or dendrimer. The branched polymer can radiate from a central attachment point or central moiety, or may include multiple branch points, such as, for example, 2, 3, 4, 5, 6, 7, 8, 9, 10, or more branch points. In some embodiments, each subunit of a polymer may optionally constitute a separate branch point.

In the polymer-nucleotide conjugate, the length and size of the branch can differ based on the type of polymer. In some branched polymers, the branch may have a length of between 1 and 1,000 nm, between 1 and 100 nm, between 1 and 200 nm, between 1 and 300 nm, between 1 and 400 nm, between 1 and 500 nm, between 1 and 600 nm, between 1 and 700 nm, between 1 and 800 nm, or between 1 and 900 nm, or more, or having a length falling within or between any of the values disclosed herein. In some branched polymers, the branch may have a size corresponding to an apparent molecular weight of 1K, 2K, 3K, 4K, 5K, 10K, 15K, 20K, 30K, 50K, 80K, 100K, or any value within a range defined by any two of the foregoing. The apparent molecular weight of a polymer may be calculated from the known molecular weight of a representative number of subunits, as determined by size exclusion chromatography, as determined by mass spectrometry, or as determined by any other method as is known in the art. The polymer can have multiple branches. The number of branches in the polymer can be 2, 3, 4, 5, 6, 7, 8, 12, 16, 24, 32, 64, 128 or more, or a number falling within a range defined by any two of these values.

For the polymer-nucleotide conjugate, the branched polymer of 4, 8, 16, 32, or 64 branches can have nucleotides attached to the ends of PEG branches, such that each end has attached thereto 0, 1, 2, 3, 4, 5, 6 or more nucleotides. In one non-limiting example, the branched polymer of between 3 and 128 PEG arms having attached to the polymer branches ends one or more nucleotides, such that each end has attached thereto 0, 1, 2, 3, 4, 5, 6 or more nucleotides or nucleotide analogs. In some embodiments, a branched polymer or dendrimer has an even number of arms. In some embodiments, a branched polymer or dendrimer has an odd number of arms.

In the polymer-nucleotide conjugate, each branch or a subset of branches of the polymer may have attached thereto a moiety comprising a nucleotide (e.g., an adenine, a thymine, a uracil, a cytosine, or a guanine residue or a derivative or mimetic thereof), and the moiety is capable of binding to a polymerase, reverse transcriptase, or other nucleotide binding domain. Optionally, the nucleotide moiety may be capable of binding to a polymerase-template-primer complex but not incorporate, or can incorporate into an elongating nucleic acid chain during a polymerase reaction. In some embodiments, the nucleotide moiety comprises a chain terminating moiety which blocks incorporation of a subsequent nucleotide during a polymerase-mediated reaction. In some embodiments, the nucleotide moiety may be unblocked (reversibly blocked) such that a subsequent nucleotide is not capable of being incorporated into an elongating nucleic acid chain during a polymerase reaction until such block is removed, after which the subsequent nucleotide is then capable of being incorporated into an elongating nucleic acid chain during a polymerase reaction.

The polymer-nucleotide conjugate can further have a binding moiety in each branch or a subset of branches. Some examples of the binding moiety include but are not limited to biotin, avidin, streptavidin or the like, polyhistidine domains, complementary paired nucleic acid domains, G-quartet forming nucleic acid domains, calmodulin, maltose-binding protein, cellulase, maltose, sucrose, glutathione-S-transferase, glutathione, O-6-methylguanine-DNA methyltransferase, benzylguanine and derivatives thereof, benzylcysteine and derivatives thereof, an antibody, an epitope, a protein A, a protein G. The binding moiety can be any interactive molecules or fragment thereof known in the art to bind to or facilitate interactions between proteins, between proteins and ligands, between proteins and nucleic acids, between nucleic acids, or between small molecule interaction domains or moieties.

In some embodiments, the polymer-nucleotide conjugate may comprise one or more elements of a complementary interaction moiety. Exemplary complementary interaction moieties include, for example, biotin and avidin; SNAP-benzylguanosine; antibody or FAB and epitope; IgG FC and Protein A, Protein G, Protein A/G, or Protein L; maltose binding protein and maltose; lectin and cognate polysaccharide; ion chelation moieties, complementary nucleic acids, nucleic acids capable of forming triplex or triple helical interactions; nucleic acids capable of forming G-quartets, and the like. One of skill in the art will readily recognize that many pairs of moieties exist and are commonly used for their property of interacting strongly and specifically with one another; and thus any such complementary pair or set is considered to be suitable for this purpose in constructing or envisioning the compositions of the present disclosure. In some embodiments, a composition as disclosed herein may comprise compositions in which one element of a complementary interaction moiety is attached to one molecule or multivalent ligand, and the other element of the complementary interaction moiety is attached to a separate molecule or multivalent ligand. In some embodiments, a composition as disclosed herein may comprise compositions in which both or all elements of a complementary interaction moiety are attached to a single molecule or multivalent ligand. In some embodiments, a composition as disclosed herein may comprise compositions in which both or all elements of a complementary interaction moiety are attached to separate arms of, or locations on, a single molecule or multivalent ligand. In some embodiments, a composition as disclosed herein may comprise compositions in which both or all elements of a complementary interaction moiety are attached to the same arm of, or locations on, a single molecule or multivalent ligand. In some embodiments, compositions comprising one element of a complementary interaction moiety and compositions comprising another element of a complementary interaction moiety may be simultaneously or sequentially mixed. In some embodiments, interactions between molecules or particles as disclosed herein allow for the association or aggregation of multiple molecules or particles such that, for example, detectable signals are increased. In some embodiments, fluorescent, colorimetric, or radioactive signals are enhanced. In other embodiments, other interaction moieties as disclosed herein or as are known in the art are contemplated. In some embodiments, a composition as provided herein may be provided such that one or more molecules comprising a first interaction moiety such as, for example, one or more imidazole or pyridine moieties, and one or more additional molecules comprising a second interaction moiety such as, for example, histidine residues, are simultaneously or sequentially mixed. In some embodiments, said composition comprises 1, 2, 3, 4, 5, 6, or more imidazole or pyridine moieties. In some embodiments, said composition comprises 1, 2, 3, 4, 5, 6, or more histidine residues. In such embodiments, interaction between the molecules or particles as provided may be facilitated by the presence of a divalent cation such as nickel, manganese, magnesium, calcium, strontium, or the like. In some embodiments, for example, a (His)3 group may interact with a (His)3 group on another molecule or particle via coordination of a nickel or manganese ion.

The polymer-nucleotide conjugate may comprise one or more buffers, salts, ions, or additives. In some embodiments, representative additives may include, but are not limited to, betaine, spermidine, detergents such as Triton X-100, Tween 20, SDS, or NP-40, ethylene glycol, polyethylene glycol, dextran, polyvinyl alcohol, vinyl alcohol, methylcellulose, heparin, heparan sulfate, glycerol, sucrose, 1,2-propanediol, DMSO, N,N,N-trimethylglycine, ethanol, ethoxyethanol, propylene glycol, polypropylene glycol, block copolymers such as the Pluronic (r) series polymers, arginine, histidine, imidazole, or any combination thereof, or any substance known in the art as a DNA "relaxer" (a compound, with the effect of altering the persistence length of DNA, altering the number of within-polymer junctions or crossings, or altering the conformational dynamics of a DNA molecule such that the accessibility of sites within the strand to DNA binding moieties is increased).

The polymer-nucleotide conjugate may include zwitterionic compounds as additives. Further representative additives may be found in Lorenz, T. C. J. Vis. Exp. (63), e3998, doi:10.3791/3998 (2012), which is hereby incorporated by reference with respect to its disclosure of additives for the facilitation of nucleic acid binding or dynamics, or the facilitation of processes involving the manipulation, use, or storage of nucleic acids.

In some embodiments, the multivalent binding compositions include at least one cations may include, but are not limited to, sodium, magnesium, strontium, barium, potassium, manganese, calcium, lithium, nickel, cobalt, or other such cations as are known in the art to facilitate nucleic acid interactions, such as self-association, secondary or tertiary structure formation, base pairing, surface association, peptide association, protein binding, or the like.

When the polymer-nucleotide conjugate is used to replace an unconjugated or untethered nucleotide to form a complex with the polymerase and the target nucleic acid, the local concentration of the nucleotide is increased many folds, which in turn enhances the signal intensity, particularly the correct signal versus mismatch. The present disclosure contemplates contacting the polymer-nucleotide conjugate with a polymerase and a primed target nucleic acid to determine the formation of a ternary binding complex.

Because of the increased local concentration of the nucleotide on the polymer-nucleotide conjugate, the binding between the polymerase, the primed target strand, and the nucleotide, when the nucleotide is complementary to the next base of the target nucleic acid, becomes more favorable. The formed binding complex has a longer persistence time which in turn helps shorten the imaging step. The high signal intensity resulted from the use of the polymer-nucleotide conjugate remain for the entire binding and imaging step. The strong binding between the polymerase, the primed target strand, and the nucleotide or nucleotide analog also means that the formed binding complex will remain stabilized during the washing step and the signal will remain at a high intensity when other reaction mixture and unmatched nucleotide analogs are washed away. After the imaging step, the binding complex can be destabilized and the primed target nucleic acid can then be extended for one base. After the extension, the binding and imaging steps can be repeated again with the use of the polymer-nucleotide conjugate to determine the identity of the next base.

The compositions and methods of the present disclosure provide a robust and controllable means of establishing and maintaining a ternary enzyme complex (e.g., during sequencing), as well as providing vastly improved means by which the presence of said complex may be identified and/or measured, and a means by which the persistence of said complex may be controlled. This provides important solutions to problems such as that of determining the identity of the N+1 base in nucleic acid sequencing applications.

Without intending to be bound by any particular theory, it has been observed that multivalent binding compositions disclosed herein associate with polymerase nucleotide complexes in order to form a ternary binding complexes with a rate that is time-dependent, though substantially slower than the rate of association known to be obtainable by nucleotides in free solution. Thus, the on-rate (Kon) is substantially and surprisingly slower than the on rate for single nucleotides or nucleotides not attached to multivalent ligand complexes. Importantly, however, the off rate (Koff) of the multivalent ligand complex is substantially slower than that observed for nucleotides in free solution. Therefore, the multivalent ligand complexes of the present disclosure provide a surprising and beneficial improvement of the persistence of ternary polymerase-polynucleotide-nucleotide complexes (especially over such complexes that are formed with free nucleotides) allowing, for example, significant improvements in imaging quality for nucleic acid sequencing applications, over currently available methods and reagents. Importantly, this property of the multivalent substrates disclosed herein renders the formation of visible ternary complexes controllable, such that subsequent visualization, modification, or processing steps may be undertaken essentially without regard to the dissociation of the complex— that is, the complex can be formed, imaged, modified, or used in other ways as necessary, and will remain stable until a user carries out an affirmative dissociation step, such as exposing the complexes to a dissociation buffer.

In various embodiments, polymerases suitable for the binding interaction (e.g., during sequencing) describe herein include may include any polymerase as is or may be known in the art. Exemplary polymerases may include but are not limited to: Klenow DNA polymerase, *Thermus aquaticus* DNA polymerase I (Taq polymerase), KlenTaq polymerase, and bacteriophage T7 DNA polymerase; human alpha, delta and epsilon DNA polymerases; bacteriophage polymerases such as T4, RB69 and phi29 bacteriophage DNA polymerases, *Pyrococcus furiosus* DNA polymerase (Pfu polymerase); *Bacillus subtilis* DNA polymerase III, and *E. coli* DNA polymerase III alpha and epsilon; 9 degree N polymerase, reverse transcriptases such as HIV type M or O reverse transcriptases, avian myeloblastosis virus reverse transcriptase, or Moloney Murine Leukemia Virus (MMLV) reverse transcriptase, or telomerase. Further non-limiting examples of DNA polymerases can include those from various Archaea genera, such as, *Aeropyrum, Archaeglobus, Desulfurococcus, Pyrobaculum, Pyrococcus, Pyrolobus, Pyrodictium, Staphylothermus, Stetteria, Sulfolobus, Thermococcus*, and *Vulcanisaeta* and the like or variants thereof, including such polymerases as are known in the art such as Vent™, Deep Vent™, Pfu, KOD, Pfx, Therminator™, and Tgo polymerases. In some embodiments, the polymerase is a Klenow polymerase.

The ternary complex has longer persistence time when the nucleotide on the polymer-nucleotide conjugate is complementary to the target nucleic acid than when non-complementary. The ternary complex also has longer persistence time when the nucleotide on the polymer-nucleotide conjugate is complementary to the target nucleic acid than a complementary nucleotide that is not conjugated or tethered. For example, in some embodiments, said ternary complexes may have a persistence time of less than is, greater than is, greater than 2s, greater than 3s, greater than 5s, greater than 10s, greater than 15s, greater than 20s, greater than 30s, greater than 60s, greater than 120s, greater than 360s, greater than 3600s, or more, or for a time lying within a range defined by any two or more of these values.

The persistence time can be measured, for example, by observing the onset and/or duration of a binding complex, such as by observing a signal from a labeled component of the binding complex. For example, a labeled nucleotide or a labeled reagent comprising one or more nucleotides may be present in a binding complex, thus allowing the signal from the label to be detected during the persistence time of the binding complex.

It has been observed that different ranges of persistence times are achievable with different salts or ions, showing, for example, that complexes formed in the presence of, for example, magnesium form more quickly than complexes formed with other ions. It has also been observed that complexes formed in the presence of, for example, strontium, form readily and dissociate completely or with substantial completeness upon withdrawal of the ion or upon washing with buffer lacking one or more components of the present compositions, such as, e.g., a polymer and/or one or more nucleotides, and/or one or more interaction moieties, or a buffer containing, for example, a chelating agent which may cause or accelerate the removal of a divalent cation from the multivalent reagent containing complex. Thus, in some embodiments, a composition of the present disclosure comprises magnesium. In some embodiments, a composition of the present disclosure comprises calcium. In some embodiments, a composition of the present disclosure comprises strontium or barium. In some embodiments, a composition of the present disclosure comprises cobalt. In some embodiments, a composition of the present disclosure comprises $MgCl_2$. In some embodiments, a composition of the present disclosure comprises $CaCl_2$. In some embodiments, a composition of the present disclosure comprises $SrCl_2$. In some embodiments, a composition of the present disclosure comprises $CoCl_2$. In some embodiments, the composition comprises no, or substantially no magnesium. In some embodiments, the composition comprises no, or substantially no calcium. In some embodiments, the methods of the present disclosure provide for the contacting of one or more nucleic acids with one or more of the compositions disclosed herein wherein said composition lacks either one of calcium or magnesium, or lacks both calcium and magnesium.

The dissociation of ternary complexes can be controlled by changing the buffer conditions. After the imaging step, a buffer with increased salt content is used to cause dissociation of the ternary complexes such that labeled polymernucleotide conjugates can be washed out, providing a means by which signals can be attenuated or terminated, such as in the transition between one sequencing cycle and the next. This dissociation may be effected, in some embodiments, by washing the complexes with a buffer lacking a necessary metal or cofactor. In some embodiments, a wash buffer may comprise one or more compositions for the purpose of maintaining pH control. In some embodiments, a wash buffer may comprise one or more monovalent cations, such as sodium. In some embodiments, a wash buffer lacks or substantially lacks a divalent cation, for example, having no or substantially no strontium, calcium, magnesium, or manganese. In some embodiments, a wash buffer further comprises a chelating agent, such as, for example, EDTA, EGTA, nitrilotriacetic acid, polyhistidine, imidazole, or the like. In some embodiments, a wash buffer may maintain the pH of the environment at the same level as for the bound complex. In some embodiments, a wash buffer may raise or lower the pH of the environment relative to the level seen for the bound complex. In some embodiments, the pH may be within a range from 2-4, 2-7, 5-8, 7-9, 7-10, or lower than 2, or higher than 10, or a range defined by any two of the values provided herein.

Addition of a particular ion may affect the binding of the polymerase to a primed target nucleic acid, the formation of a ternary complex, the dissociation of a ternary complex, or the incorporation of one or more nucleotides into an elongating nucleic acid such as during a polymerase reaction. In some embodiments, relevant anions may comprise chloride, acetate, gluconate, sulfate, phosphate, or the like. In some embodiments, an ion may be included in the compositions of the present disclosure by the addition of one or more acids, bases, or salts, such as $NiCl_2$, $CoCl_2$, $MgCl_2$, $MnCl_2$, $SrCl_2$, $CaCl_2$, $CaSO_4$, $SrCO_3$, $BaCl_2$ or the like. Representative salts, ions, solutions and conditions may be found in Remington: The Science and Practice of Pharmacy, 20th. Edition, Gennaro, A. R., Ed. (2000), which is hereby incorporated by reference in its entirety, and especially with respect to Chapter 17 and related disclosure of salts, ions, salt solutions, and ionic solutions.

The present disclosure contemplates contacting the polymer-nucleotide conjugate with one or more polymerases. The contacting can be optionally done in the presence of one or more target nucleic acids. In some embodiments, said target nucleic acids are single stranded nucleic acids. In some embodiments, the target nucleic acids are hybridized to a nucleic acid primer. In some embodiments, said target nucleic acids are double stranded nucleic acids. In some embodiments, said contacting comprises contacting the polymer-nucleotide conjugate with one polymerase. In some embodiments, said contacting comprises the contacting of said composition comprising one or more nucleotides with multiple polymerases. The polymerase can be bound to a single nucleic acid molecule.

The binding between target nucleic acid and polymer-nucleotide conjugate may be provided in the presence of a polymerase that has been rendered catalytically inactive. In one embodiment, the polymerase may have been rendered catalytically inactive by mutation. In one embodiment, the polymerase may have been rendered catalytically inactive by chemical modification. In some embodiments, the polymerase may have been rendered catalytically inactive by the absence of a necessary substrate, ion, or cofactor. In some embodiments, the polymerase enzyme may have been rendered catalytically inactive by the absence of magnesium ions.

The binding between target nucleic acid and polymer-nucleotide conjugate occur in the presence of a polymerase wherein the binding solution, reaction solution, or buffer lacks a catalytic ion such as magnesium or manganese. Alternatively, the binding between target nucleic acid and polymer-nucleotide conjugate occur in the presence of a polymerase wherein the binding solution, reaction solution, or buffer comprises a non-catalytic ion such strontium, barium or calcium.

When the catalytically inactive polymerases are used to help a nucleic acid interact with a multivalent binding composition, the interaction between said composition and said polymerase stabilizes a ternary complex so as to render the complex detectable by fluorescence or by other methods as disclosed herein or otherwise known in the art. Unbound polymer-nucleotide conjugates may optionally be washed away prior to detection of the ternary binding complex.

Contacting of one or more nucleic acids with the polymer-nucleotide conjugates disclosed herein in a solution containing either one of calcium or magnesium, or containing both calcium and magnesium. Alternatively, the contacting of one or more nucleic acids with the polymer-nucleotide conjugates disclosed herein in a solution lacking either one of calcium or magnesium, or lacking both calcium or magnesium, and in a separate step, without regard to the order of the steps, adding to the solution one of calcium or magnesium, or both calcium and magnesium. In some embodiments, the contacting of one or more nucleic acids with the polymer-nucleotide conjugates disclosed herein in a solution lacking strontium or barium, and comprises in a separate step, without regard to the order of the steps, adding to the solution strontium.

Disclosed herein are polymer-nucleotide conjugates and their use in analyzing nucleic acid including sequencing or other bioassay applications. An increase in binding of a nucleotide to an enzyme (e.g., polymerase) or an enzyme complex can be effected by increasing the effective concentration of the nucleotide. The increase can be achieved by increasing the concentration of the nucleotide in free solution, or by increasing the amount of the nucleotide in proximity to the relevant binding site. The increase can also be achieved by physically restricting a number of nucleotides into a limited volume thus resulting in a local increase in concentration, and such as structure may thus bind to the binding site with a higher apparent avidity than would be observed with unconjugated, untethered, or otherwise unrestricted individual nucleotide. One exemplary means of effecting such restriction is by providing a polymer-nucleotide conjugate in which multiple nucleotides are bound to a particle such as a polymer, a branched polymer, a dendrimer, a micelle, a liposome, a microparticle, a nanoparticle, a quantum dot, or other suitable particle known in the art.

The polymer-nucleotide conjugate disclosed herein can include a plurality of nucleotide moieties attached to the particle. In some embodiments, the plurality of nucleotides moieties is comprised of the same type of nucleotide moiety (e.g., having the same or similar base pairing properties). When the plurality of nucleotide moieties is complementary to the next nucleotide in a target nucleic acid to be identified, the polymer-nucleotide conjugate forms a binding complex (multivalent binding complex) between at least two nucleotide moieties and next nucleotide in at least two copies of the target nucleic acid sequence. In some embodiments, the multivalent binding complex comprises two or more polymerases that associate with the primed template of the target nucleic acid molecule. The multivalent binding complexes described herein exhibits increased stability and longer persistence time than the binding complex formed using a single unconjugated or untethered nucleotide. When bound to a polymerase, the multivalent binding complex can withstanding washing steps, so that the signal intensity remains high throughout the imaging and washing steps of the workflow, see for e.g., in FIG. 7. The polymer core of the polymer-nucleotide conjugate can be labeled with two or more detectable labels, which at least partially contributes to the enhanced signal that can be detected.

Figure 5A:
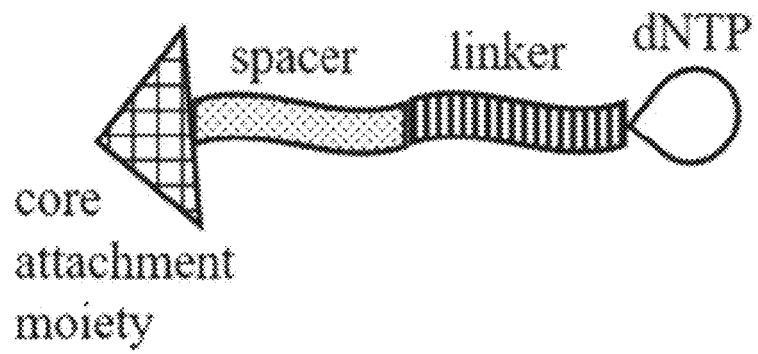
FIG. 5A is a schematic showing a nucleotide arm of a polymer-nucleotide conjugate according to an embodiment of the present disclosure.
Figure 5B:
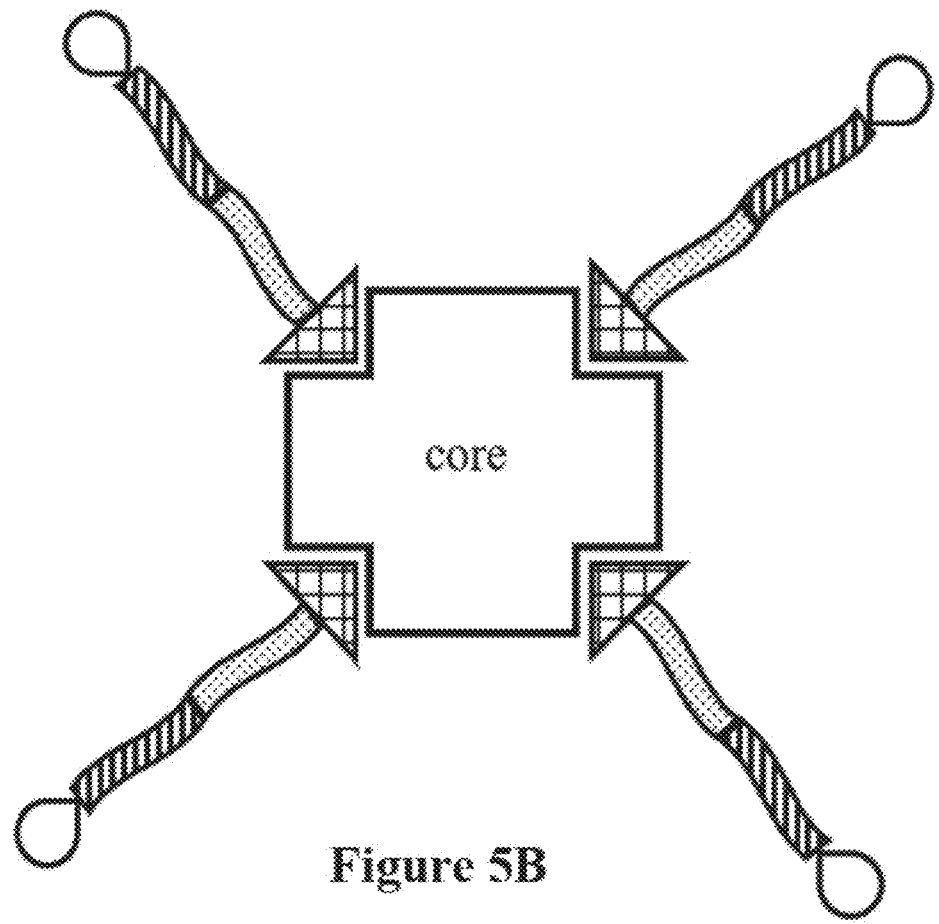
FIG. 5B is a schematic of a polymer-nucleotide conjugate comprising a core attached to a plurality of nucleotide arms where each nucleotide arm comprises (i) a core attachment moiety, (ii) a spacer, (iii) a linker, and (iv) a nucleotide unit, according to an embodiment of the present disclosure.
Figure 5C:
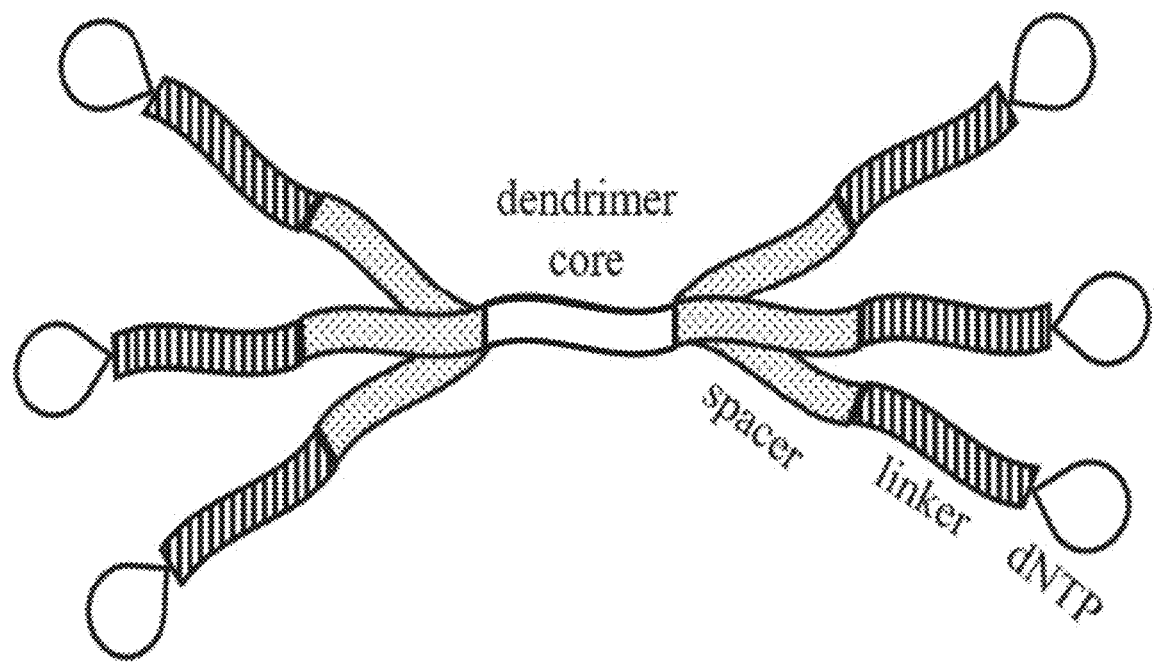
FIG. 5C is a schematic of a polymer-nucleotide conjugate, in dendrimer form, comprising a branched polymer which radiates from a central attachment point or central moiety, where a plurality of nucleotide arms radiate from the central attachment point, according to an embodiment of the present disclosure.
Figure 5D:
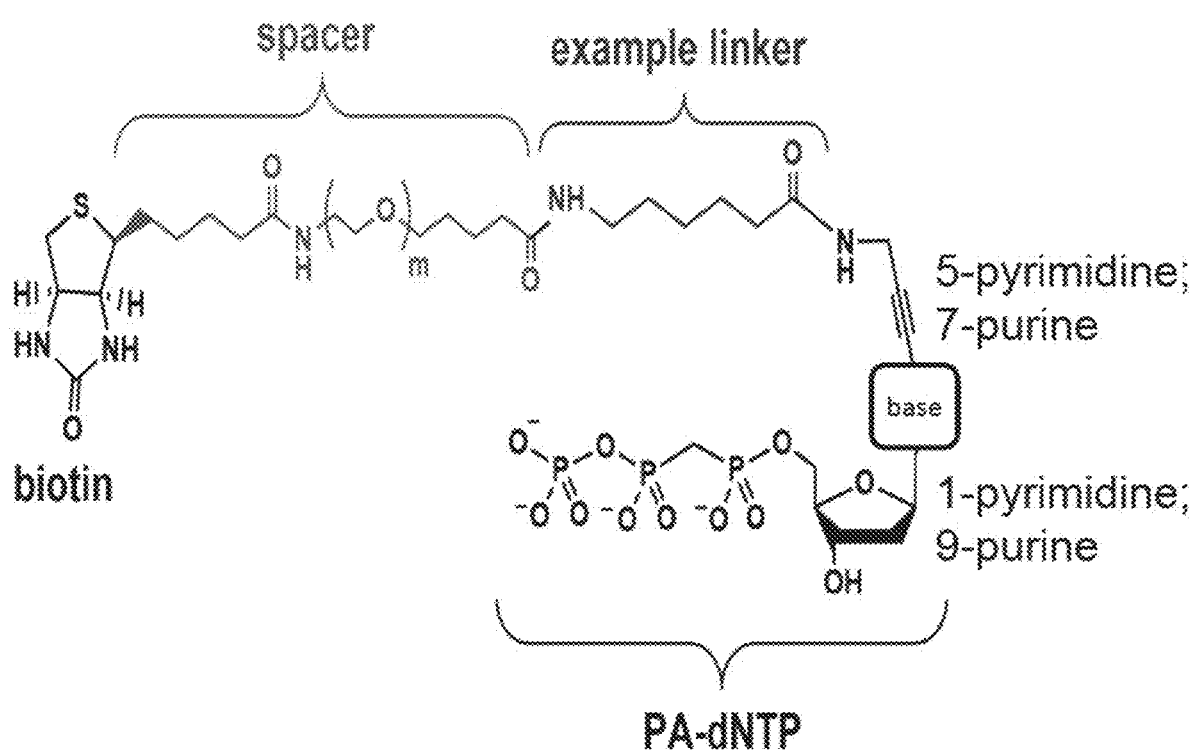
FIG. 5D is a nucleotide arm of a polymer-nucleotide conjugate comprising a biotin core attachment moiety, a spacer, an aliphatic chain linker, and a nucleotide attached to the linker via a propargyl link at the base, according to an embodiment of the present disclosure.

In some embodiments, the at least one polymer-nucleotide conjugate comprises two or more duplicates of a nucleotide moiety that are connected to a core via a linker, as shown for example, in FIG. 5A and FIG. 5B. In some embodiments, the polymer-nucleotide conjugate comprises: (a) a core, and (b) a plurality of nucleotide arms where each nucleotide arm comprises (i) a core attachment moiety, (ii) a spacer comprising a PEG moiety, (iii) a linker, and (iv) a nucleotide unit, as shown for example in FIG. 5A-D and FIG. 6A-C.

Figure 6A:
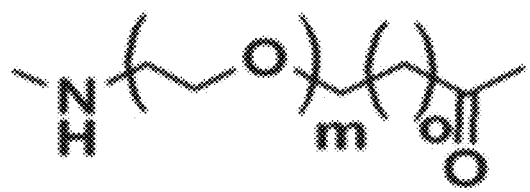
FIG. 6A shows structures of a spacer and linkers of a polymer-nucleotide conjugate according to an embodiment of the present disclosure.
Figure 6A:
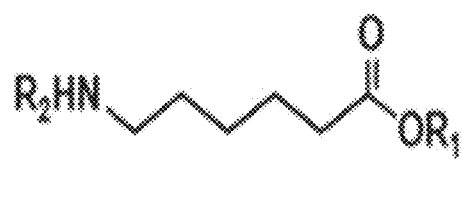
Figure 6A:
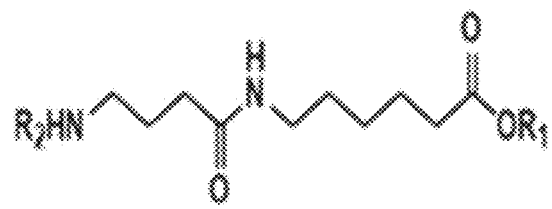
Figure 6A:
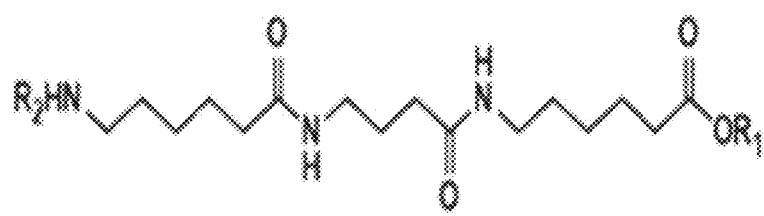
Figure 6A:
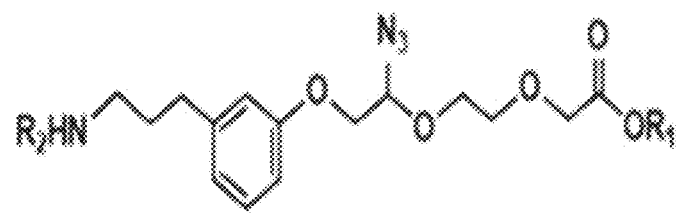
Figure 6B:
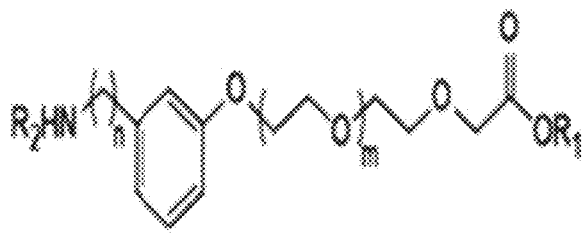
FIG. 6B-6C shows structures of additional linkers of a polymer-nucleotide conjugate according to an embodiment of the present disclosure.
Figure 6B:
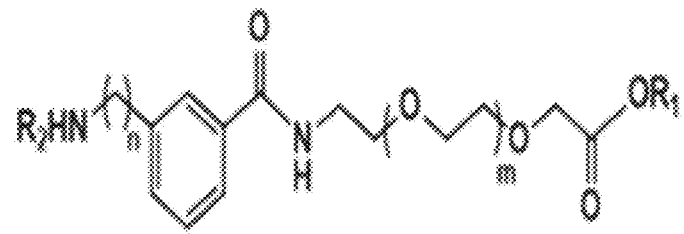
Figure 6B:
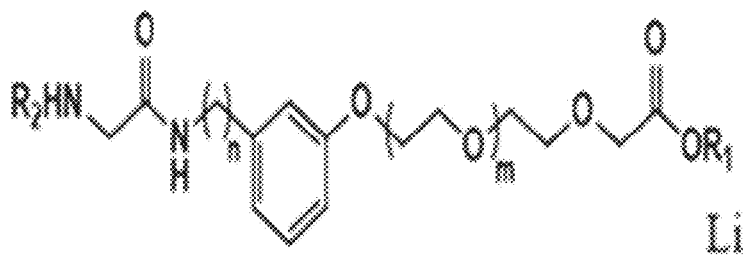
Figure 6B:
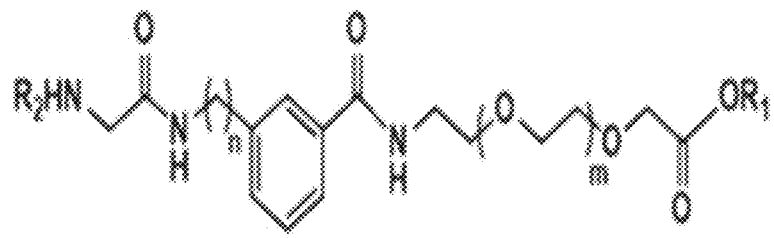
Figure 6B:
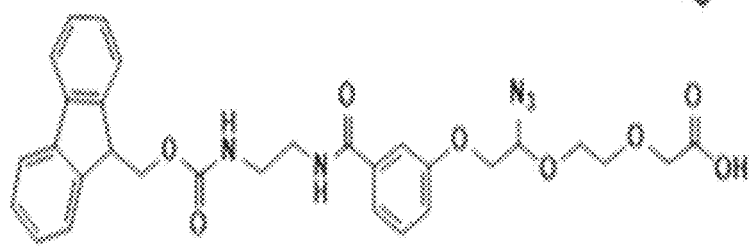
Figure 6C:
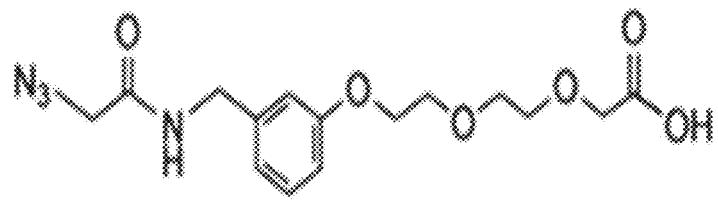
Figure 6C:
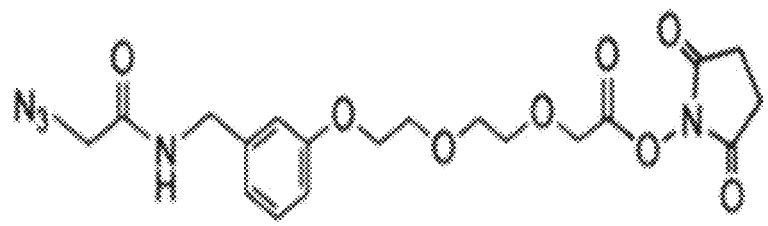
Figure 6C:
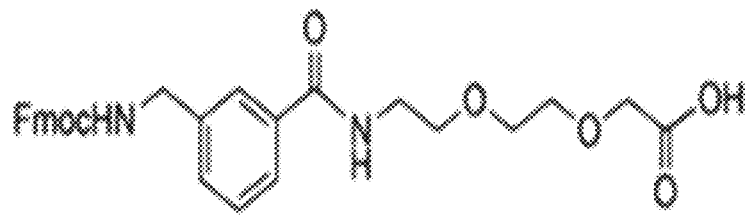
Figure 6C:
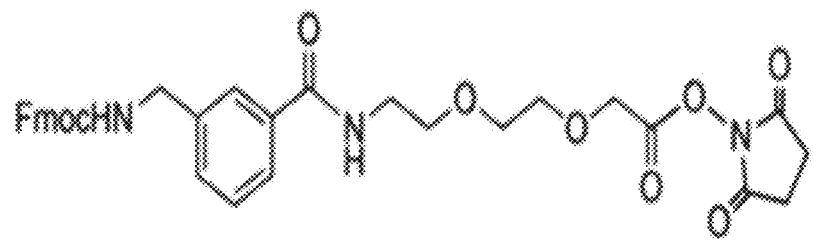

In some embodiments, the spacer is attached to the linker, wherein the linker is attached to the nucleotide unit. In some embodiments, the nucleotide unit comprises a base, sugar and at least one phosphate group. In some embodiments, the linker is attached to the nucleotide unit through the base. In some embodiments, the linker comprises an aliphatic chain or an oligo ethylene glycol chain where both linker chains having 2-6 subunits and optionally the linker includes an aromatic moiety (FIG. 6A, FIG. 6B, and FIG. 6C). In some embodiments, the polymer-nucleotide conjugate comprises a core attached to multiple nucleotide arms, and wherein the multiple nucleotide arms have the same type of nucleotide unit which is selected from a group consisting of dATP, dGTP, dCTP, dTTP and dUTP. In some embodiments, the low-binding support further comprises a plurality of polymer-nucleotide conjugates which includes a mixture of polymer-nucleotide conjugates having two or more different types of nucleotides selected from a group consisting of dATP, dGTP, dCTP, dTTP and dUTP.

In some embodiments, the polymer-nucleotide conjugate comprises a core attached to multiple nucleotide arms, wherein individual nucleotide arms comprise a nucleotide unit having a chain terminating moiety (e.g., blocking moiety) at the sugar 2' position, at the sugar 3' position, or at the sugar 2' and 3' position. In some embodiments, the chain terminating moiety is selected from a group consisting of an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group.

In some embodiments, the chain terminating moiety comprises a 3'-O-alkyl hydroxylamino group, a 3'-phosphorothioate group, a 3'-O-malonyl group, or a 3'-O-benzyl group. In some embodiments, the chain terminating moiety is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof. In some embodiments, the chain-terminating moiety comprises an azide, azido or azidomethyl group.

In some embodiments, the chain terminating moiety is cleavable/removable from the nucleotide arm, for example with a chemical compound, light or heat. In some embodiments, the chain terminating moiety comprises an alkyl, alkenyl, alkynyl or allyl group which are cleavable with tetrakis(triphenylphosphine)palladium(0) ($Pd(PPh_3)_4$), with piperidine, or with 2,3-Dichloro-5,6-dicyano-1,4-benzo-quinone (DDQ). In some embodiment, the chain terminating moiety comprises an aryl or benzyl group which are cleavable with Pd/C. In some embodiments, the chain terminating moiety comprises an amine, amide, keto, isocyanate, phosphate, thio or disulfide group which are cleavable with phosphine or with a thiol group including beta-mercaptoethanol or dithiothritol (DTT). In some embodiments, the chain terminating moiety comprises a carbonate group which is cleavable with potassium carbonate ($K_2CO_3$) in MeOH, with triethylamine in pyridine, or with Zn in acetic acid (AcOH). In some embodiments, the chain terminating moiety comprises a urea or silyl group which are cleavable with tetrabutylammonium fluoride, pyridine-HF, with ammonium fluoride, or with triethylamine trihydrofluoride. In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, the polymer-nucleotide conjugate comprises a core attached to multiple nucleotide arms, wherein the core or the nucleotide base comprises a label. In some embodiments, the label is a detectable reporter moiety. The polymer-nucleotide conjugate can have one or more labels. Examples of the detectable reporter moiety include but are not limited to fluorophores, spin labels, metals or metal ions, colorimetric labels, nanoparticles, PET labels, radioactive labels, or other such label as may render said composition detectable by such methods as are known in the art of the detection of macromolecules or molecular interactions. The detectable reporter moiety may be attached to the nucleotide (e.g. by attachment to the 5' phosphate moiety of a nucleotide), to the particle itself (e.g., to the PEG subunits), to an end of the polymer, to a central moiety, or to any other location within said polymer-nucleotide conjugate which would be recognized by one of skill in the art to be sufficient to render said composition, such as a particle, detectable by such methods as are known in the art or described elsewhere herein. In some embodiments, one or more labels are provided so as to correspond to or differentiate a particular polymer-nucleotide conjugate. The detectable reporter moiety can be a fluorophore. In some embodiments, the core can be an avidin-like moiety and the core attachment moiety can be a biotin moiety.

Exemplary polymer-nucleotide conjugates and methods of use are described in U.S. application Ser. No. 16/579,794, filed Sep. 23, 2019, the contents of the aforementioned patent application is hereby expressly incorporated by reference for all purposes.

The polymer-nucleotide conjugate (polymer-nucleotide conjugate) can be used to localize detectable signals to active regions of biochemical interactions, such as sites of protein-nucleic acid interactions, nucleic acid hybridization reactions, or enzymatic reactions, such as polymerase reactions. For example, the polymer-nucleotide conjugates described herein can be utilized to identify sites of base binding to a template or base incorporation in elongating nucleic acid chains during polymerase reactions and to provide base discrimination for sequencing and array based applications. The increased binding between the target nucleic acid and the nucleotide in the multivalent binding composition, when the nucleotide is complementary to the target nucleic acid, provides enhanced signal that greatly improve base call accuracy and shorten imaging time.

In addition, the use of polymer-nucleotide conjugates allows sequencing signals from a given sequence to originate within cluster regions containing multiple copies of the target sequence. Sequencing methods that include multiple copies of a target sequence (e.g., concatemer) have the advantage that signals can be amplified due to the presence of multiple simultaneous sequencing reactions within the defined region, each providing its own signal. The presence of multiple signals within a defined area also reduces the impact of any single skipped cycle, due to the fact that the signal from a large number of correct base calls can overwhelm the signal from a smaller number of skipped or incorrect base calls, therefore providing methods for reducing phasing errors and/or to improve read length in sequencing reactions.

The polymer-nucleotide conjugates and their use disclosed herein lead to one or more of: (i) stronger signal for better base-calling accuracy compared to conventional nucleic acid amplification and sequencing methodologies; (ii) allow greater discrimination of sequence-specific signal from background signals; (iii) reduced requirements for the amount of starting material necessary, (iv) increased sequencing rate and shortened sequencing time; (v) reducing phasing errors, and (vi) improving read length in sequencing reactions.

One of ordinary skill would recognize that in a series of iterative sequencing reactions, occasionally one or more sites will fail to incorporate a nucleotide during a given cycle, thus leading one or more sites to be unsynchronized with the bulk of the elongating nucleic acid chains. Under conditions in which sequencing signals are derived from reactions occurring on single copies of a target nucleic acid, these failures to incorporate will yield discrete errors in the output sequence. Use of the polymer-nucleotide conjugates for sequencing can reduce this type of error in sequencing reactions. For example, the use of multivalent substrates that are capable of binding to a polymerase-template-primer complex, or capable of incorporation into the elongating strand, by providing increased probabilities of rebinding upon premature dissociation of a ternary polymerase complex, can reduce the frequency of "skipped" cycles in which a base is not incorporated. Thus, in some embodiments, the present disclosure contemplates the use of multivalent substrates as disclosed herein comprising a nucleotide having a free, or reversibly modified, 5' phosphate, diphosphate, or triphosphate moiety, and wherein the nucleotide is connected to the particle or polymer as disclosed herein, through a labile or cleavable linkage. In some embodiments, the present disclosure contemplates a reduction in the intrinsic error rate due to skipped incorporations as a result of the use of the multivalent substrates disclosed herein.

The present disclosure also contemplates sequencing reactions in which sequencing signals from or relating to a given sequence are derived from or originate within definable regions containing multiple copies of the target sequence. Sequencing methods incorporating multiple copies of a target sequence have the advantage that signals can be amplified due to the presence of multiple simultaneous sequencing reactions within the defined region, each providing its own signal. The presence of multiple signals within a defined area also reduces the impact of any single skipped cycle, due to the fact that the signal from a large number of correct base calls can overwhelm the signal from a smaller number of skipped or incorrect base calls. The present disclosure further contemplates the inclusion of free, unlabeled nucleotides during elongation reactions, or during a separate part of the elongation cycle, in order to provide incorporation at sites that may have been skipped in previous cycles. For example, during or following an incorporation cycle, unlabeled blocked nucleotides may be added such that they may be incorporated at skipped sites. The unlabeled blocked nucleotides may be of the same type or types as the nucleotide attached to the multivalent binding substrate or substrates that are or were present during a particular cycle, or a mixture of 1, 2, 3, 4 or more types of unlabeled blocked nucleotides may be included.

When each sequencing cycle proceeds perfectly, each reaction within the defined region will provide an identical signal. However, as noted elsewhere herein, in a series of iterative sequencing reactions, occasionally one or more sites will fail to incorporate a nucleotide during a given cycle, thus leading one or more sites to be unsynchronized with the bulk of the elongating nucleic acid chains. This issue, referred to as "phasing," leads to degradation of the sequencing signal as the signal is contaminated with spurious signals from sites having skipped one or more cycles. This, in turn, creates the potential for errors in base identification. The progressive accumulation of skipped cycles through multiple cycles also reduces the effective read length, due to progressive degradation of the sequencing signal with each cycle. It is a further object of this disclosure to provide methods for reducing phasing errors and/or to improve read length in sequencing reactions.

The sequencing method can include contacting a target nucleic acid or multiple target nucleic acids, comprising multiple linked or unlinked copies of a target sequence, with the multivalent binding compositions described herein. Contacting said target nucleic acid, or multiple target nucleic acids comprising multiple linked or unlinked copies of a target sequence, with one or more polymer-nucleotide conjugates may provide a substantially increased local concentration of the correct nucleotide being interrogated in a given sequencing cycle, thus suppressing signals from improper incorporations or phased nucleic acid chains (i.e., those elongating nucleic acid chains which have had one or more skipped cycles).

Methods of obtaining nucleic acid sequence information can include contacting a target nucleic acid, or multiple target nucleic acids, wherein said target nucleic acid or multiple target nucleic acids comprise multiple linked or unlinked copies of a target sequence, with one or more polymer-nucleotide conjugates. This method results in a reduction in the error rate of sequencing as indicated by reduction in the misidentification of bases, the reporting of nonexistent bases, or the failure to report correct bases. In some embodiments, said reduction in the error orate of sequencing may comprise a reduction of 5%, 10%, 15%, 20% 25%, 50%, 75%, 100%, 150%, 200%, or more compared to the error rate observed using monovalent ligands, including free nucleotides, labeled free nucleotides, protein or peptide bound nucleotides, or labeled protein or peptide bound nucleotides.

The method of obtaining nucleic acid sequence information can include contacting a target nucleic acid, or multiple target nucleic acids, wherein said templet nucleic acid or multiple target nucleic acids comprise multiple linked or unlinked copies of a target sequence, with one or more polymer-nucleotide conjugates. This method results in an increase in average read length of 5%, 10%, 15%, 20% 25%, 50%, 75%, 100%, 150%, 200%, 300%, or more compared to the average read length observed using monovalent ligands, including free nucleotides, labeled free nucleotides, protein or peptide bound nucleotides, or labeled protein or peptide bound nucleotides.

Methods of obtaining nucleic acid sequence information, said methods comprising contacting a target nucleic acid, or multiple target nucleic acids, wherein said target nucleic acid or multiple target nucleic acids comprise multiple linked or unlinked copies of a target sequence, with one or more polymer-nucleotide conjugate s. This method results in an increase in average read length of 10, 20, 25, 30, 50, 75, 100, 125, 150, 200, 250, 300, 350, 400, 500 nucleotides, or more compared to the average read length observed using monovalent ligands, including free nucleotides, labeled free nucleotides, protein or peptide bound nucleotides, or labeled protein or peptide bound nucleotides.

The use of the polymer-nucleotide conjugates for sequencing effectively shortens the sequencing time. The sequencing reaction cycle comprising the contacting, detecting, and incorporating steps is performed in a total time ranging from about 5 minutes to about 60 minutes. In some embodiments, the sequencing reaction cycle is performed in at least 5 minutes, at least 10 minutes, at least 20 minutes, at least 30 minutes, at least 40 minutes, at least 50 minutes, or at least 60 minutes. In some embodiments, the sequencing reaction cycle is performed in at most 60 minutes, at most 50 minutes, at most 40 minutes, at most 30 minutes, at most 20 minutes, at most 10 minutes, or at most 5 minutes. Any of the lower and upper values described in this paragraph may be combined to form a range included within the present disclosure, for example, in some embodiments the sequencing reaction cycle may be performed in a total time ranging from about 10 minutes to about 30 minutes. Those of skill in the art will recognize that the sequencing cycle time may have any value within this range, e.g., about 16 minutes.

The use of the polymer-nucleotide conjugates for sequencing provides an more accuracy base readout. The disclosed compositions and methods for nucleic acid sequencing will provide an average Q-score for base-calling accuracy over a sequencing run that ranges from about 20 to about 50. In some embodiments, the average Q-score is at least 20, at least 25, at least 30, at least 35, at least 40, at least 45, or at least 50. Those of skill in the art will recognize that the average Q-score may have any value within this range, e.g., about 32. In some embodiments, the disclosed compositions and methods for nucleic acid sequencing will provide a Q-score of greater than 30 for at least 50%, at least 60%, at least 70%, at least 80%, at least 85%, at least 90%, at least 95%, at least 98%, or at least 99% of the terminal (or N+1) nucleotides identified. In some embodiments, the disclosed compositions and methods for nucleic acid sequencing will provide a Q-score of greater than 35 for at least 50%, at least 60%, at least 70%, at least 80%, at least 85%, at least 90%, at least 95%, at least 98%, or at least 99% of the terminal (or N+1) nucleotides identified. In some embodiments, the disclosed compositions and methods for nucleic acid sequencing will provide a Q-score of greater than 40 for at least 50%, at least 60%, at least 70%, at least 80%, at least 85%, at least 90%, at least 95%, at least 98%, or at least 99% of the terminal (or N+1) nucleotides identified. In some embodiments, the disclosed compositions and methods for nucleic acid sequencing will provide a Q-score of greater than 45 for at least 50%, at least 60%, at least 70%, at least 80%, at least 85%, at least 90%, at least 95%, at least 98%, or at least 99% of the terminal (or N+1) nucleotides identified. In some embodiments, the disclosed compositions and methods for nucleic acid sequencing will provide a Q-score of greater than 50 for at least 50%, at least 60%, at least 70%, at least 80%, at least 85%, at least 90%, at least 95%, at least 98%, or at least 99% of the terminal (or N+1) nucleotides identified.

The present disclosure relates to polymer-nucleotide conjugates each having a plurality of nucleotides conjugated to a particle or core (e.g., a polymer, branched polymer, dendrimer, or equivalent structure). Contacting the polymer-nucleotide conjugate with a polymerase and a primed target nucleic acid may result in the formation of a ternary complex which may be detected and in turn achieve a more accurate determination of the bases of the target nucleic acid.

When the polymer-nucleotide conjugate is used in replacement of single unconjugated or untethered nucleotide to form a complex with the polymerase and the target nucleic acid, the local concentration of the nucleotide is increased many fold, which in turn enhances the signal intensity, particularly the correct signal versus mismatch. The polymer-nucleotide conjugate described herein can include at least one polymer-nucleotide conjugate for interacting with the target nucleic acid. The multivalent composition can also include two, three, or four different polymer-nucleotide conjugate s, each having a different nucleotide conjugated to the particle.

In a polymer-nucleotide conjugate having a polymer-nucleotide conjugate form or a core-nucleotide conjugate form, multiple copies of the same nucleotide may be covalently bound to or noncovalently bound to the particle. Examples of the particle can include a branched polymer; a dendrimer; a cross linked polymer particle such as an agarose, polyacrylamide, acrylate, methacrylate, cyanoacrylate, methyl methacrylate particle; a glass particle; a ceramic particle; a metal particle; a quantum dot; a liposome; an emulsion particle, or any other particle (e.g., nanoparticles, microparticles, or the like) known in the art. In a preferred embodiment, the particle is a branched polymer.

The nucleotide can be linked to the particle or core through a linker, and the nucleotide can be attached to one end or location of a polymer. The nucleotide can be conjugated to the particle through the base or the 5' end of the nucleotide. In some polymer-nucleotide conjugate s, one nucleotide attached to one end or location of a polymer. In some polymer-nucleotide conjugate, multiple nucleotides are attached to one end or location of a polymer. The conjugated nucleotide is sterically accessible to one or more proteins, one or more enzymes, and nucleotide binding moieties. In some embodiments, a nucleotide may be provided separately from a nucleotide binding moiety such as a polymerase. In some embodiments, the linker does not comprise a photo emitting or photo absorbing group.

The particle or core can also have a binding moiety. In some embodiments, particles or cores may self-associate without the use of a separate interaction moiety. In some embodiments, particles or cores may self-associate due to buffer conditions or salt conditions, e.g., as in the case of calcium-mediated interactions of hydroxyapatite particles, lipid or polymer mediated interactions of micelles or liposomes, or salt-mediated aggregation of metallic (such as iron or gold) nanoparticles.

The polymer-nucleotide conjugates can have one or more labels (e.g., detectable reporter moieties). Examples of the labels include but are not limited to fluorophores, spin labels, metals or metal ions, colorimetric labels, nanoparticles, PET labels, radioactive labels, or other such label as may render said composition detectable by such methods as are known in the art of the detection of macromolecules or molecular interactions. The label may be attached to the nucleotide (e.g. by attachment to the base or the 5' phosphate moiety of a nucleotide), to the particle itself (e.g., to the PEG subunits) or to the core (e.g., to the streptavidin core), to an end of the polymer, to a central moiety, or to any other location within said polymer-nucleotide conjugate which would be recognized by one of skill in the art to be sufficient to render said composition, such as a particle, detectable by such methods as are known in the art or described elsewhere herein. In some embodiments, one or more labels are provided so as to correspond to or differentiate a particular polymer-nucleotide conjugate.

One example of the polymer-nucleotide conjugate (e.g., polymer-nucleotide conjugate) is a polymer-nucleotide conjugate. Examples of the branched polymer include polyethylene glycol (PEG), polypropylene glycol, polyvinyl alcohol, polylactic acid, polyglycolic acid, polyglycine, polyvinyl acetate, a dextran, or other such polymers. In one embodiment, the polymer is a PEG. In another embodiment, the polymer can have PEG branches.

Suitable polymers may be characterized by a repeating unit having a functional group suitable for derivatization such as an amine, a hydroxyl, a carbonyl, or an allyl group. The polymer can also have one or more pre-derivatized substituents such that one or more particular subunits comprise a site of derivatization or a branch site, whether or not other subunits include the same site, substituent, or moiety. A pre-derivatized substituent may comprise or may further comprise, for example, a nucleotide, a nucleoside, a nucleotide analog, a label such as a fluorescent label, radioactive label, or spin label, an interaction moiety, an additional polymer moiety, or the like, or any combination of the foregoing.

In the polymer-nucleotide conjugate (e.g., polymer-nucleotide conjugate), the polymer can have a plurality of branches. The branched polymer can have various configurations, including but are not limited to stellate ("starburst") forms, aggregated stellate ("helter skelter") forms, bottle brush, or dendrimer. The branched polymer can radiate from a central attachment point or central moiety, or may include multiple branch points, such as, for example, 2, 3, 4, 5, 6, 7, 8, 9, 10, or more branch points. In some embodiments, each subunit of a polymer may optionally constitute a separate branch point.

In the polymer-nucleotide conjugate, the length and size of the branch can differ based on the type of polymer. In some branched polymers, the branch may have a length of between 1 and 1,000 nm, between 1 and 100 nm, between 1 and 200 nm, between 1 and 300 nm, between 1 and 400 nm, between 1 and 500 nm, between 1 and 600 nm, between 1 and 700 nm, between 1 and 800 nm, or between 1 and 900 nm, or more, or having a length falling within or between any of the values disclosed herein. In some branched polymers, the branch may have a size corresponding to an apparent molecular weight of 1K, 2K, 3K, 4K, 5K, 10K, 15K, 20K, 30K, 50K, 80K, 100K, or any value within a range defined by any two of the foregoing. The apparent molecular weight of a polymer may be calculated from the known molecular weight of a representative number of subunits, as determined by size exclusion chromatography, as determined by mass spectrometry, or as determined by any other method as is known in the art. The polymer can have multiple branches. The number of branches in the polymer can be 2, 3, 4, 5, 6, 7, 8, 12, 16, 24, 32, 64, 128 or more, or a number falling within a range defined by any two of these values.

For the polymer-nucleotide conjugate (e.g., polymer-nucleotide conjugate), the branched polymer of 4, 8, 16, 32, or 64 branches can have nucleotides attached to the ends of PEG branches, such that each end has attached thereto 0, 1, 2, 3, 4, 5, 6 or more nucleotides. In one non-limiting example, the branched polymer of between 3 and 128 PEG arms having attached to the polymer branches ends one or more nucleotides, such that each end has attached thereto 0, 1, 2, 3, 4, 5, 6 or more nucleotides or nucleotide analogs. In some embodiments, a branched polymer or dendrimer has an even number of arms. In some embodiments, a branched polymer or dendrimer has an odd number of arms.

In the polymer-nucleotide conjugate (e.g., polymer-nucleotide conjugate), each branch or a subset of branches of the polymer may have attached thereto a moiety comprising a nucleotide (e.g., an adenine, a thymine, a uracil, a cytosine, or a guanine residue or a derivative or mimetic thereof), and the moiety is capable of binding to a polymerase, reverse transcriptase, or other nucleotide binding domain. Optionally, the nucleotide moiety may be capable of binding to a polymerase-template-primer complex but not incorporate, or can incorporate into an elongating nucleic acid chain during a polymerase reaction. In some embodiments, the nucleotide moiety comprises a chain terminating moiety which blocks incorporation of a subsequent nucleotide during a polymerase-mediated reaction. In some embodiments, the nucleotide moiety may be unblocked (reversibly blocked) such that a subsequent nucleotide is not capable of being incorporated into an elongating nucleic acid chain during a polymerase reaction until such block is removed, after which the subsequent nucleotide is then capable of being incorporated into an elongating nucleic acid chain during a polymerase reaction.

The polymer-nucleotide conjugate can further have a binding moiety in each branch or a subset of branches. Some examples of the binding moiety include but are not limited to biotin, avidin, streptavidin or the like, polyhistidine domains, complementary paired nucleic acid domains, G-quartet forming nucleic acid domains, calmodulin, maltose-binding protein, cellulase, maltose, sucrose, glutathione-S-transferase, glutathione, O-6-methylguanine-DNA methyltransferase, benzylguanine and derivatives thereof, benzylcysteine and derivatives thereof, an antibody, an epitope, a protein A, a protein G. The binding moiety can be any interactive molecules or fragment thereof known in the art to bind to or facilitate interactions between proteins, between proteins and ligands, between proteins and nucleic acids, between nucleic acids, or between small molecule interaction domains or moieties.

In some embodiments, the polymer-nucleotide conjugate may comprise one or more elements of a complementary interaction moiety. Exemplary complementary interaction moieties include, for example, biotin and avidin; SNAP-benzylguanosine; antibody or FAB and epitope; IgG FC and Protein A, Protein G, Protein A/G, or Protein L; maltose binding protein and maltose; lectin and cognate polysaccharide; ion chelation moieties, complementary nucleic acids, nucleic acids capable of forming triplex or triple helical interactions; nucleic acids capable of forming G-quartets, and the like. One of skill in the art will readily recognize that many pairs of moieties exist and are commonly used for their property of interacting strongly and specifically with one another; and thus any such complementary pair or set is considered to be suitable for this purpose in constructing or envisioning the compositions of the present disclosure. In some embodiments, a composition as disclosed herein may comprise compositions in which one element of a complementary interaction moiety is attached to one molecule or multivalent ligand, and the other element of the complementary interaction moiety is attached to a separate molecule or multivalent ligand. In some embodiments, a composition as disclosed herein may comprise compositions in which both or all elements of a complementary interaction moiety are attached to a single molecule or multivalent ligand. In some embodiments, a composition as disclosed herein may comprise compositions in which both or all elements of a complementary interaction moiety are attached to separate arms of, or locations on, a single molecule or multivalent ligand. In some embodiments, a composition as disclosed herein may comprise compositions in which both or all elements of a complementary interaction moiety are attached to the same arm of, or locations on, a single molecule or multivalent ligand. In some embodiments, compositions comprising one element of a complementary interaction moiety and compositions comprising another element of a complementary interaction moiety may be simultaneously or sequentially mixed. In some embodiments, interactions between molecules or particles as disclosed herein allow for the association or aggregation of multiple molecules or particles such that, for example, detectable signals are increased. In some embodiments, fluorescent, colorimetric, or radioactive signals are enhanced. In other embodiments, other interaction moieties as disclosed herein or as are known in the art are contemplated. In some embodiments, a composition as provided herein may be provided such that one or more molecules comprising a first interaction moiety such as, for example, one or more imidazole or pyridine moieties, and one or more additional molecules comprising a second interaction moiety such as, for example, histidine residues, are simultaneously or sequentially mixed. In some embodiments, said composition comprises 1, 2, 3, 4, 5, 6, or more imidazole or pyridine moieties. In some embodiments, said composition comprises 1, 2, 3, 4, 5, 6, or more histidine residues. In such embodiments, interaction between the molecules or particles as provided may be facilitated by the presence of a divalent cation such as nickel, manganese, magnesium, calcium, strontium, or the like. In some embodiments, for example, a (His)3 group may interact with a (His)3 group on another molecule or particle via coordination of a nickel or manganese ion.

The polymer-nucleotide conjugate may comprise one or more buffers, salts, ions, or additives. In some embodiments, representative additives may include, but are not limited to, betaine, spermidine, detergents such as Triton X-100, Tween 20, SDS, or NP-40, ethylene glycol, polyethylene glycol, dextran, polyvinyl alcohol, vinyl alcohol, methylcellulose, heparin, heparan sulfate, glycerol, sucrose, 1,2-propanediol, DMSO, N,N,N-trimethylglycine, ethanol, ethoxyethanol, propylene glycol, polypropylene glycol, block copolymers such as the Pluronic (r) series polymers, arginine, histidine, imidazole, or any combination thereof, or any substance known in the art as a DNA "relaxer" (a compound, with the effect of altering the persistence length of DNA, altering the number of within-polymer junctions or crossings, or altering the conformational dynamics of a DNA molecule such that the accessibility of sites within the strand to DNA binding moieties is increased).

The polymer-nucleotide conjugate may include zwitterionic compounds as additives. Further representative additives may be found in Lorenz, T. C. J. Vis. Exp. (63), e3998, doi:10.3791/3998 (2012), which is hereby incorporated by reference with respect to its disclosure of additives for the facilitation of nucleic acid binding or dynamics, or the facilitation of processes involving the manipulation, use, or storage of nucleic acids.

In some embodiments, the multivalent binding compositions include at least one cations may include, but are not limited to, sodium, magnesium, strontium, barium, potassium, manganese, calcium, lithium, nickel, cobalt, or other such cations as are known in the art to facilitate nucleic acid interactions, such as self-association, secondary or tertiary structure formation, base pairing, surface association, peptide association, protein binding, or the like.

When the polymer-nucleotide conjugate is used to replace an unconjugated or untethered nucleotide to form a complex with the polymerase and the target nucleic acid, the local concentration of the nucleotide is increased many folds, which in turn enhances the signal intensity, particularly the correct signal versus mismatch. The present disclosure contemplates contacting the polymer-nucleotide conjugate with a polymerase and a primed target nucleic acid to determine the formation of a ternary binding complex.

Because of the increased local concentration of the nucleotide on the polymer-nucleotide conjugate, the binding between the polymerase, the primed target strand, and the nucleotide, when the nucleotide is complementary to the next base of the target nucleic acid, becomes more favorable. The formed binding complex has a longer persistence time which in turn helps shorten the imaging step. The high signal intensity resulted from the use of the polymer-nucleotide conjugate remain for the entire binding and imaging step. The strong binding between the polymerase, the primed target strand, and the nucleotide or nucleotide analog also means that the formed binding complex will remain stabilized during the washing step and the signal will remain at a high intensity when other reaction mixture and unmatched nucleotide analogs are washed away. After the imaging step, the binding complex can be destabilized and the primed target nucleic acid can then be extended for one base. After the extension, the binding and imaging steps can be repeated again with the use of the polymer-nucleotide conjugate to determine the identity of the next base.

The compositions and methods of the present disclosure provide a robust and controllable means of establishing and maintaining a ternary enzyme complex (e.g., during sequencing), as well as providing vastly improved means by which the presence of said complex may be identified and/or measured, and a means by which the persistence of said complex may be controlled. This provides important solutions to problems such as that of determining the identity of the N+1 base in nucleic acid sequencing applications.

Without intending to be bound by any particular theory, it has been observed that multivalent binding compositions disclosed herein associate with polymerase nucleotide complexes in order to form a ternary binding complexes with a rate that is time-dependent, though substantially slower than the rate of association known to be obtainable by nucleotides in free solution. Thus, the on-rate (Kon) is substantially and surprisingly slower than the on rate for single nucleotides or nucleotides not attached to multivalent ligand complexes. Importantly, however, the off rate (Koff) of the multivalent ligand complex is substantially slower than that observed for nucleotides in free solution. Therefore, the multivalent ligand complexes of the present disclosure provide a surprising and beneficial improvement of the persistence of ternary polymerase-polynucleotide-nucleotide complexes (especially over such complexes that are formed with free nucleotides) allowing, for example, significant improvements in imaging quality for nucleic acid sequencing applications, over currently available methods and reagents. Importantly, this property of the multivalent substrates disclosed herein renders the formation of visible ternary complexes controllable, such that subsequent visualization, modification, or processing steps may be undertaken essentially without regard to the dissociation of the complex— that is, the complex can be formed, imaged, modified, or used in other ways as necessary, and will remain stable until a user carries out an affirmative dissociation step, such as exposing the complexes to a dissociation buffer.

In various embodiments, polymerases suitable for the binding interaction (e.g., during sequencing) describe herein include may include any polymerase as is or may be known in the art. Exemplary polymerases may include but are not limited to: Klenow DNA polymerase, *Thermus aquaticus* DNA polymerase I (Taq polymerase), KlenTaq polymerase, and bacteriophage T7 DNA polymerase; human alpha, delta and epsilon DNA polymerases; bacteriophage polymerases such as T4, RB69 and phi29 bacteriophage DNA polymerases, *Pyrococcus furiosus* DNA polymerase (Pfu polymerase); *Bacillus subtilis* DNA polymerase III, and *E. coli* DNA polymerase III alpha and epsilon; 9 degree N polymerase, reverse transcriptases such as HIV type M or O reverse transcriptases, avian myeloblastosis virus reverse transcriptase, or Moloney Murine Leukemia Virus (MMLV) reverse transcriptase, or telomerase. Further non-limiting examples of DNA polymerases can include those from various Archaea genera, such as, *Aeropyrum, Archaeglobus, Desulfurococcus, Pyrobaculum, Pyrococcus, Pyrolobus, Pyrodictium, Staphylothermus, Stetteria, Sulfolobus, Thermococcus,* and *Vulcanisaeta* and the like or variants thereof, including such polymerases as are known in the art such as Vent™, Deep Vent™, Pfu, KOD, Pfx, Therminator™, and Tgo polymerases. In some embodiments, the polymerase is a Klenow polymerase.

The ternary complex has longer persistence time when the nucleotide on the polymer-nucleotide conjugate is complementary to the target nucleic acid than when a non-complementary nucleotide. The ternary complex also has longer persistence time when the nucleotide on the polymer-nucleotide conjugate is complementary to the target nucleic acid than a complementary nucleotide that is not conjugated or tethered. For example, in some embodiments, said ternary complexes may have a persistence time of less than 1s, greater than 1s, greater than 2s, greater than 3s, greater than 5s, greater than 10s, greater than 15s, greater than 20s, greater than 30s, greater than 60s, greater than 120s, greater than 360s, greater than 3600s, or more, or for a time lying within a range defined by any two or more of these values.

The persistence time can be measured, for example, by observing the onset and/or duration of a binding complex, such as by observing a signal from a labeled component of the binding complex. For example, a labeled nucleotide or a labeled reagent comprising one or more nucleotides may be present in a binding complex, thus allowing the signal from the label to be detected during the persistence time of the binding complex.

It has been observed that different ranges of persistence times are achievable with different salts or ions, showing, for example, that complexes formed in the presence of, for example, magnesium form more quickly than complexes formed with other ions. It has also been observed that complexes formed in the presence of, for example, strontium, form readily and dissociate completely or with substantial completeness upon withdrawal of the ion or upon washing with buffer lacking one or more components of the present compositions, such as, e.g., a polymer and/or one or more nucleotides, and/or one or more interaction moieties, or a buffer containing, for example, a chelating agent which may cause or accelerate the removal of a divalent cation from the multivalent reagent containing complex. Thus, in some embodiments, a composition of the present disclosure comprises magnesium. In some embodiments, a composition of the present disclosure comprises calcium. In some embodiments, a composition of the present disclosure comprises strontium or barium. In some embodiments, a composition of the present disclosure comprises cobalt. In some embodiments, a composition of the present disclosure comprises $MgCl_2$. In some embodiments, a composition of the present disclosure comprises $CaCl_2$). In some embodiments, a composition of the present disclosure comprises $SrCl_2$. In some embodiments, a composition of the present disclosure comprises $CoCl_2$. In some embodiments, the composition comprises no, or substantially no magnesium. In some embodiments, the composition comprises no, or substantially no calcium. In some embodiments, the methods of the present disclosure provide for the contacting of one or more nucleic acids with one or more of the compositions disclosed herein wherein said composition lacks either one of calcium or magnesium, or lacks both calcium and magnesium.

The dissociation of ternary complexes can be controlled by changing the buffer conditions. After the imaging step, a buffer with increased salt content is used to cause dissociation of the ternary complexes such that labeled polymer-nucleotide conjugates can be washed out, providing a means by which signals can be attenuated or terminated, such as in the transition between one sequencing cycle and the next. This dissociation may be effected, in some embodiments, by washing the complexes with a buffer lacking a necessary metal or cofactor. In some embodiments, a wash buffer may comprise one or more compositions for the purpose of maintaining pH control. In some embodiments, a wash buffer may comprise one or more monovalent cations, such as sodium. In some embodiments, a wash buffer lacks or substantially lacks a divalent cation, for example, having no or substantially no strontium, calcium, magnesium, or manganese. In some embodiments, a wash buffer further comprises a chelating agent, such as, for example, EDTA, EGTA, nitrilotriacetic acid, polyhistidine, imidazole, or the like. In some embodiments, a wash buffer may maintain the pH of the environment at the same level as for the bound complex. In some embodiments, a wash buffer may raise or lower the pH of the environment relative to the level seen for the bound complex. In some embodiments, the pH may be within a range from 2-4, 2-7, 5-8, 7-9, 7-10, or lower than 2, or higher than 10, or a range defined by any two of the values provided herein.

Addition of a particular ion may affect the binding of the polymerase to a primed target nucleic acid, the formation of a ternary complex, the dissociation of a ternary complex, or the incorporation of one or more nucleotides into an elongating nucleic acid such as during a polymerase reaction. In some embodiments, relevant anions may comprise chloride, acetate, gluconate, sulfate, phosphate, or the like. In some embodiments, an ion may be included in the compositions of the present disclosure by the addition of one or more acids, bases, or salts, such as NiCl2, CoCl2, MgCl2, MnCl2, SrCl2, CaCl2), CaSO4, SrCO3, BaCl2 or the like. Representative salts, ions, solutions and conditions may be found in Remington: The Science and Practice of Pharmacy, 20th. Edition, Gennaro, A. R., Ed. (2000), which is hereby incorporated by reference in its entirety, and especially with respect to Chapter 17 and related disclosure of salts, ions, salt solutions, and ionic solutions.

The present disclosure contemplates contacting the polymer-nucleotide conjugate with one or more polymerases. The contacting can be optionally done in the presence of one or more target nucleic acids. In some embodiments, said target nucleic acids are single stranded nucleic acids. In some embodiments, the target nucleic acids are hybridized to a nucleic acid primer. In some embodiments, said target nucleic acids are double stranded nucleic acids. In some embodiments, said contacting comprises contacting the polymer-nucleotide conjugate with one polymerase. In some embodiments, said contacting comprises the contacting of said composition comprising one or more nucleotides with multiple polymerases. The polymerase can be bound to a single nucleic acid molecule.

The binding between target nucleic acid and polymer-nucleotide conjugate may be provided in the presence of a polymerase that has been rendered catalytically inactive. In one embodiment, the polymerase may have been rendered catalytically inactive by mutation. In one embodiment, the polymerase may have been rendered catalytically inactive by chemical modification. In some embodiments, the polymerase may have been rendered catalytically inactive by the absence of a necessary substrate, ion, or cofactor. In some embodiments, the polymerase enzyme may have been rendered catalytically inactive by the absence of magnesium ions.

The binding between target nucleic acid and polymer-nucleotide conjugate occur in the presence of a polymerase wherein the binding solution, reaction solution, or buffer lacks a catalytic ion such as magnesium or manganese. Alternatively, the binding between target nucleic acid and polymer-nucleotide conjugate occur in the presence of a polymerase wherein the binding solution, reaction solution, or buffer comprises a non-catalytic ion such strontium, barium or calcium.

When the catalytically inactive polymerases are used to help a nucleic acid interact with a multivalent binding composition, the interaction between said composition and said polymerase stabilizes a ternary complex so as to render the complex detectable by fluorescence or by other methods as disclosed herein or otherwise known in the art. Unbound polymer-nucleotide conjugates may optionally be washed away prior to detection of the ternary binding complex.

Contacting of one or more nucleic acids with the polymer-nucleotide conjugates disclosed herein in a solution containing either one of calcium or magnesium, or containing both calcium and magnesium. Alternatively, the contacting of one or more nucleic acids with the polymer-nucleotide conjugates disclosed herein in a solution lacking either one of calcium or magnesium, or lacking both calcium or magnesium, and in a separate step, without regard to the order of the steps, adding to the solution one of calcium or magnesium, or both calcium and magnesium. In some embodiments, the contacting of one or more nucleic acids with the polymer-nucleotide conjugates disclosed herein in a solution lacking strontium or barium, and comprises in a separate step, without regard to the order of the steps, adding to the solution strontium.

Provided herein are methods for analyzing nucleic acids comprising determining the sequence of the immobilized target nucleic acid molecule (e.g., concatemer molecule) by: (1) contacting the immobilized concatemer molecule with (i) a plurality of polymerases, (ii) a plurality of nucleotides, and (iii) a plurality of sequencing primers that hybridize with the sequencing primer binding sequence, under a condition suitable for binding at least one polymerase and at least one sequencing primer to a portion of the immobilized concatemer molecule, and suitable for binding at least one of the nucleotides to the 3' end of the sequencing primer at a position that is opposite a complementary nucleotide in the immobilized concatemer molecule wherein the bound nucleotide incorporates into the 3' end of the sequencing primer; (2) detecting and identifying the incorporated nucleotide thereby determining the sequence of the immobilized concatemer molecule; and (3) optionally repeating steps (1) and (2) at least once. In some embodiments, the determining the sequence of the immobilized concatemer molecule comprises sequencing the target sequence and the spatial barcode sequence. In some embodiments, the condition that is suitable to bind the nucleotide to the at least one of the nucleotides from the plurality to the 3' ends of the hybridized sequencing primers and suitable to incorporate the bound nucleotide into the hybridized sequencing primer (step (1)) comprises at least one catalytic cation including magnesium and/or manganese.

In some embodiments, the method for analyzing biological molecules from a cellular biological sample further comprise step (g): sequencing at least a portion of the nucleic acid concatemer, including sequencing the target sequence and the spatial barcode sequence, to determine the spatial location of the target nucleic acid in the cellular biological sample.

In some embodiments, the sequencing of step (g) comprises sequencing at least a portion of the nucleic acid concatemers using an optical imaging system comprising a field-of-view (FOV) greater than 1.0 mm$^2$. In some embodiments, the sequencing of step (g) includes placing the cellular biological sample in a flow cell having walls (e.g., top or first wall, and bottom or second wall) and a gap in-between, where the gap can be filled with a fluid, where the flow cell is positioned in a fluorescence optical imaging system. The cellular biological sample has a thickness that may require using the imaging system to focus separately on the first and second surfaces of the flow cell, when using a traditional imaging system. For improved imaging of the sequencing reaction of the nucleic acids from the cellular biological sample, the flow cell can be positioned in a high performance fluorescence imaging system, which comprises two or more tube lenses which are designed to provide optimal imaging performance for the first and second surfaces of the flow cell at two or more fluorescence wavelengths. In some embodiments, the high-performance imaging system further comprises a focusing mechanism configured to refocus the optical system between acquiring images of the first and second surfaces of the flow cell. In some embodiments, the high performance imaging system is configured to image two or more fields-of-view on at least one of the first flow cell surface or the second flow cell surface.

In some embodiments, the sequencing of step (g) comprises: contacting the plurality of nucleic acid concatemers with a plurality of sequencing primers, a plurality of polymerases, and a plurality of multivalent molecules, wherein each of the multivalent molecules comprise two or more duplicates of a nucleotide moiety that are connected to a core via a linker (FIGS. 5A and 5B).

In some embodiments, the multivalent molecule comprises multiple nucleotides that are bound to a particle (or core) such as a polymer, a branched polymer, a dendrimer (FIG. 5C), a micelle, a liposome, a microparticle, a nanoparticle, a quantum dot, or other suitable particle known in the art.

In some embodiments, the multivalent molecule comprises: (a) a core, and (b) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms (FIGS. 5A-D and 6A-C). In some embodiments, the spacer is attached to the linker. In some embodiments, the linker is attached to the nucleotide unit. In some embodiments, the nucleotide unit comprises a base, sugar and at least one phosphate group, and wherein the linker is attached to the nucleotide unit through the base. In some embodiments, the linker comprises an aliphatic chain or an oligo ethylene glycol chain where both linker chains having 2-6 subunits and optionally the linker includes an aromatic moiety.

In some embodiments, the multivalent molecule comprises a core attached to multiple nucleotide arms, and wherein the multiple nucleotide arms have the same type of nucleotide unit which is selected from a group consisting of dATP, dGTP, dCTP, dTTP and dUTP.

In some embodiments, the multivalent molecule further comprises a plurality of multivalent molecules which includes a mixture of multivalent molecules having two or more different types of nucleotides selected from a group consisting of dATP, dGTP, dCTP, dTTP and dUTP.

In some embodiments, the multivalent molecule comprises a core attached to multiple nucleotide arms, and wherein individual nucleotide arms comprise a nucleotide unit having a chain terminating moiety (e.g., blocking moiety) at the sugar 2' position, at the sugar 3' position, or at the sugar 2' and 3' position.

In some embodiments, the chain terminating moiety comprise an azide, azido or azidomethyl group. In some embodiments, the chain terminating moiety is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, the chain terminating moiety is cleavable/removable from the nucleotide unit.

In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, the multivalent molecule comprises a core attached to multiple nucleotide arms, wherein the core is labeled with detectable reporter moiety. In some embodiments, the detectable reporter moiety comprises a fluorophore.

In some embodiments, the core of the multivalent molecule comprises an avidin-like moiety and the core attachment moiety comprises biotin.

In some embodiments, the sequencing of step (g) comprises: (1) contacting the plurality of nucleic acid concatemers with (i) a plurality of polymerases, (ii) at least one multivalent molecule comprising two or more duplicates of a nucleotide moiety that are connected to a core via a linker, and (iii) a plurality of sequencing primers that hybridize with a portion of the concatemers, under a condition suitable for binding at least one polymerase and at least one sequencing primer to a portion of one of the nucleic acid concatemer molecules, and suitable for binding at least one of the nucleotide moieties of the multivalent molecule to the 3' end of the sequencing primer at a position that is opposite a complementary nucleotide in the concatemer molecule wherein the bound nucleotide moiety does not incorporate into the sequencing primer; (2) detecting and identifying the bound nucleotide moiety of the multivalent molecule thereby determining the sequence of the concatemer molecule; (3) optionally repeating steps (1) and (2) at least once; (4) contacting the concatemer molecule with (i) a plurality of polymerases, and (ii) a plurality of nucleotides, under a condition suitable binding at least one polymerase to at least a portion of the concatemer molecule and suitable for binding at least one of the nucleotides from the plurality to the 3' ends of the hybridized sequencing primers at a position that is opposite a complementary nucleotide in the concatemer molecule wherein the bound nucleotides incorporate into the hybridized sequencing primers; (5) optionally detecting the incorporated nucleotides; (6) optionally identifying the incorporation nucleotides thereby determining or confirming the sequence of the concatemer; and (7) repeating steps (1)-(6) at least once.

In some embodiments, the sequencing of step (g) comprises: (1) contacting the plurality of immobilized concatemers with a plurality of sequencing primers that hybridize with the sequencing primer binding sequence, a plurality of polymerases, and a plurality of nucleotides, under a condition suitable for binding at least one polymerase and at least one sequencing primer to a portion of the immobilized concatemer, and suitable for binding at least one of the nucleotides to the 3' end of the sequencing primer at a position that is opposite a complementary nucleotide in the immobilized concatemer wherein the bound nucleotide incorporates into the 3' end of the sequencing primer; (2) detecting and identifying the incorporated nucleotide thereby determining the sequence of the immobilized concatemer molecule; and (3) optionally repeating steps (1) and (2) at least once. In some embodiments, at least one of the nucleotides in the plurality of nucleotides comprises a chain terminating moiety at the sugar 2' or 3' position. In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In Situ Single Cell Sequencing. The present disclosure provides a method for in situ analysis of nucleic acids in a cellular biological sample, wherein the cells of the cellular biological sample comprise cellular RNA and at least one cell in the sample having a target RNA, the method comprising step (a): conducting a reverse transcription reaction in the cellular biological sample under a condition that is suitable for generating at least one cDNA corresponding to the target RNA, wherein the suitable condition comprises contacting the target RNA in the at least one cell with (i) a high efficiency hybridization buffer, (ii) a reverse transcriptase enzyme, (iii) a plurality of nucleotides, and (iv) a plurality of reverse transcriptase primers that bind at least a portion of the target RNA.

In some embodiments, the cellular biological sample comprises a sample that is fresh, frozen, fresh frozen, or archived (e.g., formalin-fixed paraffin-embedded; FFPE).

In some embodiments, at least some of the target RNA remains inside the cells of the cellular biological sample. In some embodiments, the target RNA is not immobilized to any type of support that is exterior to the cellular biological sample.

In some embodiments, the cellular biological sample is treated to fix the location of the nucleic acids, including the target RNA, inside the cells of the sample. For example, the cellular biological sample can be treated with formalin. The cellular biological sample can be treated with formaldehyde, ethanol, methanol or picric acid. The cellular biological sample can be embedded in a paraffin wax.

In some embodiments, the plurality of reverse transcriptase primers in step (a) can be modified so they bind to cells or bind to cellular components in a cell, such that the cDNA generated by conducting the reverse transcriptase reaction binds a cellular component and remains in the cell. For example, the reverse transcriptase primers can be modified to include a reactive moiety at their 5' ends or can include nucleotide residues that are modified to include a reactive moiety. The reactive moiety comprise nucleophilic functional groups (e.g., amines, alcohols, thiols and hydrazides), electrophilic functional groups (e.g., aldehydes, esters, epoxides, isocyanates, maleimides and vinyl ketones), functional groups capable of cycloaddition reactions, forming disulfide bonds, or binding to metals. The reactive moiety comprises primary or secondary amines, lower alkylamine group, acetyl group, hydroxamic acids, N-hydroxysuccinimidyl esters, N-hydroxysuccinimidyl carbonates, maleimides, oxycarbonylimidazoles, nitrophenylesters, trifluoroethyl esters, glycidyl ethers or vinylsulfones. The reactive moiety comprises an affinity binding group such as biotin. The reactive moiety comprises fluorescein or acridine.

In some embodiments, the reverse transcription reaction of step (a) comprises a plurality of nucleotides and an enzyme having reverse transcription activity, including reverse transcriptase enzymes from AMV (avian myeloblastosis virus), M-MLV (moloney murine leukemia virus), or HIV (human immunodeficiency virus). In some embodiments, the reverse transcriptase can be a commercially-available enzyme, including MultiScribe™, ThermoScript™, or ArrayScript™. In some embodiments, the reverse transcriptase enzyme comprises Superscript I, II, III, or IV enzymes. In some embodiments, the reverse transcription reaction can include an RNase inhibitor. In some embodiments, the plurality of reverse transcription primers are resistant to ribonuclease degradation. For example, the reverse transcription primers can be modified to include two or more phosphorothioate bonds, or 2'-O-methyl, 2' fluorobases, phosphorylated 3' ends, or locked nucleic acid residues.

In some embodiments, the high efficiency high efficiency hybridization buffer of step (a) comprises: (i) a first polar aprotic solvent having a dielectric constant that is no greater than 40 and having a polarity index of 4-9; (ii) a second polar aprotic solvent having a dielectric constant that is no greater than 115 and is present in the high efficiency high efficiency hybridization buffer formulation in an amount effective to denature double-stranded nucleic acids; (iii) a pH buffer system that maintains the pH of the high efficiency high efficiency hybridization buffer formulation in a range of about 4-8; and (iv) a crowding agent in an amount sufficient to enhance or facilitate molecular crowding. In some embodiments, the high efficiency high efficiency hybridization buffer of step (a) comprises: (i) the first polar aprotic solvent comprises acetonitrile at 25-50% by volume of the high efficiency high efficiency hybridization buffer; (ii) the second polar aprotic solvent comprises formamide at 5-10% by volume of the high efficiency high efficiency hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the high efficiency high efficiency hybridization buffer. In some embodiments, the high efficiency hybridization buffer further comprises betaine.

In some embodiments, the high efficiency high efficiency hybridization buffer of step (a) promotes high stringency (e.g., specificity), speed, and efficacy of nucleic acid hybridization reactions and increases the efficiency of the subsequent amplification and sequencing steps. In some embodiments, the high efficiency hybridization buffer significantly shortens nucleic acid hybridization times, and decreases sample input requirements. Nucleic acid annealing can be performed at isothermal conditions and eliminate the cooling step for annealing.

In some embodiments, the method for in situ analysis of nucleic acids in a cellular biological sample further comprises step (b): degrading some or all of the cellular RNA and retaining at least the cell membrane of the cellular biological sample. In some embodiment, the cellular RNA is degraded with a ribonuclease.

In some embodiments, the method for in situ analysis of nucleic acids in a cellular biological sample further comprises step (c): contacting the at least one cDNA with a plurality of padlock probes each comprising two terminal regions that bind to portions of the at least one cDNA to generate at least one cDNA-padlock probe complex having the two probe terminal regions hybridized to the adjacent regions of the cDNA to form a nick or gap.

In some embodiments, the padlock probe of step (c) comprises a single oligonucleotide strand which includes target capture sequences at its 5'terminal-end and 3'terminal-end that are complementary to contiguous regions of the target nucleic acid molecule (e.g., RNA). The padlock probe can also include any one or any combination of two or more adaptor sequences including an amplification primer binding sequence, a sequencing primer binding sequence, an immobilization sequence and/or a sample index sequence. The various adaptor sequences can be located in any region, for example the internal portion of the padlock probe. The 5' and 3' ends of the padlock probe can hybridize to adjacent positions on the target nucleic acid molecule to form an open circularized molecule with a nick or gap between the hybridized 5' and 3' ends.

In some embodiments, the method for in situ analysis of nucleic acids in a cellular biological sample further comprises step (d): conducting a gap-filling reaction and/or a ligation reaction on the at least one cDNA-padlock probe complex to generate a covalently closed circularized padlock probe.

In some embodiments, the gap-filling reaction comprises contacting the open circularized molecule with a DNA polymerase and a plurality of nucleotides, where the DNA polymerase comprises *E. coli* DNA polymerase I, Klenow fragment of *E. coli* DNA polymerase I, T7 DNA polymerase, or T4 DNA polymerase. In some embodiments, the ligation reaction comprises use of a ligase enzyme, including a T3, T4, T7 or Taq DNA ligase enzyme.

In some embodiments, the method for in situ analysis of nucleic acids in a cellular biological sample further comprises step (e): conducting a rolling circle amplification reaction on the circularized padlock probes to generate a plurality of nucleic acid concatemers.

In some embodiments, the rolling circle amplification reaction of step (e) comprises contacting the covalently closed circularized padlock probes (e.g., circularized nucleic acid template molecule(s)) with an amplification primer, a DNA polymerase, a plurality of nucleotides, and at least one catalytic divalent cation, under a condition suitable for generating at least one nucleic acid concatemer, wherein the at least one catalytic divalent cation comprises magnesium or manganese.

In some embodiments, the rolling circle amplification reaction of step (e) comprises: (1) contacting the covalently closed circularized padlock probes (e.g., circularized nucleic acid template molecule(s)) with an amplification primer, a DNA polymerase, a plurality of nucleotides, and at least one non-catalytic divalent cation that does not promote polymerase-catalyzed nucleotide incorporation into the amplification primer, wherein the non-catalytic divalent cation comprises strontium or barium; and (2) contacting the covalently closed circularized padlock probes with at least one catalytic divalent cation, under a condition suitable for generating at least one nucleic acid concatemer, wherein the at least one catalytic divalent cation comprises magnesium or manganese.

In some embodiments, the rolling circle amplification reaction of step (e) is conducted at a constant temperature (e.g., isothermal) ranging from room temperature to about 50° C., or from room temperature to about 65° C.

In some embodiments, the rolling circle amplification reaction of step (e) can be conducted in the presence of a plurality of compaction oligonucleotides which compacts the size and/or shape of the immobilized concatemer to form an immobilized compact nanoball.

In some embodiments, the rolling circle amplification reaction of step (e) comprises a DNA polymerase having a strand displacing activity which is selected from a group consisting of phi29 DNA polymerase, large fragment of Bst DNA polymerase, large fragment of Bsu DNA polymerase, and Bca (exo-) DNA polymerase, Klenow fragment of *E.* coli DNA polymerase, T5 polymerase, M-MuLV reverse transcriptase, HIV viral reverse transcriptase, or Deep Vent DNA polymerase. In some embodiments, the phi29 DNA polymerase can be wild type phi29 DNA polymerase (e.g., MagniPhi from Expedeon), or variant EquiPhi29 DNA polymerase (e.g., from Thermo Fisher Scientific), and chimeric QualiPhi DNA polymerase (e.g., from 4basebio).

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with at least one amplification primer comprising a random sequence, a DNA polymerase having strand displacement activity, a plurality of nucleotides, and a catalytic divalent cation comprising magnesium or manganese.

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with a DNA primase-polymerase enzyme, a DNA polymerase having strand displacement activity, a plurality of nucleotides, and a catalytic divalent cation comprising magnesium or manganese. In some embodiments, a DNA primase-polymerase comprises an enzyme having activities of a DNA polymerase and an RNA primase. A DNA primase-polymerase enzyme can utilize deoxyribonucleotide triphosphates to synthesize a DNA primer on a single-stranded DNA template in a template-sequence dependent manner, and can extend the primer strand via nucleotide polymerization (e.g., primer extension), in the presence of a catalytic divalent cation (e.g., magnesium and/or manganese). The DNA primase-polymerase include enzymes that are members of DnaG-like primases (e.g., bacteria) and AEP-like primases (Archaea and Eukaryotes). An exemplary DNA primase-polymerase enzyme is Tth PrimPol from *Thermus thermophilus* HB27.

In some embodiments, the method for in situ analysis of nucleic acids in a cellular biological sample further comprises step (f): sequencing at least a portion of the nucleic acid concatemers. In some embodiments, the sequencing comprises sequencing at least a portion of the nucleic acid concatemers using an optical imaging system comprising a field-of-view (FOV) greater than 1.0 mm$^2$.

In some embodiments, the sequencing of step (f) includes placing the cellular biological sample in a flow cell having walls (e.g., top or first wall, and bottom or second wall) and a gap in-between, where the gap can be filled with a fluid, where the flow cell is positioned in a fluorescence optical imaging system. The cellular biological sample has a thickness that may require using the imaging system to focus separately on the first and second surfaces of the flow cell, when using a traditional imaging system. For improved imaging of the sequencing reaction in the cellular biological sample, the flow cell can be positioned in a high performance fluorescence imaging system, which comprises two or more tube lenses which are designed to provide optimal imaging performance for the first and second surfaces of the flow cell at two or more fluorescence wavelengths. In some embodiments, the high-performance imaging system further comprises a focusing mechanism configured to refocus the optical system between acquiring images of the first and second surfaces of the flow cell. In some embodiments, the high performance imaging system is configured to image two or more fields-of-view on at least one of the first flow cell surface or the second flow cell surface.

In some embodiments, steps (a)-(f) are conducted inside the cellular biological sample. In some embodiments, the cellular biological sample is positioned on a support prior to step (a), where the support lacks immobilized capture oligonucleotides. In some embodiments, the target RNA or cDNA is not immobilized to any type of support. In some embodiments, at least some of the target RNA and/or cDNA remains inside the cellular biological sample throughout steps (a)-(f).

In some embodiments, the sequencing of step (f) comprises: contacting the plurality of nucleic acid concatemers with a plurality of sequencing primers, a plurality of polymerases, and a plurality of multivalent molecules, wherein each of the multivalent molecules comprise two or more duplicates of a nucleotide moiety that are connected to a core via a linker.

In some embodiments, the multivalent molecule comprises multiple nucleotides that are bound to a particle (or core) such as a polymer, a branched polymer, a dendrimer, a micelle, a liposome, a microparticle, a nanoparticle, a quantum dot, or other suitable particle known in the art.

In some embodiments, the multivalent molecule comprises: (1) a core, and (2) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms. In some embodiments, the spacer is attached to the linker. In some embodiments, the linker is attached to the nucleotide unit. In some embodiments, the nucleotide unit comprises a base, sugar and at least one phosphate group, and wherein the linker is attached to the nucleotide unit through the base. In some embodiments, the linker comprises an aliphatic chain or an oligo ethylene glycol chain where both linker chains having 2-6 subunits and optionally the linker includes an aromatic moiety.

In some embodiments, the multivalent molecule comprises a core attached to multiple nucleotide arms, and wherein the multiple nucleotide arms have the same type of nucleotide unit which is selected from a group consisting of dATP, dGTP, dCTP, dTTP and dUTP.

In some embodiments, the multivalent molecule further comprises a plurality of multivalent molecules which includes a mixture of multivalent molecules having two or more different types of nucleotides selected from a group consisting of dATP, dGTP, dCTP, dTTP and dUTP.

In some embodiments, the multivalent molecule comprises a core attached to multiple nucleotide arms, and wherein individual nucleotide arms comprise a nucleotide unit having a chain terminating moiety (e.g., blocking moiety) at the sugar 2' position, at the sugar 3' position, or at the sugar 2' and 3' position.

In some embodiments, the chain terminating moiety comprise an azide, azido or azidomethyl group. In some embodiments, the chain terminating moiety is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, the chain terminating moiety is cleavable/removable from the nucleotide unit.

In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, the multivalent molecule comprises a core attached to multiple nucleotide arms, wherein the core is labeled with detectable reporter moiety. In some embodiments, the detectable reporter moiety comprises a fluorophore.

In some embodiments, the core of the multivalent molecule comprises an avidin-like moiety and the core attachment moiety comprises biotin.

In some embodiments, the sequencing of step (f) comprises: (1) contacting the plurality of nucleic acid concatemers with (i) a plurality of polymerases, (ii) at least one multivalent molecule comprising two or more duplicates of a nucleotide moiety that are connected to a core via a linker, and (iii) a plurality of sequencing primers that hybridize with a portion of the concatemers, under a condition suitable for binding at least one polymerase and at least one sequencing primer to a portion of one of the nucleic acid concatemer molecules, and suitable for binding at least one of the nucleotide moieties of the multivalent molecule to the 3' end of the sequencing primer at a position that is opposite a complementary nucleotide in the concatemer molecule wherein the bound nucleotide moiety does not incorporate into the sequencing primer; (2) detecting and identifying the bound nucleotide moiety of the multivalent molecule thereby determining the sequence of the concatemer molecule; (3) optionally repeating steps (1) and (2) at least once; (4) contacting the concatemer molecule with (i) a plurality of polymerases, and (ii) a plurality of nucleotides, under a condition suitable binding at least one polymerase to at least a portion of the concatemer molecule and suitable for binding at least one of the nucleotides from the plurality to the 3' ends of the hybridized sequencing primers at a position that is opposite a complementary nucleotide in the concatemer molecule wherein the bound nucleotides incorporate into the hybridized sequencing primers; (5) optionally detecting the incorporated nucleotides; (6) optionally identifying the incorporation nucleotides thereby determining or confirming the sequence of the concatemer; and (7) repeating steps (1)-(6) at least once.

In some embodiments, the sequencing of step (f) comprises: (1) contacting the plurality of immobilized concatemers with a plurality of sequencing primers that hybridize with the sequencing primer binding sequence, a plurality of polymerases, and a plurality of nucleotides, under a condition suitable for binding at least one polymerase and at least one sequencing primer to a portion of the immobilized concatemer, and suitable for binding at least one of the nucleotides to the 3' end of the sequencing primer at a position that is opposite a complementary nucleotide in the immobilized concatemer wherein the bound nucleotide incorporates into the 3' end of the sequencing primer; (2) detecting and identifying the incorporated nucleotide thereby determining the sequence of the immobilized concatemer molecule; and (3) optionally repeating steps (1) and (2) at least once. In some embodiments, at least one of the nucleotides in the plurality of nucleotides comprises a chain terminating moiety at the sugar 2' or 3' position. In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In situ Single Cell Sequencing. The present disclosure provides a method for in situ analysis of nucleic acids in a single cell wherein the single cell is placed in a cell media, and wherein the single cell comprises cellular RNA including a target RNA, the method comprising: (a) conducting a reverse transcription reaction in the single cell under a condition that is suitable for generating at least one cDNA corresponding to the target RNA, wherein the suitable condition comprises contacting the target RNA in the single cell with (i) a high efficiency hybridization buffer, (ii) a reverse transcriptase enzyme, (iii) a plurality of nucleotides, and (iv) a plurality of reverse transcriptase primers that bind at least a portion of the target RNA.

In some embodiments, the single cell is a cell sample that is fresh, frozen, fresh frozen, or archived (e.g., formalin-fixed paraffin-embedded; FFPE).

In some embodiments, the target RNA remains inside the single cell. In some embodiments, the target RNA is not immobilized to any type of support that is exterior to the single cell.

In some embodiments, the single cell can be treated to fix the location of the nucleic acids, including the target RNA, inside the single cell. For example, the single cell can be treated with formalin. The single cell can be treated with formaldehyde, ethanol, methanol or picric acid. The single cell can be embedded in a paraffin wax.

In some embodiments, the plurality of reverse transcriptase primers in step (a) can be modified so they bind to cells or bind to cellular components in a cell, such that the cDNA generated by conducting the reverse transcriptase reaction binds a cellular component and remains in the cell. For example, the reverse transcriptase primers can be modified to include a reactive moiety at their 5' ends or can include nucleotide residues that are modified to include a reactive moiety. The reactive moiety comprise nucleophilic functional groups (e.g., amines, alcohols, thiols and hydrazides), electrophilic functional groups (e.g., aldehydes, esters, epoxides, isocyanates, maleimides and vinyl ketones), functional groups capable of cycloaddition reactions, forming disulfide bonds, or binding to metals. The reactive moiety comprises primary or secondary amines, lower alkylamine group, acetyl group, hydroxamic acids, N-hydroxysuccinimidyl esters, N-hydroxysuccinimidyl carbonates, maleimides, oxycarbonylimidazoles, nitrophenylesters, trifluoroethyl esters, glycidyl ethers or vinylsulfones. The reactive moiety comprises an affinity binding group such as biotin. The reactive moiety comprises fluorescein or acridine.

In some embodiments, the reverse transcription reaction of step (a) comprises a plurality of nucleotides and an enzyme having reverse transcription activity, including reverse transcriptase enzymes from AMV (avian myeloblastosis virus), M-MLV (moloney murine leukemia virus), or HIV (human immunodeficiency virus). In some embodiments, the reverse transcriptase can be a commercially-available enzyme, including MultiScribe™, ThermoScript™, or ArrayScript™. In some embodiments, reverse transcriptase enzyme comprises Superscript I, II, III, or IV enzymes. In some embodiments, the reverse transcription reaction can include an RNase inhibitor. In some embodiments, the plurality of reverse transcription primers are resistant to ribonuclease degradation. For example, the reverse transcription primers can be modified to include two or more phosphorothioate bonds, or 2'-O-methyl, 2' fluoro-bases, phosphorylated 3' ends, or locked nucleic acid residues.

In some embodiments, the plurality of reverse transcription primers are resistant to ribonuclease degradation. For example, the reverse transcription primers can be modified to include two or more phosphorothioate bonds, or 2'-O-methyl, 2' fluoro-bases, phosphorylated 3' ends, or locked nucleic acid residues.

In some embodiments, the high efficiency high efficiency hybridization buffer of step (a) comprises: (i) a first polar aprotic solvent having a dielectric constant that is no greater than 40 and having a polarity index of 4-9; (ii) a second polar aprotic solvent having a dielectric constant that is no greater than 115 and is present in the high efficiency high efficiency hybridization buffer formulation in an amount effective to denature double-stranded nucleic acids; (iii) a pH buffer system that maintains the pH of the high efficiency high efficiency hybridization buffer formulation in a range of about 4-8; and (iv) a crowding agent in an amount sufficient to enhance or facilitate molecular crowding. In some embodiments, the high efficiency high efficiency hybridization buffer of step (a) comprises: (i) the first polar aprotic solvent comprises acetonitrile at 25-50% by volume of the high efficiency high efficiency hybridization buffer; (ii) the second polar aprotic solvent comprises formamide at 5-10% by volume of the high efficiency high efficiency hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the high efficiency high efficiency hybridization buffer. In some embodiments, the high efficiency hybridization buffer further comprises betaine.

In some embodiments, the high efficiency high efficiency hybridization buffer of step (a) promotes high stringency (e.g., specificity), speed, and efficacy of nucleic acid hybridization reactions and increases the efficiency of the subsequent amplification and sequencing steps. In some embodiments, the high efficiency hybridization buffer significantly shortens nucleic acid hybridization times, and decreases sample input requirements. Nucleic acid annealing can be performed at isothermal conditions and eliminate the cooling step for annealing.

In some embodiments, the single cell is placed in a cell media which comprises a complex cell media having a fluid obtained from a biological fluid which is selected from a group consisting of fetal bovine serum, blood plasma, blood serum, lymph fluid, human placental cord serum and amniotic fluid, and wherein the complex cell media can support cell growth and/or proliferation. In some embodiments, the complex cell media comprises a serum-containing media, a serum-free media, a chemically-defined media, or a protein-free media. In some embodiments, the complex cell media comprises RPMI-1640, MEM, DMEM or IMDM.

In some embodiments, the single cell is placed in a cell media which comprises a simple cell media which includes any one or any combination of two or more of a buffer, a phosphate compound, a sodium compound, a potassium compound, a calcium compound, a magnesium compound and/or glucose, and wherein the simple cell media cannot support cell growth and/or proliferation. In some embodiments, the simple cell media comprise PBS, DPBS, HBSS, DMEM, EMEM or EBSS.

In some embodiments, the method for in situ analysis of nucleic acids in a single cell further comprise step (b): degrading some or all of the cellular RNA and retaining at least the cell membrane of the single cell. In some embodiment, the cellular RNA is degraded with a ribonuclease.

In some embodiments, the method for in situ analysis of nucleic acids in a single cell further comprise step (c): contacting the at least one cDNA with a plurality of padlock probes each comprising two terminal regions that bind to portions of the at least one cDNA to generate at least one cDNA-padlock probe complex having the two probe terminal regions hybridized to the adjacent regions of the cDNA to form a nick or gap.

In some embodiments, the padlock probe of step (c) comprises a single oligonucleotide strand which includes target capture sequences at its 5'terminal-end and 3'terminal-end that are complementary to contiguous regions of the target nucleic acid molecule (e.g., RNA). The padlock probe can also include any one or any combination of two or more adaptor sequences including an amplification primer binding sequence, a sequencing primer binding sequence, an immobilization sequence and/or a sample index sequence. The various adaptor sequences can be located in any region, for example the internal portion of the padlock probe. The 5' and 3' ends of the padlock probe can hybridize to adjacent positions on the target nucleic acid molecule to form an open circularized molecule with a nick or gap between the hybridized 5' and 3' ends.

In some embodiments, the method for in situ analysis of nucleic acids in a single cell further comprise step (d): conducting a gap-filling reaction and/or a ligation reaction on the at least one cDNA-padlock probe complex to generate a covalently closed circularized padlock probe.

In some embodiments, the gap-filling reaction comprises contacting the open circularized molecule with a DNA polymerase and a plurality of nucleotides, where the DNA polymerase comprises E. coli DNA polymerase I, Klenow fragment of E. coli DNA polymerase I, T7 DNA polymerase, or T4 DNA polymerase. In some embodiments, the ligation reaction comprises use of a ligase enzyme, including a T3, T4, T7 or Taq DNA ligase enzyme.

In some embodiments, the method for in situ analysis of nucleic acids in a single cell further comprise step (e): conducting a rolling circle amplification reaction on the covalently closed circularized padlock probes to generate a plurality of nucleic acid concatemers.

In some embodiments, the rolling circle amplification reaction of step (e) comprises contacting the covalently closed circularized padlock probes (e.g., circularized nucleic acid template molecule(s)) with an amplification primer, a DNA polymerase, a plurality of nucleotides, and at least one catalytic divalent cation, under a condition suitable for generating at least one nucleic acid concatemer, wherein the at least one catalytic divalent cation comprises magnesium or manganese.

In some embodiments, the rolling circle amplification reaction of step (e) comprises: (1) contacting the covalently closed circularized padlock probes (e.g., circularized nucleic acid template molecule(s)) with an amplification primer, a DNA polymerase, a plurality of nucleotides, and at least one non-catalytic divalent cation that does not promote polymerase-catalyzed nucleotide incorporation into the amplification primer, wherein the non-catalytic divalent cation comprises strontium or barium; and (2) contacting the covalently closed circularized padlock probes with at least one catalytic divalent cation, under a condition suitable for generating at least one nucleic acid concatemer, wherein the at least one catalytic divalent cation comprises magnesium or manganese.

In some embodiments, the rolling circle amplification reaction of step (e) is conducted at a constant temperature (e.g., isothermal) ranging from room temperature to about 50° C., or from room temperature to about 65° C.

In some embodiments, the rolling circle amplification reaction of step (e) can be conducted in the presence of a plurality of compaction oligonucleotides which compacts the size and/or shape of the immobilized concatemer to form an immobilized compact nanoball.

In some embodiments, the rolling circle amplification reaction of step (e) comprises a DNA polymerase having a strand displacing activity which is selected from a group consisting of phi29 DNA polymerase, large fragment of Bst DNA polymerase, large fragment of Bsu DNA polymerase, and Bca (exo-) DNA polymerase, Klenow fragment of E. coli DNA polymerase, T5 polymerase, M-MuLV reverse transcriptase, HIV viral reverse transcriptase, or Deep Vent DNA polymerase. In some embodiments, the phi29 DNA polymerase can be wild type phi29 DNA polymerase (e.g., MagniPhi from Expedeon), or variant EquiPhi29 DNA polymerase (e.g., from Thermo Fisher Scientific), and chimeric QualiPhi DNA polymerase (e.g., from 4basebio).

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with at least one amplification primer comprising a random sequence, a DNA polymerase having strand displacement activity, a plurality of nucleotides, and a catalytic divalent cation comprising magnesium or manganese.

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with a DNA primase-polymerase enzyme, a DNA polymerase having strand displacement activity, a plurality of nucleotides, and a catalytic divalent cation comprising magnesium or manganese. In some embodiments, a DNA primase-polymerase comprises an enzyme having activities of a DNA polymerase and an RNA primase. A DNA primase-polymerase enzyme can utilize deoxyribonucleotide triphosphates to synthesize a DNA primer on a single-stranded DNA template in a template-sequence dependent manner, and can extend the primer strand via nucleotide polymerization (e.g., primer extension), in the presence of a catalytic divalent cation (e.g., magnesium and/or manganese). The DNA primase-polymerase include enzymes that are members of DnaG-like primases (e.g., bacteria) and AEP-like primases (Archaea and Eukaryotes). An exemplary DNA primase-polymerase enzyme is Tth PrimPol from *Thermus thermophilus* HB27.

In some embodiments, the method for in situ analysis of nucleic acids in a single cell further comprise step (f): sequencing at least a portion of the nucleic acid concatemers. In some embodiments, the sequencing comprises sequencing at least a portion of the nucleic acid concatemers using an optical imaging system comprising a field-of-view (FOV) greater than 1.0 mm$^2$.

In some embodiments, the sequencing of step (f) includes placing the single cell in a flow cell having walls (e.g., top or first wall, and bottom or second wall) and a gap in-between, where the gap can be filled with a fluid, where the flow cell is positioned in a fluorescence optical imaging system. The single cell has a thickness that may require using the imaging system to focus separately on the first and second surfaces of the flow cell, when using a traditional imaging system. For improved imaging of the sequencing reaction in the single cell, the flow cell can be positioned in a high performance fluorescence imaging system, which comprises two or more tube lenses which are designed to provide optimal imaging performance for the first and second surfaces of the flow cell at two or more fluorescence wavelengths. In some embodiments, the high-performance imaging system further comprises a focusing mechanism configured to refocus the optical system between acquiring images of the first and second surfaces of the flow cell. In some embodiments, the high performance imaging system is configured to image two or more fields-of-view on at least one of the first flow cell surface or the second flow cell surface.

In some embodiments, steps (a)-(f) are conducted inside the single cell. In some embodiments, the target RNA or cDNA is not immobilized to any type of support. In some embodiments, at least some of the target RNA and/or cDNA remains inside the cellular biological sample throughout steps (a)-(f).

In some embodiments, the single cell is positioned on a support prior to any of steps (a)-(f), where the support lacks immobilized capture oligonucleotides. For example, the method comprises: (1) positioning the single cell on a low non-specific binding coating that lacks immobilized capture oligonucleotides under a condition suitable for immobilizing the single cell to the surface of the low non-specific binding support, wherein the positioning is conducted prior to step (a), and wherein the cellular RNA remains inside the single cell; (2) positioning the single cell on a low non-specific binding coating that lacks immobilized capture oligonucleotides under a condition suitable for immobilizing the single cell to the surface of the low non-specific binding support, wherein the positioning is conducted prior to step (b), and wherein the at least one cDNA remains inside the single cell; (3) positioning the single cell on a low non-specific binding coating that lacks immobilized capture oligonucleotides under a condition suitable for immobilizing the single cell to the surface of the low non-specific binding support, wherein the positioning is conducted prior to step (e), and wherein the circularized padlock probe remains inside the single cell; or (4) positioning the single cell on a low non-specific binding coating that lacks immobilized capture oligonucleotides under a condition suitable for immobilizing the single cell to the surface of the low non-specific binding support, wherein the positioning is conducted prior to step (f), and wherein the plurality of nucleic acid concatemers remain inside the single cell.

In some embodiments, the low non-specific binding support comprises a support with a coating, wherein the coating comprises at least one hydrophilic polymer layer having a water contact angle of no more than 45 degrees.

In some embodiments, the sequencing of step (f) comprises: contacting the plurality of nucleic acid concatemers with a plurality of sequencing primers, a plurality of polymerases, and a plurality of multivalent molecules, wherein each of the multivalent molecules comprise two or more duplicates of a nucleotide moiety that are connected to a core via a linker.

In some embodiments, the multivalent molecule comprises multiple nucleotides that are bound to a particle (or core) such as a polymer, a branched polymer, a dendrimer, a micelle, a liposome, a microparticle, a nanoparticle, a quantum dot, or other suitable particle known in the art.

In some embodiments, the multivalent molecule comprises: (1) a core, and (2) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms. In some embodiments, the spacer is attached to the linker. In some embodiments, the linker is attached to the nucleotide unit. In some embodiments, the nucleotide unit comprises a base, sugar and at least one phosphate group, and wherein the linker is attached to the nucleotide unit through the base. In some embodiments, the linker comprises an aliphatic chain or an oligo ethylene glycol chain where both linker chains having 2-6 subunits and optionally the linker includes an aromatic moiety.

In some embodiments, the multivalent molecule comprises a core attached to multiple nucleotide arms, and wherein the multiple nucleotide arms have the same type of nucleotide unit which is selected from a group consisting of dATP, dGTP, dCTP, dTTP and dUTP.

In some embodiments, the multivalent molecule further comprises a plurality of multivalent molecules which includes a mixture of multivalent molecules having two or more different types of nucleotides selected from a group consisting of dATP, dGTP, dCTP, dTTP and dUTP.

In some embodiments, the multivalent molecule comprises a core attached to multiple nucleotide arms, and wherein individual nucleotide arms comprise a nucleotide unit having a chain terminating moiety (e.g., blocking moiety) at the sugar 2' position, at the sugar 3' position, or at the sugar 2' and 3' position.

In some embodiments, the chain terminating moiety comprise an azide, azido or azidomethyl group. In some embodiments, the chain terminating moiety is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, the chain terminating moiety is cleavable/removable from the nucleotide unit.

In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, the multivalent molecule comprises a core attached to multiple nucleotide arms, wherein the core is labeled with detectable reporter moiety. In some embodiments, the detectable reporter moiety comprises a fluorophore.

In some embodiments, the core of the multivalent molecule comprises an avidin-like moiety and the core attachment moiety comprises biotin.

In some embodiments, the sequencing of step (f) comprises: (1) contacting the plurality of nucleic acid concatemers with (i) a plurality of polymerases, (ii) at least one multivalent molecule comprising two or more duplicates of a nucleotide moiety that are connected to a core via a linker, and (iii) a plurality of sequencing primers that hybridize with a portion of the concatemers, under a condition suitable for binding at least one polymerase and at least one sequencing primer to a portion of one of the nucleic acid concatemer molecules, and suitable for binding at least one of the nucleotide moieties of the multivalent molecule to the 3' end of the sequencing primer at a position that is opposite a complementary nucleotide in the concatemer molecule wherein the bound nucleotide moiety does not incorporate into the sequencing primer; (2) detecting and identifying the bound nucleotide moiety of the multivalent molecule thereby determining the sequence of the concatemer molecule; (3) optionally repeating steps (1) and (2) at least once; (4) contacting the concatemer molecule with (i) a plurality of polymerases, and (ii) a plurality of nucleotides, under a condition suitable binding at least one polymerase to at least a portion of the concatemer molecule and suitable for binding at least one of the nucleotides from the plurality to the 3' ends of the hybridized sequencing primers at a position that is opposite a complementary nucleotide in the concatemer molecule wherein the bound nucleotides incorporate into the hybridized sequencing primers; (5) optionally detecting the incorporated nucleotides; (6) optionally identifying the incorporation nucleotides thereby determining or confirming the sequence of the concatemer; and (7) repeating steps (1)-(6) at least once.

In some embodiments, the sequencing of step (f) comprises: (1) contacting the plurality of immobilized concatemers with a plurality of sequencing primers that hybridize with the sequencing primer binding sequence, a plurality of polymerases, and a plurality of nucleotides, under a condition suitable for binding at least one polymerase and at least one sequencing primer to a portion of the immobilized concatemer, and suitable for binding at least one of the nucleotides to the 3' end of the sequencing primer at a position that is opposite a complementary nucleotide in the immobilized concatemer wherein the bound nucleotide incorporates into the 3' end of the sequencing primer; (2) detecting and identifying the incorporated nucleotide thereby determining the sequence of the immobilized concatemer molecule; and (3) optionally repeating steps (1) and (2) at least once. In some embodiments, at least one of the nucleotides in the plurality of nucleotides comprises a chain terminating moiety at the sugar 2' or 3' position. In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

Biological Molecule Capture on a Low Binding Coating and Analysis. The present disclosure provides method for analyzing biological molecules from a cellular biological sample, wherein the cells in the cellular biological sample comprise cellular nucleic acids and polypeptides, and wherein at least one cell in the sample includes a target nucleic acid that encodes a target polypeptide, the method comprising the general step of: (a) providing a support comprising a low non-specific binding coating to which a plurality of capture oligonucleotides and optionally a plurality of circularization oligonucleotides are immobilized, wherein the plurality of immobilized capture oligonucleotides comprise (i) a target capture region that hybridizes to at least a portion of a target nucleic acid molecule, and (ii) a spatial barcode sequence, wherein the low non-specific binding coating comprises at least one hydrophilic polymer layer having a water contact angle of no more than 45 degrees.

In some embodiments, the low non-specific binding coating in step (a) exhibits low background fluorescence signals or high contrast to noise (CNR) ratios relative to known surfaces in the art. In some embodiments, the low non-specific binding coating exhibits a level of non-specific Cy3 dye absorption of less than about 0.25 molecules/$\mu m^2$, where no more than 5% of the target nucleic acid is associated with the surface coating without hybridizing to an immobilized capture oligonucleotide. In some embodiments, a fluorescence image of the surface coating having a plurality of clonally-amplified clusters of nucleic acid exhibits a contrast-to-noise ratio (CNR) of at least 20, or at least 50, or higher contrast-to-noise ratios (CNR), when using a fluorescence imaging system under non-signal saturating conditions.

In some embodiments, the low non-specific binding coating of step (a) has regions (e.g., features) located at predetermined locations on the coating. The low non-specific binding coating comprises a plurality of features including at least a first and second feature, where each feature includes a plurality of capture oligonucleotide and optionally a plurality of circularization oligonucleotides that are immobilized to the coating. In some embodiments, the first feature comprises a plurality of first capture oligonucleotides having a first target capture region and a first spatial barcode sequence. In some embodiments, the second feature comprises a plurality of second capture oligonucleotides having a second target capture region and a second spatial barcode sequence. In some embodiments, the sequence of the first target capture region in the first feature is the same or different from the sequence of the second target capture region in the second feature. In some embodiments, the first spatial barcode sequence in the first feature differs from the second spatial barcode sequence in the second feature.

In some embodiments, the method for analyzing biological molecules from a cellular biological sample further comprise step (b): contacting the low non-specific binding coating with the cellular biological sample in the presence of a high efficiency hybridization buffer under conditions suitable to promote migration of the cellular nucleic acids, including the target nucleic acid molecule, from the cellular biological sample to one of the immobilized capture oligonucleotides thereby forming an immobilized target nucleic acid duplex, wherein the target nucleic acid molecule is immobilized to the low non-specific binding coating in a manner that preserves spatial location information of the target nucleic acid molecule in the cellular biological sample.

In some embodiments, the cellular biological sample in step (b) comprises a cellular biological sample that is fresh, frozen, fresh frozen, or archived (e.g., formalin-fixed paraffin-embedded; FFPE).

In some embodiments, the cellular biological sample in step (b) is subjected to a permeabilizing reaction to promote migration of the cellular nucleic acid molecules (e.g., DNA and/or RNA), including the target nucleic acid molecule, from the cellular biological sample to one of the immobilized capture oligonucleotides.

In some embodiments, the target nucleic acid comprises RNA. In some embodiments, the spatial location of the target RNA in the cellular biological sample corresponds to the spatial location of at least one cell in the cellular biological sample that expresses the target RNA which encodes the target polypeptide.

In some embodiments, the high efficiency high efficiency hybridization buffer of step (b) comprises: (i) a first polar aprotic solvent having a dielectric constant that is no greater than 40 and having a polarity index of 4-9; (ii) a second polar aprotic solvent having a dielectric constant that is no greater than 115 and is present in the high efficiency high efficiency hybridization buffer formulation in an amount effective to denature double-stranded nucleic acids; (iii) a pH buffer system that maintains the pH of the high efficiency high efficiency hybridization buffer formulation in a range of about 4-8; and (iv) a crowding agent in an amount sufficient to enhance or facilitate molecular crowding.

In some embodiments, the high efficiency high efficiency hybridization buffer of step (b) comprises: (i) the first polar aprotic solvent comprises acetonitrile at 25-50% by volume of the high efficiency high efficiency hybridization buffer; (ii) the second polar aprotic solvent comprises formamide at 5-10% by volume of the high efficiency high efficiency hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the high efficiency high efficiency hybridization buffer. In some embodiments, the high efficiency hybridization buffer further comprises betaine.

In some embodiments, the high efficiency high efficiency hybridization buffer of step (b) promotes high stringency (e.g., specificity), speed, and efficacy of nucleic acid hybridization reactions and increases the efficiency of the subsequent amplification and sequencing steps. In some embodiments, the high efficiency hybridization buffer significantly shortens nucleic acid hybridization times, and decreases sample input requirements. Nucleic acid annealing can be performed at isothermal conditions and eliminate the cooling step for annealing.

In some embodiments, the method for analyzing biological molecules from a cellular biological sample further comprise step (c): conducting a primer extension reaction on the immobilized target nucleic acid duplex thereby forming an immobilized target extension product.

In some embodiments, the primer extension reaction of step (c) can be a reverse transcription reaction which comprises (i) a reverse transcriptase enzyme, (ii) a plurality of nucleotides, and (iii) a plurality of reverse transcriptase primers that bind at least a portion of the target RNA. In some embodiments, the reverse transcription reaction of step (a) comprises a plurality of nucleotides and an enzyme having reverse transcription activity, including reverse transcriptase enzymes from AMV (avian myeloblastosis virus), M-MLV (moloney murine leukemia virus), or HIV (human immunodeficiency virus). In some embodiments, the reverse transcriptase can be a commercially-available enzyme, including MultiScribe™, ThermoScript™, or ArrayScript™. In some embodiments, the reverse transcriptase enzyme comprises Superscript I, II, III, or IV enzymes. In some embodiments, the reverse transcription reaction can include an RNase inhibitor.

In some embodiments, the plurality of reverse transcription primers are resistant to ribonuclease degradation. For example, the reverse transcription primers can be modified to include two or more phosphorothioate bonds, or 2'-O-methyl, 2' fluoro-bases, phosphorylated 3' ends, or locked nucleic acid residues.

In some embodiments, the method for analyzing biological molecules from a cellular biological sample further comprise step (d): forming an open circular target molecule using the immobilized circularization oligonucleotide, or if the low non-specific binding coating does not already include an immobilized circularization oligonucleotide then immobilizing a soluble circularization oligonucleotide to the low non-specific binding coating in proximity to the immobilized target extension product and forming an open circular target molecule using the now-immobilized circularization oligonucleotide;

In some embodiments, the method for analyzing biological molecules from a cellular biological sample further comprise step (e): forming a covalently closed circular target molecule which is immobilized to the low non-specific binding coating.

In some embodiments, the forming the covalently closed circular target molecule comprises a polymerase-mediated gap-filling reaction, an enzymatic ligation reaction, or a polymerase-mediated gap-filling reaction and enzymatic ligation reaction. In some embodiments, the polymerase-mediate gap-filling reaction comprises contacting the open circular target molecule with a DNA polymerase and a plurality of nucleotides, where the DNA polymerase comprises E. coli DNA polymerase I, Klenow fragment of E. coli DNA polymerase I, T7 DNA polymerase, or T4 DNA polymerase. In some embodiments, the enzymatic ligation reaction comprises use of a ligase enzyme, including a T3, T4, T7 or Taq DNA ligase enzyme. In some embodiments, the forming the covalently closed circular target molecule comprises contacting the open circular target molecule with a CircLigase or CircLigase II enzyme.

In some embodiments, the method for analyzing biological molecules from a cellular biological sample further comprise step (f): conducting a rolling circle amplification reaction on the immobilized covalently closed circular target molecule to form an immobilized nucleic acid concatemer molecule having tandem repeat regions comprising the target sequence and the spatial barcode sequence.

In some embodiments, the rolling circle amplification reaction of step (f) comprises contacting the covalently closed circularized padlock probes (e.g., circularized nucleic acid template molecule(s)) with an amplification primer, a DNA polymerase, a plurality of nucleotides, and at least one catalytic divalent cation, under a condition suitable for generating at least one nucleic acid concatemer, wherein the at least one catalytic divalent cation comprises magnesium or manganese.

In some embodiments, the rolling circle amplification reaction of step (f) comprises: (1) contacting the covalently closed circularized padlock probes (e.g., circularized nucleic acid template molecule(s)) with an amplification primer, a DNA polymerase, a plurality of nucleotides, and at least one non-catalytic divalent cation that does not promote polymerase-catalyzed nucleotide incorporation into the amplification primer, wherein the non-catalytic divalent cation comprises strontium or barium; and (2) contacting the covalently closed circularized padlock probes with at least one catalytic divalent cation, under a condition suitable for generating at least one nucleic acid concatemer, wherein the at least one catalytic divalent cation comprises magnesium or manganese.

In some embodiments, the rolling circle amplification reaction of step (f) is conducted at a constant temperature (e.g., isothermal) ranging from room temperature to about 50° C., or from room temperature to about 65° C.

In some embodiments, the rolling circle amplification reaction of step (f) can be conducted in the presence of a plurality of compaction oligonucleotides which compacts the size and/or shape of the immobilized concatemer to form an immobilized compact nanoball.

In some embodiments, the rolling circle amplification reaction of step (f) comprises a DNA polymerase having a strand displacing activity which is selected from a group consisting of phi29 DNA polymerase, large fragment of Bst DNA polymerase, large fragment of Bsu DNA polymerase, and Bca (exo-) DNA polymerase, Klenow fragment of E. coli DNA polymerase, T5 polymerase, M-MuLV reverse transcriptase, HIV viral reverse transcriptase, or Deep Vent DNA polymerase. In some embodiments, the phi29 DNA polymerase can be wild type phi29 DNA polymerase (e.g., MagniPhi from Expedeon), or variant EquiPhi29 DNA polymerase (e.g., from Thermo Fisher Scientific), and chimeric QualiPhi DNA polymerase (e.g., from 4basebio).

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with at least one amplification primer comprising a random sequence, a DNA polymerase having strand displacement activity, a plurality of nucleotides, and a catalytic divalent cation comprising magnesium or manganese.

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with a DNA primase-polymerase enzyme, a DNA polymerase having strand displacement activity, a plurality of nucleotides, and a catalytic divalent cation comprising magnesium or manganese. In some embodiments, a DNA primase-polymerase comprises an enzyme having activities of a DNA polymerase and an RNA primase. A DNA primase-polymerase enzyme can utilize deoxyribonucleotide triphosphates to synthesize a DNA primer on a single-stranded DNA template in a template-sequence dependent manner, and can extend the primer strand via nucleotide polymerization (e.g., primer extension), in the presence of a catalytic divalent cation (e.g., magnesium and/or manganese). The DNA primase-polymerase include enzymes that are members of DnaG-like primases (e.g., bacteria) and AEP-like primases (Archaea and Eukaryotes). An exemplary DNA primase-polymerase enzyme is Tth PrimPol from *Thermus thermophilus* HB27.

In some embodiment, the rolling circle amplification reaction can be followed by a flexing amplification reaction instead of a multiple displacement amplification (MDA) reaction. In some embodiments, the flexing amplification reaction comprises: (1) forming a nucleic acid relaxant reaction mixture by contacting the nucleic acid concatemer with one or a combination of two or more compounds selected from a group consisting of formamide, acetonitrile, ethanol, guanidine hydrochloride, urea, potassium iodide and/or polyamines, to generate a relaxed nucleic acid concatemer, wherein the forming a nucleic acid relaxant reaction mixture is conducted with a temperature ramp-up, a relaxant incubation temperature, and a temperature ramp-down; (2) washing the relaxed concatemer; (3) forming a flexing amplification reaction mixture by contacting the relaxed concatemer with a strand-displacing DNA polymerase, a plurality of nucleotides, a catalytic divalent cation, (in the absence of added amplification primers), to generate double-stranded concatemers, wherein the forming a flexing amplification reaction mixture is conducted with a temperature ramp-up, a flexing incubation temperature, and a temperature ramp-down; (4) washing the double-stranded concatemer; and (5) repeating steps (1)-(4) at least once.

In some embodiments, the method for analyzing biological molecules from a cellular biological sample further comprise step (g): sequencing at least a portion of the nucleic acid concatemer, including sequencing the target sequence and the spatial barcode sequence, to determine the spatial location of the target nucleic acid in the cellular biological sample.

In some embodiments, the sequencing of step (g) comprises sequencing at least a portion of the nucleic acid concatemers using an optical imaging system comprising a field-of-view (FOV) greater than 1.0 mm$^2$. In some embodiments, the sequencing of step (g) includes placing the cellular biological sample in a flow cell having walls (e.g., top or first wall, and bottom or second wall) and a gap in-between, where the gap can be filled with a fluid, where the flow cell is positioned in a fluorescence optical imaging system. The cellular biological sample has a thickness that may require using the imaging system to focus separately on the first and second surfaces of the flow cell, when using a traditional imaging system. For improved imaging of the sequencing reaction of the nucleic acids from the cellular biological sample, the flow cell can be positioned in a high performance fluorescence imaging system, which comprises two or more tube lenses which are designed to provide optimal imaging performance for the first and second surfaces of the flow cell at two or more fluorescence wavelengths. In some embodiments, the high-performance imaging system further comprises a focusing mechanism configured to refocus the optical system between acquiring images of the first and second surfaces of the flow cell. In some embodiments, the high performance imaging system is configured to image two or more fields-of-view on at least one of the first flow cell surface or the second flow cell surface.

In some embodiments, the sequencing of step (g) comprises: contacting the plurality of nucleic acid concatemers with a plurality of sequencing primers, a plurality of polymerases, and a plurality of multivalent molecules, wherein each of the multivalent molecules comprise two or more duplicates of a nucleotide moiety that are connected to a core via a linker.

In some embodiments, the multivalent molecule comprises multiple nucleotides that are bound to a particle (or core) such as a polymer, a branched polymer, a dendrimer, a micelle, a liposome, a microparticle, a nanoparticle, a quantum dot, or other suitable particle known in the art.

In some embodiments, the multivalent molecule comprises: (1) a core, and (2) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms. In some embodiments, the spacer is attached to the linker. In some embodiments, the linker is attached to the nucleotide unit. In some embodiments, the nucleotide unit comprises a base, sugar and at least one phosphate group, and wherein the linker is attached to the nucleotide unit through the base. In some embodiments, the linker comprises an aliphatic chain or an oligo ethylene glycol chain where both linker chains having 2-6 subunits and optionally the linker includes an aromatic moiety.

In some embodiments, the multivalent molecule comprises a core attached to multiple nucleotide arms, and wherein the multiple nucleotide arms have the same type of nucleotide unit which is selected from a group consisting of dATP, dGTP, dCTP, dTTP and dUTP.

In some embodiments, the multivalent molecule further comprises a plurality of multivalent molecules which includes a mixture of multivalent molecules having two or more different types of nucleotides selected from a group consisting of dATP, dGTP, dCTP, dTTP and dUTP.

In some embodiments, the multivalent molecule comprises a core attached to multiple nucleotide arms, and wherein individual nucleotide arms comprise a nucleotide unit having a chain terminating moiety (e.g., blocking moiety) at the sugar 2' position, at the sugar 3' position, or at the sugar 2' and 3' position.

In some embodiments, the chain terminating moiety comprise an azide, azido or azidomethyl group. In some embodiments, the chain terminating moiety is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, the chain terminating moiety is cleavable/removable from the nucleotide unit.

In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, the multivalent molecule comprises a core attached to multiple nucleotide arms, wherein the core is labeled with detectable reporter moiety. In some embodiments, the detectable reporter moiety comprises a fluorophore.

In some embodiments, the core of the multivalent molecule comprises an avidin-like moiety and the core attachment moiety comprises biotin.

In some embodiments, the sequencing of step (g) comprises: (1) contacting the plurality of nucleic acid concatemers with (i) a plurality of polymerases, (ii) at least one multivalent molecule comprising two or more duplicates of a nucleotide moiety that are connected to a core via a linker, and (iii) a plurality of sequencing primers that hybridize with a portion of the concatemers, under a condition suitable for binding at least one polymerase and at least one sequencing primer to a portion of one of the nucleic acid concatemer molecules, and suitable for binding at least one of the nucleotide moieties of the multivalent molecule to the 3' end of the sequencing primer at a position that is opposite a complementary nucleotide in the concatemer molecule wherein the bound nucleotide moiety does not incorporate into the sequencing primer; (2) detecting and identifying the bound nucleotide moiety of the multivalent molecule thereby determining the sequence of the concatemer molecule; (3) optionally repeating steps (1) and (2) at least once; (4) contacting the concatemer molecule with (i) a plurality of polymerases, and (ii) a plurality of nucleotides, under a condition suitable binding at least one polymerase to at least a portion of the concatemer molecule and suitable for binding at least one of the nucleotides from the plurality to the 3' ends of the hybridized sequencing primers at a position that is opposite a complementary nucleotide in the concatemer molecule wherein the bound nucleotides incorporate into the hybridized sequencing primers; (5) optionally detecting the incorporated nucleotides; (6) optionally identifying the incorporation nucleotides thereby determining or confirming the sequence of the concatemer; and (7) repeating steps (1)-(6) at least once.

In some embodiments, the sequencing of step (g) comprises: (1) contacting the plurality of immobilized concatemers with a plurality of sequencing primers that hybridize with the sequencing primer binding sequence, a plurality of polymerases, and a plurality of nucleotides, under a condition suitable for binding at least one polymerase and at least one sequencing primer to a portion of the immobilized concatemer, and suitable for binding at least one of the nucleotides to the 3' end of the sequencing primer at a position that is opposite a complementary nucleotide in the immobilized concatemer wherein the bound nucleotide incorporates into the 3' end of the sequencing primer; (2) detecting and identifying the incorporated nucleotide thereby determining the sequence of the immobilized concatemer molecule; and (3) optionally repeating steps (1) and (2) at least once. In some embodiments, at least one of the nucleotides in the plurality of nucleotides comprises a chain terminating moiety at the sugar 2' or 3' position. In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

Capturing Nucleic Acids from A Single Cell and Analysis. The present disclosure provides a method for analyzing nucleic acids from a single cell (e.g., a cellular biological sample) wherein the single cell is placed in a cell media, and wherein the single cell includes cellular nucleic acids and polypeptides, and wherein the single cell includes a target nucleic acid that encodes a target polypeptide, the method comprising the general steps of: (a) providing a support comprising a low non-specific binding coating to which a plurality of capture oligonucleotides and optionally a plurality of circularization oligonucleotides are immobilized, wherein the plurality of immobilized capture oligonucleotides comprise (i) a target capture region that hybridizes to at least a portion of a target nucleic acid molecule, and (ii) a spatial barcode sequence, wherein the low non-specific binding coating comprises at least one hydrophilic polymer layer having a water contact angle of no more than 45 degrees.

In some embodiments, the low non-specific binding coating in step (a) exhibits low background fluorescence signals or high contrast to noise (CNR) ratios relative to known surfaces in the art. In some embodiments, the low non-specific binding coating exhibits a level of non-specific Cy3 dye absorption of less than about 0.25 molecules/$\mu m^2$, where no more than 5% of the target nucleic acid is associated with the surface coating without hybridizing to an immobilized capture oligonucleotide. In some embodiments, a fluorescence image of the surface coating having a plurality of clonally-amplified clusters of nucleic acid exhibits a contrast-to-noise ratio (CNR) of at least 20, or at least 50, or higher contrast-to-noise ratios (CNR), when using a fluorescence imaging system under non-signal saturating conditions.

In some embodiments, the low non-specific binding coating of step (a) has regions (e.g., features) located at predetermined locations on the coating. The low non-specific binding coating comprises a plurality of features including at least a first and second feature, where each feature includes a plurality of capture oligonucleotide and optionally a plurality of circularization oligonucleotides that are immobilized to the coating. In some embodiments, the first feature comprises a plurality of first capture oligonucleotides having a first target capture region and a first spatial barcode sequence. In some embodiments, the second feature comprises a plurality of second capture oligonucleotides having a second target capture region and a second spatial barcode sequence. In some embodiments, the sequence of the first target capture region in the first feature is the same or different from the sequence of the second target capture region in the second feature. In some embodiments, the first spatial barcode sequence in the first feature differs from the second spatial barcode sequence in the second feature.

In some embodiments, the single cell is placed in a cell media which comprises a complex cell media having a fluid obtained from a biological fluid which is selected from a group consisting of fetal bovine serum, blood plasma, blood serum, lymph fluid, human placental cord serum and amniotic fluid, and wherein the complex cell media can support cell growth and/or proliferation. In some embodiments, the complex cell media comprises a serum-containing media, a serum-free media, a chemically-defined media, or a protein-free media. In some embodiments, the complex cell media comprises RPMI-1640, MEM, DMEM or IMDM.

In some embodiments, the single cell is placed in a cell media which comprises a simple cell media which includes any one or any combination of two or more of a buffer, a phosphate compound, a sodium compound, a potassium compound, a calcium compound, a magnesium compound and/or glucose, and wherein the simple cell media cannot support cell growth and/or proliferation. In some embodiments, the simple cell media comprise PBS, DPBS, HBSS, DMEM, EMEM or EBSS.

In some embodiments, the method for analyzing nucleic acids from a single cell further comprise the step (b): contacting the low non-specific binding coating with the single cell in the presence of a high efficiency hybridization buffer under conditions suitable to promote migration of the cellular nucleic acids, including the target nucleic acid molecule, from the single cell to one of the immobilized capture oligonucleotides thereby forming an immobilized target nucleic acid duplex, wherein the target nucleic acid molecule from the single cell is immobilized to the low non-specific binding coating in a manner that preserves spatial location information of the target nucleic acid molecule in the single cell.

In some embodiments, the single cell in step (b) comprises a single cell sample that is fresh, frozen, fresh frozen, or archived (e.g., formalin-fixed paraffin-embedded; FFPE).

In some embodiments, the single cell in step (b) is subjected to a permeabilizing reaction to promote migration of the cellular nucleic acid molecules (e.g., DNA and/or RNA), including the target nucleic acid molecule, from the single cell to one of the immobilized capture oligonucleotides.

In some embodiments, the target nucleic acid comprises RNA. In some embodiments, the spatial location of the target RNA in the single cell corresponds to the spatial location of the target RNA which encodes the target polypeptide.

In some embodiments, the high efficiency high efficiency hybridization buffer of step (b) comprises: (i) a first polar aprotic solvent having a dielectric constant that is no greater than 40 and having a polarity index of 4-9; (ii) a second polar aprotic solvent having a dielectric constant that is no greater than 115 and is present in the high efficiency high efficiency hybridization buffer formulation in an amount effective to denature double-stranded nucleic acids; (iii) a pH buffer system that maintains the pH of the high efficiency high efficiency hybridization buffer formulation in a range of about 4-8; and (iv) a crowding agent in an amount sufficient to enhance or facilitate molecular crowding.

In some embodiments, the high efficiency high efficiency hybridization buffer of step (b) comprises: (i) the first polar aprotic solvent comprises acetonitrile at 25-50% by volume of the high efficiency high efficiency hybridization buffer; (ii) the second polar aprotic solvent comprises formamide at 5-10% by volume of the high efficiency high efficiency hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the high efficiency high efficiency hybridization buffer. In some embodiments, the high efficiency hybridization buffer further comprises betaine.

In some embodiments, the high efficiency high efficiency hybridization buffer of step (b) promotes high stringency (e.g., specificity), speed, and efficacy of nucleic acid hybridization reactions and increases the efficiency of the subsequent amplification and sequencing steps. In some embodiments, the high efficiency hybridization buffer significantly shortens nucleic acid hybridization times, and decreases sample input requirements. Nucleic acid annealing can be performed at isothermal conditions and eliminate the cooling step for annealing.

In some embodiments, the method for analyzing nucleic acids from a single cell further comprise the step (c): conducting a primer extension reaction on the immobilized target nucleic acid duplex thereby forming an immobilized target extension product.

In some embodiments, the primer extension reaction of step (c) can be a reverse transcription reaction which comprises (i) a reverse transcriptase enzyme, (ii) a plurality of nucleotides, and (iii) a plurality of reverse transcriptase primers that bind at least a portion of the target RNA. In some embodiments, the reverse transcription reaction of step (a) comprises a plurality of nucleotides and an enzyme having reverse transcription activity, including reverse transcriptase enzymes from AMV (avian myeloblastosis virus), M-MLV (moloney murine leukemia virus), or HIV (human immunodeficiency virus). In some embodiments, the reverse transcriptase can be a commercially-available enzyme, including MultiScribe™, ThermoScript™, or Array-Script™. In some embodiments, the reverse transcriptase enzyme comprises Superscript I, II, III, or IV enzymes. In some embodiments, the reverse transcription reaction can include an RNase inhibitor.

In some embodiments, the plurality of reverse transcription primers are resistant to ribonuclease degradation. For example, the reverse transcription primers can be modified to include two or more phosphorothioate bonds, or 2'-O-methyl, 2' fluoro-bases, phosphorylated 3' ends, or locked nucleic acid residues.

In some embodiments, the method for analyzing nucleic acids from a single cell further comprise the step (d): forming an open circular target molecule using the immobilized circularization oligonucleotide, or if the low non-specific binding coating does not already include an immobilized circularization oligonucleotide then immobilizing a soluble circularization oligonucleotide to the low non-specific binding coating in proximity to the immobilized target extension product and forming an open circular target molecule using the now-immobilized circularization oligonucleotide.

In some embodiments, the method for analyzing nucleic acids from a single cell further comprise the step (e): forming a covalently closed circular target molecule which is immobilized to the low non-specific binding coating.

In some embodiments, the forming the covalently closed circular target molecule comprises a polymerase-mediated gap-filling reaction, an enzymatic ligation reaction, or a polymerase-mediated gap-filling reaction and enzymatic ligation reaction. In some embodiments, the polymerase-mediate gap-filling reaction comprises contacting the open circular target molecule with a DNA polymerase and a plurality of nucleotides, where the DNA polymerase comprises E. coli DNA polymerase I, Klenow fragment of E. coli DNA polymerase I, T7 DNA polymerase, or T4 DNA polymerase. In some embodiments, the enzymatic ligation reaction comprises use of a ligase enzyme, including a T3, T4, T7 or Taq DNA ligase enzyme. In some embodiments, the forming the covalently closed circular target molecule comprises contacting the open circular target molecule with a CircLigase or CircLigase II enzyme.

In some embodiments, the method for analyzing nucleic acids from a single cell further comprise the step (f): conducting a rolling circle amplification reaction on the immobilized covalently closed circular target molecule to form an immobilized nucleic acid concatemer molecule having tandem repeat regions comprising the target sequence and the spatial barcode sequence.

In some embodiments, the rolling circle amplification reaction of step (f) comprises contacting the covalently closed circularized padlock probes (e.g., circularized nucleic acid template molecule(s)) with an amplification primer, a DNA polymerase, a plurality of nucleotides, and at least one catalytic divalent cation, under a condition suitable for generating at least one nucleic acid concatemer, wherein the at least one catalytic divalent cation comprises magnesium or manganese.

In some embodiments, the rolling circle amplification reaction of step (f) comprises: (1) contacting the covalently closed circularized padlock probes (e.g., circularized nucleic acid template molecule(s)) with an amplification primer, a DNA polymerase, a plurality of nucleotides, and at least one non-catalytic divalent cation that does not promote polymerase-catalyzed nucleotide incorporation into the amplification primer, wherein the non-catalytic divalent cation comprises strontium or barium; and (2) contacting the covalently closed circularized padlock probes with at least one catalytic divalent cation, under a condition suitable for generating at least one nucleic acid concatemer, wherein the at least one catalytic divalent cation comprises magnesium or manganese.

In some embodiments, the rolling circle amplification reaction of step (f) is conducted at a constant temperature (e.g., isothermal) ranging from room temperature to about 50° C.

In some embodiments, the rolling circle amplification reaction of step (f) can be conducted in the presence of a plurality of compaction oligonucleotides which compacts the size and/or shape of the immobilized concatemer to form an immobilized compact nanoball.

In some embodiments, the rolling circle amplification reaction of step (f) comprises a DNA polymerase having a strand displacing activity which is selected from a group consisting of phi29 DNA polymerase, large fragment of Bst DNA polymerase, large fragment of Bsu DNA polymerase, and Bca (exo-) DNA polymerase, Klenow fragment of E. coli DNA polymerase, T5 polymerase, M-MuLV reverse transcriptase, HIV viral reverse transcriptase, or Deep Vent DNA polymerase. In some embodiments, the phi29 DNA polymerase can be wild type phi29 DNA polymerase (e.g., MagniPhi from Expedeon), or variant EquiPhi29 DNA polymerase (e.g., from Thermo Fisher Scientific), and chimeric QualiPhi DNA polymerase (e.g., from 4basebio).

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with at least one amplification primer comprising a random sequence, a DNA polymerase having strand displacement activity, a plurality of nucleotides, and a catalytic divalent cation comprising magnesium or manganese.

In some embodiments, the rolling circle amplification reaction can be followed by a multiple displacement amplification (MDA) reaction. In some embodiments, the method further comprises: conducting a multiple displacement amplification (MDA) reaction prior to step (f), wherein the MDA reaction comprises contacting at least one nucleic acid concatemer with a DNA primase-polymerase enzyme, a DNA polymerase having strand displacement activity, a plurality of nucleotides, and a catalytic divalent cation comprising magnesium or manganese. In some embodiments, a DNA primase-polymerase comprises an enzyme having activities of a DNA polymerase and an RNA primase. A DNA primase-polymerase enzyme can utilize deoxyribonucleotide triphosphates to synthesize a DNA primer on a single-stranded DNA template in a template-sequence dependent manner, and can extend the primer strand via nucleotide polymerization (e.g., primer extension), in the presence of a catalytic divalent cation (e.g., magnesium and/or manganese). The DNA primase-polymerase include enzymes that are members of DnaG-like primases (e.g., bacteria) and AEP-like primases (Archaea and Eukaryotes). An exemplary DNA primase-polymerase enzyme is Tth PrimPol from *Thermus thermophilus* HB27.

In some embodiment, the rolling circle amplification reaction can be followed by a flexing amplification reaction instead of a multiple displacement amplification (MDA) reaction. In some embodiments, the flexing amplification reaction comprises: (1) forming a nucleic acid relaxant reaction mixture by contacting the nucleic acid concatemer with one or a combination of two or more compounds selected from a group consisting of formamide, acetonitrile, ethanol, guanidine hydrochloride, urea, potassium iodide and/or polyamines, to generate a relaxed nucleic acid concatemer, wherein the forming a nucleic acid relaxant reaction mixture is conducted with a temperature ramp-up, a relaxant incubation temperature, and a temperature ramp-down; (2) washing the relaxed concatemer; (3) forming a flexing amplification reaction mixture by contacting the relaxed concatemer with a strand-displacing DNA polymerase, a plurality of nucleotides, a catalytic divalent cation, (in the absence of added amplification primers), to generate double-stranded concatemers, wherein the forming a flexing amplification reaction mixture is conducted with a temperature ramp-up, a flexing incubation temperature, and a temperature ramp-down; (4) washing the double-stranded concatemer; and (5) repeating steps (1)-(4) at least once.

In some embodiments, the method for analyzing nucleic acids from a single cell further comprise the step (g): sequencing at least a portion of the nucleic acid concatemer, including sequencing the target sequence and the spatial barcode sequence, to determine the spatial location of the target nucleic acid in the single cell.

In some embodiments, the sequencing of step (g) comprises sequencing at least a portion of the nucleic acid concatemers using an optical imaging system comprising a field-of-view (FOV) greater than 1.0 mm$^2$. In some embodiments, the sequencing of step (g) includes placing the single cell in a flow cell having walls (e.g., top or first wall, and bottom or second wall) and a gap in-between, where the gap can be filled with a fluid, where the flow cell is positioned in a fluorescence optical imaging system. The single cell has a thickness that may require using the imaging system to focus separately on the first and second surfaces of the flow cell, when using a traditional imaging system. For improved imaging of the sequencing reaction of the nucleic acids from the single cell, the flow cell can be positioned in a high performance fluorescence imaging system, which comprises two or more tube lenses which are designed to provide optimal imaging performance for the first and second surfaces of the flow cell at two or more fluorescence wavelengths. In some embodiments, the high-performance imaging system further comprises a focusing mechanism configured to refocus the optical system between acquiring images of the first and second surfaces of the flow cell. In some embodiments, the high performance imaging system is configured to image two or more fields-of-view on at least one of the first flow cell surface or the second flow cell surface.

In some embodiments, the sequencing of step (g) comprises: contacting the plurality of nucleic acid concatemers with a plurality of sequencing primers, a plurality of polymerases, and a plurality of multivalent molecules, wherein each of the multivalent molecules comprise two or more duplicates of a nucleotide moiety that are connected to a core via a linker.

In some embodiments, the multivalent molecule comprises multiple nucleotides that are bound to a particle (or core) such as a polymer, a branched polymer, a dendrimer, a micelle, a liposome, a microparticle, a nanoparticle, a quantum dot, or other suitable particle known in the art.

In some embodiments, the multivalent molecule comprises: (1) a core, and (2) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms. In some embodiments, the spacer is attached to the linker. In some embodiments, the linker is attached to the nucleotide unit. In some embodiments, the nucleotide unit comprises a base, sugar and at least one phosphate group, and wherein the linker is attached to the nucleotide unit through the base. In some embodiments, the linker comprises an aliphatic chain or an oligo ethylene glycol chain where both linker chains having 2-6 subunits and optionally the linker includes an aromatic moiety.

In some embodiments, the multivalent molecule comprises a core attached to multiple nucleotide arms, and wherein the multiple nucleotide arms have the same type of nucleotide unit which is selected from a group consisting of dATP, dGTP, dCTP, dTTP and dUTP.

In some embodiments, the multivalent molecule further comprises a plurality of multivalent molecules which includes a mixture of multivalent molecules having two or more different types of nucleotides selected from a group consisting of dATP, dGTP, dCTP, dTTP and dUTP.

In some embodiments, the multivalent molecule comprises a core attached to multiple nucleotide arms, and wherein individual nucleotide arms comprise a nucleotide unit having a chain terminating moiety (e.g., blocking moiety) at the sugar 2' position, at the sugar 3' position, or at the sugar 2' and 3' position.

In some embodiments, the chain terminating moiety comprise an azide, azido or azidomethyl group. In some embodiments, the chain terminating moiety is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, the chain terminating moiety is cleavable/removable from the nucleotide unit.

In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, the multivalent molecule comprises a core attached to multiple nucleotide arms, wherein the core is labeled with detectable reporter moiety. In some embodiments, the detectable reporter moiety comprises a fluorophore.

In some embodiments, the core of the multivalent molecule comprises an avidin-like moiety and the core attachment moiety comprises biotin.

In some embodiments, the sequencing of step (g) comprises: (1) contacting the plurality of nucleic acid concatemers with (i) a plurality of polymerases, (ii) at least one multivalent molecule comprising two or more duplicates of a nucleotide moiety that are connected to a core via a linker, and (iii) a plurality of sequencing primers that hybridize with a portion of the concatemers, under a condition suitable for binding at least one polymerase and at least one sequencing primer to a portion of one of the nucleic acid concatemer molecules, and suitable for binding at least one of the nucleotide moieties of the multivalent molecule to the 3' end of the sequencing primer at a position that is opposite a complementary nucleotide in the concatemer molecule wherein the bound nucleotide moiety does not incorporate into the sequencing primer; (2) detecting and identifying the bound nucleotide moiety of the multivalent molecule thereby determining the sequence of the concatemer molecule; (3) optionally repeating steps (1) and (2) at least once; (4) contacting the concatemer molecule with (i) a plurality of polymerases, and (ii) a plurality of nucleotides, under a condition suitable binding at least one polymerase to at least a portion of the concatemer molecule and suitable for binding at least one of the nucleotides from the plurality to the 3' ends of the hybridized sequencing primers at a position that is opposite a complementary nucleotide in the concatemer molecule wherein the bound nucleotides incorporate into the hybridized sequencing primers; (5) optionally detecting the incorporated nucleotides; (6) optionally identifying the incorporation nucleotides thereby determining or confirming the sequence of the concatemer; and (7) repeating steps (1)-(6) at least once.

In some embodiments, the sequencing of step (g) comprises: (1) contacting the plurality of immobilized concatemers with a plurality of sequencing primers that hybridize with the sequencing primer binding sequence, a plurality of polymerases, and a plurality of nucleotides, under a condition suitable for binding at least one polymerase and at least one sequencing primer to a portion of the immobilized concatemer, and suitable for binding at least one of the nucleotides to the 3' end of the sequencing primer at a position that is opposite a complementary nucleotide in the immobilized concatemer wherein the bound nucleotide incorporates into the 3' end of the sequencing primer; (2) detecting and identifying the incorporated nucleotide thereby determining the sequence of the immobilized concatemer molecule; and (3) optionally repeating steps (1) and (2) at least once. In some embodiments, at least one of the nucleotides in the plurality of nucleotides comprises a chain terminating moiety at the sugar 2' or 3' position. In some embodiments, the chain terminating moiety is an azide, azido or azidomethyl group which are cleavable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP).

In some embodiments, in any of the sequencing steps can be conducted by performing a sequencing-by-binding procedure which comprises: (1) contacting a primed template nucleic acid (e.g., a primer hybridized to a nucleic acid concatemer) with a polymerase and a first combination of two or three types of test nucleotides under conditions that form a stabilized ternary complex between the polymerase, primed template nucleic acid and a test nucleotide that is complementary to the next base of the primed template nucleic acid; (2) detecting the ternary complex while precluding incorporation of test nucleotides into the primer; (3) repeating steps (1) and (2) using the primed template nucleic acid, a polymerase and a second combination of two or three types of test nucleotides, wherein the second combination is different from the first combination: (4) incorporating into the primer, after step (c), a nucleotide that is complimentary to the next base; and (5) repeating steps (1) through (4) to identify/determine the sequence of the primed template nucleic acid.

In some embodiments, the first combination of two or three types of test nucleotides includes two, and only two, types of test nucleotides. Optionally, the second combination can also include two, and only two, types of test nucleotides.

In some embodiments, steps (1) and (2) are carried out serially for four different combinations of two types of test nucleotides, wherein each different nucleotide type is contacted with the primed template nucleic acid two times in aggregate. Alternatively, steps (1) and (2) can be carried out serially for six different combinations of two types of test nucleotides, wherein each different nucleotide type is present three times in aggregate.

Further provided is a method of determining the identity of the next correct nucleotide for a primed template nucleic acid molecule (e.g., a primer hybridized to a nucleic acid concatemer). The method includes the steps of: (1) providing a template nucleic acid molecule primed with a primer (e.g., a primer hybridized to a nucleic acid concatemer); (2) contacting the primed template nucleic acid molecule from step (1) with a first reaction mixture including a polymerase and at least one test nucleotide under conditions that (i) stabilize ternary complexes including the primed template nucleic acid molecule, the polymerase and a next correct nucleotide, while precluding incorporation of any nucleotide into the primer, and (ii) destabilize binary complexes including the primed template nucleic acid molecule and the polymerase but not the next correct nucleotide; (3) detecting (e.g., monitoring) interaction of the polymerase with the primed template nucleic acid molecule without chemical incorporation of any nucleotide into the primer of the primed template nucleic acid molecule, to determine whether a ternary complex formed in step (2); and (4) determining whether any of the test nucleotides is the next correct nucleotide for the primed template nucleic acid molecule using the result of step (3). According to one generally preferred embodiment, the conditions that stabilize ternary complexes while precluding incorporation of any nucleotide into the primer can be provided by including in the first reaction mixture a non-catalytic metal ion that inhibits polymerization.

Single and multichannel fluorescence imaging modules and systems: Disclosed herein are single- and multichannel imaging systems that provide improved performance in terms of field-of-view, image resolution, image quality across the field-of-view, dual-surface imaging, imaging duty cycle time, and imaging throughput for genomics applications such as nucleic acid sequencing. In some instances, the imaging modules or systems disclosed herein may comprise fluorescence imaging modules or systems.

In some instances, the fluorescence imaging systems disclosed herein may comprise a single fluorescence excitation light source (for providing excitation light at a single wavelength or within a single excitation wavelength range) and an optical path configured to deliver the excitation light to a sample (e.g., fluorescently-tagged nucleic acid molecules or clusters thereof disposed on a substrate surface). In some instances, the fluorescence imaging systems disclosed herein may comprise a single fluorescence emission imaging and detection channel, e.g., an optical path configured to collect fluorescence emitted by the sample and deliver an image of the sample (e.g., an image of a substrate surface on which fluorescently-tagged nucleic acid molecules or clusters thereof are disposed) to an image sensor or other photodetection device. In some instances, the fluorescence imaging systems may comprise two, three, four, or more than four fluorescence excitation light sources and/or optical paths configured to deliver excitation light at two, three, four, or more than four excitation wavelengths (or within two, three, four, or more than four excitation wavelength ranges). In some instances, the fluorescence imaging systems disclosed herein may comprise two, three, four, or more than four fluorescence emission imaging and detection channels configured to collect fluorescence emitted by the sample at two, three, four, or more than four emission wavelengths (or within two, three, four, or more than four emission wavelength ranges and deliver an image of the sample (e.g., an image of a substrate surface on which fluorescently-tagged nucleic acid molecules or clusters thereof are disposed) to two, three, four, or more than four image sensors or other photodetection devices.

Figure 8A:
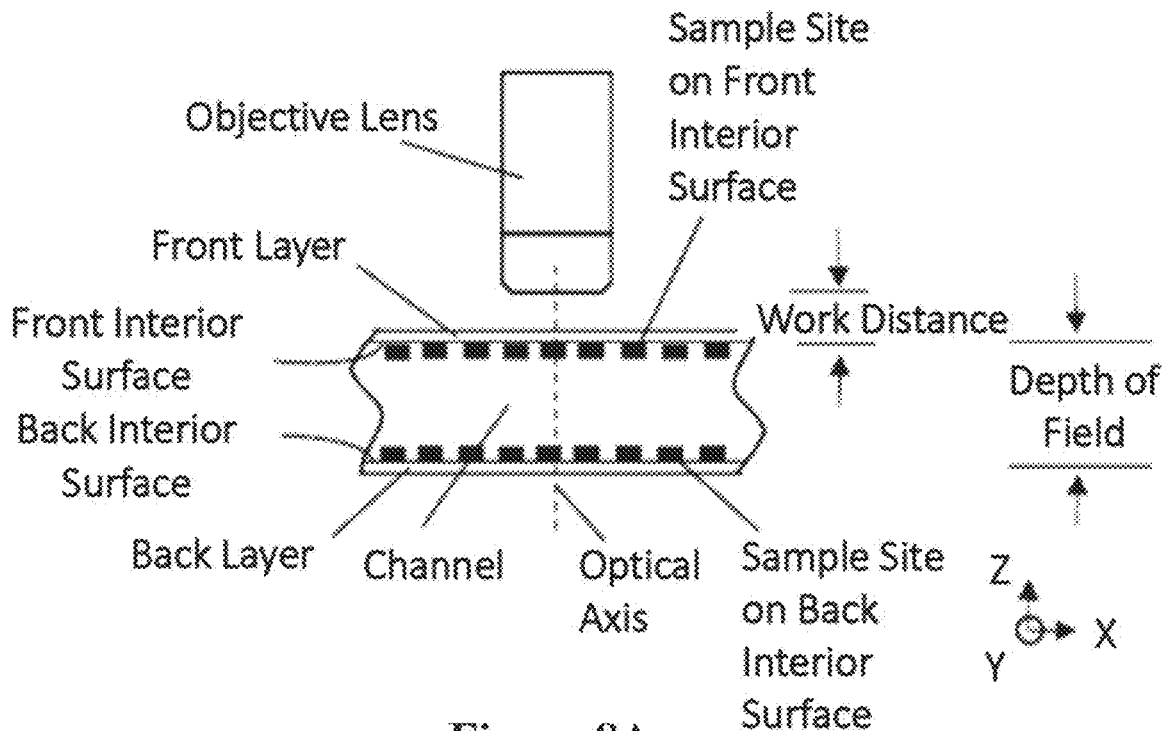
FIGS. 8A-8B schematically illustrate non-limiting examples of imaging dual surface support structures for presenting sample sites for imaging by the imaging systems disclosed herein.
Figure 8B:
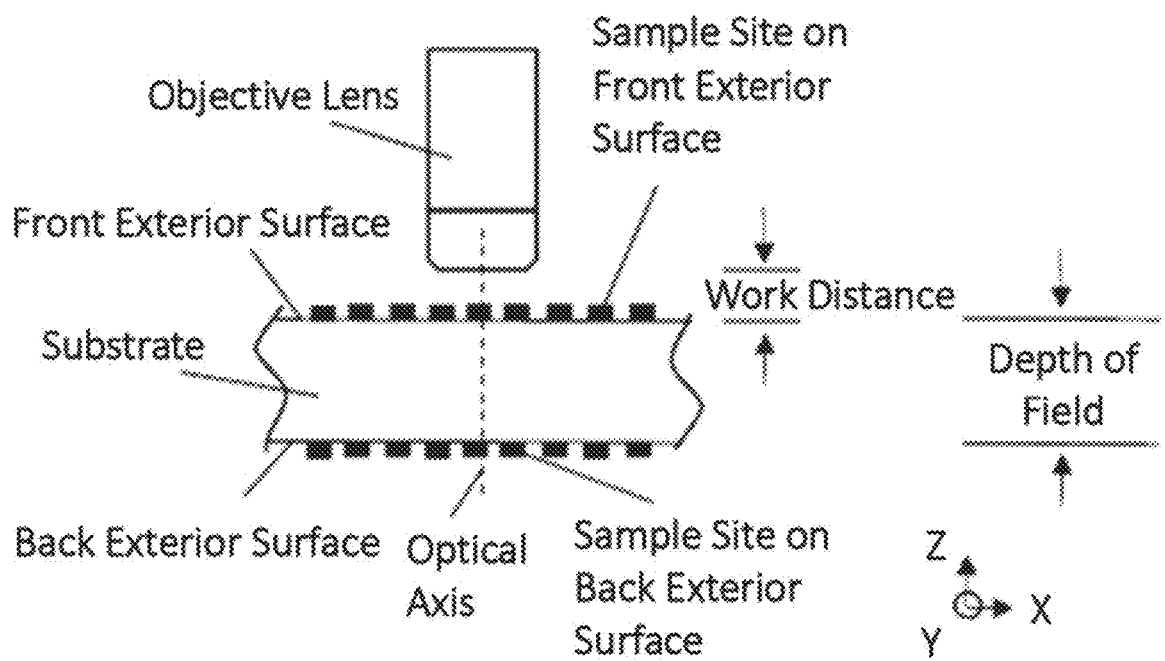

Dual surface imaging: In some instances, the imaging systems disclosed herein, including fluorescence imaging systems, may be configured to acquire high-resolution images of a single sample support structure or substrate surface. In some instances, the imaging systems disclosed herein, including fluorescence imaging systems, may be configured to acquire high-resolution images of two or more sample support structures or substrate surfaces, e.g., two or more surfaces of a flow cell. In some instances, the high-resolution images provided by the disclosed imaging systems may be used to monitor reactions occurring on the two or more surfaces of the flow cell (e.g., nucleic acid hybridization, amplification, and/or sequencing reactions) as various reagents flow through the flow cell or around a flow cell substrate. FIG. 8A and FIG. 8B provide schematic illustrations of such dual surface support structures. FIG. 8A shows a dual surface support structure such as a flow cell that includes an internal flow channel through which an analyte or reagent can be flowed. The flow channel may be formed between first and second, top and bottom, and/or front and back layers such as first and second, top and bottom, and/or front and back plates as shown. One or more of the plates may include a glass plate, such as a coverslip, or the like. In some implementations, the layer comprises borosilicate glass, quartz, or plastic. Interior surfaces of these top and bottom layers provide walls of the flow channel that assist in confining the flow of analyte or reagent through the flow channel of the flow cell. In some designs, these interior surfaces are planar. Similarly, the top and bottom layers may be planar. In some designs, at least one additional layer (not shown) is disposed between the top and bottom layers. This additional layer may have one or more pathways cut therein that assist in defining one or more flow channels and controlling the flow of the analyte or reagent within the flow channel. Additional discussion of sample support structures, e.g., flow cells, can be found below.

FIG. 8A schematically illustrates a plurality of fluorescing sample sites on the first and second, top and bottom, and/or front and back interior surfaces of the flow cell. In some implementations, reactions may occur at these at these sites to bind sample such that fluorescence is emitted from these sites (note that FIG. 8A is schematic and not drawn to scale; for example, the size and spacing of the fluorescing sample sites may be smaller than shown).

FIG. 8B shows another dual surface support structure having two surfaces containing fluorescing sample sites to be imaged. The sample support structure comprises a substrate having first and second, top and bottom, and/or front and back exterior surfaces. In some designs, these exterior surfaces are planar. In various implementations, the analyte or reagent is flowed across these first and second exterior surfaces. FIG. 8B schematically illustrates a plurality of fluorescing sample sites on the first and second, top and bottom, and/or front and back exterior surfaces of the sample support structure. In some implementations, reactions may occur at these at these sites to bind sample such that fluorescence is emitted from these sites (note that FIG. 8B is schematic and not drawn to scale; for example, the size and spacing of the fluorescing sample sites may be smaller than shown).

In some instances, the fluorescence imaging modules and systems described herein may be configured to image such fluorescing sample sites on first and second surfaces at different distances from the objective lens. In some designs, only one of the first or second surfaces is in focus at a time. Accordingly, in such designs, one of the surfaces is imaged at a first time, and the other surface is imaged at a second time. The focus of the fluorescence imaging module may be changed after imaging one of the surfaces in order to image the other surface with comparable optical resolution, as the images of the two surfaces are not simultaneously in focus. In some designs, an optical compensation element may be introduced into the optical path between the sample support structure and the image sensor in order to image one of the two surfaces. The depth of field in such fluorescence imaging configurations may not be sufficiently large to include both the first and second surfaces. In some implementations of the fluorescence imaging modules described herein, both the first and second surfaces may be imaged at the same time, i.e., simultaneously. For example, the fluorescence imaging module may have a depth of field that is sufficiently large to include both surfaces. In some instances, this increased depth of field may be provided by, for example, reducing the numerical aperture of the objective lens (or microscope objective) as will be discussed in more detail below.

As shown in FIGS. 8A and 8B, the imaging optics (e.g., an objective lens) may be positioned at a suitable distance (e.g., a distance corresponding to the working distance) from the first and second surfaces to form in-focus images of the first and second surfaces on an image sensor of a detection channel. As shown in the example of FIGS. 8A and 8B, the first surface may be between said objective lens and the second surface. For example, as illustrated, the objective lens is disposed above both the first and second surfaces, and the first surface is disposed above the second surface. The first and second surfaces, for example, are at different depths. The first and second surfaces are at different distances from any one or more of the fluorescence imaging module, the illumination and imaging module, imaging optics, or the objective lens. The first and second surfaces are separated from each other with the first surface spaced apart above the second surface. In the example shown, the first and second surfaces are planar surfaces and are separated from each other along a direction normal to said first and second planar surfaces. Also, in the example shown, said objective lens has an optical axis and said first and second surfaces are separated from each other along the direction of said optical axis. Similarly, the separation between the first and second surfaces may correspond to the longitudinal distance such as along the optical path of the excitation beam and/or along an optical axis through the fluorescence imaging module and/or the objective lens. Accordingly, these two surfaces may be separated by a distance from each other in the longitudinal (Z) direction, which may be along the direction of the central axis of the excitation beam and/or the optical axis of the objective lens and/or the fluorescence imaging module. This separation may correspond, for example, to a flow channel within a flow cell in some implementations.

In various designs, the objective lens (possibly in combination with another optical component, e.g., a tube lens) have a depth of field and/or depth of focus that is at least as large as the longitudinal separation (in the Z direction) between the first and second surfaces. The objective lens, alone or in combination with the additional optical component, may thus simultaneously form in-focus images of both the first and the second surface on an image sensor of one or more detection channels where these images have comparable optical resolution. In some implementations, the imaging module may or may not need to be re-focused to capture images of both the first and second surfaces with comparable optical resolution. In some implementations, compensation optics need not be moved into or out of an optical path of the imaging module to form in-focus images of the first and second surfaces. Similarly, in some implementations, one or more optical elements (e.g., lens elements) in the imaging module (e.g., the objective lens and/or a tube lens) need not be moved, for example, in the longitudinal direction along the first and/or second optical paths (e.g., along the optical axis of the imaging optics) to form in-focus images of the first surface in comparison to the location of said one or more optical element when used to form in-focus images of the second surface. In some implementations, however, the imaging module includes an autofocus system configured to provide both the first and second surface in focus at the same time. In various implementations, the sample is in focus to sufficiently resolve the sample sites, which are closely spaced together in lateral directions (e.g., the X and Y directions). Accordingly, in various implementations, no optical element enters an optical path between the sample support structure (e.g., between a translation stage that supports the sample support structure) and an image sensor (or photodetector array) in the at least one detection channel in order to form in-focus images of fluorescing sample sites on a first surface of the sample support structure and on a second surface of said sample support structure. Similarly, in various implementations, no optical compensation is used to form an in-focus image of fluorescing sample sites on a first surface of the sample support structure on the image sensor or photodetector array that is not identical to optical compensation used to form an in-focus image of fluorescing sample sites on a second surface of the sample support structure on the image sensor or photodetector array. Additionally, in certain implementations, no optical element in an optical path between the sample support structure (e.g., between a translation stage that supports the sample support structure) and an image sensor in the at least one detection channel is adjusted differently to form an in-focus image of fluorescing sample sites on a first surface of the sample support structure than to form an in-focus image of fluorescing sample sites on a second surface of the sample support structure. Similarly, in some various implementations, no optical element in an optical path between the sample support structure (e.g., between a translation stage that supports the sample support structure) and an image sensor in the at least one detection channel is moved a different amount or a different direction to form an in-focus image of fluorescing sample sites on the a first surface of the sample support structure on the image sensor than to form an in-focus image of fluorescing sample sites on a second surface of said sample support structure on the image sensor. Any combination of the features is possible. For example, in some implementations, in-focus images of the upper interior surface and the lower interior surface of the flow cell can be obtained without moving an optical compensator into or out of an optical path between the flow cell and the at least one image sensor and without moving one or more optical elements of the imaging system (e.g., the objective and/or tube lens) along the optical path (e.g., optical axis) therebetween. For example, in-focus images of the upper interior surface and the lower interior surface of the flow cell can be obtained without moving one or more optical elements of the tube lens into or out of the optical path, or without moving one or more optical elements of the tube lens along the optical path (e.g., optical axis) therebetween.

Any one or more of the fluorescence imaging module, the illumination optical path, the imaging optical path, the objective lens, or the tube lens may be designed to reduce or minimize optical aberration at two locations such as two planes corresponding to two surfaces on a flow cell or other sample support structure, for example, where fluorescing sample sites are located. Any one or more of the fluorescence imaging module, the illumination optical path, the imaging optical path, the objective lens, or the tube lens may be designed to reduce or minimize optical aberration at the selected locations or planes relative to other locations or planes, such as first and second surfaces containing fluorescing sample sites on a dual surface flow cell. For example, any one or more of the fluorescence imaging module, the illumination optical path, the imaging optical path, the objective lens, or the tube lens may be designed to reduce or minimize optical aberration at two depths or planes located at different distances from the objective lens as compared to the aberrations associated with other depths or planes at other distances from the objective lens. For example, optical aberration may be less for imaging the first and second surfaces than elsewhere in a region ranging from about 1 to about 10 mm from the objective lens. Additionally, any one or more of the fluorescence imaging module, the illumination optical path, the imaging optical path, the objective lens, or the tube lens may, in some instances, be configured to compensate for optical aberration induced by transmission of emission light through one or more portions of the sample support structure such as a layer that includes one of the surfaces on which sample adheres as well as possibly a solution that is in contact with the sample. This layer (e.g., a coverslip or the wall of a flow cell) may comprise, e.g., glass, quartz, plastic, or other transparent material having a refractive index and that introduces optical aberration.

Accordingly, the imaging performance may be substantially the same when imaging the first surface and second surface. For example, the optical transfer functions (OTF) and/or modulation transfer functions (MTF) may be the substantially the same for imaging of the first and second surfaces. Either or both of these transfer functions may, for example, be within 200%, within 15%, within 10%, within 5%, within 2.5%, or within 1% of each other, or within any range formed by any of these values at one or more specified spatial frequencies or when averaged over a range of spatial frequencies. Accordingly, an imaging performance metric may be substantially the same for imaging the upper interior surface or the lower interior surface of the flow cell without moving an optical compensator into or out of an optical path between the flow cell and the at least one image sensor, and without moving one or more optical elements of the imaging system (e.g., the objective and/or tube lens) along the optical path (e.g., optical axis) therebetween. For example, an imaging performance metric may be substantially the same for imaging the upper interior surface or the lower interior surface of the flow cell without moving one or more optical elements of the tube lens into or out of the optical path or without moving one or more optical elements of the tube lens along the optical path (e.g., optical axis) therebetween. Additional discussion of MTF is included below and in U.S. Provisional Application No. 62/962,723 filed Jan. 17, 2020, which is incorporated herein by reference in its entirety.

It will be understood by those of skill in the art that the disclosed imaging modules or systems may, in some instances, be stand-alone optical systems designed for imaging a sample or substrate surface. In some instances, they may comprise one or more processors or computers. In some instances, they may comprise one or more software packages that provide instrument control functionality and/or image processing functionality. In some instances, in addition to optical components such as light sources (e.g., solid-state lasers, dye lasers, diode lasers, arc lamps, tungsten-halogen lamps, etc.), lenses, prisms, mirrors, dichroic reflectors, beam splitters, optical filters, optical bandpass filters, light guides, optical fibers, apertures, and image sensors (e.g., complementary metal oxide semiconductor (CMOS) image sensors and cameras, charge-coupled device (CCD) image sensors and cameras, etc.), they may also include mechanical and/or optomechanical components, such as X-Y translation stages, X-Y-Z translation stages, piezoelectric focusing mechanisms, electro-optical phase plates, and the like. In some instances, they may function as modules, components, sub-assemblies, or sub-systems of larger systems designed for, e.g., genomics applications (e.g., genetic testing and/or nucleic acid sequencing applications). For example, in some instances, they may function as modules, components, sub-assemblies, or sub-systems of larger systems that further comprise light-tight and/or other environmental control housings, temperature control modules, flow cells and cartridges, fluidics control modules, fluid dispensing robotics, cartridge- and/or microplate-handling (pick-and-place) robotics, one or more processors or computers, one or more local and/or cloud-based software packages (e.g., instrument/system control software packages, image processing software packages, data analysis software packages), data storage modules, data communication modules (e.g., Bluetooth, WiFi, intranet, or internet communication hardware and associated software), display modules, etc., or any combination thereof. These additional components of larger systems, e.g., systems designed for genomics applications, will be discussed in more detail below.

Figure 9A:
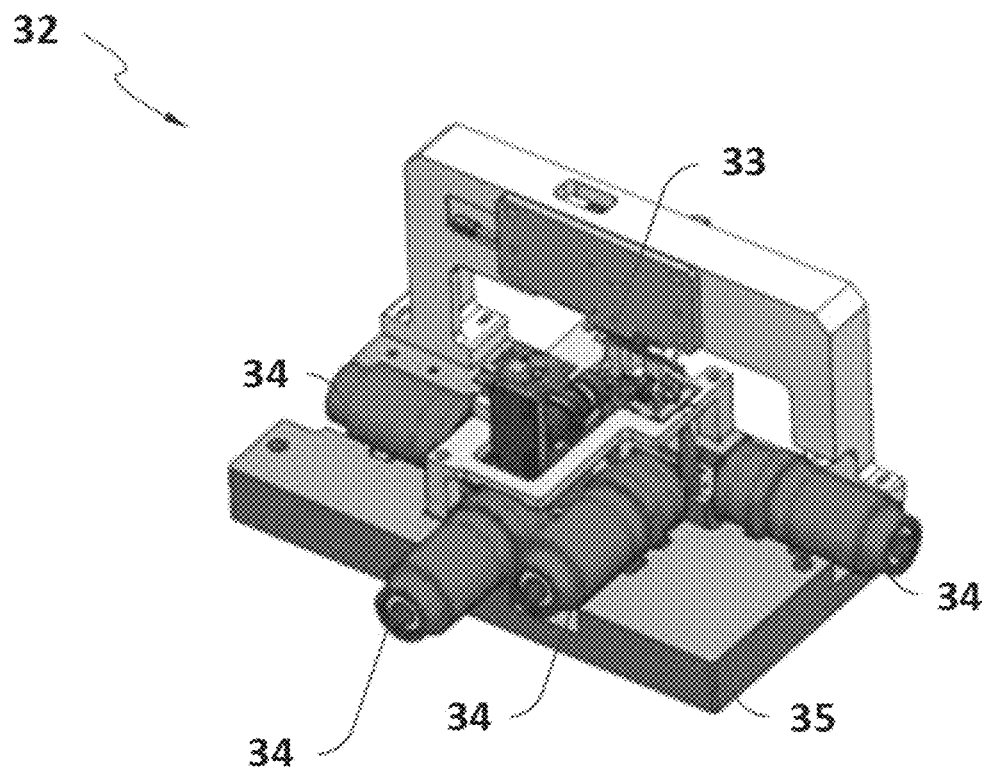
FIGS. 9A-9B illustrate a non-limiting example of a multi-channel fluorescence imaging module comprising a dichroic beam splitter for transmitting an excitation light beam to a sample, and for receiving and redirecting by reflection the resultant fluorescence emission to four detection channels configured for detection of fluorescence emission at four different respective wavelengths or wavelength bands.
Figure 9B:
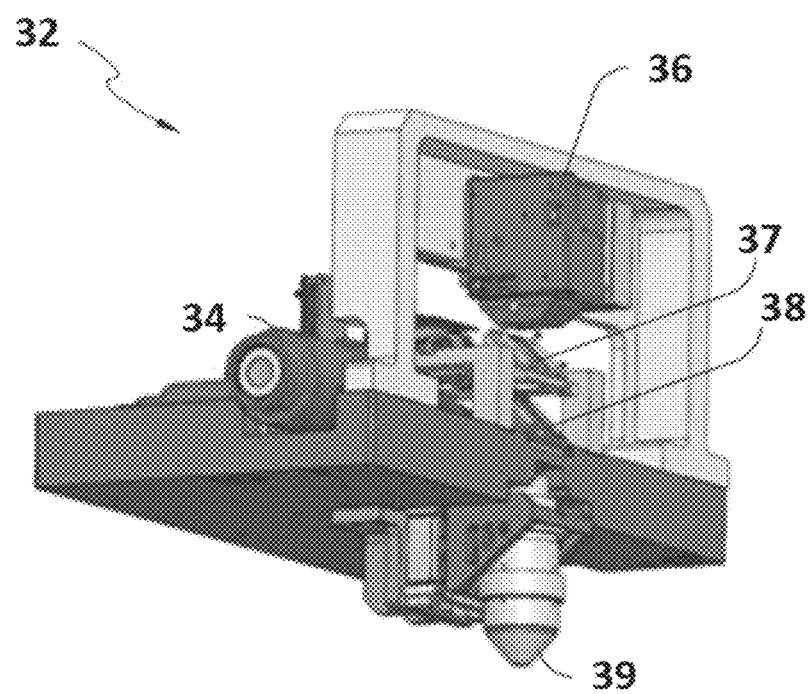

FIGS. 9A and 9B illustrate a non-limiting example of an illumination and imaging module 32 for multi-channel fluorescence imaging. The illumination and imaging module 32 includes an objective lens 39, an illumination source 36, a plurality of detection channels 34, and a first dichroic filter 38, which may comprise a dichroic reflector or beam splitter. An autofocus system, which may include an autofocus laser 33, for example, that projects a spot the size of which is monitored to determine when the imaging system is in-focus may be included in some designs. Some or all components of the illumination and imaging module 32 may be coupled to a baseplate 35.

The illumination or light source 36 may include any suitable light source configured to produce light of at least a desired excitation wavelength (discussed in more detail below). The light source may be a broadband source that emits light within one or more excitation wavelength ranges (or bands). The light source may be a narrowband source that emits light within one or more narrower wavelength ranges. In some instances, the light source may produce a single isolated wavelength (or line) corresponding to the desired excitation wavelength, or multiple isolated wavelengths (or lines). In some instances, the lines may have some very narrow bandwidth. Example light sources that may be suitable for use in the illumination source 36 include, but are not limited to, an incandescent filament, xenon arc lamp, mercury-vapor lamp, a light-emitting diode, a laser source such as a laser diode or a solid-state laser, or other types of light sources. As discussed below, in some designs, the light source may comprise a polarized light source such as a linearly polarized light source. In some implementations, the orientation of the light source is such that s-polarized light is incident on one or more surfaces of one or more optical components such as the dichroic reflective surface of one or more dichroic filters.

The illumination source 36 may further include one or more additional optical components such as lenses, filters, optical fibers, or any other suitable transmissive or reflective optics as appropriate to output an excitation light beam having suitable characteristics toward a first dichroic filter 38. For example, beam shaping optics may be included, for example, to receive light from a light emitter in the light source and produce a beam and/or provide a desired beam characteristic. Such optics may, for example, comprise a collimating lens configured to reduce the divergence of light and/or increase collimation and/or to collimate the light.

In some implementations, multiple light sources are included in the illumination and imaging module 32. In some such implementations, different light sources may produce light having different spectral characteristics, for example, to excite different fluorescence dyes. In some implementations, light produced by the different light sources may directed to coincide and form an aggregate excitation light beam. This composite excitation light beam may be composed of excitation light beams from each of the light sources. The composite excitation light beam will have more optical power than the individual beams that overlap to form the composite beam. For example, in some implementations that include two light sources that produce two excitation light beams, the composite excitation light beam formed from the two individual excitation light beams may have optical power that is the sum of the optical power of the individual beams. Similarly, in some implementations, three, four, five or more light sources may be included, and these light sources may each output excitation light beams that together form a composite beam that that has an optical power that is the sum of the optical power of the individual beams.

In some implementations, the light source 36 outputs a sufficiently large amount of light to produce sufficiently strong fluorescence emission. Stronger fluorescence emission can increase the signal-to-noise ratio (SNR) and the contrast-to-noise ratio (CNR) of images acquired by the fluorescence imaging module. In some implementations, the output of the light source and/or an excitation light beam derived therefrom (including a composite excitation light beam) may range in power from about 0.5 W to about 5.0 W, or more (as will be discussed in more detail below).

Referring again to FIGS. 9A and 9B, the first dichroic filter 38 is disposed with respect to the light source to receive light therefrom. The first dichroic filter may comprise a dichroic mirror, dichroic reflector, dichroic beam splitter, or dichroic beam combiner configured to transmit light in a first spectral region (or wavelength range) and reflect light having a second spectral region (or wavelength range). The first spectral region may include one or more spectral bands, e.g., one or more spectral bands in the ultraviolet and blue wavelength ranges. Similarly, a second spectral region may include one or more spectral bands, e.g., one or more spectral bands extending from the green to red and infrared wavelengths. Other spectral regions or wavelength ranges are also possible.

In some implementations, the first dichroic filter may be configured to transmit light from the light source to a sample support structure such as to a microscope slide, a capillary, a flow cell, a microfluidic chip, or other substrate or support structure. The sample support structure supports and positions the sample, e.g., a composition comprising a fluorescently-labeled nucleic acid molecule or complement thereof, with respect to the illumination and imaging module 32. Accordingly, a first optical path extends from the light source to the sample via the first dichroic filter. In various implementations, the sample support structure includes at least one surface on which the sample is disposed or to which the sample binds. In some instances, the sample may be disposed within or bound to different localized regions or sites on the at least one surface of the sample support structure.

In some instances, the support structure may include two surfaces located at different distances from objective lens 39 (i.e., at different positions or depths along the optical axis of objective lens 39) on which the sample is disposed. As discussed below, for example, a flow cell may comprise a fluid channel formed at least in part by first and second (e.g., upper and lower) interior surfaces, and the sample may be disposed at localized sites on the first interior surface, the second interior surface, or both interior surfaces. The first and second surface may be separated by the region corresponding to the fluid channel through which a solution flows, and thus be at different distances or depth with respect to objective lens 39 of the illumination and imaging module 32.

The objective lens 39 may be included in the first optical path between the first dichroic filter and the sample. This objective lens may be configured, for example, to have a focal length, working distance, and/or be positioned to focus light from the light source(s) onto the sample, e.g., onto a surface of the microscope slide, capillary, flow cell, microfluidic chip, or other substrate or support structure. Similarly, the objective lens 39 may be configured to have suitable focal length, working distance, and/or be positioned to collect light reflected, scattered, or emitted from the sample (e.g., fluorescence emission) and to form an image of the sample (e.g., a fluorescence image).

In some implementations, objective lens 39 may comprise a microscope objective such as an off-the-shelf objective. In some implementations, objective lens 39 may comprise a custom objective. An example of a custom objective lens and/or custom objective—tube lens combination is described below and in U.S. Provisional Application No. 62/962,723 filed on Jan. 17, 2020, which is incorporated herein by reference in its entirety. The objective lens 39 may be designed to reduce or minimize optical aberration at two locations such as two planes corresponding to two surfaces of a flow cell or other sample support structure. The objective lens 39 may be designed to reduce the optical aberration at the selected locations or planes, e.g., the first and second surfaces of a dual surface flow cell, relative to other locations or planes in the optical path. For example, the objective lens 39 may be designed to reduce the optical aberration at two depths or planes located at different distances from the objective lens as compared to the optical aberrations associated with other depths or planes at other distances from the objective. For example, in some instances, optical aberration may be less for imaging the first and second surfaces of a flow cell than that exhibited elsewhere in a region spanning from 1 to 10 mm from the front surface of the objective lens. Additionally, a custom objective lens 39 may in some instances be configured to compensate for optical aberration induced by transmission of fluorescence emission light through one or more portions of the sample support structure, such as a layer that includes one or more of the flow cell surfaces on which a sample is disposed, or a layer comprising a solution filling the fluid channel of a flow cell. These layers may comprise, e.g., glass, quartz, plastic, or other transparent material having a refractive index, and which may introduce optical aberration.

In some implementations, objective lens 39 may have a numerical aperture (NA) of 0.6 or more (as discussed in more detail below). Such a numerical aperture may provide for reduced depth of focus and/or depth of field, improved background discrimination, and increased imaging resolution.

In some implementations, objective lens 39 may have a numerical aperture (NA) of 0.6 or less (as discussed in more detail below). Such a numerical aperture may provide for increased depth of focus and/or depth of field. Such increased depth of focus and/or depth of field may increase the ability to image planes separated by a distance such as that that separates the first and second surfaces of a dual surface flow cell.

As discussed above, a flow cell may comprise, for example, first and second layers comprising first and second interior surfaces respectively that are separated by a fluid channel through which an analyte or reagent can flow. In some implementations, the objective lens 39 and/or illumination and imaging module 32 may be configured to provide a depth of field and/or depth of focus sufficiently large to image both the first and second interior surfaces of the flow cell, either sequentially by re-focusing the imaging module between imaging the first and second surfaces, or simultaneously by ensuring a sufficiently large depth of field and/or depth of focus, with comparable optical resolution. In some instances, the depth of field and/or depth of focus may be at least as large or larger than the distance separating the first and second surfaces of the flow cell to be imaged, such as the first and second interior surfaces of the flow cell. In some instances, the first and second surfaces, e.g., the first and second interior surfaces of a dual surface flow cell or other sample support structure, may be separated, for example, by a distance ranging from about 10 µm to about 700 µm, or more (as will be discussed in more detail below). In some instances, the depth of field and/or depth of focus may thus range from about 10 µm to about 700 µm, or more (as will be discussed in more detail below).

In some designs, compensation optics (e.g., an "optical compensator" or "compensator") may be moved into or out of an optical path in the imaging module, for example, an optical path by which light collected by the objective lens 39 is delivered to an image sensor, to enable the imaging module to image the first and second surfaces of the dual surface flow cell. The imaging module may be configured, for example, to image the first surface when the compensation optics is included in the optical path between the objective lens and an image sensor or photodetector array configured to capture an image of the first surface. In such a design, the imaging module may be configured to image the second surface when the compensation optics is removed from or not included in the optical path between the objective lens 39 and the image sensor or photodetector array configured to capture an image of the second surface. The need for an optical compensator may be more pronounced when using an objective lens 39 with a high numerical aperture (NA) value, e.g., for numerical aperture values of at least 0.6, least 0.65, at least 0.7, at least 0.75, at least 0.8, at least 0.85, at least 0.9, at least 0.95, at least 1.0, or higher. In some implementations, the optical compensation optics (e.g., an optical compensator or compensator) comprises a refractive optical element such as a lens, a plate of optically-transparent material such as glass, a plate of optically-transparent material such as glass, or in the case of polarized light beams, a quarter-wave plate or half-wave plate, etc. Other configurations may be employed to enable the first and second surfaces to be imaged at different times. For example, one or more lenses or optical elements may be configured to be translated in and out of, or along, an optical path between the objective lens 39 and the image sensor.

In certain designs, however, the objective lens 39 is configured to provide sufficiently large depth of focus and/or depth of field to enable the first and second surfaces to be imaged with comparable optical resolution without such compensation optics moving into and out of an optical path in the imaging module, such as an optical path between the objective lens and the image sensor or photodetector array. Similarly, in various designs, the objective lens 39 is configured to provide sufficiently large depth of focus and/or depth of field to enable the first and second surfaces to be imaged with comparable optical resolution without optics being moved, such as one or more lenses or other optical components being translated along an optical path in the imaging module, such as an optical path between the objective lens and the image sensor or photodetector array. Examples of such objective lenses will be described in more detail below.

In some implementations, the objective lens (or microscope objective) 39 may be configured to have reduced magnification. The objective lens 39 may be configured, for example, such that the fluorescence imaging module has a magnification of from less than 2× to less than 10× (as will be discussed in more detail below). Such reduced magnification may alter design constraints such that other design parameters can be achieved. For example, the objective lens 39 may also be configured such that the fluorescence imaging module has a large field-of-view (FOV) ranging, for example, from about 1.0 mm to about 5.0 mm (e.g., in diameter, width, length, or longest dimension) as will be discussed in more detail below.

In some implementations, the objective lens 39 may be configured to provide the fluorescence imaging module with a field-of-view as indicated above such that the FOV has diffraction-limited performance, e.g., less than 0.15 waves of aberration over at least 60%, 70%, 80%, 900, or 95% of the field, as will be discussed in more detail below.

In some implementations, the objective lens 39 may be configured to provide the fluorescence imaging module with a field-of-view as indicated above such that the FOV has diffraction-limited performance, e.g., a Strehl ratio of greater than 0.8 over at least 60%, 70%, 80%, 90%, or 95% of the field, as will be discussed in more detail below.

Referring again to FIGS. 9A and 9B, the first dichroic beam splitter or beam combiner is disposed in the first optical path between the light source and the sample so as to illuminate the sample with one or more excitation beams. This first dichroic beam splitter or combiner is also in one or more second optical path(s) from the sample to the different optical channels used to detect the fluorescence emission. Accordingly, the first dichroic filter 38 couples the first optical path of the excitation beam emitted by the illumination source 36 and second optical path of the emission light emitted by a sample specimen to the various optical channels where the light is directed to respective image sensors or photodetector arrays for capturing images of the sample.

In various implementations, the first dichroic filter 38, e.g., first dichroic reflector or beam splitter or beam combiner, has a passband selected to transmit light from the illumination source 36 only within a specified wavelength band or possibly a plurality of wavelength bands that include the desired excitation wavelength or wavelengths. For example, the first dichroic beam splitter 38 includes a reflective surface comprising a dichroic reflector that has spectral transmissivity response that is, e.g., configured to transmit light having at least some of the wavelengths output by the light source that form part of the excitation beam. The spectral transmissivity response may be configured not to transmit (e.g., instead to reflect) light of one or more other wavelengths, for example, of one or more other fluorescence emission wavelengths. In some implementations, the spectral transmissivity response may also be configured not to transmit (e.g., instead to reflect) light of one or more other wavelengths output by the light source. Accordingly, the first dichroic filter 38 may be utilized to select which wavelength or wavelengths of light output by the light source reach the sample. Conversely, the dichroic reflector in the first dichroic beam splitter 38 has a spectral reflectivity response that reflects light having one or more wavelengths corresponding to the desired fluorescence emission from the sample and possible reflects light having one or more wavelengths output from the light source that is not intended to reach the sample. Accordingly, in some implementations, the dichroic reflector has a spectral transmissivity that includes one or more pass bands to transmit the light to be incident on the sample and one or more stop bands that reflects light outside the pass bands, for example, light at one or more emission wavelengths and possibly one or more wavelengths output by the light source that are not intended to reach the sample. Likewise, in some implementations the dichroic reflector has a spectral reflectivity that includes one or more spectral regions configured to reflect one or more emission wavelengths and possible one or more wavelengths output by the light source that are not intended to reach the sample and includes one or more regions that transmit light outside these reflection regions. The dichroic reflector included in the first dichroic filter 38 may comprise a reflective filter such as an interference filter (e.g., a quarter-wave stack) configured to provide the appropriate spectral transmission and reflection distributions. FIGS. 9A and 9B also show a dichroic filter 38, which may comprise for example a dichroic beam splitter or beam combiner, that may be used to direct the autofocus laser 33 though the objective and to the sample support structure.

Although the imaging module 32 shown in FIGS. 9A and 9B and discussed above is configured such that the excitation beam is transmitted by the first dichroic filter 38 to the objective lens 39, in some designs the illumination source 36 may be disposed with respect to the first dichroic filter 38 and/or the first dichroic filter is configured (e.g., oriented) such that the excitation beam is reflected by the first dichroic filter 38 to the objective lens 39. Similarly, in some such designs, the first dichroic filter 38 is configured to transmit fluorescence emission from the sample and possibly transmit light having one or more wavelengths output from the light source that is not intended to reach the sample. As will be discussed below, a design where the fluorescence emission is transmitted instead of reflected may potentially reduce wavefront error in the detected emission and/or possibly have other advantages. In either case, in various implementations the first dichroic reflector 38 is disposed in the second optical path so as to receive fluorescence emission from the sample, at least some of which continues on to the detection channels 34.

Figure 10A:
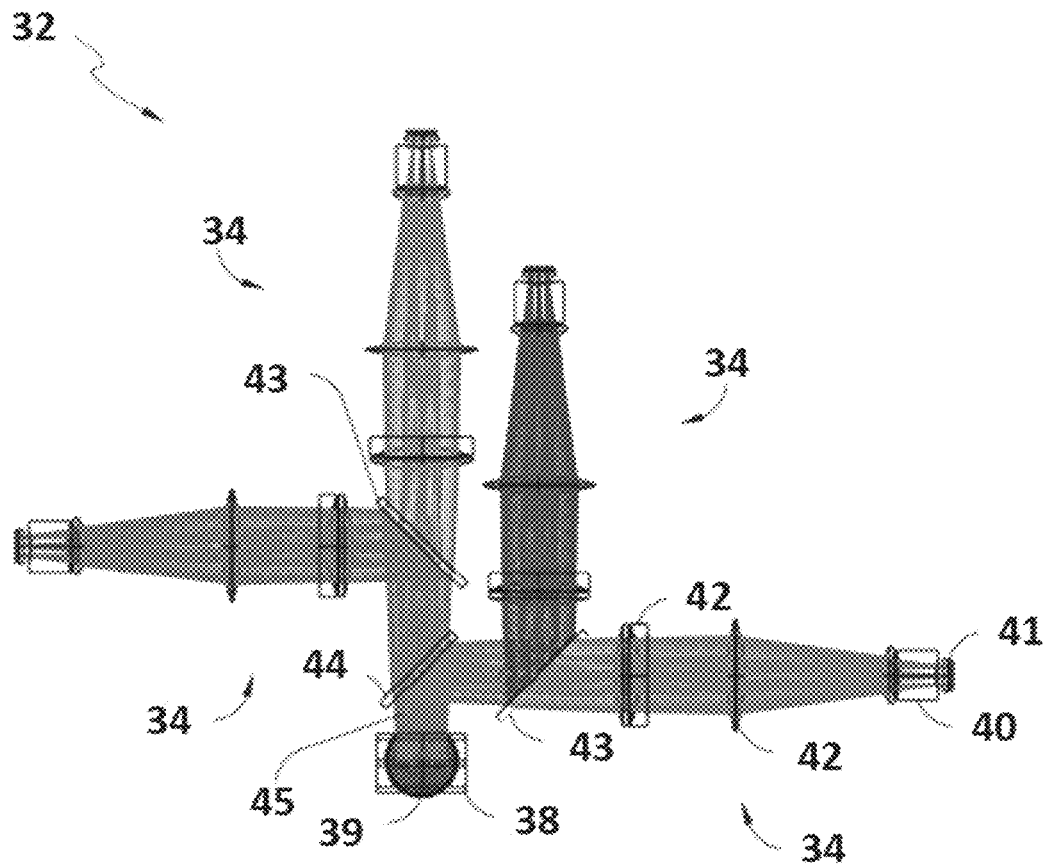
FIGS. 10A-10B illustrate the optical paths within the multi-channel fluorescence imaging module of FIGS. 10A and 10B comprising a dichroic beam splitter for transmitting an excitation light beam to a sample, and for receiving and redirecting by reflection a resultant fluorescence emission to four detection channels for detection of fluorescence emission at four different respective wavelengths or wavelength bands.
Figure 10B:
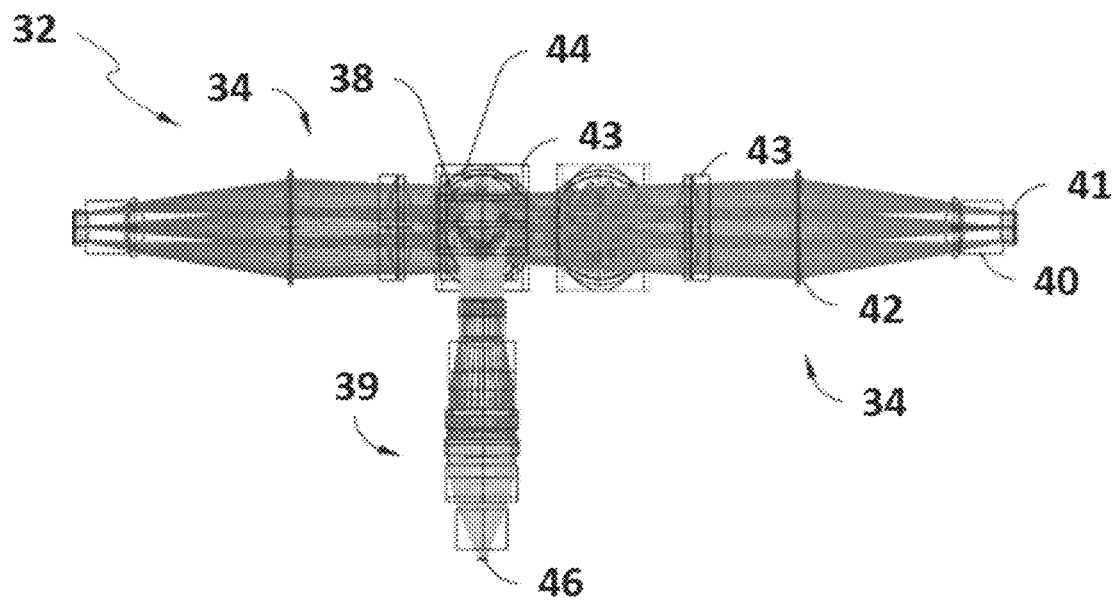

FIGS. 10A and 10B illustrate the optical paths within the multi-channel fluorescence imaging module of FIGS. 10A and 10B. In the example show in FIG. 10A and FIG. 10A, the detection channels 34 are disposed to receive fluorescence emission from a sample specimen that is transmitted by the objective lens 39 and reflected by the first dichroic filter 38. As referred to above and described more below, in some designs the detection channels 34 may be disposed to receive the portion of the emission light that is transmitted, rather than reflected, by the first dichroic filter. In either case, the detection channels 34 may include optics for receiving at least a portion of the emission light. For example, the detection channels 34 may include one or more lenses, such as tube lenses, and may include one or more image sensors or detectors such as photodetector arrays (e.g., CCD or CMOS sensor arrays) for imaging or otherwise producing a signal based on the received light. The tube lenses may, for example, comprise one or more lens elements configured to form an image of the sample onto the sensor or photodetector array to capture an image thereof. Additional discussion of detection channels is included below and in U.S. Provisional Application No. 62/962,723, filed Jan. 17, 2020, which is incorporated herein by reference in its entirety. In some instances, improved optical resolution may be achieved using an image sensor having relatively high sensitivity, small pixels, and high pixel count, in conjunction with a suitable sampling scheme, which may include oversampling or undersampling.

FIGS. 10A and 10B are ray tracing diagrams illustrating optical paths of the illumination and imaging module 32 of FIGS. 9A and 9B. FIG. 10A corresponds to a top view of the illumination and imaging module 32. FIG. 10B corresponds to a side view of the illumination and imaging module 32. The illumination and imaging module 32 illustrated in these figures includes four detection channels 34. However, it will be understood that the disclosed illumination and imaging modules may equally be implemented in systems including more or fewer than four detection channels 34. For example, the multi-channel systems disclosed herein may be implemented with as few as one detection channel 34, or as many as two detection channels 34, three detection channels 34, four detection channels 34, five detection channels 34, six detection channels 34, seven detection channels 34, eight detection channels 34, or more than eight detection channels 34, without departing from the spirit or scope of the present disclosure.

The non-limiting example of imaging module 32 illustrated in FIGS. 10A and 10B includes four detection channels 34, a first dichroic filter 38 that reflects a beam 45 of emission light, a second dichroic filter (e.g., a dichroic beam splitter) 44 that splits the beam 45 into a transmitted portion and a reflected portion, and two channel-specific dichroic filters (e.g., dichroic beam splitters) 43 that further split the transmitted and reflected portions of the beam 45 among individual detection channels 34. The dichroic reflecting surface in the dichroic beam splitters 44 and 43 for splitting the beam 45 among detection channels are shown disposed at 45 degrees relative to a central beam axis of the beam 45 or an optical axis of the imaging module. However, as discussed below, an angle smaller than 45 degrees may be employed and may offer advantages such as sharper transitions from pass band to stop band.

The different detection channels 34 includes imaging devices 41, which may include an image sensor or photodetector array (e.g., a CCD or CMOS detector array). The different detection channels 34 further include optics 42 such as lenses (e.g., one or more tube lenses each comprising one or more lens elements) disposed to focus the portion of the emission light entering the detection channel 34 at a focal plane coincident with a plane of the photodetector array 41. The optics 42 (e.g., a tube lens) combined with the objective lens 39 are configured to form an image of the sample onto the photodetector array 41 to capture an image of the sample, for example, an image of a surface on the flow cell or other sample support structure after the sample has bound to that surface. Accordingly, such an image of the sample may comprise a plurality of fluorescent emitting spots or regions across a spatial extent of the sample support structure where the sample is emitting fluorescence light. The objective lens 39 together with the optics 42 (e.g., tube lens) may provide a field of view (FOV) that includes a portion of the sample or the entire sample. Similarly, the photodetector array 41 of the different detection channels 34 may be configured to capture images of a full field of view (FOV) provided by the objective lens and the tube lens, or a portion thereof. In some implementations, the photodetector array 41 of some or all detection channels 34 can detect the emission light emitted by a sample disposed on the sample support structure, e.g., a surface of the flow cell, or a portion thereof and record electronic data representing an image thereof. In some implementations, the photodetector array 41 of some or all detection channels 34 can detect features in the emission light emitted by a specimen without capturing and/or storing an image of the sample disposed on the flow cell surface and/or of the full field of view (FOV) provided by the objective lens and optics 42 and/or 40 (e.g., elements of a tube lens). In some implementations, the FOV of the disclosed imaging modules (e.g., that provided by the combination of objective lens 39 and optics 42 and/or 40) may range, for example, between about 1 mm and 5 mm (e.g., in diameter, width, length, or longest dimension) as will be discussed below. The FOV may be selected, for example, to provide a balance between magnification and resolution of the imaging module and/or based on one or more characteristics of the image sensors and/or objective lenses. For example, a relatively smaller FOV may be provided in conjunction with a smaller and faster imaging sensor to achieve high throughput.

Referring again to FIGS. 10A and 10B, in some implementations, the optics 42 in the detection channel (e.g., the tube lens) may be configured to reduce optical aberration in images acquired using optics 42 in combination with objective lens 39. In some implementations comprising multiple detection channels for imaging at different emission wavelengths, the optics 42 (e.g., the tube lens) for different detection channels have different designs to reduce aberration for the respective emission wavelengths at which that particular channel is configured to image. In some implementations, the optics 42 (e.g., the tube lens) may be configured to reduce aberrations when imaging a specific surface (e.g., a plane, object plane, etc.) on the sample support structure comprising fluorescing sample sites disposed thereon as compared to other locations (e.g., other planes in object space). Similarly, in some implementations, the optics 42 (e.g., the tube lens) may be configured to reduce aberrations when imaging first and second surfaces (e.g., first and second planes, first and second object planes, etc.) on a dual surface sample support structure (e.g., a dual surface flow cell) having fluorescing sample sites disposed thereon as compared to other locations (e.g., other planes in object space). For example, the optics 42 in the detection channel (e.g., tube lens) may be designed to reduce the aberration at two depths or planes located at different distances from the objective lens as compared to the aberrations associated with other depths or planes at other distances from the objective. For example, optical aberration may be less for imaging the first and second surfaces than elsewhere in a region from about 1 to about 10 mm from the objective lens. Additionally, custom optic 42 in the detection channel (e.g., a tube lens) may in some embodiments be configured to compensate for aberration induced by transmission of emission light through one or more portions of the sample support structure such as a layer that includes one of the surfaces on which the sample is disposed as well as possibly a solution adjacent to and in contact with the surface on which the sample is disposed. The layer comprising one of the surfaces on which the sample is disposed may comprise, e.g., glass, quartz, plastic, or other transparent material having a refractive index, and which introduces optical aberration. Custom optic 42 in the detection channel (e.g., the tube lens), for example, may in some implementations be configured to compensate for optical aberration induced by a sample support structure, e.g., a coverslip or flow cell wall, or other sample support structure components, as well as possibly a solution adjacent to and in contact with the surface on which the sample is disposed.

In some implementations, the optics 42 in the detection channel (e.g., a tube lens) are configured to have reduced magnification. The optics 42 in the detection channel (e.g., a tube lens) may be configured, for example, such that the fluorescence imaging module has a magnification of less than, for example, 10×, as will be discussed further below. Such reduced magnification may alter design constraints such that other design parameters can be achieved. For example, the optics 42 (e.g., a tube lens) may also be configured such that the fluorescence imaging module has a large field-of-view (FOV), for example, of at least 1.0 mm or larger (e.g., in diameter, width, length, or longest dimension), as will be discussed further below.

In some implementations, the optics 42 (e.g., a tube lens) may be configured to provide the fluorescence imaging module with a field-of-view as indicated above such that the FOV has less than 0.15 waves of aberration over at least 60%, 70%, 80%, 90%, or 95% of the field, as will be discussed further below.

Referring again to FIGS. 10A and 10B, in various implementations, a sample is located at or near a focal position 46 of the objective lens 39. As described above with reference to FIGS. 9A and 9B, a light source such as a laser source provides an excitation beam to the sample to induce fluorescence. At least a portion of fluorescence emission is collected by the objective lens 39 as emission light. The objective lens 39 transmits the emission light toward the first dichroic filter 38, which reflects some or all of the emission light as the beam 45 incident upon the second dichroic filter 44 and to the different detection channels, each comprising optics 42 that form an image of the sample (e.g., a plurality of fluorescing sample sites on a surface of a sample support structure) onto a photodetector array 41.

As discussed above, in some implementations, the sample support structure comprises a flow cell such as a dual surface flow cell having two surfaces (e.g., two interior surfaces, a first surface and a second surface, etc.) containing sample sites that emit fluorescent emission. These two surfaces may be separated by a distance from each other in the longitudinal (Z) direction along the direction of the central axis of the excitation beam and/or the optical axis of the objective lens. This separation may correspond, for example, to a flow channel within the flow cell. Analytes or reagents may be flowed through the flow channel and contact the first and second interior surfaces of the flow cell, which may thereby be contacted with a binding composition such that fluorescence emission is radiated from a plurality of sites on the first and second interior surfaces. The imaging optics (e.g., objective lens 39) may be positioned at a suitable distance (e.g., a distance corresponding to the working distance) from the sample to form in-focus images of the sample on one or more detector arrays 41. As discussed above, in various designs, the objective lens 39 (possibly in combination with the optics 42) may have a depth of field and/or depth of focus that is at least as large as the longitudinal separation between the first and second surfaces. The objective lens 39 and the optics 42 (of each detection channel) can thus simultaneously form images of both the first and the second flow cell surfaces on the photodetector array 41, and these images of the first and second surfaces are both in focus and have comparable optical resolution (or may be brought into focus with only minor refocusing of the objects to acquire images of the first and second surfaces that have comparable optical resolution). In various implementations, compensation optics need not be moved into or out of an optical path of the imaging module (e.g., into or out of the first and/or second optical paths) to form in-focus images of the first and second surfaces that are of comparable optical resolution. Similarly, in various implementations, one or more optical elements (e.g., lens elements) in the imaging module (e.g., the objective lens 39 or optics 42) need not be moved, for example, in the longitudinal direction along the first and/or second optical paths to form in-focus images of the first surface in comparison to the location of said one or more optical elements when used to form in-focus images of the second surface. In some implementations, the imaging module includes an autofocus system configured to quickly and sequentially refocus the imaging module on the first and/or second surface such that the images have comparable optical resolution. In some implementations, objective lens 39 and/or optics 42 are configured such that both the first and second flow cell surfaces are in focus simultaneously with comparable optical resolution without moving an optical compensator into or out of the first and/or second optical path, and without moving one or more lens elements (e.g., objective lens 39 and/or optics 42 (such as a tube lens) longitudinally along the first and/or second optics path. In some implementations, images of the first and/or second surfaces, acquired either sequentially (e.g., with refocusing between surfaces) or simultaneously (e.g., without refocusing between surfaces) using the novel objective lens and/or tube lens designs disclosed herein, may be further processed using a suitable image processing algorithm to enhance the effective optical resolution of the images such that the images of the first and second surfaces have comparable optical resolution. In various implementations, the sample plane is sufficiently in focus to resolve sample sites on the first and/or second flow cell surfaces, the sample sites being closely spaced in lateral directions (e.g., in the X and Y directions).

As discussed above, the dichroic filters may comprise interference filters that selectively transmit and reflect light of different wavelengths based on the principle of thin-film interference, using layers of optical coatings having different refractive indices and particular thickness. Accordingly, the spectral response (e.g., transmission and/or reflection spectra) of the dichroic filters implemented within multi-channel fluorescence imaging modules may be at least partially dependent upon the angle of incidence, or range of angles of incidence (e.g., dependent on beam diameter and/or beam divergence), at which the light of the excitation and/or emission beams are incident upon the dichroic filters. Such effects may be especially significant with respect to the dichroic filters of the detection optical path (e.g., the dichroic filters 44 and 43 of FIGS. 10A and 10B).

In some implementations, the focal length of the objective lens that is suitable for producing a narrow beam diameter with minimal divergence that results in sharper may be longer than those typically employed in fluorescence microscopes or imaging systems. For example, in some implementations, the focal length of the objective lens may range between 20 mm and 40 mm, as will be discussed further below. In one example, an objective lens 39 having a focal length of 36 mm may produce a beam 45 characterized by a divergence small enough that light across the full diameter of the beam 45 is incident upon the second dichroic filter 38 at angles within 2.5 degrees of the angle of incidence of the central beam axis.

In some implementations of the disclosed imaging modules, the polarization state of the excitation beam may be utilized to further improve the performance of the multi-channel fluorescence imaging modules disclosed herein. Referring again to FIGS. 9A and 9B, for example, some implementations of the multi-channel fluorescence imaging modules disclosed herein have an epifluorescence configuration in which a first dichroic filter 38 merges the optical paths of the excitation beam and the beam of emission light such that both the excitation and emission light are transmitted through the objective lens 39. As discussed above, the illumination source 36 may include a light source such as a laser or other source which provides the light that forms the excitation beam. In some designs, the light source comprises a linearly polarized light source and the excitation beam may be linearly polarized. In some designs, polarization optics are included to polarize the light and/or rotate the polarization of the light. For example, a polarizer such as a linear polarizer may be included in an optical path of the excitation beam to polarize the excitation beam. Retarders such as half wave retarders or a plurality of quarter wave retarders or retarders having other amounts of retardance may be included to rotate the linear polarization in some designs.

The linearly polarized excitation beam, when it is incident upon any dichroic filter or other planar interface, may be p-polarized (e.g., having an electric field component parallel to the plane of incidence), s-polarized (e.g., having an electric field component normal to the plane of incidence), or may have a combination of p-polarization and s-polarization states within the beam. The p- or s-polarization state of the excitation beam may be selected and/or changed by selecting the orientation of the illumination source 36 and/or one or more components thereof with respect to the first dichroic filter 38 and/or with respect to any other surfaces with which the excitation beam will interact. In some implementations where the light source output linearly polarized light, the light source can be configured to provide s-polarized light. For example, the light source may comprise an emitter such as a solid-state laser or a laser diode that may be rotated about its optical axis or the central axis of the beam to orient the linearly polarized light output therefrom. Alternatively, or in addition, retarders may be employed to rotate the linear polarization about the optical axis or the central axis of the beam. As discussed above, in some implementations, for example when the light source does not output polarized light, a polarizer disposed in the optical path of the excitation beam can polarize the excitation beam. In some designs, for example, a linear polarizer is disposed in the optical path of the excitation beam. This polarizer may be rotated to provide the proper orientation of the linear polarization to provide s-polarized light.

In some designs, the linear polarization is rotated about the optical axis or the central axis of the beam such that s-polarization is incident on the dichroic reflector of the dichroic beam splitter. When s-polarized light is incident on the dichroic reflector of the dichroic beam splitter the transition between the pass band and the stop band is sharper as opposed to when p-polarized light is incident on the dichroic reflector of the dichroic beam splitter.

As discussed above, in some implementation, a polarizer such as a linear polarizer may be used to polarize the excitation beam. This polarizer may be rotated to provide an orientation of the linearly polarized light corresponding to s-polarized light. Also as discussed above, in some implementations, other approaches to rotating the linearly polarized light may be used. For example, optical retarders such as half wave retarders or multiple quarter wave retarders may be used to rotate the polarization direction. Other arrangements are also possible.

Figure 11A:
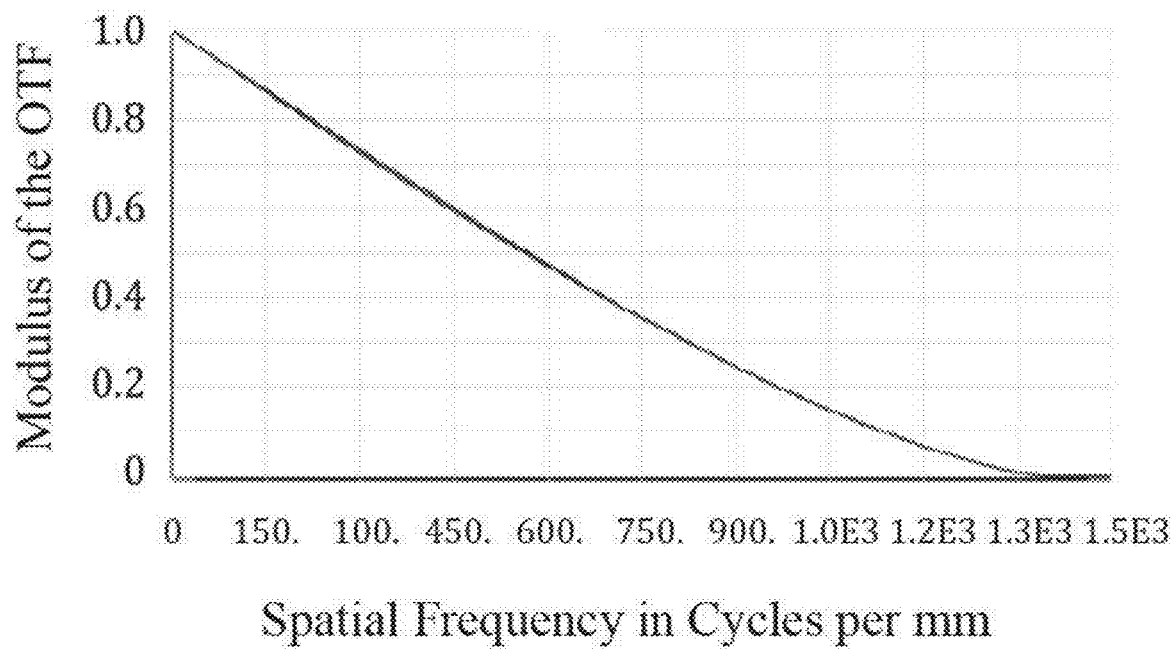
FIGS. 11A-11B illustrate the modulation transfer function (MTF) of an example dual surface imaging system disclosed herein having a numerical aperture (NA) of 0.3.
Figure 11B:
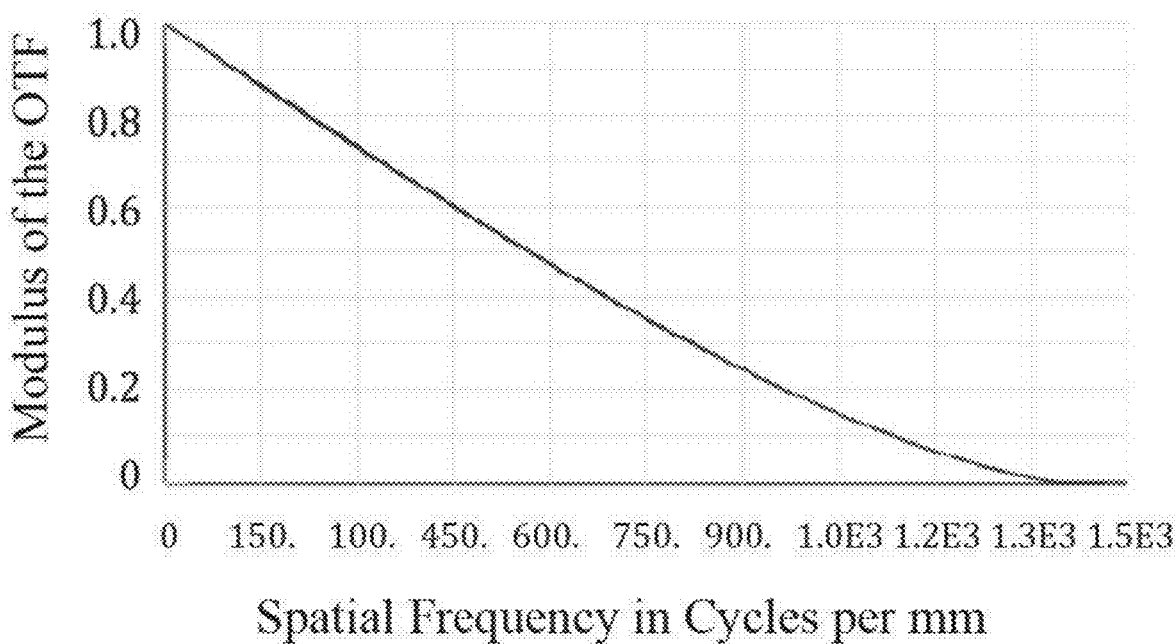
Figure 12A:
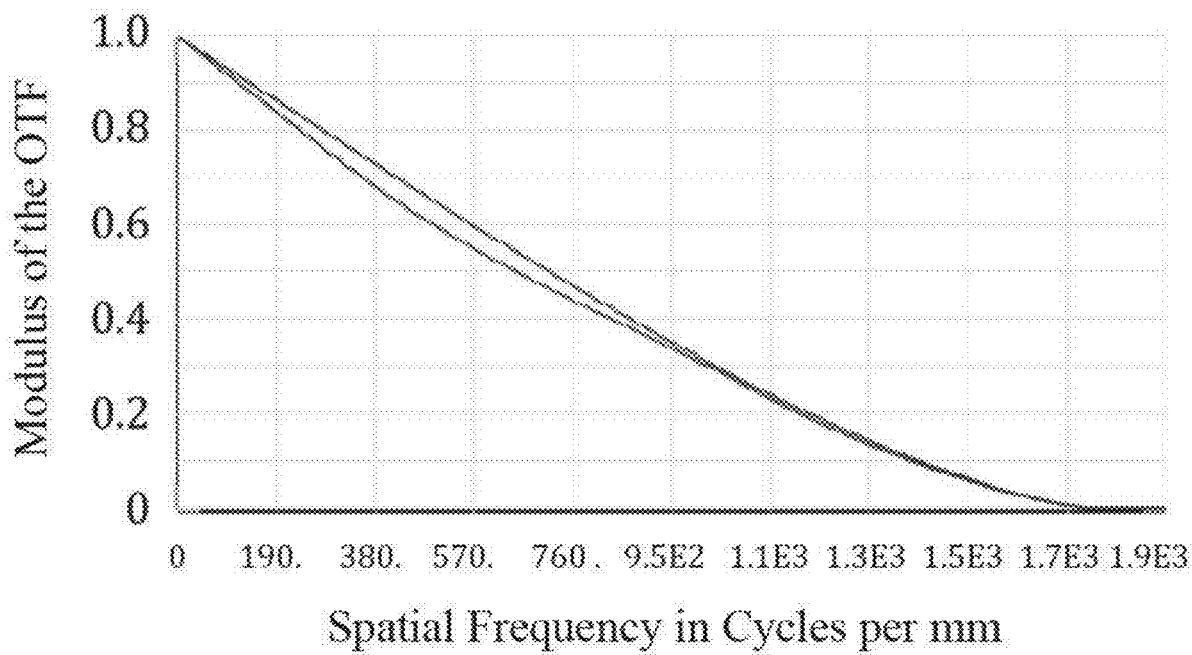
FIGS. 12A-12B illustrate the MTF of an example dual surface imaging system disclosed herein having an NA of 0.5.
Figure 12B:
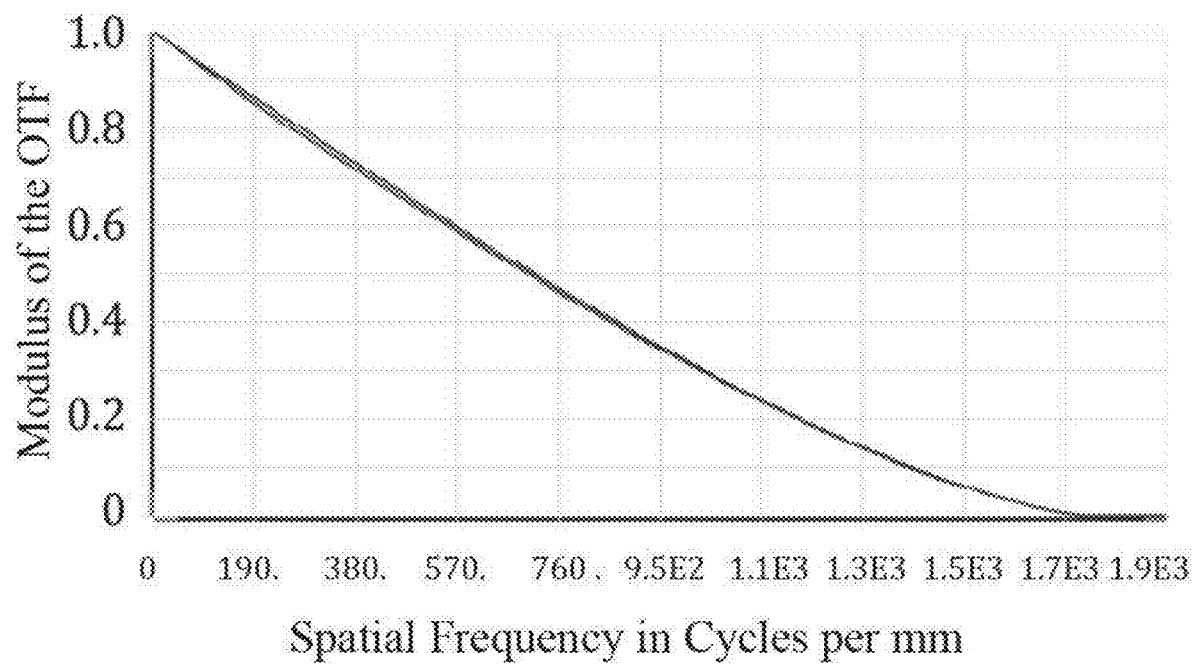
Figure 13A:
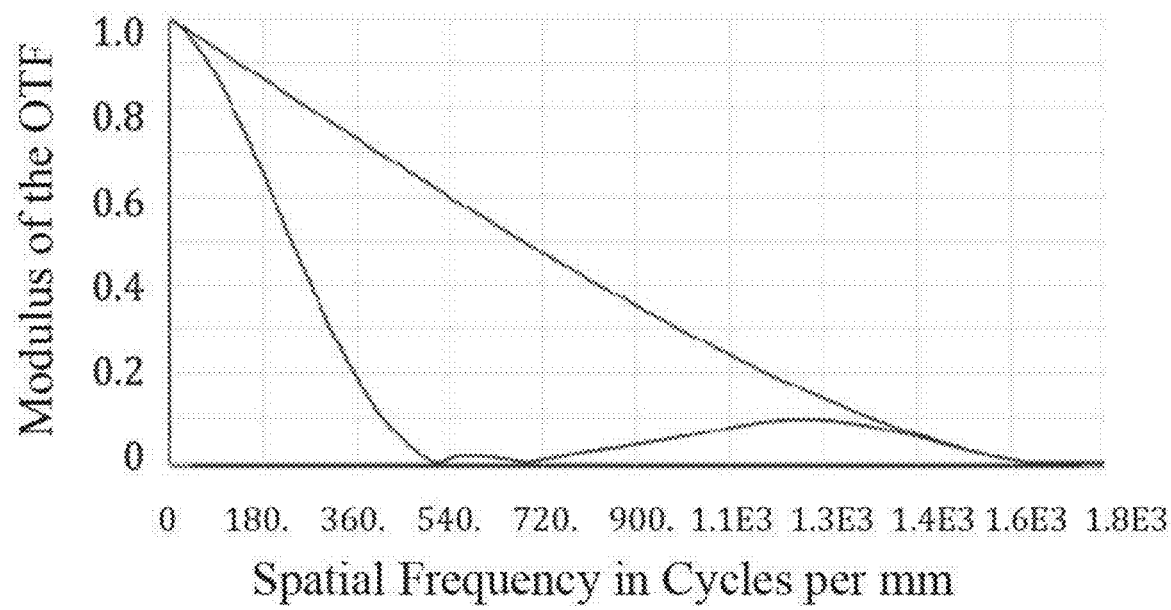
FIGS. 13A-13B illustrate the MTF of an example dual surface imaging system disclosed herein having an NA of 0.7.
Figure 13B:
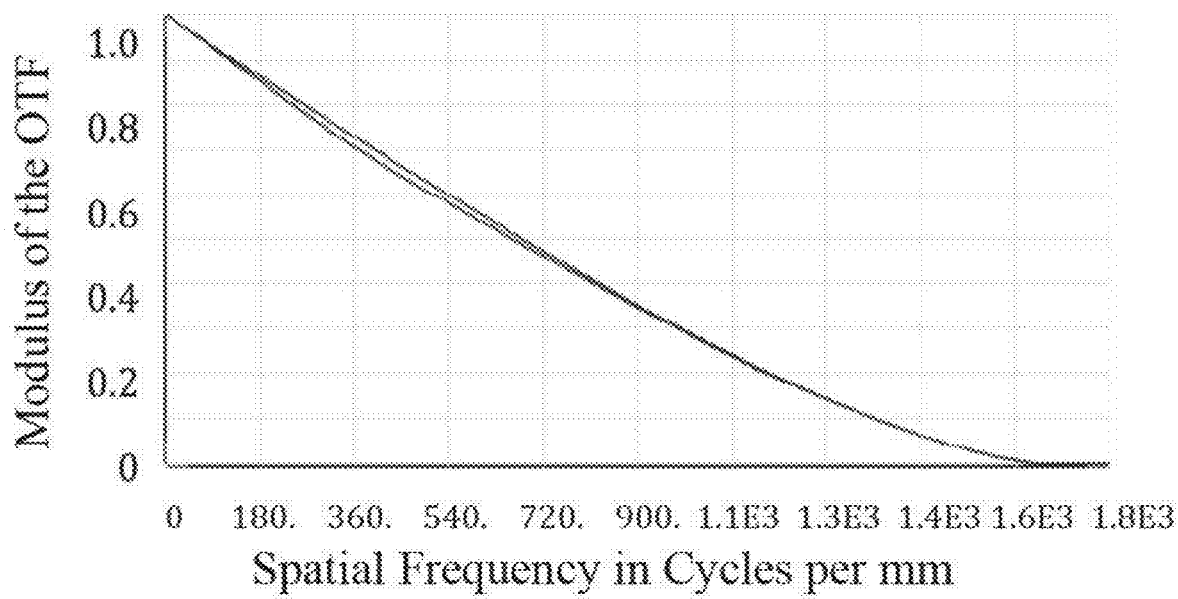

As discussed elsewhere herein, reducing the numerical aperture (NA) of the fluorescence imaging module and/or of the objective lens may increase the depth of field to enable the comparable imaging of the two surfaces. FIGS. 11A-B, FIGS. 11A-B, and FIGS. 13A-B show how the MTF is more similar at first and second surfaces separated by 1 mm of glass for lower numerical apertures than for larger numerical apertures. FIGS. 11A and 11B show the MTF at first (FIG. 11A) and second (FIG. 11B) surfaces for an NA of 0.3. FIGS. 12A and 12B show the MTF at first (FIG. 12A) and second (FIG. 12B) surfaces for an NA of 0.5. FIGS. 13A and 13B show the MTF at first (FIG. 13A) and second (FIG. 13B) surfaces for an NA of 0.7. The first and second surfaces in each of these figures correspond to, e.g., the top and bottom surfaces of a flow cell.

Figure 14A:
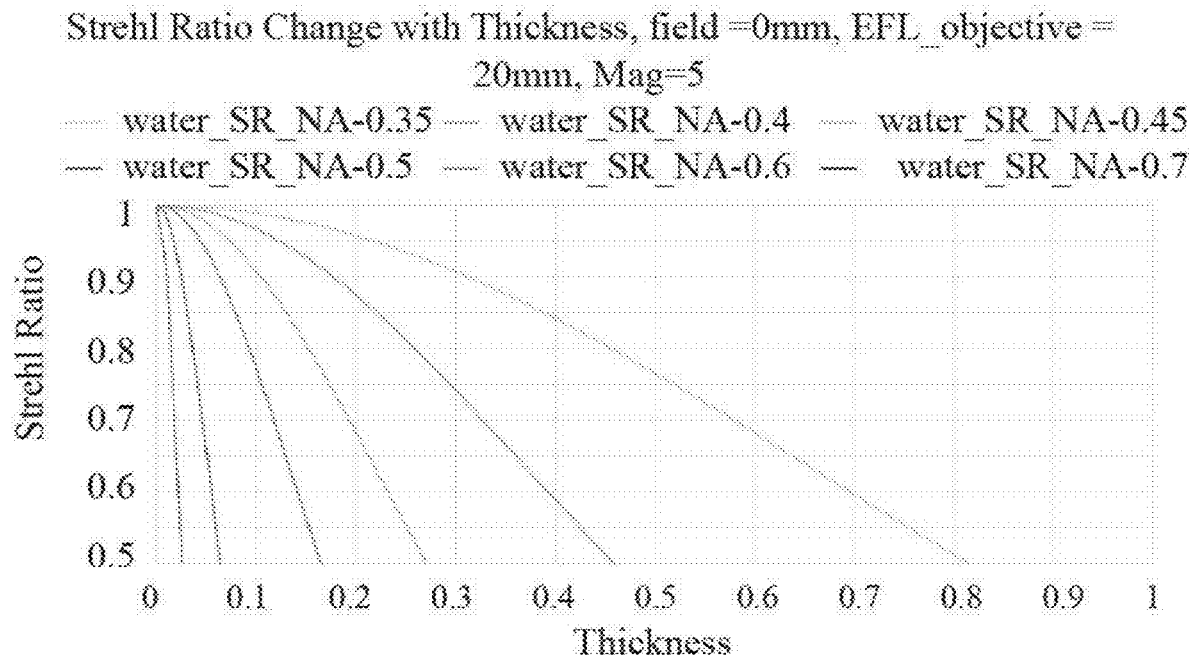
FIGS. 14A-14B provide plots of the calculated Strehl ratio for imaging a second flow cell surface through a first flow cell surface.
Figure 14B:
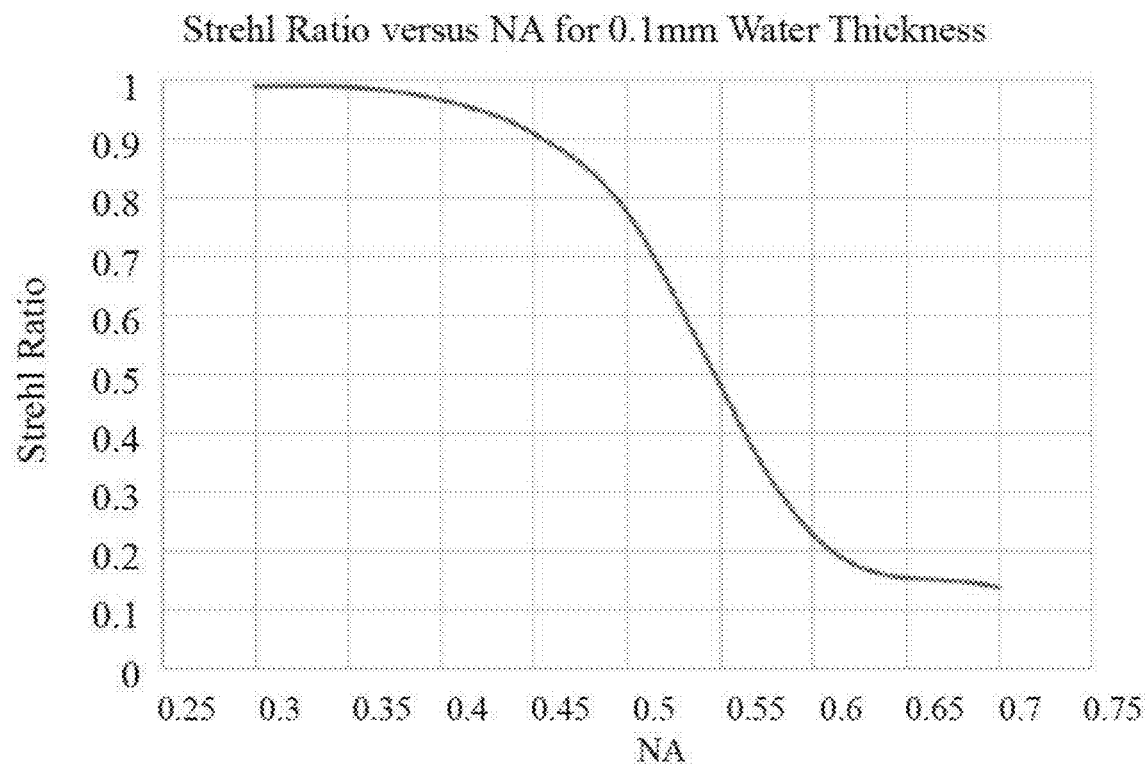

FIGS. 14A-B provide plots of the calculated Strehl ratio (i.e., the ratio of peak light intensity focused or collected by the optical system versus that focused or collected by an ideal optical system and point light source) for imaging a second flow cell surface through a first flow cell surface. FIG. 14A shows a plot of the Strehl ratios for imaging a second flow cell surface through a first flow cell surface as a function of the thickness of the intervening fluid layer (fluid channel height) for different objective lens and/or optical system numerical apertures. As shown, the Strehl ratio decreases with increasing separation between the first and second surfaces. One of the surfaces would thus have deteriorated image quality with increasing separation between the two surfaces. The decrease in second surface imaging performance with increased separation distance between the two surfaces is reduced for imaging systems having smaller numeral apertures as compared to those having larger numerical apertures. FIG. 14B shows a plot of the Strehl ratio as a function of numerical aperture for imaging a second flow cell surface through a first flow cell surface and an intervening layer of water having a thickness of 0.1 mm. The loss of imaging performance at higher numerical apertures may be attributed to the increased optical aberration induced by the fluid for the second surface imaging. With increasing NA, the increased optical aberration introduced by the fluid for the second surface imaging degrades the image quality significantly. In general, however, reducing the numeral aperture of the optical system reduces the achievable resolution. This loss of image quality can be at least partially offset by providing an increased sample plane (or object plane) contrast-to-noise ratio, for example, by using chemistries for nucleic acid sequencing applications that enhance the fluorescence emission for labeled nucleic acid clusters and/or that reduce background fluorescence emission. In some instances, for example, sample support structures comprising hydrophilic substrate materials and/or hydrophilic coatings may be employed. In some cases, such hydrophilic substrates and/or hydrophilic coatings may reduce background noise. Additional discussion of sample support structures, hydrophilic surfaces and coatings, and methods for enhancing contrast-to-noise ratios, e.g., for nucleic acid sequencing applications, can be found below.

In some implementations, any one or more of the fluorescence imaging system, the illumination and imaging module 32, the imaging optics (e.g., optics 42), the objective lens, and/or the tube lens is configured to have reduced magnification, such as a magnification of less than 10×, as will be discussed further below. Such reduced magnification may adjust design constraints such that other design parameters can be achieved. For example, any one or more of the fluorescence microscope, illumination and imaging module 32, the imaging optics (e.g., optics 42), the objective lens or the tube lens may also be configured such that the fluorescence imaging module has a large field-of-view (FOV), for example, a field-of-view of at least 3.0 mm or larger (e.g., in diameter, width, height, or longest dimension), as will be discussed further below. Any one or more of the fluorescence imaging system, the illumination and imaging module 32, the imaging optics (e.g., optics 42), the objective lens and/or the tube lens may be configured to provide the fluorescence microscope with such a field-of-view such that the FOV has less than, e.g., 0.1 waves of aberration over at least 80% of field. Similarly, any one or more of the fluorescence imaging system, illumination and imaging module 32, the imaging optics (e.g., optics 42), the objective lens and/or the tube lens may be configured such that the fluorescence imaging module has such a FOV and is diffraction limited or is diffraction limited over such an FOV.

As discussed above, in various implementations, a large field-of-view (FOV) is provided by the disclosed optical systems. In some implementations, obtaining an increased FOV is facilitated in part by the use of larger image sensors or photodetector arrays. The photodetector array, for example, may have an active area with a diagonal of at least 15 mm or larger, as will be discussed further below. As discussed above, in some implementations the disclosed optical imaging systems provide a reduced magnification, for example, of less than 10× which may facilitate large FOV designs. Despite the reduced magnification, the optical resolution of the imaging module may still be sufficient as detector arrays having small pixel size or pitch may be used. The pixel size and/or pitch may, for example, be about 5 μm or less, as will be discussed in more detail below. In some implementations, the pixel size is smaller than twice the optical resolution provided by the optical imaging system (e.g., objective and tube lens) to satisfy the Nyquist theorem. Accordingly, the pixel dimension and/or pitch for the image sensor(s) may be such that a spatial sampling frequency for the imaging module is at least twice an optical resolution of the imaging module. For example, the spatial sampling frequency for the photodetector array may be is at least 2 times, at least 2.5 times, at least 3 times, at least 4 times, or at least 5 times the optical resolution of the fluorescence imaging module (e.g., the illumination and imaging module, the objective and tube lens, the object lens and optics 42 in the detection channel, the imaging optics between the sample support structure or stage configured to support the sample support stage and the photodetector array) or any spatial sampling frequency in a range between any of these values.

Although a wide range of features are discussed herein with respect to fluorescence imaging modules, any of the features and designs describe herein may be applied to other types of optical imaging systems including without limitation bright-field and dark-field imaging and may apply to luminescence or phosphorescence imaging.

Improved or optimized objective and/or tube lens for use with thicker coverslips: Existing design practice includes the design of objective lenses and/or use of commonly available off-the-shelf microscope objectives to optimize image quality when images are acquired through thin (e.g., <200 µm thick) microscope coverslips. When used to image on both sides of a fluidic channel or flow cell, the extra height of the gap between the two surfaces (i.e., the height of the fluid channel; typically, about 50 µm to 200 µm) introduces optical aberration in images captured for the non-optimal side of the fluidic channel, thereby causing lower optical resolution. This is primarily because the additional gap height is significant compared to the optimal coverslip thickness (typical fluid channel or gap heights of 50-200 µm vs. coverslip thicknesses of <200 µm). Another common design practice is to utilize an additional "compensator" lens in the optical path when imaging is to be performed on the non-optimal side of the fluid channel or flow cell. This "compensator" lens and the mechanism required to move it in or out of the optical path so that either side of the flow cell may be imaged further increases system complexity and imaging system down time, and potentially degrades image quality due to vibration, etc.

In the present disclosure, the imaging system is designed for compatibility with flow cell consumables that comprise a thicker coverslip or flow cell wall (thickness ≥700 µm). The objective lens design may be improved or optimized for a coverslip that is equal to the true cover slip thickness plus half of the effective gap thickness (e.g., 700 µm+½*fluid channel (gap) height). This design significantly reduces the effect of gap height on image quality for the two surfaces of the fluid channel and balances the optical quality for images of the two surfaces, as the gap height is small relative to the total coverslip thickness and thus its impact on optical quality is reduced.

Additional advantages of using a thicker coverslip include improved control of thickness tolerance error during manufacturing, and a reduced likelihood that the coverslip undergoes deformation due to thermal and mounting-induced stress. Coverslip thickness error and deformation adversely impact imaging quality for both the top surface and the bottom surface of a flow cell.

To further improve the dual surface imaging quality for sequencing applications, our optical system design places a strong emphasis on improving or optimizing MTF (e.g., through improving or optimizing the objective lens and/or tube lens design) in the mid- to high-spatial frequency range that is most suitable for imaging and resolving small spots or clusters.

Improved or optimized tube lens design for use in combination with commercially-available, off-the-shelf objectives: For low-cost sequencer design, the use of a commercially-available, off-the-shelf objective lens may be preferred due to its relatively low price. However, as noted above, low-cost, off-the-shelf objectives are mostly optimized for use with thin coverslips of about 170 µm in thickness. In some instances, the disclosed optical systems may utilize a tube lens design that compensates for a thicker flow cell coverslip while enabling high image quality for both interior surfaces of a flow cell in dual-surface imaging applications. In some instances, the tube lens designs disclosed herein enable high quality imaging for both interior surfaces of a flow cell without moving an optical compensator into or out of the optical path between the flow cell and an image sensor, without moving one or more optical elements or components of the tube lens along the optical path, and without moving one or more optical elements or components of the tube lens into or out of the optical path.

Figure 15:
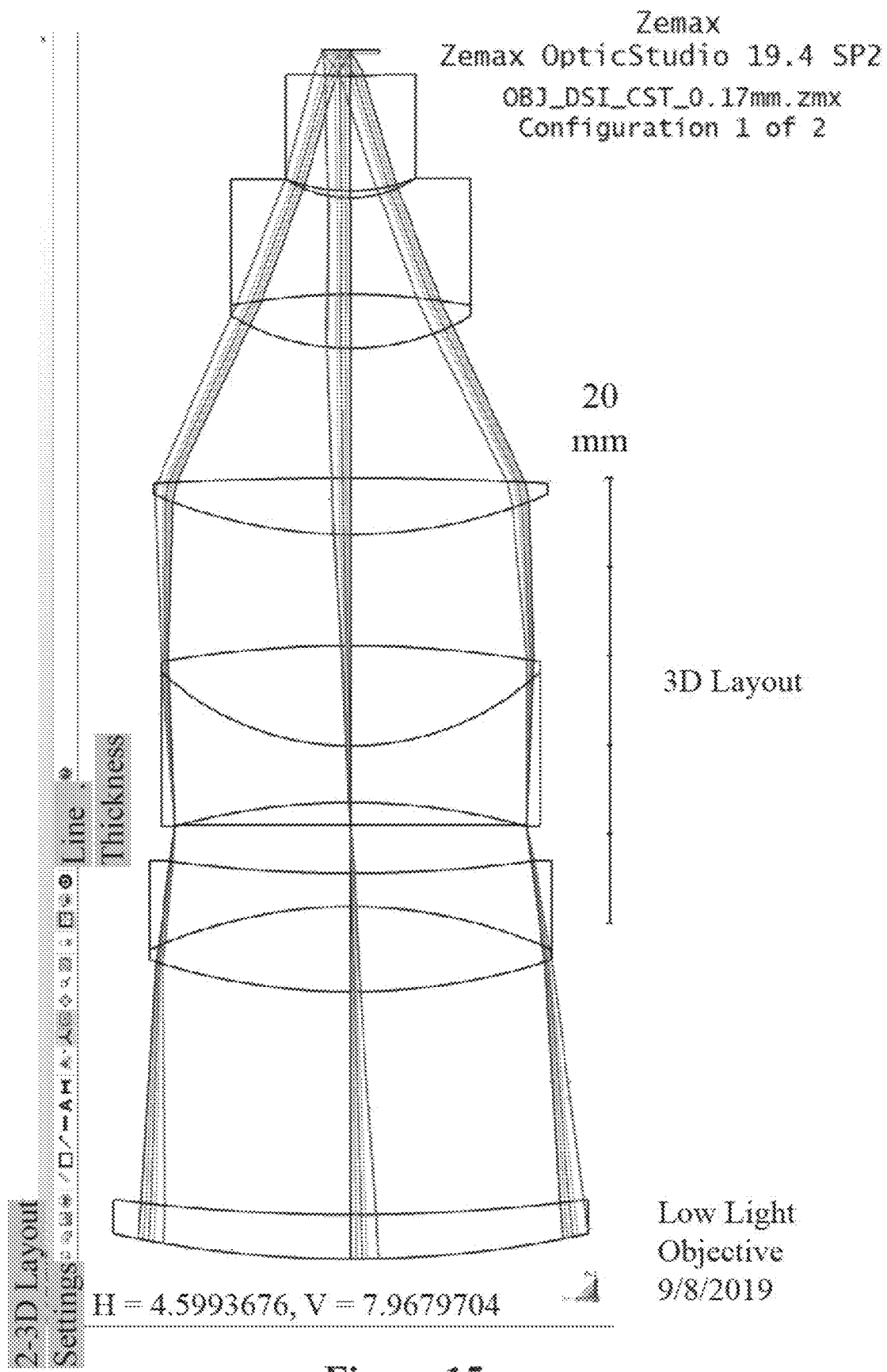
FIG. 15 provides an optical ray tracing diagram for an objective lens design that has been designed for imaging a surface on the opposite side of a 0.17 mm thick coverslip.
Figure 16:
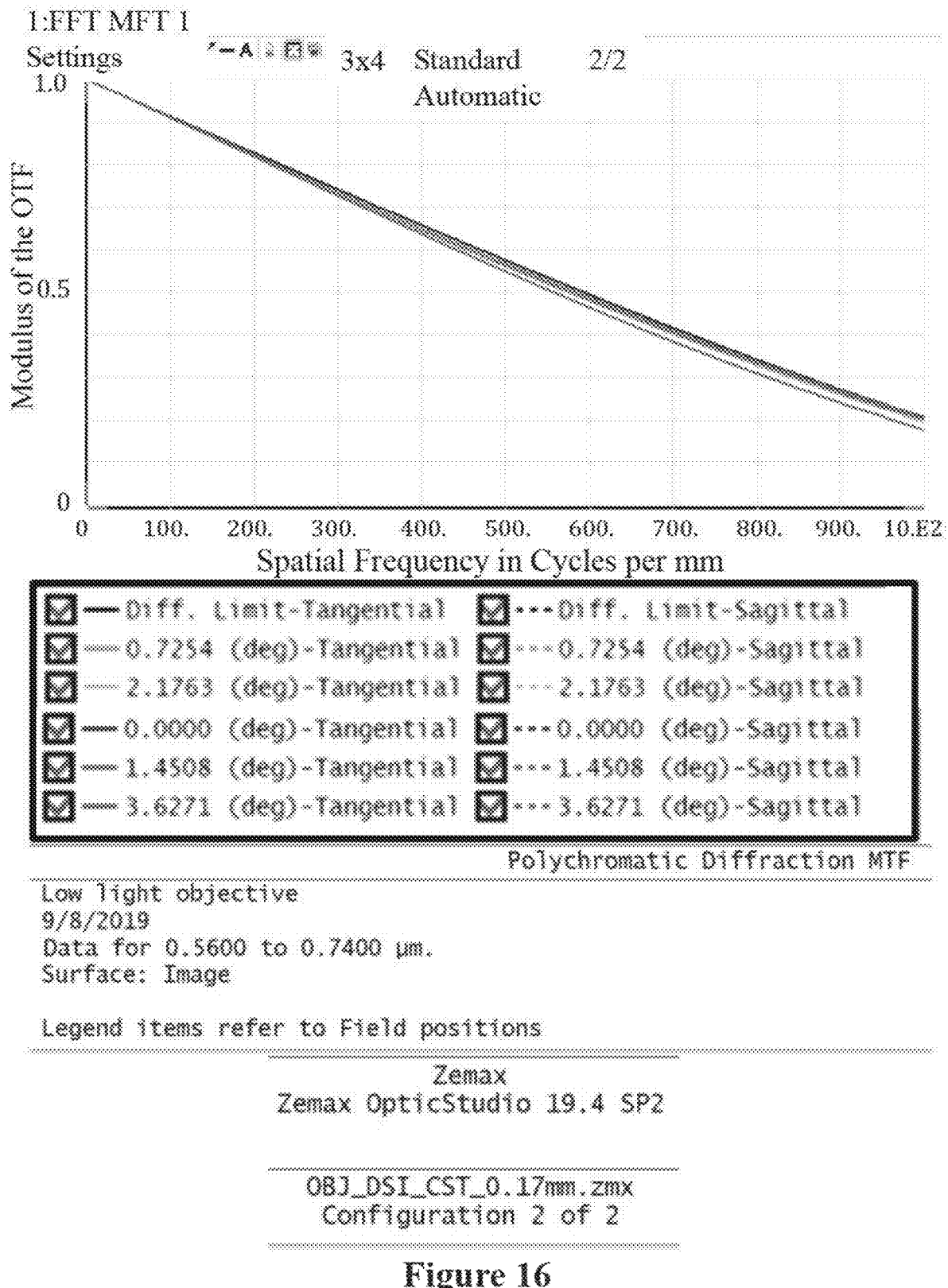
FIG. 16 provides a plot of the modulation transfer function for the objective lens illustrated in FIG. 15 as a function of spatial frequency when used to image a surface on the opposite side of a 0.17 mm thick coverslip.

FIG. 15 provides an optical ray tracing diagram for a low light objective lens design that has been improved or optimized for imaging a surface on the opposite side of a 0.17 mm thick coverslip. The plot of modulation transfer function for this objective, shown in FIG. 16, indicates near-diffraction limited imaging performance when used with the designed—for 0.17 mm thick coverslip.

Figure 17:
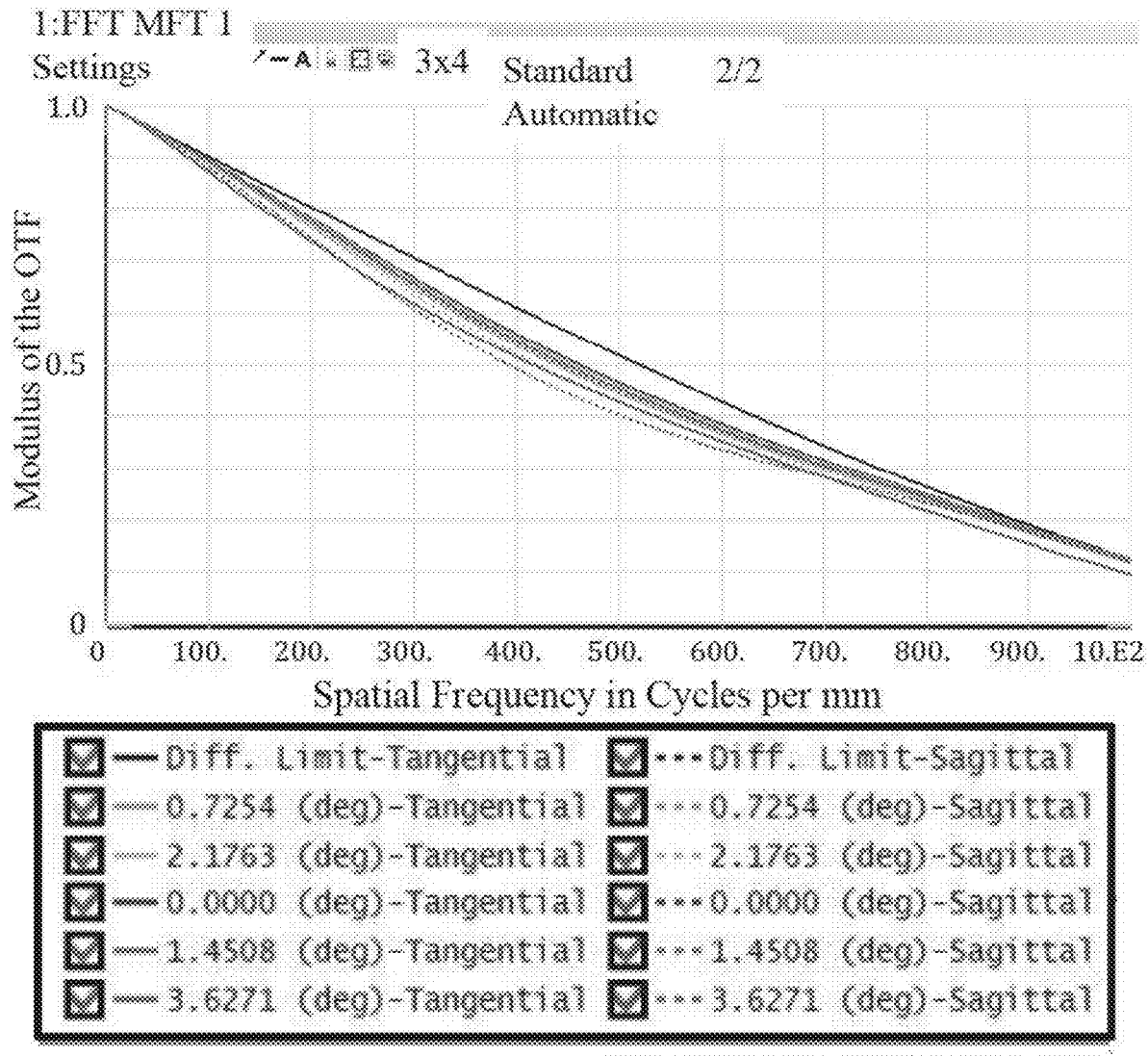
FIG. 17 provides a plot of the modulation transfer function for the objective lens illustrated in FIG. 19 as a function of spatial frequency when used to image a surface on the opposite side of a 0.3 mm thick coverslip.

FIG. 17 provides a plot of the modulation transfer function for the same objective lens illustrated in FIG. 15 as a function of spatial frequency when used to image a surface on the opposite side of a 0.3 mm thick coverslip. The relatively minor deviations of MTF value over the spatial frequency range of about 100 to about 800 lines/mm (or cycles/mm) indicates that the image quality obtained even when using a 0.3 mm thick coverslip is still reasonable.

Figure 18:
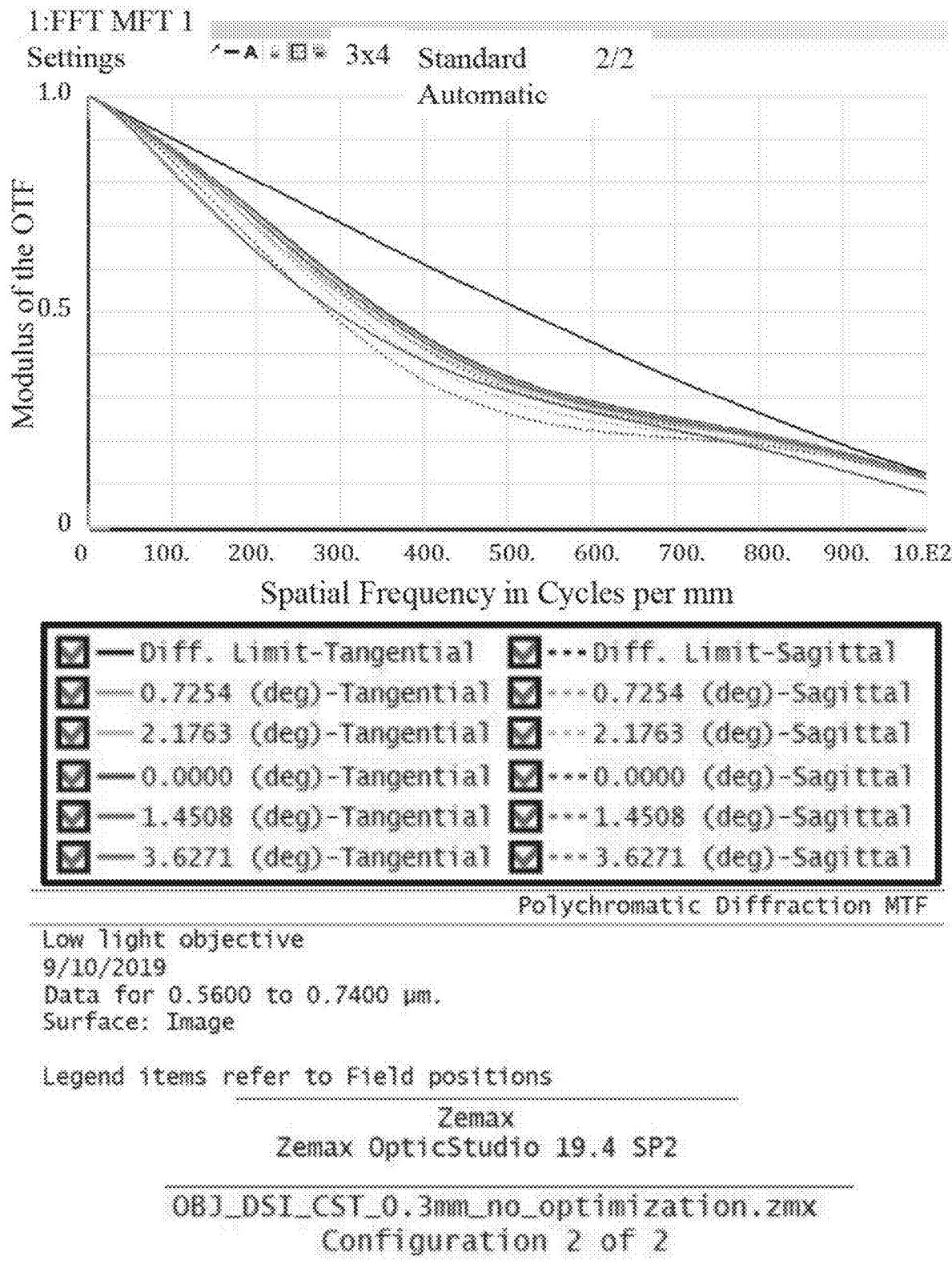
FIG. 18 provides a plot of the modulation transfer function for the objective lens illustrated in FIG. 15 as a function of spatial frequency when used to image a surface that is separated from that on the opposite side of a 0.3 mm thick coverslip by a 0.1 mm thick layer of aqueous fluid.

FIG. 18 provides a plot of the modulation transfer function for the same objective lens illustrated in FIG. 15 as a function of spatial frequency when used to image a surface that is separated from that on the opposite side of a 0.3 mm thick coverslip by a 0.1 mm thick layer of aqueous fluid (i.e., under the kind of conditions encountered for dual-side imaging of a flow cell when imaging the far surface). As can be seen in the plot of FIG. 18, imaging performance is degraded, as indicated by the deviations of the MTF curves from those for the an ideal, diffraction-limited case over the spatial frequency range of about 50 lp/mm to about 900 lp/mm.

Figure 19:
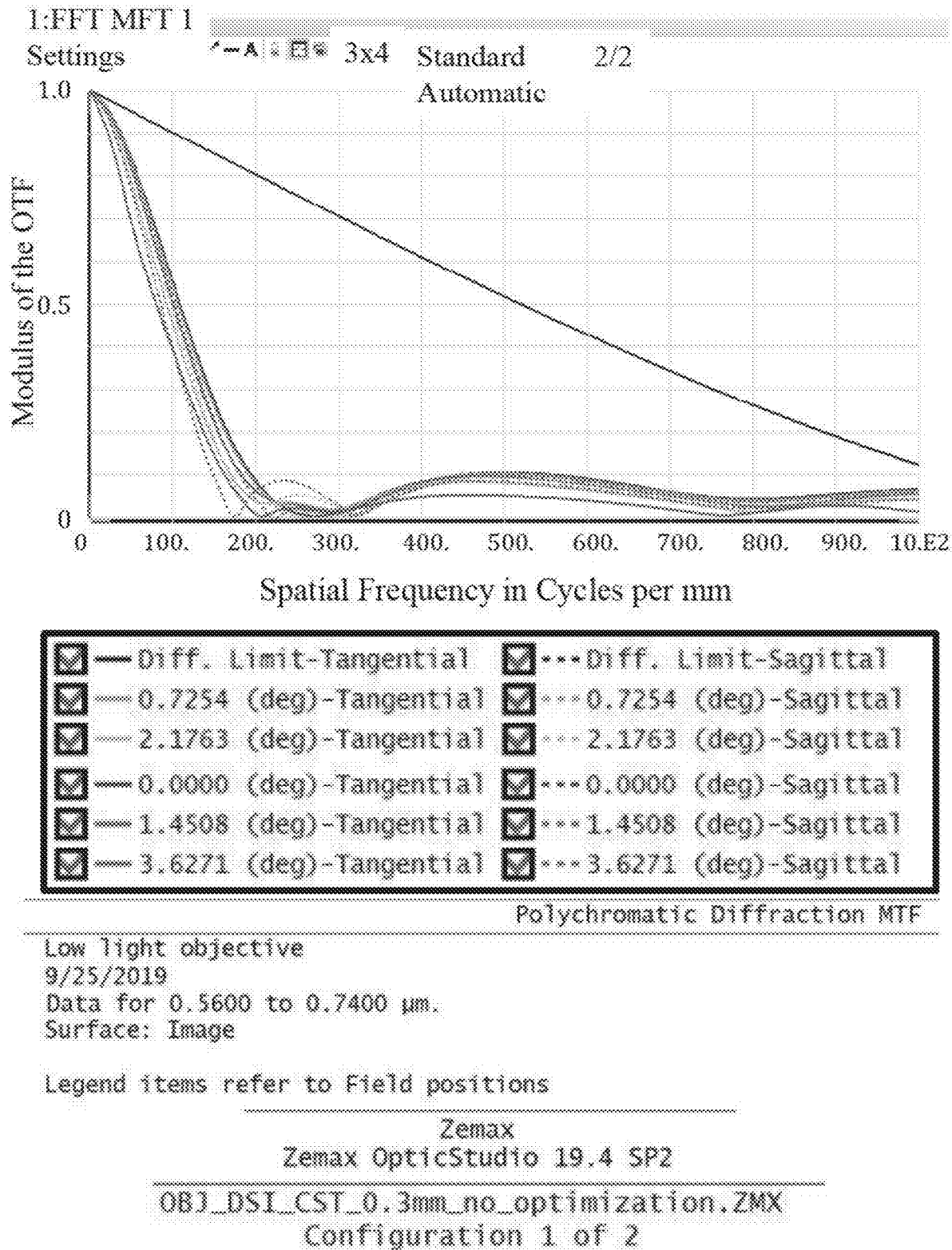
FIG. 19 provides a plot of the modulation transfer function for the objective lens illustrated in FIG. 15 as a function of spatial frequency when used to image a surface on the opposite side of a 1.0 mm thick coverslip.
Figure 20:
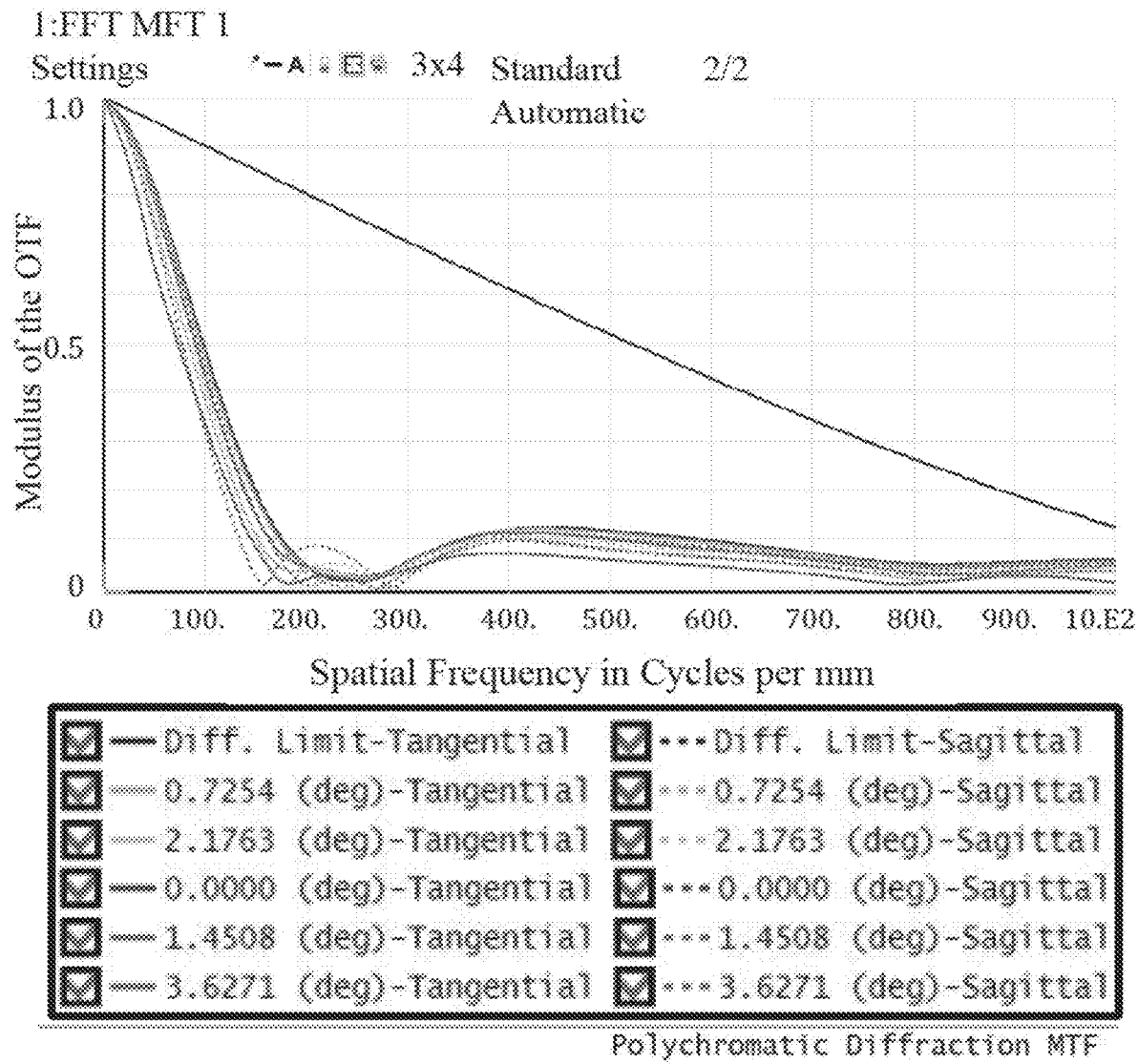
FIG. 20 provides a plot of the modulation transfer function for the objective lens illustrated in FIG. 15 as a function of spatial frequency when used to image a surface that is separated from that on the opposite side of a 1.0 mm thick coverslip by a 0.1 mm thick layer of aqueous fluid.

FIG. 19 and FIG. 20 provide plots of the modulation transfer function as a function of spatial frequency for the upper (or near) interior surface (FIG. 19) and lower (or far) interior surface (FIG. 20) of a flow cell when imaged using the objective lens illustrated in FIG. 15 through a 1.0 mm thick coverslip, and when the upper and lower interior surfaces are separated by a 0.1 mm thick layer of aqueous fluid. As can be seen, imaging performance is significantly degraded for both surfaces.

Figure 21:
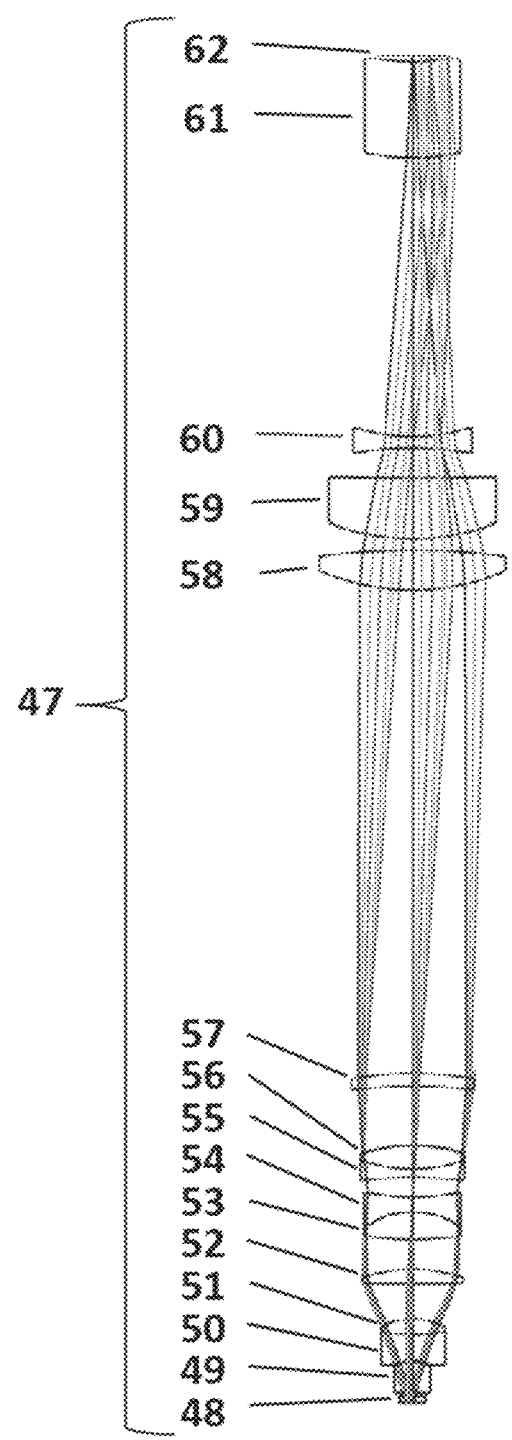
FIG. 21 provides a ray tracing diagram for a tube lens design which, if used in conjunction with the objective lens illustrated in FIG. 15, provides for improved dual-side imaging through a 1 mm thick coverslip.

FIG. 21 provides a ray tracing diagram for a tube lens design which, if used in conjunction with the objective lens illustrated in FIG. 15, provides for improved dual-side imaging through a 1 mm thick coverslip. The optical design 47 comprising a compound objective (lens elements 49, 50, 51, 52, 53, 54, 55, 56, and 57) and a tube lens (lens elements 58, 59, 60, and 61) is improved or optimized for use with flow cells comprising a thick coverslip (or wall), e.g., greater than 700 µm thick, and a fluid channel thickness of at least 50 µm, and transfers the image of an interior surface from the flow cell 48 to the image sensor 62 with dramatically improved optical image quality and higher CNR.

In some instances, the tube lens (or tube lens assembly) may comprise at least two optical lens elements, at least three optical lens elements, at least four optical lens elements, at least five optical lens elements, at least six optical lens elements, at least seven optical lens elements, at least eight optical lens elements, at least nine optical lens elements, at least ten optical lens elements, or more, where the number of optical lens elements, the surface geometry of each element, and the order in which they are placed in the assembly is improved or optimized to correct for optical aberrations induced by the thick wall of the flow cell, and in some instances, allows one to use a commercially-available, off-the-shelf objective while still maintaining high-quality, dual-side imaging capability.

In some instances, as illustrated in FIG. 21, the tube lens assembly may comprise, in order, a first asymmetric convex-convex lens 58, a second convex-plano lens 59, a third asymmetric concave-concave lens 60, and a fourth asymmetric convex-concave lens 61.

Figure 22:
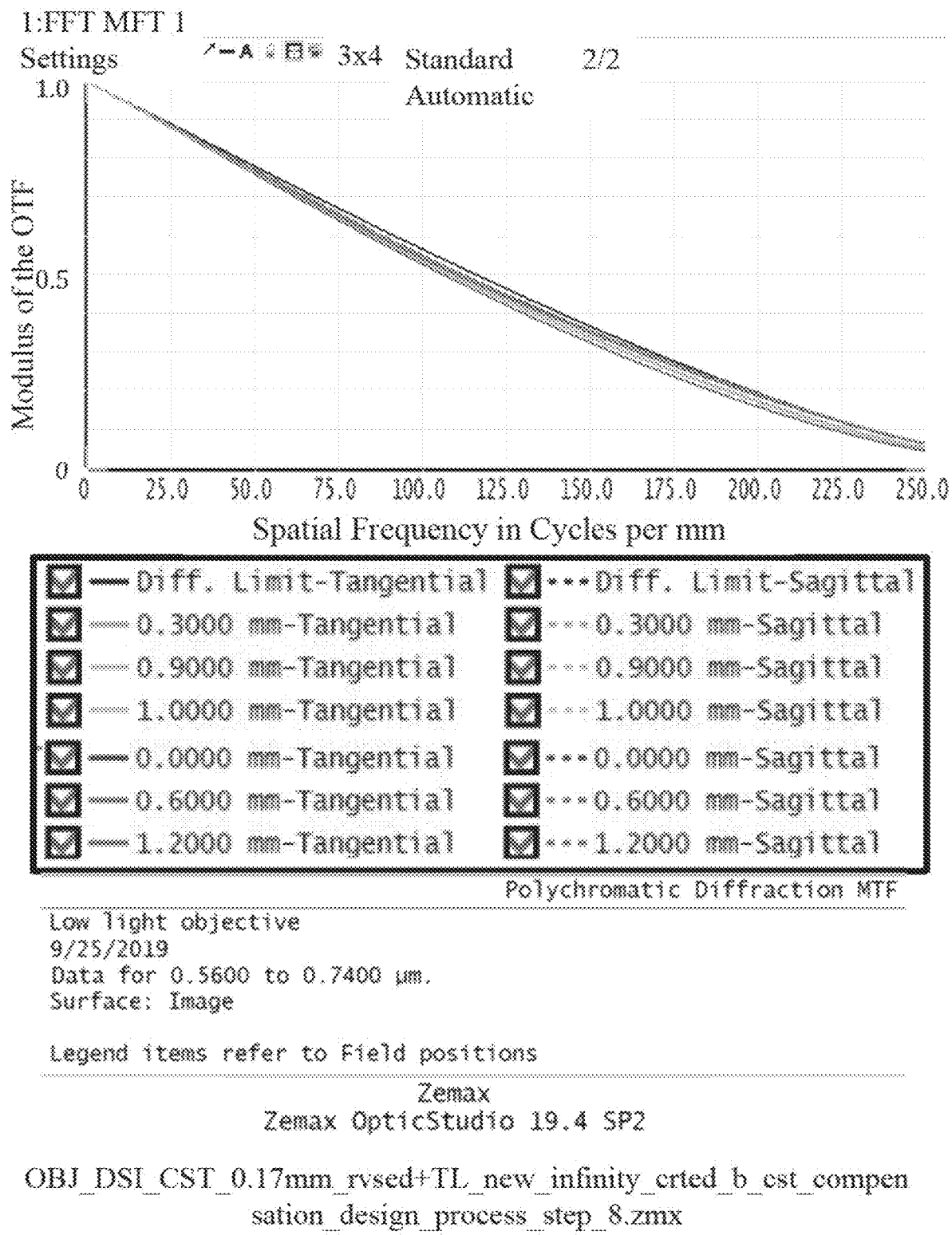
FIG. 22 provides a plot of the modulation transfer function for the combination of objective lens and tube lens illustrated in FIG. 15 as a function of spatial frequency when used to image a surface on the opposite side of a 1.0 mm thick coverslip.
Figure 23:
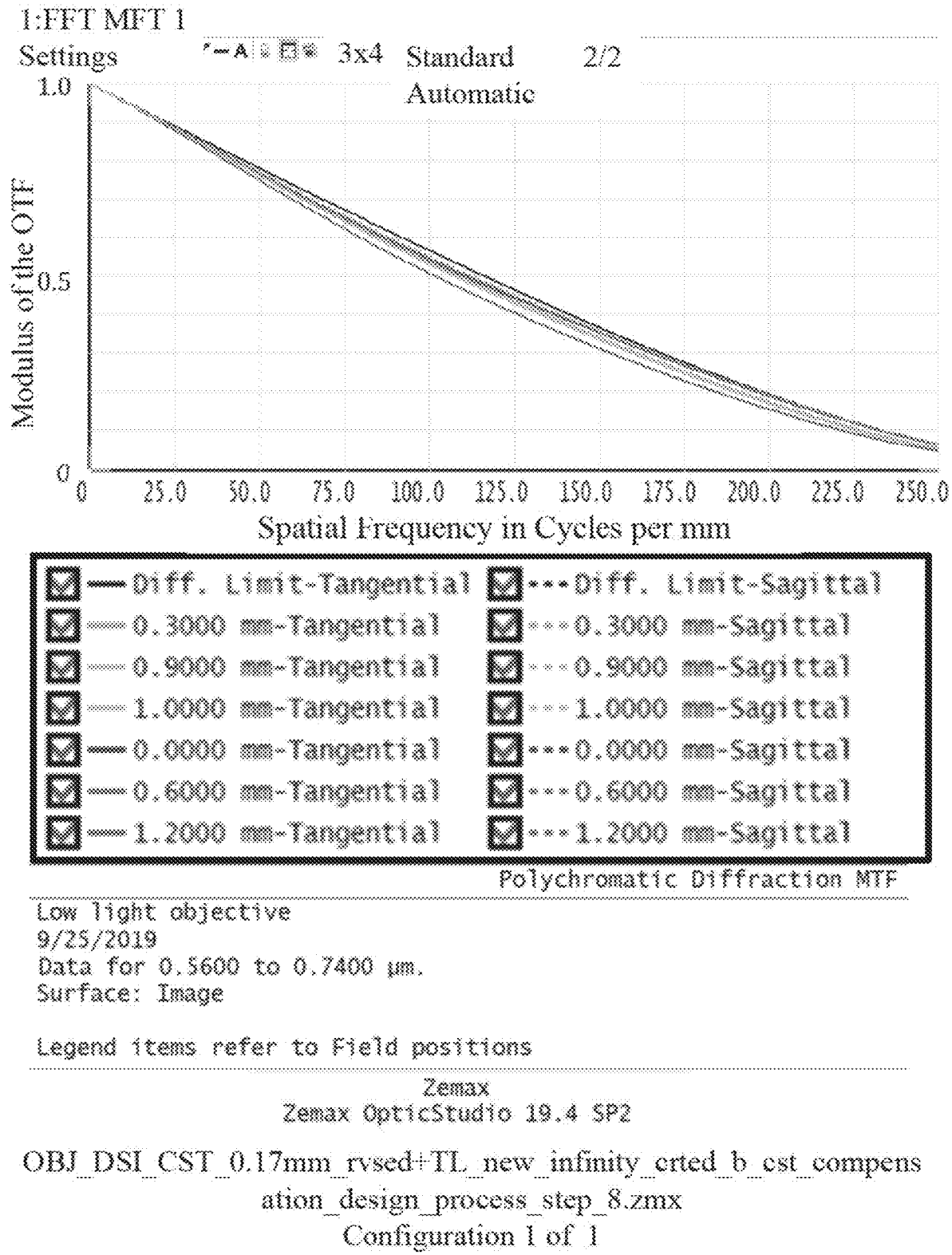
FIG. 23 provides a plot of the modulation transfer function for the combination of objective lens and tube lens illustrated in FIG. 15 as a function of spatial frequency when used to image a surface that is separated from that on the opposite side of a 1.0 mm thick coverslip by a 0.1 mm thick layer of aqueous fluid.

FIG. 22 and FIG. 23 provide plots of the modulation transfer function as a function of spatial frequency for the upper (or near) interior surface (FIG. 22) and lower (or far) interior surface (FIG. 23) of a flow cell when imaged using the objective lens (corrected for a 0.17 mm coverslip) and tube lens combination illustrated in FIG. 21 through a 1.0 mm thick coverslip, and when the upper and lower interior surfaces are separated by a 0.1 mm thick layer of aqueous fluid. As can be seen, the imaging performance achieved is nearly that expected for a diffraction-limited optical design.

Imaging channel-specific tube lens adaptation or optimization: In imaging system design, it is possible to improve or optimize both the objective lens and the tube lens in the same wavelength region for all imaging channels. Typically, the same objective lens is shared by all imaging channels, and each imaging channel either uses the same tube lens or has a tube lens that shares the same design.

In some instances, the imaging systems disclosed herein may further comprise a tube lens for each imaging channel where the tube lens has been independently improved or optimized for the specific imaging channel to improve image quality, e.g., to reduce or minimize distortion and field curvature, and improve depth-of-field (DOF) performance for each channel. Because the wavelength range (or bandpass) for each specific imaging channel is much narrower than the combined wavelength range for all channels, the wavelength- or channel-specific adaptation or optimization of the tube lens used in the disclosed systems results in significant improvements in imaging quality and performance. This channel-specific adaptation or optimization results in improved image quality for both the top and bottom surfaces of the flow cell in dual-side imaging applications.

Dual-side imaging w/o fluid present in flow cell: For optimal imaging performance of both top and bottom interior surfaces of a flow cell, a motion-actuated compensator is typically required to correct for optical aberrations induced by the fluid in the flow cell (typically comprising a fluid layer thickness of about 50-200 μm). In some instances of the disclosed optical system designs, the top interior surface of the flow cell may be imaged with fluid present in the flow cell. Once the sequencing chemistry cycle has been completed, the fluid may be extracted from the flow cell for imaging of the bottom interior surface. Thus, in some instances, even without the use of a compensator, the image quality for the bottom surface is maintained.

Compensation for optical aberration and/or vibration using electro-optical phase plates: In some instances, dual-surface image quality may be improved without requiring the removal of the fluid from the flow cell by using an electro-optical phase plate (or other corrective lens) in combination with the objective to cancel the optical aberrations induced by the presence of the fluid. In some instances, the use of an electro-optical phase plate (or lens) may be used to remove the effects of vibration arising from the mechanical motion of a motion-actuated compensator and may provide faster image acquisition times and sequencing cycle times for genomic sequencing applications.

Improved contrast-to-noise ratio (CNR), field-of-view (FOV), spectral separation, and timing design to increase or maximize information transfer and throughput: Another way to increase or maximize information transfer in imaging systems designed for genomics applications is to increase the size of the field-of-view (FOV) and reduce the time required to image a specific FOV. With typical large NA optical imaging systems, it may be common to acquire images for fields-of-view that are on the order of 1 mm$^2$ in area, where in the presently disclosed imaging system designs large FOV objectives with long working distances are specified to enable imaging of areas of 2 mm$^2$ or larger.

In some cases, the disclosed imaging systems are designed for use in combination with proprietary low-binding substrate surfaces and DNA amplification processes that reduce fluorescence background arising from a variety of confounding signals including, but are not limited to, nonspecific adsorption of fluorescent dyes to substrate surfaces, nonspecific nucleic acid amplification products (e.g., nucleic acid amplification products that arise the substrate surface in areas between the spots or features corresponding to clonally-amplified clusters of nucleic acid molecules (i.e., specifically amplified colonies), nonspecific nucleic acid amplification products that may arise within the amplified colonies, phased and pre-phased nucleic acid strands, etc. The use of low-binding substrate surfaces and DNA amplification processes that reduce fluorescence background in combination with the disclosed optical imaging systems may significantly cut down on the time required to image each FOV.

The presently disclosed system designs may further reduce the required imaging time through imaging sequence improvement or optimization where multiple channels of fluorescence images are acquired simultaneously or with overlapping timing, and where spectral separation of the fluorescence signals is designed to reduce cross-talks between fluorescence detection channels and between the excitation light and the fluorescence signal(s).

The presently disclosed system designs may further reduce the required imaging time through improvement or optimization of scanning motion sequence. In the typical approach, an X-Y translation stage is used to move the target FOV into position underneath the objective, an autofocus step is performed where optimal focal position is determined and the objective is moved in the Z direction to the determined focal position, and an image is acquired. A sequence of fluorescence images is acquired by cycling through a series of target FOV positions. From an information transfer duty cycle perspective, information is only transferred during the fluorescence image acquisition portion of the cycle. In the presently disclosed imaging system designs, a single-step motion in which all axes (X-Y-Z) are repositioned simultaneously is performed, and the autofocus step is used to check focal position error. The additional Z motion is only commanded if the focal position error (i.e., the difference between the focal plane position and the sample plane position) exceeds a certain limit (e.g., a specified error threshold). Coupled with high speed X-Y motion, this approach increases the duty cycle of the system, and thus increases the imaging throughput per unit time.

Furthermore, by matching the optical collection efficiency, modulation transfer function, and image sensor performance characteristics of the design with the fluorescence photon flux expected for the input excitation photon flux, dye efficiency (related to dye extinction coefficient and fluorescence quantum yield), while accounting for background signal and system noise characteristics, the time required to acquire high quality (high contrast-to-noise ratio (CNR) images) may be reduced or minimized.

The combination of efficient image acquisition and improved or optimized translation stage step and settle times leads to fast imaging times (i.e., the overall time required per field-of-view) and higher throughput imaging system performance.

Along with the large FOV and fast image acquisition duty cycle, the disclosed designs may comprise also specifying image plane flatness, chromatic focus performance between fluorescence detection channels, sensor flatness, image distortion, and focus quality specifications.

Chromatic focus performance is further improved by individually aligning the image sensors for different fluorescence detection channels such that the best focal plane for each detection channel overlaps. The design goal is to ensure that images across more than 90 percent of the field-of-view are acquired within ±100 nm (or less) relative to the best focal plane for each channel, thus increasing or maximizing the transfer of individual spot intensity signals. In some instances, the disclosed designs further ensure that images across 99 percent of the field-of-view are acquired within ±150 nm (or less) relative to the best focal plane for each channel, and that images across more the entire field-of-view are acquired within ±200 nm (or less) relative to the best focal plane for each imaging channel.

Illumination optical path design: Another factor for improving signal-to-noise ratio (SNR), contrast-to-noise ratio (CNR), and/or increasing throughput is to increase illumination power density to the sample. In some instances, the disclosed imaging systems may comprise an illumination path design that utilizes a high-power laser or laser diode coupled with a liquid light guide. The liquid light guide removes optical speckle that is intrinsic to coherent light sources such as lasers and laser diodes. Furthermore, the coupling optics are designed in such a way as to underfill the entrance aperture of the liquid light guide. The underfilling of the liquid light guide entrance aperture reduces the effective numerical aperture of the illumination beam entering the objective lens, and thus improves light delivery efficiency through the objective onto the sample plane. With this design innovation, one can achieve illumination power densities up to 3× that for conventional designs over a large field-of-view (FOV).

By utilizing the angle-dependent discrimination of s- and p-polarization, in some instances, the illumination beam polarization may be orientated to reduce the amount of back-scattered and back-reflected illumination light that reaches the imaging sensors.

Assessing image quality: For any of the embodiments of the optical imaging designs disclosed herein, imaging performance or imaging quality may be assessed using any of a variety of performance metrics known to those of skill in the art. Examples include, but are not limited to, measurements of modulation transfer function (MTF) at one or more specified spatial frequencies, defocus, spherical aberration, chromatic aberration, coma, astigmatism, field curvature, image distortion, contrast-to-noise ratio (CNR), or any combination thereof.

In some instances, the disclosed optical designs for dual-side imaging (e.g., the disclosed objective lens designs, tube lens designs, the use of an electro-optical phase plate in combination with an objective, etc., alone or in combination) may yield significant improvements for image quality for both the upper (near) and lower (far) interior surfaces of a flow cell, such that the difference in an imaging performance metric for imaging the upper interior surface and the lower interior surface of the flow cell is less than 20%, less than 15%, less than 10%, less than 5%, less than 4%, less than 3%, less than 2%, or less than 1% for any of the imaging performance metrics listed above, either individually or in combination.

In some instances, the disclosed optical designs for dual-side imaging (e.g., comprising the disclosed tube lens designs, the use of an electro-optical phase plate in combination with an objective, etc.) may yield significant improvements for image quality such that an image quality performance metric for dual-side imaging provides for an at least 1%, at least 2%, at least 3%, at least 4%, at least 5%, at least 10%, at least 15%, at least 20%, at least 25%, or at least 30% improvement in the imaging performance metric for dual-side imaging compared to that for a conventional system comprising, e.g., an objective lens, a motion-actuated compensator (that is moved out of or into the optical path when imaging the near or far interior surfaces of a flow cell), and an image sensor for any of the imaging performance metrics listed above, either individually or in combination. In some instances, fluorescence imaging systems comprising one or more of the disclosed tube lens designs provides for an at least equivalent or better improvement in an imaging performance metric for dual-side imaging compared to that for a conventional system comprising an objective lens, a motion-actuated compensator, and an image sensor. In some instances, fluorescence imaging systems comprising one or more of the disclosed tube lens designs provides for an at least 5%, 10%, 15%, 20%, 25%, 30%, 35%, 40%, 45%, or 50% improvement in an imaging performance metric for dual-side imaging compared to that for a conventional system comprising an objective lens, a motion-actuated compensator, and an image sensor.

Imaging Module Specifications:

Excitation light wavelength(s): In any of the disclosed optical imaging module designs, the light source(s) of the disclosed imaging modules may produce visible light, such as green light and/or red light. In some instances, the light source(s), alone or in combination with one or more optical components, e.g., excitation optical filters and/or dichroic beam splitters, may produce excitation light at about 350 nm, 375 nm, 400 nm, 425 nm, 450 nm, 475 nm, 500 nm, 525 nm, 550 m, 575 nm, 600 nm, 625 nm, 650 nm, 675 nm, 700 nm, 725 nm, 750 nm, 775 nm, 800 nm, 825 nm, 850 nm, 875 nm, or 900 nm. Those of skill in the art will recognize that the excitation wavelength may have any value within this range, e.g., about 620 nm.

Excitation light bandwidths: In any of the disclosed optical imaging module designs, the light source(s), alone or in combination with one or more optical components, e.g., excitation optical filters and/or dichroic beam splitters, may produce light at the specified excitation wavelength within a bandwidth of ±2 nm, ±5 nm, 10 nm, ±20 nm, ±40 nm, ±80 nm, or greater. Those of skill in the art will recognize that the excitation bandwidths may have any value within this range, e.g., about ±18 nm.

Light source power output: In any of the disclosed optical imaging module designs, the output of the light source(s) and/or an excitation light beam derived therefrom (including a composite excitation light beam) may range in power from about 0.5 W to about 5.0 W, or more (as will be discussed in more detail below). In some instances, the output of the light source and/or the power of an excitation light beam derived therefrom may be at least 0.5 W, at least 0.6 W, at least 0.7 W, at least 0.8 W, at least 1 W, at least 1.1 W, at least 1.2 W, at least 1.3 W, at least 1.4 W, at least 1.5 W, at least 1.6 W, at least 1.8 W, at least 2.0 W, at least 2.2 W, at least 2.4 W, at least 2.6 W, at least 2.8 W, at least 3.0 W, at least 3.5 W, at least 4.0 W, at least 4.5 W, or at least 5.0 W. In some implementations, the output of the light source and/or the power of an excitation light beam derived therefrom (including a composite excitation light beam) may be at most 5.0 W, at most 4.5 W, at most 4.0 W, at most 3.5 W, at most 3.0 W, at most 2.8 W, at most 2.6 W, at most 2.4 W, at most 2.2 W, at most 2.0 W, at most 1.8 W, at most 1.6 W, at most 1.5 W, at most 1.4 W, at most 1.3 W, at most 1.2 W, at most 1.1 W, at most 1 W, at most 0.8 W, at most 0.7 W, at most 0.6

W, or at most 0.5 W. Any of the lower and upper values described in this paragraph may be combined to form a range included within the present disclosure, for example, in some instances the output of the light source and/or the power of an excitation light beam derived therefrom (including a composite excitation light beam) may range from about 0.8 W to about 2.4 W. Those of skill in the art will recognize that the output of the light source and/or the power of an excitation light beam derived therefrom (including a composite excitation light beam) may have any value within this range, e.g., about 1.28 W.

Light source output power and CNR: In some implementations of the disclosed optical imaging module designs, the output power of the light source(s) and/or the power of excitation light beam(s) derived therefrom (including a composite excitation light beam) is sufficient, in combination with an appropriate sample, to provide for a contrast-to-noise ratio (CNR) in images acquired by the illumination and imaging module of at least 5, at least 10, at least 15, at least 20, at least 21, at least 22, at least 23, at least 24, at least 25, at least 30, at least 35, at least 40, or at least 50 or more, or any CNR within any range formed by any of these values.

Fluorescence emission bands: In some instances, the disclosed fluorescence optical imaging modules may be configured to detect fluorescence emission produced by any of a variety of fluorophores known to those of skill in the art. Examples of suitable fluorescence dyes for use in, e.g., genotyping and nucleic acid sequencing applications (e.g., by conjugation to nucleotides, oligonucleotides, or proteins) include, but are not limited to, fluorescein, rhodamine, coumarin, cyanine, and derivatives thereof, including the cyanine derivatives cyanine dye-3 (Cy3), cyanine dye-5 (Cy5), cyanine dye-7 (Cy7), etc.

Fluorescence emission wavelengths: In any of the disclosed optical imaging module designs, the detection channel or imaging channel of the disclosed optical systems may include one or more optical components, e.g., emission optical filters and/or dichroic beam splitters, configured to collect emission light at about 350 nm, 375 nm, 400 nm, 425 nm, 450 nm, 475 nm, 500 nm, 525 nm, 550 m, 575 nm, 600 nm, 625 nm, 650 nm, 675 nm, 700 nm, 725 nm, 750 nm, 775 nm, 800 nm, 825 nm, 850 nm, 875 nm, or 900 nm. Those of skill in the art will recognize that the emission wavelength may have any value within this range, e.g., about 825 nm.

Fluorescence emission light bandwidths: In any of the disclosed optical imaging module designs, the detection channel or imaging channel may comprise one or more optical components, e.g., emission optical filters and/or dichroic beam splitters, configured to collect light at the specified emission wavelength within a bandwidth of ±2 nm, +5 nm, ±10 nm, ±20 nm, ±40 nm, ±80 nm, or greater. Those of skill in the art will recognize that the excitation bandwidths may have any value within this range, e.g., about ±18 nm.

Numerical aperture: In some instances, the numerical aperture of the objective lens and/or optical imaging module (e.g., comprising an objective lens and/or tube lens) in any of the disclosed optical system designs may range from about 0.1 to about 1.4. In some instances, the numerical aperture may be at least 0.1, at least 0.2, at least 0.3, at least 0.4, at least 0.5, at least 0.6, at least 0.7, at least 0.8, at least 0.9, at least 1.0, at least 1.1, at least 1.2, at least 1.3, or at least 1.4. In some instances, the numerical aperture may be at most 1.4, at most 1.3, at most 1.2, at most 1.1, at most 1.0, at most 0.9, at most 0.8, at most 0.7, at most 0.6, at most 0.5, at most 0.4, at most 0.3, at most 0.2, or at most 0.1. Any of the lower and upper values described in this paragraph may be combined to form a range included within the present disclosure, for example, in some instances the numerical aperture may range from about 0.1 to about 0.6. Those of skill in the art will recognize that the numerical aperture may have any value within this range, e.g., about 0.55.

Optical resolution: In some instances, depending on the numerical aperture of the objective lens and/or optical system (e.g., comprising an objective lens and/or tube lens), the minimum resolvable spot (or feature) separation distance at the sample plane achieved by any of the disclosed optical system designs may range from about 0.5 μm to about 2 μm. In some instances, the minimum resolvable spot separation distance at the sample plane may be at least 0.5 μm, at least 0.6 μm, at least 0.7 μm, at least 0.8 μm, at least 0.9 μm, at least 1.0 μm, at least 1.2 μm, at least 1.4 μm, at least 1.6 μm, at least 1.8 μm, or at least 1.0 μm. In some instances, the minimum resolvable spot separation distance may be at most 2.0 μm, at most 1.8 μm, at most 1.6 μm, at most 1.4 μm, at most 1.2 μm, at most 1.0 μm, at most 0.9 μm, at most 0.8 μm, at most 0.7 μm, at most 0.6 μm, or at most 0.5 μm. Any of the lower and upper values described in this paragraph may be combined to form a range included within the present disclosure, for example, in some instances the minimum resolvable spot separation distance may range from about 0.8 μm to about 1.6 μm. Those of skill in the art will recognize that the minimum resolvable spot separation distance may have any value within this range, e.g., about 0.95 μm.

Optical resolution of first and second surfaces at different depths: In some instances, the use of the novel objective lens and/or tube lens designs disclosed herein, in any of the optical modules or systems disclosed herein, may confer comparable optical resolution for first and second surfaces (e.g. the upper and lower interior surfaces of a flow cell) with or without the need to refocus between acquiring the images of the first and second surfaces. In some instances, the optical resolution of the images thus obtained of the first and second surfaces may be with 20%, 18%, 16%, 14%, 12%, 10%, 8%, 6%, 4%, 2%, or 1% of each other, or within any value within this range.

Magnification: In some instances, the magnification of the objective lens and/or tube lens, and/or optical system (e.g., comprising an objective lens and/or tube lens) in any of the disclosed optical configurations may range from about 2× to about 20×. In some instances, the optical system magnification may be at least 2×, at least 3×, at least 4×, at least 5×, at least 6×, at least 7×, at least 8×, at least 9×, at least 10×, at least 15×, or at least 20×. In some instances, the optical system magnification may be at most 20×, at most 15×, at most 10×, at most 9×, at most 8×, at most 7×, at most 6×, at most 5×, at most 4×, at most 3×, or at most 2×. Any of the lower and upper values described in this paragraph may be combined to form a range included within the present disclosure, for example, in some instances the optical system magnification may range from about 3× to about 10×. Those of skill in the art will recognize that the optical system magnification may have any value within this range, e.g., about 7.5×.

Objective lens focal length: In some implementations of the disclosed optical designs, the focal length of the objective lens may range between 20 mm and 40 mm. In some instances, the focal length of the objective lens may be at least 20 mm, at least 25 mm, at least 30 mm, at least 35 mm, or at least 40 mm. In some instances, the focal length of the objective lens may be at most 40 mm, at most 35 mm, at most 30 mm, at most 25 mm, or at most 20 mm. Any of the lower and upper values described in this paragraph may be combined to form a range included within the present disclosure, for example, in some instances the focal length of the objective lens may range from 25 mm to 35 mm. Those of skill in the art will recognize that the focal length of the objective lens may have any value within the range of values specified above, e.g., about 37 mm.

Objective lens working distance: In some implementations of the disclosed optical designs, the working distance of the objective lens may range between about 100 μm and 30 mm. In some instances, the working distance may be at least 100 μm, at least 200 μm, at least 300 μm, at least 400 μm, at least 500 μm, at least 600 μm, at least 700 μm, at least 800 μm, at least 900 μm, at least 1 mm, at least 2 mm, at least 4 mm, at least 6 mm, at least 8 mm, at least 10 mm, at least 15 mm, at least 20 mm, at least 25 mm, or at least 30 mm. In some instances, the working distance may be at most 30 mm, at most 25 mm, at most 20 mm, at most 15 mm, at most 10 mm, at most 8 mm, at most 6 mm, at most 4 mm, at most 2 mm, at most 1 mm, at most 900 μm, at most 800 μm, at most 700 μm, at most 600 μm, at most 500 μm, at most 400 μm, at most 300 μm, at most 200 μm, at most 100 μm. Any of the lower and upper values described in this paragraph may be combined to form a range included within the present disclosure, for example, in some instances the working distance of the objective lens may range from 500 μm to 2 mm. Those of skill in the art will recognize that the working distance of the objective lens may have any value within the range of values specified above, e.g., about 1.25 mm.

Objectives optimized for imaging through thick coverslips: In some instances of the disclosed optical designs, the design of the objective lens may be improved or optimized for a different coverslip of flow cell thickness. For example, in some instances the objective lens may be designed for optimal optical performance for a coverslip that is from about 200 μm to about 1,000 μm thick. In some instances, the objective lens may be designed for optimal performance with a coverslip that is at least 200 μm, at least 300 μm, at least 400 μm, at least 500 μm, at least 600 μm, at least 700 μm, at least 800 μm, at least 900 μm, or at least 1,000 μm thick. In some instances, the objective lens may be designed for optimal performance with a coverslip that is at most 1,000 μm, at most 900 μm, at most 800 μm, at most 700 μm, at most 600 μm, at most 500 μm, at most 400 μm, at most 300 μm, or at most 200 μm thick. Any of the lower and upper values described in this paragraph may be combined to form a range included within the present disclosure, for example, in some instances the objective lens may be designed for optimal optical performance for a coverslip that may range from about 300 μm to about 900 μm. Those of skill in the art will recognize that the objective lens may be designed for optimal optical performance for a coverslip that may have any value within this range, e.g., about 725 μm.

Depth of field and depth of focus: In some instances, the depth of field and/or depth of focus for any of the disclosed imaging module (e.g., comprising an objective lens and/or tube lens) designs may range from about 10 μm to about 800 μm, or more. In some instances, the depth of field and/or depth of focus may be at least 10 μm, at least 20 μm, at least 30 μm, at least 40 μm, at least 50 μm, at least 75 μm, at least 100 μm, at least 125 μm, at least 150 μm, at least 175 μm, at least 200 μm, at least 250 μm, at least 300 μm, at least 300 μm, at least 400 μm, at least 500 μm, at least 600 μm, at least 700 μm, or at least 800 μm, or more. In some instances, the depth of field and/or depth of focus be at most 800 μm, at most 700 μm, at most 600 μm, at most 500 μm, at most 400 μm, at most 300 μm, at most 250 μm, at most 200 μm, at most 175 μm, at most 150 μm, at most 125 μm, at most 100 μm, at most 75 μm, at most 50 μm, at most 40 μm, at most 30 μm, at most 20 μm, at most 10 μm, or less. Any of the lower and upper values described in this paragraph may be combined to form a range included within the present disclosure, for example, in some instances the depth of field and/or depth of focus may range from about 100 μm to about 175 μm. Those of skill in the art will recognize that the depth of field and/or depth of focus may have any value within the range of values specified above, e.g., about 132 μm.

Field of view (FOP): In some implementations, the FOV of any of the disclosed imaging module designs (e.g., that provided by a combination of objective lens and detection channel optics (such as a tube lens)) may range, for example, between about 1 mm and 5 mm (e.g., in diameter, width, length, or longest dimension). In some instances, the FOV may be at least 1.0 mm, at least 1.5 mm, at least 2.0 mm, at least 2.5 mm, at least 3.0 mm, at least 3.5 mm, at least 4.0 mm, at least 4.5 mm, or at least 5.0 mm (e.g., in diameter, width, length, or longest dimension). In some instances, the FOV may be at most 5.0 mm, at most 4.5 mm, at most 4.0 mm, at most 3.5 mm, at most 3.0 mm, at most 2.5 mm, at most 2.0 mm, at most 1.5 mm, or at most 1.0 mm (e.g., in diameter, width, length, or longest dimension). Any of the lower and upper values described in this paragraph may be combined to form a range included within the present disclosure, for example, in some instances the FOV may range from about 1.5 mm to about 3.5 mm (e.g., in diameter, width, length, or longest dimension). Those of skill in the art will recognize that the FOV may have any value within the range of values specified above, e.g., about 3.2 mm (e.g., in diameter, width, length, or longest dimension).

Field-of-view (FOV) area. In some instances of the disclosed optical system designs, the area of the field-of-view may range from about 2 mm$^2$ to about 5 mm$^2$. In some instances, the field-of-view may be at least 2 mm$^2$, at least 3 mm$^2$, at least 4 mm$^2$, or at least 5 mm$^2$ in area. In some instances, the field-of-view may be at most 5 mm$^2$, at most 4 mm$^2$, at most 3 mm$^2$, or at most 2 mm$^2$ in area. Any of the lower and upper values described in this paragraph may be combined to form a range included within the present disclosure, for example, in some instances the field-of-view may range from about 3 mm$^2$ to about 4 mm$^2$ in area. Those of skill in the art will recognize that the area of the field-of-view may have any value within this range, e.g., 2.75 mm$^2$.

Optimization of objective lens and/or tube lens MTF: In some instances, the design of the objective lens and/or at least one tube lens in the disclosed imaging modules and systems is configured to optimize the modulation transfer function in the mid to high spatial frequency range. For example, in some instances, the design of the objective lens and/or at least one tube lens in the disclosed imaging modules and systems is configured to optimize the modulation transfer function in the spatial frequency range from 500 cycles per mm to 900 cycles per mm, from 700 cycles per mm to 1100 cycles per mm, from 800 cycles per mm to 1200 cycles per mm, or from 600 cycles per mm to 1000 cycles per mm in the sample plane.

Optical aberration and diffraction-limited imaging performance: In some implementations of any of the optical imaging module designs disclosed herein, the objective lens and/or tube lens may be configured to provide the imaging module with a field-of-view as indicated above such that the FOV has less than 0.15 waves of aberration over at least 60%, 70%, 80%, 90%, or 95% of the field. In some implementations, the objective lens and/or tube lens may be configured to provide the imaging module with a field-of-view as indicated above such that the FOV has less than 0.1 waves of aberration over at least 60%, 70%, 80%, 90%, or 95% of the field. In some implementations, the objective lens and/or tube lens may be configured to provide the imaging module with a field-of-view as indicated above such that the FOV has less than 0.075 waves of aberration over at least 60%, 70%, 800, 90%, or 95% of the field. In some implementations, the objective lens and/or tube lens may be configured to provide the imaging module with a field-of-view as indicated above such that the FOV is diffraction-limited over at least 60%, 70%, 80%, 90%, or 95% of the field.

Angle of incidence of light beams on dichroic reflectors, beam splitter, and beam combiners: In some instances of the disclosed optical designs, the angles of incidence for a light beam incident on a dichroic reflector, beam splitter, or beam combiner may range between about 20 degrees and about 45 degrees. In some instances, the angles of incidence may be at least 20 degrees, at least 25 degrees, at least 30 degrees, at least 35 degrees, at least 40 degrees, or at least 45 degrees. In some instances, the angles of incidence may be at most 45 degrees, at most 40 degrees, at most 35 degrees, at most 30 degrees, at most 25 degrees, or at most 20 degrees. Any of the lower and upper values described in this paragraph may be combined to form a range included within the present disclosure, for example, in some instances the angles of incidence may range from about 25 degrees to about 40 degrees. Those of skill in the art will recognize that the angles of incidence may have any value within the range of values specified above, e.g., about 43 degrees.

Image sensor (photodetector array) size: In some instances, the disclosed optical systems may comprise image sensor(s) having an active area with a diagonal ranging from about 10 mm to about 30 mm, or larger. In some instances, the image sensors may have an active area with a diagonal of at least 10 mm, at least 12 mm, at least 14 mm, at least 16 mm, at least 18 mm, at least 20 mm, at least 22 mm, at least 24 mm, at least 26 mm, at least 28 mm, or at least 30 mm. In some instances, the image sensors may have an active area with a diagonal of at most 30 mm, at most 28 mm, at most 26 mm, at most 24 mm, at most 22 mm, at most 20 mm, at most 18 mm, at most 16 mm, at most 14 mm, at most 12 mm, or at most 10 mm. Any of the lower and upper values described in this paragraph may be combined to form a range included within the present disclosure, for example, in some instances the image sensor(s) may have an active area with a diagonal ranging from about 12 mm to about 24 mm. Those of skill in the art will recognize that the image sensor(s) may have an active area with a diagonal having any value within the range of values specified above, e.g., about 28.5 mm.

Image sensor pixel size and pitch: In some instances, the pixel size and/or pitch selected for the image sensor(s) used in the disclosed optical system designs may range in at least one dimension from about 1 µm to about 10 µm. In some instances, the pixel size and/or pitch may be at least 1 µm, at least 2 µm, at least 3 µm, at least 4 µm, at least 5 µm, at least 6 µm, at least 7 µm, at least 8 µm, at least 9 µm, or at least 10 µm. In some instances, the pixel size and/or pitch may be at most 10 µm, at most 9 µm, at most 8 µm, at most 7 µm, at most 6 µm, at most 5 µm, at most 4 µm, at most 3 µm, at most 2 µm, or at most 1 µm. Any of the lower and upper values described in this paragraph may be combined to form a range included within the present disclosure, for example, in some instances the pixel size and/or pitch may range from about 3 µm to about 9 µm. Those of skill in the art will recognize that the pixel size and/or pitch may have any value within this range, e.g., about 1.4 µm.

Oversampling: In some instances of the disclosed optical designs, a spatial oversampling scheme is utilized wherein the spatial sampling frequency is at least 2×, 2.5×, 3×, 3.5×, 4×, 4.5×, 5×, 6×, 7×, 8×, 9×, or 10× the optical resolution X (lp/mm).

Maximum translation stage velocity: In some instances of the disclosed optical imaging modules, the maximum translation stage velocity on any one axis may range from about 1 mm/sec to about 5 mm/sec. In some instances, the maximum translation stage velocity may be at least 1 mm/sec, at least 2 mm/sec, at least 3 mm/sec, at least 4 mm/sec, or at least 5 mm/sec. In some instances, the maximum translation stage velocity may be at most 5 mm/sec, at most 4 mm/sec, at most 3 mm/sec, at most 2 mm/sec, or at most 1 mm/sec. Any of the lower and upper values described in this paragraph may be combined to form a range included within the present disclosure, for example, in some instances the maximum translation stage velocity may range from about 2 mm/sec to about 4 mm/sec. Those of skill in the art will recognize that the maximum translation stage velocity may have any value within this range, e.g., about 2.6 mm/sec.

Maximum translation stage acceleration: In some instances of the disclosed optical imaging modules, the maximum acceleration on any one axis of motion may range from about 2 mm/sec$^2$ to about 10 mm/sec$^2$. In some instances, the maximum acceleration may be at least 2 mm/sec$^2$, at least 3 mm/sec$^2$, at least 4 mm/sec$^2$, at least 5 mm/sec$^2$, at least 6 mm/sec$^2$, at least 7 mm/sec$^2$, at least 8 mm/sec$^2$, at least 9 mm/sec$^2$, or at least 10 mm/sec$^2$. In some instances, the maximum acceleration may be at most 10 mm/sec$^2$, at most 9 mm/sec$^2$, at most 8 mm/sec$^2$, at most 7 mm/sec$^2$, at most 6 mm/sec$^2$, at most 5 mm/sec$^2$, at most 4 mm/sec$^2$, at most 3 mm/sec$^2$, or at most 2 mm/sec$^2$. Any of the lower and upper values described in this paragraph may be combined to form a range included within the present disclosure, for example, in some instances the maximum acceleration may range from about 2 mm/sec$^2$ to about 8 mm/sec$^2$. Those of skill in the art will recognize that the maximum acceleration may have any value within this range, e.g., about 3.7 mm/sec$^2$.

Translation stage positioning repeatability: In some instances of the disclosed optical imaging modules, the repeatability of positioning for any one axis may range from about 0.1 µm to about 2 µm. In some instances, the repeatability of positioning may be at least 0.1 µm, at least 0.2 µm, at least 0.3 µm, at least 0.4 µm, at least 0.5 µm, at least 0.6 µm, at least 0.7 µm, at least 0.8 µm, at least 0.9 µm, at least 1.0 µm, at least 1.2 µm, at least 1.4 µm, at least 1.6 µm, at least 1.8 µm, or at least 2.0 µm. In some instances, the repeatability of positioning may be at most 2.0 µm, at most 1.8 µm, at most 1.6 µm, at most 1.4 µm, at most 1.2 µm, at most 1.0 µm, at most 0.9 µm, at most 0.8 µm, at most 0.7 µm, at most 0.6 µm, at most 0.5 µm, at most 0.4 µm, at most 0.3 µm, at most 0.2 µm, or at most 0.1 µm. Any of the lower and upper values described in this paragraph may be combined to form a range included within the present disclosure, for example, in some instances the repeatability of positioning may range from about 0.3 µm to about 1.2 µm. Those of skill in the art will recognize that the repeatability of positioning may have any value within this range, e.g., about 0.47 µm.

FOV repositioning time: In some instances of the disclosed optical imaging modules, the maximum time required to reposition the sample plane (field-of-view) relative to the optics, or vice versa, may range from about 0.1 sec to about 0.5 sec. In some instances, the maximum repositioning time (i.e., the scan stage step and settle time) may be at least 0.1 sec, at least 0.2 sec, at least 0.3 sec, at least 0.4 sec, or at least 0.5 sec. In some instances, the maximum repositioning time may be at most 0.5 sec, at most 0.4 sec, at most 0.3 sec, at most 0.2 sec, or at most 0.1 sec. Any of the lower and upper values described in this paragraph may be combined to form a range included within the present disclosure, for example, in some instances the maximum repositioning time may range from about 0.2 sec to about 0.4 sec. Those of skill in the art will recognize that the maximum repositioning time may have any value within this range, e.g., about 0.45 sec.

Error threshold for autofocus correction: In some instances of the disclosed optical imaging modules, the specified error threshold for triggering an autofocus correction may range from about 50 nm to about 200 nm. In some instances, the error threshold may be at least 50 nm, at least 75 nm, at least 100 nm, at least 125 nm, at least 150 nm, at least 175 nm, or at least 200 nm. In some instances, the error threshold may be at most 200 nm, at most 175 nm, at most 150 nm, at most 125 nm, at most 100 nm, at most 75 nm, or at most 50 nm. Any of the lower and upper values described in this paragraph may be combined to form a range included within the present disclosure, for example, in some instances the error threshold may range from about 75 nm to about 150 nm. Those of skill in the art will recognize that the error threshold may have any value within this range, e.g., about 105 nm.

Image acquisition time: In some instances of the disclosed optical imaging modules, the image acquisition time may range from about 0.001 sec to about 1 sec. In some instances, the image acquisition time may be at least 0.001 sec, at least 0.01 sec, at least 0.1 sec, or at least 1 sec. in some instances, the image acquisition time may be at most 1 sec, at most 0.1 sec, at most 0.01 sec, or at most 0.001 sec. Any of the lower and upper values described in this paragraph may be combined to form a range included within the present disclosure, for example, in some instances the image acquisition time may range from about 0.01 sec to about 0.1 sec. Those of skill in the art will recognize that the image acquisition time may have any value within this range, e.g., about 0.250 seconds.

Imaging time per FOV: In some instances, the imaging times may range from about 0.5 seconds to about 3 seconds per field-of-view. In some instances, the imaging time may be at least 0.5 seconds, at least 1 second, at least 1.5 seconds, at least 2 seconds, at least 2.5 seconds, or at least 3 seconds per FOV. In some instances, the imaging time may be at most 3 seconds, at most 2.5 seconds, at most 2 seconds, at most 1.5 seconds, at most 1 second, or at most 0.5 seconds per FOV. Any of the lower and upper values described in this paragraph may be combined to form a range included within the present disclosure, for example, in some instances the imaging time may range from about 1 second to about 2.5 seconds. Those of skill in the art will recognize that the imaging time may have any value within this range, e.g., about 1.85 seconds.

Flatness of field: In some instances, images across 80%, 90%, 95%, 98%, 99%, or 100% percent of the field-of-view are acquired within ±200 nm, ±175 nm, ±150 nm, ±125 nm, ±100 nm, ±75 nm, or ±50 nm relative to the best focal plane for each fluorescence (or other imaging mode) detection channel.

Analysis systems and system components for genomics and other applications: As noted above, in some implementations, the disclosed optical imaging modules may function as modules, components, sub-assemblies, or sub-systems of larger systems (e.g., analysis systems) configured for performing, e.g., genomics applications (e.g., genetic testing and/or nucleic acid sequencing applications) or other chemical analysis, biochemical analysis, nucleic acid analysis, cell analysis or tissue analysis applications. In addition to one, two, three, four, or more than four imaging modules as disclosed herein (each of which may comprise one or more illumination optical paths and/or one or more detection optical paths (e.g., one or more detection channels configured for imaging fluorescence emission within a specified wavelength range onto an image sensor)), such systems may comprise one or more X-Y translation stages, one or more X-Y-Z translation stages, flow cells or cartridges, fluidics systems and fluid flow control modules, temperature control modules, fluid dispensing robotics, cartridge- and/or microplate-handling (pick-and-place) robotics, light-tight housings and/or environmental control chambers, one or more processors or computers, data storage modules, data communication modules (e.g., Bluetooth, WiFi, intranet, or internet communication hardware and associated software), display modules, one or more local and/or cloud-based software packages (e.g., instrument/system control software packages, image processing software packages, data analysis software packages), etc., or any combination thereof.

Translation stages: In some implementations of the imaging and analysis systems (e.g., nucleic acid sequencing systems) disclosed herein, the system may comprise one or more (e.g., one, two, three, four, or more than four) high precision X-Y (or in some cases, X-Y-Z) translation stage(s) for re-positioning one or more sample support structure(s) (e.g., flow cell(s)) in relation to the one or more imaging modules, for example, in order to tile one or more images, each corresponding to a field-of-view of the imaging module, to reconstruct composite image(s) of an entire flow cell surface. In some implementations of the imaging systems and genomics analysis systems (e.g., nucleic acid sequencing systems) disclosed herein, the system may comprise one or more (e.g., one, two, three, four, or more than four) high precision X-Y (or in some cases, X-Y-Z) translation stage(s) for re-positioning the one or more imaging modules in relation to one or more sample support structure(s) (e.g., flow cell(s)), for example, in order to tile one or more images, each corresponding to a field-of-view of the imaging module, to reconstruct composite image(s) of an entire flow cell surface.

Suitable translation stages are commercially available from a variety of vendors, for example, Parker Hannifin. Precision translation stage systems typically comprise a combination of several components including, but not limited to, linear actuators, optical encoders, servo and/or stepper motors, and motor controllers or drive units. High precision and repeatability of stage movement is required for the systems and methods disclosed herein in order to ensure accurate and reproducible positioning and imaging of, e.g., fluorescence signals when interspersing repeated steps of reagent delivery and optical detection.

Consequently, the systems disclosed herein may comprise specifying the precision with which the translation stage is configured to position a sample support structure in relation to the illumination and/or imaging optics (or vice versa). In one aspect of the present disclosure, the precision of the one or more translation stages is between about 0.1 µm and about 10 µm. In other aspects, the precision of the translation stage is about 10 µm or less, about 9 µm or less, about 8 µm or less, about 7 µm or less, about 6 µm or less, about 5 µm or less, about 4 µm or less, about 3 µm or less, about 2 µm or less, about 1 µm or less, about 0.9 µm or less, about 0.8 µm or less, about 0.7 µm or less, about 0.6 µm or less, about 0.5 µm or less, about 0.4 µm or less, about 0.3 µm or less, about 0.2 µm or less, or about 0.1 µm or less. Those of skill in the art will appreciate that, in some instances, the positioning precision of the translation stage may fall within any range bounded by any of two of these values (e.g. from about 0.5 µm to about 1.5 µm). In some instances, the positioning precision of the translation stage may have any value within the range of values included in this paragraph, e.g., about 0.12 µm.

Flow cells, microfluidic devices, and cartridges: As noted above, in some instances, a sample support structure for the disclosed imaging modules may be configured as a flow cell device comprising, e.g., one, two, three, four, or more than four sample support surfaces (or simply surfaces) upon which cells, tissue slices, or nucleic acid molecules derived therefrom may be tethered or immobilized. The flow cell devices and flow cell cartridges disclosed herein may be used as components of analysis systems designed for a variety of chemical analysis, biochemical analysis, nucleic acid analysis, cell analysis, or tissue analysis application. In general, such analysis systems may comprise one or more one or more of the disclosed single capillary flow cell devices, multiple capillary flow cell devices, capillary flow cell cartridges, and/or microfluidic devices and cartridges described herein. Additional description of the disclosed flow cell devices and cartridges may be found in PCT Patent Application Publication WO 2020/118255, which is incorporated herein by reference in its entirety.

In some instances, the systems disclosed herein may comprise 1, 2, 3, 4, 5, 6, 7, 8, 9, 10, or more than 10 single capillary flow cell devices, multiple capillary flow cell devices, capillary flow cell cartridges, and/or microfluidic devices and cartridges. In some instances, the single capillary flow cell devices, multiple capillary flow cell devices, and/or microfluidic devices and cartridges may be fixed components of the disclosed systems. In some instances, the single capillary flow cell devices, multiple capillary flow cell devices, and/or microfluidic devices and cartridges may be removable, exchangeable components of the disclosed systems. In some instances, the single capillary flow cell devices, multiple capillary flow cell devices, and/or microfluidic devices and cartridges may be disposable or consumable components of the disclosed systems.

In some implementations, the disclosed single capillary flow cell devices (or single capillary flow cell cartridges) comprise a single capillary, e.g., a glass or fused-silica capillary, the lumen of which forms a fluid flow path through which reagents or solutions may flow, and the interior surface of which may form a sample support structure to which samples of interest are bound or tethered. In some implementations, the multi-capillary capillary flow cell devices (or multi-capillary flow cell cartridges) disclosed herein may comprise 2, 3, 4, 5, 6, 7, 8, 9, 10, 11, 12, 13, 14, 15, 16, 17, 18, 19, 20, or more than 20 capillaries configured for performing an analysis technique that further comprises imaging as a detection method.

In some instances, one or more capillaries may be packaged within a chassis to form a cartridge that facilitates ease-of-handling, incorporates adapters or connectors for making external fluid connections, and may optionally include additional integrated functionality such as reagent reservoirs, waste reservoirs, valves (e.g., microvalves), pumps (e.g., micropumps), etc., or any combination thereof.

Figure 24:
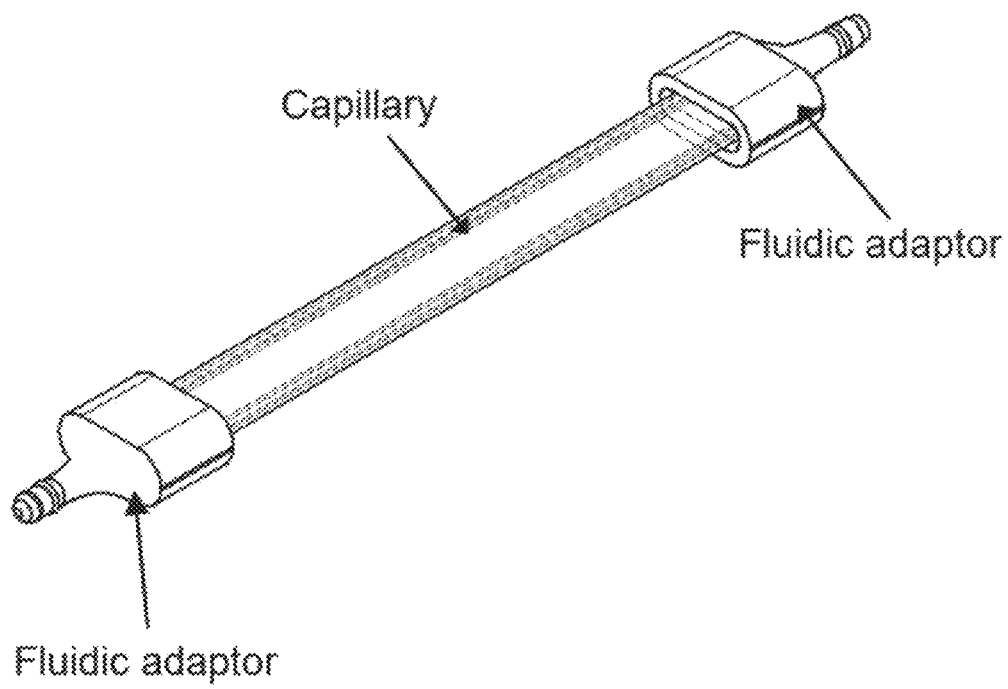
FIG. 24 illustrates one non-limiting example of a single capillary flow cell having 2 fluidic adaptors.

FIG. 24 illustrates one non-limiting example of a single glass capillary flow cell device that comprises two fluidic adaptors—one affixed to each end of the piece of glass capillary—that are designed to mate with standard OD fluidic tubing to provide for convenient, interchangeable fluid connections with an external fluid flow control system. The fluidic adaptors can be attached to the capillary using any of a variety of techniques known to those of skill in the art including, but not limited to, press fit, adhesive bonding, solvent bonding, laser welding, etc., or any combination thereof.

In general, the capillaries used in the disclosed capillary flow cell devices and capillary flow cell cartridges will have at least one internal, axially-aligned fluid flow channel (or "lumen") that runs the full length of the capillary. In some instances, the capillary may have two, three, four, five, or more than five internal, axially-aligned fluid flow channels (or "lumen").

A number specified cross-sectional geometries for suitable capillaries (or the lumen thereof) are consistent with the disclosure herein including, but not limited to, circular, elliptical, square, rectangular, triangular, rounded square, rounded rectangular, or rounded triangular cross-sectional geometries. In some instances, the capillary (or lumen thereof) may have any specified cross-sectional dimension or set of dimensions. For example, in some instances the largest cross-sectional dimension of the capillary lumen (e.g. the diameter if the lumen is circular in shape, or the diagonal if the lumen is square or rectangular in shape) may range from about 10 µm to about 10 mm. In some aspects, the largest cross-sectional dimension of the capillary lumen may be at least 10 µm, at least 25 µm, at least 50 µm, at least 75 µm, at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In some aspects, the largest cross-sectional dimension of the capillary lumen may be at most 10 mm, at most 9 mm, at most 8 mm, at most 7 mm, at most 6 mm, at most 5 mm, at most 4 mm, at most 3 mm, at most 2 mm, at most 1 mm, at most 900 µm, at most 800 µm, at most 700 µm, at most 600 µm, at most 500 µm, at most 400 µm, at most 300 µm, at most 200 µm, at most 100 µm, at most 75 µm, at most 50 µm, at most 25 µm, or at most 10 µm. Any of the lower and upper values described in this paragraph may be combined to form a range included within the present disclosure, for example, in some instances the largest cross-sectional dimension of the capillary lumen may range from about 100 µm to about 500 µm. Those of skill in the art will recognize that the largest cross-sectional dimension of the capillary lumen may have any value within this range, e.g., about 124 µm.

In some instances, e.g., wherein the lumen of the one or more capillaries in a flow cell device or cartridge has a square or rectangular cross-section, the distance between a first interior surface (e.g., a top or upper surface) and a second interior surface (e.g., a bottom or lower surface) that defines the gap height or thickness of a fluid flow channel may range from about 10 µm to about 500 µm. In some instances, the gap height may be at least 10 µm, at least 20 µm, at least 30 µm, at least 40 µm, at least 50 µm, at least 60 µm, at least 70 µm, at least 80 µm, at least 90 µm, at least 100 µm, at least 125 µm, at least 150 µm, at least 175 µm, at least 200 µm, at least 225 µm, at least 250 µm, at least 275 µm, at least 300 µm, at least 325 µm, at least 350 µm, at least 375 µm, at least 400 µm, at least 425 µm, at least 450 µm, at least 475 µm, or at least 500 µm. In some instances, the gap height may be at most 500 µm, at most 475 µm, at most 450 µm, at most 425 µm, at most 400 µm, at most 375 µm, at most 350 µm, at most 325 µm, at most 300 µm, at most 275 µm, at most 250 µm, at most 225 µm, at most 200 µm, at most 175 µm, at most 150 µm, at most 125 µm, at most 100 µm, at most 90 µm, at most 80 µm, at most 70 µm, at most 60 µm, at most 50 µm, at most 40 µm, at most 30 µm, at most 20 µm, or most 10 µm. Any of the lower and upper values described in this paragraph may be combined to form a range included within the present disclosure, for example, in some instances the gap height may range from about 40 µm to about 125 µm. Those of skill in the art will recognize that the gap height may have any value within the range of values in this paragraph, e.g., about 122 µm.

In some instances, the length of the one or more capillaries used to fabricate the disclosed capillary flow cell devices or flow cell cartridges may range from about 5 mm to about 5 cm or greater. In some instances, the length of the one or more capillaries may be less than 5 mm, at least 5 mm, at least 1 cm, at least 1.5 cm, at least 2 cm, at least 2.5 cm, at least 3 cm, at least 3.5 cm, at least 4 cm, at least 4.5 cm, or at least 5 cm. In some instances, the length of the one or more capillaries may be at most 5 cm, at most 4.5 cm, at most 4 cm, at most 3.5 cm, at most 3 cm, at most 2.5 cm, at most 2 cm, at most 1.5 cm, at most 1 cm, or at most 5 mm. Any of the lower and upper values described in this paragraph may be combined to form a range included within the present disclosure, for example, in some instances the length of the one or more capillaries may range from about 1.5 cm to about 2.5 cm. Those of skill in the art will recognize that the length of the one or more capillaries may have any value within this range, e.g., about 1.85 cm. In some instances, devices or cartridges may comprise a plurality of two or more capillaries that are the same length. In some instances, devices or cartridges may comprise a plurality of two or more capillaries that are of different lengths.

The capillaries used for constructing the disclosed capillary flow cell devices or capillary flow cell cartridges may be fabricated from any of a variety of materials known to those of skill in the art including, but not limited to, glass (e.g., borosilicate glass, soda lime glass, etc.), fused silica (quartz), polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), polydimethylsiloxane (PDMS), etc.), polyetherimide (PEI) and perfluoroelastomer (FFKM) as more chemically inert alternatives, or any combination thereof. PEI is somewhere between polycarbonate and PEEK in terms of both cost and chemical compatibility. FFKM is also known as Kalrez.

The one or more materials used to fabricate the capillaries are often optically transparent to facilitate use with spectroscopic or imaging-based detection techniques. In some instances, the entire capillary will be optically transparent. Alternately, in some instances, only a portion of the capillary (e.g., an optically transparent "window") will be optically transparent.

The capillaries used for constructing the disclosed capillary flow cell devices and capillary flow cell cartridges may be fabricated using any of a variety of techniques known to those of skill in the art, where the choice of fabrication technique is often dependent on the choice of material used, and vice versa. Examples of suitable capillary fabrication techniques include, but are not limited to, extrusion, drawing, precision computer numerical control (CNC) machining and boring, laser photoablation, and the like.

In some implementations, the capillaries used in the disclosed capillary flow cell devices and cartridges may be off-the-shelf commercial products. Examples of commercial vendors that provide precision capillary tubing include Accu-Glass (St. Louis, MO; precision glass capillary tubing), Polymicro Technologies (Phoenix, AZ; precision glass and fused-silica capillary tubing), Friedrich & Dimmock, Inc. (Millville, NJ; custom precision glass capillary tubing), and Drummond Scientific (Broomall, PA; OEM glass and plastic capillary tubing).

The fluidic adapters that are attached to the capillaries of the capillary flow cell devices and cartridges disclosed herein, and other components of the capillary flow cell devices or cartridges, may be fabricated using any of a variety of suitable techniques (e.g., extrusion molding, injection molding, compression molding, precision CNC machining, etc.) and materials (e.g., glass, fused-silica, ceramic, metal, polydimethylsiloxane, polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), etc.), where again the choice of fabrication technique is often dependent on the choice of material used, and vice versa.

Figure 25:
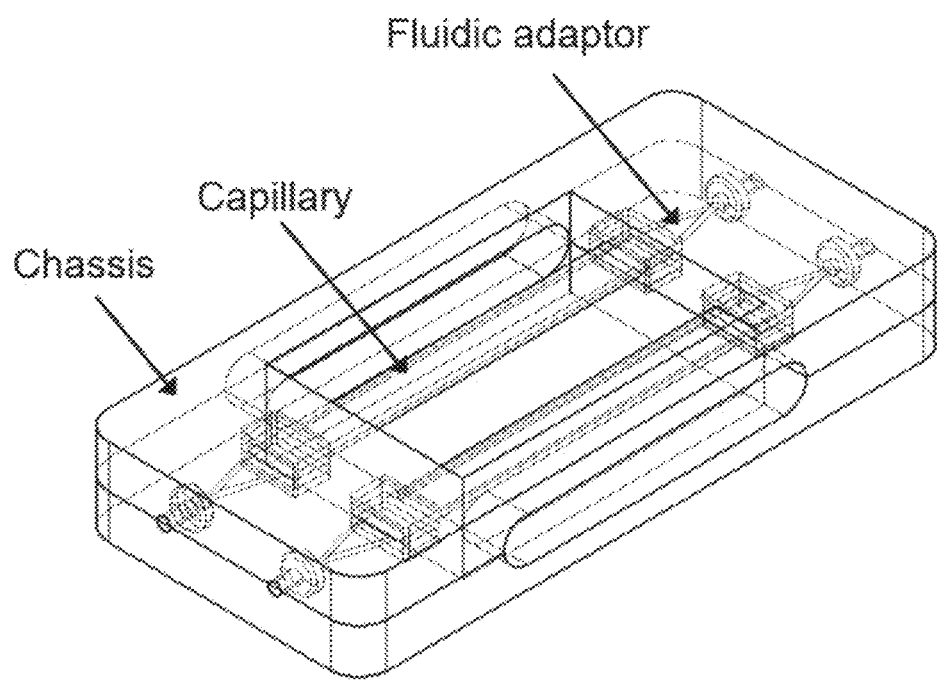
FIG. 25 illustrates one non-limiting example of a flow cell cartridge comprising a chassis, fluidic adapters, and optionally other components, that is designed to hold two capillaries.

FIG. 25 provides a non-limiting example of capillary flow cell cartridge that comprises two glass capillaries, fluidic adaptors (two per capillary in this example), and a cartridge chassis that mates with the capillaries and/or fluidic adapters such that the capillaries are held in a fixed orientation relative to the cartridge. In some instances, the fluidic adaptors may be integrated with the cartridge chassis. In some instances, the cartridge may comprise additional adapters that mate with the capillaries and/or capillary fluidic adapters. As noted elsewhere herein, in some instances, the cartridge may comprise additional functional components. In some instances, the capillaries are permanently mounted in the cartridge. In some instances, the cartridge chassis is designed to allow one or more capillaries of the flow cell cartridge to be interchangeable removed and replaced. For example, in some instances, the cartridge chassis may comprise a hinged "clamshell" configuration which allows it to be opened so that one or more capillaries may be removed and replaces. In some instances, the cartridge chassis is configured to mount on, for example, the stage of a fluorescence microscope or within a cartridge holder of a fluorescence imaging module or instrument system of the present disclosure.

In some instances, the disclosed flow cell devices may comprise microfluidic devices (or "microfluidic chips") and cartridges, where the microfluidic devices are fabricated by forming fluid channels in one or more layers of a suitable material and comprise one or more fluid channels (e.g., "analysis" channels) configured for performing an analysis technique that further comprises imaging as a detection method. In some implementations, the microfluidic devices or cartridges disclosed herein may comprise 1, 2, 3, 4, 5, 6, 7, 8, 9, 10, 11, 12, 13, 14, 15, 16, 17, 18, 19, 20, or more than 20 fluid channels (e.g., "analysis" fluid channels) configured for performing an analysis technique that further comprises imaging as a detection method. In some instances, the disclosed microfluidic devices may further comprise additional fluid channels (e.g., for dilution or mixing of reagents), reagent reservoirs, waste reservoirs, adapters for making external fluid connections, and the like, to provide integrated "lab-on-a-chip" functionality within the device.

A non-limiting example of microfluidic flow cell cartridge comprises a chip having two or more parallel glass channels formed on the chip, fluidic adaptors coupled to the chip, and a cartridge chassis that mates with the chip and/or fluidic adapters such that the chip is posited in a fixed orientation relative to the cartridge. In some instances, the fluidic adaptors may be integrated with the cartridge chassis. In some instances, the cartridge may comprise additional adapters that mate with the chip and/or fluidic adapters. In some instances, the chip is permanently mounted in the cartridge. In some instances, the cartridge chassis is designed to allow one or more chips of the flow cell cartridge to be interchangeably removed and replaced. For example, in some instances, the cartridge chassis may comprise a hinged "clamshell" configuration which allows it to be opened so that one or more chips may be removed and replaces. In some instances, the cartridge chassis is configured to mount on, for example, the stage of a microscope system or within a cartridge holder of an imaging system. Even through only one chip is described in the non-limiting example, it is understood that more than one chip can be used in the microfluidic flow cell cartridge. The flow cell cartridges of the present disclosure may comprise a single microfluidic chip or a plurality of microfluidic chips. In some instances, the flow cell cartridges of the present disclosure may comprise 2, 3, 4, 5, 6, 7, 8, 9, 10, 11, 12, 13, 14, 15, 16, 17, 18, 19, 20, or more than 20 microfluidic chips. The packaging of one or more microfluidic devices within a cartridge may facilitate ease-of-handling and correct positioning of the device within the optical imaging system.

The fluid channels within the disclosed microfluidic devices and cartridges may have an of a variety of cross-sectional geometries including, but not limited to, circular, elliptical, square, rectangular, triangular, rounded square, rounded rectangular, or rounded triangular cross-sectional geometries. In some instances, the fluid channels may have any specified cross-sectional dimension or set of dimensions. For example, in some instances, the height (e.g., gap height), width, or largest cross-sectional dimension of the fluid channels (e.g., the diagonal if the fluid channel has a square, rounded square, rectangular, or rounded rectangular cross-section) may range from about 10 μm to about 10 mm. In some aspects, the height (e.g., gap height), width, or largest cross-sectional dimension of the fluid channels may be at least 10 μm, at least 25 μm, at least 50 μm, at least 75 μm, at least 100 μm, at least 200 μm, at least 300 μm, at least 400 μm, at least 500 μm, at least 600 μm, at least 700 μm, at least 800 μm, at least 900 μm, at least 1 mm, at least 2 mm, at least 3 mm, at least 4 mm, at least 5 mm, at least 6 mm, at least 7 mm, at least 8 mm, at least 9 mm, or at least 10 mm. In some aspects, the height (e.g., gap height), width, or largest cross-sectional dimension of the fluid channels may be at most 10 mm, at most 9 mm, at most 8 mm, at most 7 mm, at most 6 mm, at most 5 mm, at most 4 mm, at most 3 mm, at most 2 mm, at most 1 mm, at most 900 μm, at most 800 μm, at most 700 μm, at most 600 μm, at most 500 μm, at most 400 μm, at most 300 μm, at most 200 μm, at most 100 μm, at most 75 μm, at most 50 μm, at most 25 μm, or at most 10 μm. Any of the lower and upper values described in this paragraph may be combined to form a range included within the present disclosure, for example, in some instances the height (e.g., gap height), width, or largest cross-sectional dimension of the fluid channels may range from about 20 μm to about 200 μm. Those of skill in the art will recognize that the height (e.g., gap height), width, or largest cross-sectional dimension of the fluid channels may have any value within this range, e.g., about 122 μm.

In some instances, the length of the fluid channels in the disclosed microfluidic devices and cartridges may range from about 5 mm to about 10 cm or greater. In some instances, the length of the fluid channels may be less than 5 mm, at least 5 mm, at least 1 cm, at least 1.5 cm, at least 2 cm, at least 2.5 cm, at least 3 cm, at least 3.5 cm, at least 4 cm, at least 4.5 cm, at least 5 cm, at least 6 cm, at least 7 cm, at least 8 cm, at least 9 cm, or at least 10 cm. In some instances, the length of the fluid channels may be at most 10 cm, at most 9 cm, at most 8 cm, at most 7 cm, at most 6 cm, at most 5 cm, at most 4.5 cm, at most 4 cm, at most 3.5 cm, at most 3 cm, at most 2.5 cm, at most 2 cm, at most 1.5 cm, at most 1 cm, or at most 5 mm. Any of the lower and upper values described in this paragraph may be combined to form a range included within the present disclosure, for example, in some instances the length of the fluid channels may range from about 1.5 cm to about 2.5 cm. Those of skill in the art will recognize that the length of the fluid channels may have any value within this range, e.g., about 1.35 cm. In some instances, the microfluidic devices or cartridges may comprise a plurality of fluid channels that are the same length. In some instances, the microfluidic devices or cartridges may comprise a plurality of fluid channels that are of different lengths.

The disclosed microfluidic devices will comprise at least one layer of material having one or more fluid channels formed therein. In some instances, the microfluidic chip may include two layers bonded together to form one or more fluid channels. In some instances, the microfluidic chip may include three or more layers bonded together to form one or more fluid channels. In some instances, the microfluidic fluid channels may have an open top. In some instances, the microfluidic fluid channels may be fabricated within one layer, e.g., the top surface of a bottom layer, and sealed by bonding the top surface of the bottom layer to the bottom surface of a top layer of material. In some instances, the microfluidic channels may be fabricated within one layer, e.g., as patterned channels the depth of which extends through the full thickness of the layer, which is then sandwiched between and bonded to two non-patterned layers to seal the fluid channels. In some instances, the microfluidic channels are fabricated by the removal of a sacrificial layer on the surface of a substrate. This method does not require the bulk substrate (e.g., a glass or silicon wafer) to be etched away. Instead, the fluid channels are located on the surface of the substrate. In some instances, the microfluidic channels may be fabricated in or on the surface of a substrate and then sealed by deposition of a conformal film or layer on the surface of the substrate to create sub-surface or buried fluid channels in the chip.

The microfluidic chips can be manufactured using a combination of microfabrication processes. Because the devices are microfabricated, substrate materials will typically be selected based upon their compatibility with known microfabrication techniques, e.g., photolithography, wet chemical etching, laser ablation, laser irradiation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electromagnetic (e.g. light) or electric fields.

The disclosed microfluidic chips may be fabricated from any of a variety of materials known to those of skill in the art including, but not limited to, glass (e.g., borosilicate glass, soda lime glass, etc.), fused-silica (quartz), silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), polydimethylsiloxane (PDMS), etc.), polyetherimide (PEI) and perfluoroelastomer (FFKM) (as more chemically inert alternatives), or any combination thereof. In some preferred instances, the substrate material(s) may include silica-based substrates, such as borosilicate glass, and quartz, as well as other substrate materials.

The disclosed microfluidic devices may be fabricated using any of a variety of techniques known to those of skill in the art, where the choice of fabrication technique is often dependent on the choice of material used, and vice versa. The microfluidic channels on the chip can be constructed using techniques suitable for forming micro-structures or micro-patterns on the surface of a substrate. In some instances, the fluid channels are formed by laser irradiation. In some instances, the microfluidic channels are formed by focused femtosecond laser radiation. In some instances, the microfluidic channels are formed by photolithography and etching including, but not limited to, chemical etching, plasma etching, or deep reactive ion etching. In some instances, the microfluidic channels are formed using laser etching. In some instances, the microfluidic channels are formed using a direct-write lithography technique. Examples of direct-write lithography include electron beam direct-write and focused ion beam milling.

In additional preferred instances, the substrate material(s) may comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates may be readily patterned or micromachined using available microfabrication techniques, such as those described above. In some instances, microfluidic chips may be fabricated from polymeric materials, e.g., from microfabricated masters, using well known molding techniques, such as injection molding, embossing, stamping, or by polymerizing the polymeric precursor material within a mold (see, e.g., U.S. Pat. No. 5,512,131). In some instances, such polymeric substrate materials are preferred for their ease of manufacture, low cost, and disposability, as well as their general inertness to most extreme reaction conditions. As with flow cell devices fabricated from other materials, e.g., glass, flow cell devices fabricated from these polymeric materials may include treated surfaces, e.g., derivatized or coated surfaces, to enhance their utility in the microfluidic system, as will be discussed in more detail below.

The fluid channels and/or fluid chambers of the microfluidic devices are typically fabricated into the upper surface of a first substrate as microscale channels (e.g., grooves, indentations, etc.) using the above described microfabrication techniques. The first substrate comprises a top side having a first planar surface and a bottom side. In the microfluidic devices prepared in accordance with the methods described herein, the plurality of fluid channels (e.g., grooves and/or indentations) are formed on the first planar surface. In some instances, the fluid channels (e.g., grooves and/or indentations) formed in the first planar surface (prior to bonding to a second substrate) have a bottom and side walls, with the top remaining open. In some instances, the fluid channels (e.g., grooves and/or indentations) formed in the first planar surface (prior to bonding to a second substrate) have a bottom and side walls and the top remaining closed. In some instances, the fluid channels (e.g., grooves and/or indentations) formed in the first planar surfaces (prior to bonding to a second substrate) have only side walls and no top or bottom surface (i.e., the fluid channels span the full thickness of the first substrate.

Fluid channels and chambers may be sealed by placing the first planar surface of the first substrate in contact with, and bonding to, the planar surface of a second substrate to form the channels and/or chambers (e.g., the interior portion) of the device at the interface of these two components. In some instances, after the first substrate is bonded to a second substrate, the structure may further be placed in contact with and bonded to a third substrate. In some instances, the third substrate may be placed in contact with the side of the first substrate that is not in contact with the second substrate. In some instances, the first substrate is placed between the second substrate and the third substrate. In some instances, the second substrate and the third substrate can cover and/or seal the grooves, indentations, or apertures formed on the first substrate to form the channels and/or chambers (e.g., the interior portion) of the device at the interface of these components.

The device can have openings that are oriented such that they are in fluid communication with at least one of the fluid channels and/or fluid chambers formed in the interior portion of the device, thereby forming fluid inlets and/or fluid outlets. In some instances, the openings are formed on the first substrate. In some instances, the openings are formed on the first and the second substrate. In some instances, the openings are formed on the first, the second, and the third substrate. In some instances, the openings are positioned at the top side of the device. In some instances, the openings are positioned at the bottom side of the device. In some instances, the openings are positioned at the first and/or the second ends of the device, and the channels run along the direction from the first end to the second end.

Conditions under which substrates may be bonded together are generally widely understood by those of skill in the art, and such bonding of substrates is generally carried out by any of a variety of methods, the choice of which may vary depending upon the nature of the substrate materials used. For example, thermal bonding of substrates may be applied to a number of substrate materials including, e.g., glass or silica-based substrates, as well as some polymer based-substrates. Such thermal bonding techniques typically comprise mating the substrate surfaces that are to be bonded under conditions of elevated temperature and, in some cases, application of external pressure. The precise temperatures and pressures utilized will generally vary depending upon the nature of the substrate materials used.

For example, for silica-based substrate materials, i.e., glass (borosilicate glass, Pyrex™, soda lime glass, etc.), fused-silica (quartz), and the like, thermal bonding of substrates is typically carried out at temperatures ranging from about 500° C. to about 1400° C., and preferably, from about 500° C. to about 1200° C. For example, soda lime glass is typically bonded at temperatures of around 550° C., whereas borosilicate glass is typically thermally bonded at or near 800° C. Quartz substrates, on the other hand, are typically thermally bonded at temperatures at or near 1200° C. These bonding temperatures are typically achieved by placing the substrates to be bonded into high temperature annealing ovens.

Polymeric substrates that are thermally bonded, on the other hand, will typically utilize lower temperatures and/or pressures than silica-based substrates, in order to prevent excessive melting of the substrates and/or distortion, e.g., flattening of the interior portion of the device (i.e., the fluid channels or chambers). Generally, such elevated temperatures for bonding polymeric substrates will vary from about 80° C. to about 200° C., depending upon the polymeric material used, and will preferably be between about 90° C. and about 150° C. Because of the significantly reduced temperatures required for bonding polymeric substrates, such bonding may typically be carried out without the need for the high temperature ovens used in the bonding of silica-based substrates. This allows incorporation of a heat source within a single integrated bonding system, as described in greater detail below.

Adhesives may also be used to bond substrates together according to well-known methods, which typically comprise applying a layer of adhesive between the substrates that are to be bonded and pressing them together until the adhesive sets. A variety of adhesives may be used in accordance with these methods, including, e.g., UV curable adhesives, that are commercially available. Alternative methods may also be used to bond substrates together in accordance with the present invention, including e.g., acoustic or ultrasonic welding and/or solvent welding of polymeric parts.

Typically, a plurality of the described microfluidic chips or devices will be manufactured at the same time in parallel, e.g., using "wafer-scale" fabrication. For example, polymeric substrates may be stamped or molded in large separable sheets which can then be mated and bonded together. Individual devices or bonded substrates may then be separated from the larger sheet by cutting or dicing. Similarly, for silica-based substrates, individual devices can be fabricated from larger substrate wafers or plates, allowing higher throughput of the manufacturing process. Specifically, a plurality of fluid channel structures can be fabricated on a first substrate wafer or plate, which is then overlaid with and bonded to a second substrate wafer or plate, and optionally further overlaid with and bonded to a third substrate wafer or plate. The individual devices are then segmented from the larger substrates using known methods, such as sawing, scribing and breaking, and the like.

As noted above, the top or second substrate is overlaid upon the bottom or first substrate to seal the various channels and chambers. In carrying out the bonding process according to the methods of the present disclosure, the bonding of the first and second substrates may be carried out using vacuum and/or pressure to maintain the two substrate surfaces in optimal contact. In particular, the bottom substrate may be maintained in optimal contact with the top substrate by, e.g., mating the planar surface of the bottom substrate with the planar surface of the top substrate and applying a vacuum through holes that are disposed through the top substrate. Typically, application of a vacuum to holes in the top substrate is carried out by placing the top substrate on a vacuum chuck, which typically comprises a mounting table or surface, having an integrated vacuum source. In the case of silica-based substrates, the bonded substrates are subjected to elevated temperatures in order to create an initial bond, so that the bonded substrates may then be transferred to the annealing oven, without any shifting relative to each other.

Alternate bonding systems for incorporation with the apparatus described herein include, e.g., adhesive dispensing systems, for applying adhesive layers between the two planar surfaces of the substrates. This may be done by applying the adhesive layer prior to mating the substrates, or by placing an amount of the adhesive at one edge of the adjoining substrates and allowing the wicking action of the two mated substrates to draw the adhesive across the space between the two substrates.

In certain instances, the overall bonding system can include automatable systems for placing the top and bottom substrates on the mounting surface and aligning them for subsequent bonding. Typically, such systems include translation systems for moving either the mounting surface or one or more of the top and bottom substrates relative to each other. For example, robotic systems may be used to lift, translate and place each of the top and bottom substrates upon the mounting table, and within the alignment structures, in turn. Following the bonding process, such systems also can remove the finished product from the mounting surface and transfer these mated substrates to a subsequent operation, e.g., a separation or dicing operation, an annealing oven for silica-based substrates, etc., prior to placing additional substrates thereon for bonding.

In some instances, the manufacturing of the microfluidic chip includes the layering or laminating of two or more layers of substrate, e.g., patterned and non-patterned polymeric sheets, in order to produce the chip. For example, in microfluidic devices, the microfluidic features of the device are typically produced by laser irradiation, etching, or otherwise fabricating features into the surface of a first layer. A second layer is then laminated or bonded to the surface of the first to seal these features and provide the fluidic elements of the device, e.g., the fluid channels.

As noted above, in some instances one or more capillary flow cell devices or microfluidic chips may be mounted in a cartridge chassis to form a capillary flow cell cartridge or microfluidic cartridge. In some instances, the capillary flow cell cartridge or microfluidic cartridge may further comprise additional components that are integrated with the cartridge to provide enhanced performance for specific applications. Examples of additional components that may be integrated into the cartridge include, but are not limited to, adapters or connectors for making fluidic connections to other components of the system, fluid flow control components (e.g., miniature valves, miniature pumps, mixing manifolds, etc.), temperature control components (e.g., resistive heating elements, metal plates that serve as heat sources or sinks, piezoelectric (Peltier) devices for heating or cooling, temperature sensors), or optical components (e.g., optical lenses, windows, filters, mirrors, prisms, fiber optics, and/or light-emitting diodes (LEDs) or other miniature light sources that may collectively be used to facilitate spectroscopic measurements and/or imaging of one or more capillary or fluid flow channels.

The fluidic adaptors, cartridge chassis, and other cartridge components may be attached to the capillaries, capillary flow cell device(s), microfluidic chip(s) (or fluid channels within the chip) using any of a variety of techniques known to those of skill in the art including, but not limited to, press fit, adhesive bonding, solvent bonding, laser welding, etc., or any combination thereof. In some instances, the inlet(s) and/or outlet(s) of the microfluidic channels in the microfluidic chip are apertures on the top surface of the chip, and the fluidic adaptors can be attached or coupled to the inlet(s) and/or outlet(s) of the microfluidic channels within the chip. In some instances, the cartridge may comprise additional adapters (i.e., in addition to the fluidic adapters) that mate with the chip and/or fluidic adapters and help to position the chip within the cartridge. These adapters may be constructed using the same fabrication techniques and materials as those outlined above for the fluidic adapters.

The cartridge chassis (or "housing") may be fabricated from metal and/or polymer materials such as aluminum, anodized aluminum, polycarbonate (PC), acrylic (PMMA), or Ultem (PEI), while other materials are also consistent with the present disclosure. A housing may be fabricated using CNC machining and/or molding techniques, and designed so that one, two, or more than two capillaries or microfluidic chips are constrained by the chassis in a fixed orientation to create one or more independent flow channels. The capillaries or chips may be mounted in the chassis using, e.g., a compression fit design, or by mating with compressible adapters made of silicone or a fluoroelastomer. In some instances, two or more components of the cartridge chassis (e.g., an upper half and a lower half) are assembled using, e.g., screws, clips, clamps, or other fasteners so that the two halves are separable. In some instances, two or more components of the cartridge chassis are assembled using, e.g., adhesives, solvent bonding, or laser welding so that the two or more components are permanently attached.

Flow cell surface coatings: In some instances, one or more interior surfaces of the capillary lumens or microfluidic channels in the disclosed flow cell devices (e.g., single- or multi-capillary flow cells, flow cell cartridges, microfluidic devices, or microfluidic cartridges) may be coated using any of a variety of surface modification techniques or polymer coatings described elsewhere herein. In some instances, the coatings may be formulated to increase or maximize the number of available binding sites (e.g., tethered oligonucleotide adapter/primer sequences) on the one or more interior surfaces to increase or maximize a foreground signal, e.g., a fluorescence signal arising from labeled nucleic acid molecules hybridized to tethered oligonucleotide adapter/primer sequences. In some instances, the coatings may be formulated to decrease or minimize nonspecific binding of fluorophores and other small molecules, or labeled or unlabeled nucleotides, proteins, enzymes, antibodies, oligonucleotides, or nucleic acid molecules (e.g., DNA, RNA, etc.), in order to decrease or minimize a background signal, e.g., background fluorescence arising from the nonspecific binding of labeled biomolecules or from autofluorescence of a sample support structure. The combination of increased foreground signal and reduced background signal that may be achieved in some instances through the use of the disclosed coatings may thus provide improved signal-to-noise ratio (SNR) in spectroscopic measurements or improved contrast-to-noise ratio (CNR) in imaging methods.

Fluidics systems and fluid flow control modules: in some implementations, the disclosed imaging and/or analysis systems may provide fluid flow control capability for delivering samples or reagents to the one or more flow cell devices or flow cell cartridges (e.g., single capillary flow cell device or microfluidic channel flow cell device) connected to the system. Reagents and buffers may be stored in bottles, reagent and buffer cartridges, or other suitable containers that are connected to the flow cell inlets by means of tubing and valve manifolds. The disclosed systems may also include processed sample and waste reservoirs in the form of bottles, cartridges, or other suitable containers for collecting fluids downstream of the capillary flow cell devices or capillary flow cell cartridges. In some embodiments, the fluid flow (or "fluidics") control module may provide programmable switching of flow between different sources, e.g. sample or reagent reservoirs or bottles located in the instrument, and the inlet(s) to a central region (e.g., a capillary flow cell or microfluidic device, or a large fluid chamber such as a large fluid chamber within a microfluidic device). In some instances, the fluid flow control module may provide programmable switching of flow between outlet(s) from the central region (e.g., a capillary flow cell or microfluidic device) and different collection points, e.g., processed sample reservoirs, waste reservoirs, etc., connected to the system. In some instances, samples, reagents, and/or buffers may be stored within reservoirs that are integrated into the flow cell cartridge or microfluidic cartridge itself. In some instances, processed samples, spent reagents, and/or used buffers may be stored within reservoirs that are integrated into the flow cell cartridge or microfluidic device cartridge itself.

In some implementations, one or more fluid flow control modules may be configured to control the delivery of fluids to one or more capillary flow cells, capillary flow cell cartridges, microfluidic devices, microfluidic cartridges, or any combination thereof. In some instances, the one or more fluidics controllers may be configured to control volumetric flow rates for one or more fluids or reagents, linear flow velocities for one or more fluids or reagents, mixing ratios for one or more fluids or reagents, or any combination thereof. Control of fluid flow through the disclosed systems will typically be performed using pumps (or other fluid actuation mechanisms) and valves (e.g., programmable pumps and valves). Examples of suitable pumps include, but are not limited to, syringe pumps, programmable syringe pumps, peristaltic pumps, diaphragm pumps, and the like. Examples of suitable valves include, but are not limited to, check valves, electromechanical two-way or three-way valves, pneumatic two-way and three-way valves, and the like. In some instances, fluid flow through the system may be controlled by means of applying positive pneumatic pressure to one or more inlets of the reagent and buffer containers, or to inlets incorporated into flow cell cartridge (s) (e.g., capillary flow cell or microfluidic cartridges). In some embodiments, fluid flow through the system may be controlled by means of drawing a vacuum at one or more outlets of waste reservoir(s), or at one or more outlets incorporated into flow cell cartridge(s) (e.g., capillary flow cell or microfluidic cartridges).

In some instances, different modes of fluid flow control are utilized at different points in an assay or analysis procedure, e.g. forward flow (relative to the inlet and outlet for a given capillary flow cell device), reverse flow, oscillating or pulsatile flow, or combinations thereof. In some applications, oscillating or pulsatile flow may be applied, for example, during assay wash/rinse steps to facilitate complete and efficient exchange of fluids within the one or more flow cell devices or flow cell cartridges (e.g., capillary flow cell devices or cartridges, and microfluidic devices or cartridges).

Similarly, in some cases different fluid flow rates may be utilized at different locations within a flow cell device or at different points in the assay or analysis process workflow, for example, in some instances, the volumetric flow rate may vary from −100 ml/sec to +100 ml/sec. In some embodiment, the absolute value of the volumetric flow rate may be at least 0.001 ml/sec, at least 0.01 ml/sec, at least 0.1 ml/sec, at least 1 ml/sec, at least 10 ml/sec, or at least 100 ml/sec. In some embodiments, the absolute value of the volumetric flow rate may be at most 100 ml/sec, at most 10 ml/sec, at most 1 ml/sec, at most 0.1 ml/sec, at most 0.01 ml/sec, or at most 0.001 ml/sec. The volumetric flow rate at a given location with the flow cell device or at a given point in time may have any value within this range, e.g. a forward flow rate of 2.5 ml/sec, a reverse flow rate of −0.05 ml/sec, or a value of 0 ml/sec (i.e., stopped flow).

In some implementations, the fluidics system may be designed to minimize the consumption of key reagents (e.g., expensive reagents) required for performing, e.g., genomic analysis applications. For example, in some implementations the disclosed fluidics systems may comprise a first reservoir housing a first reagent or solution, a second reservoir housing a second reagent or solution, and a central region, e.g., a central capillary flow cell or microfluidic device, where an outlet from the first reservoir and an outlet from the second reservoir are fluidically coupled to an inlet of the central capillary flow cell or microfluidic device through at least one valve such that the volume of the first reagent or solution flowing per unit time from the outlet of the first reservoir to the inlet of the central capillary flow cell or microfluidic device is less than the volume of the second reagent or solution flowing per unit time from the outlet of the second reservoir to the inlet of the central region. In some implementations, the first reservoir and second reservoir may be integrated into a capillary flow cell cartridge or microfluidic cartridge. In some instances, the at least one valve may also be integrated into the capillary flow cell cartridge or microfluidic cartridge.

In some instances, the first reservoir is fluidically coupled to the central capillary flow cell or microfluidic device through a first valve, and the second reservoir is fluidically coupled to the central capillary flow cell or microfluidic device through a second valve. In some instances, the first and/or second valves may be, e.g., a diaphragm valve, pinch valve, gate valve, or other suitable valve. In some instances, the first reservoir is positioned in close proximity to the inlet of the central capillary flow cell or microfluidic device to reduce dead volume for delivery of the first reagent solution. In some instances, the first reservoir is placed in closer proximity to the inlet of the central capillary flow cell or microfluidic device than is the second reservoir. In some instances, the first reservoir is positioned in close proximity to the second valve so as to reduce the dead volume for delivery of the first reagent relative to that for delivery of a plurality of "second" reagents (e.g., two, three, four, five, or six or more "second" reagents) from a plurality of "second" reservoirs (e.g., two, three, four, five, or six or more "second" reservoirs).

The first and second reservoirs described above may be used to house the same or different reagents or solutions. In some instances, the first reagent that is housed in the first reservoir is different from the second reagent that is housed in the second reservoir, and the second reagent comprises at least one reagent that is used in common by a plurality of reactions occurring in the central a central capillary flow cell or microfluidic device. In some instances, e.g., in fluidics systems configured for performing nucleic acid sequencing chemistry within the central capillary flow cell or microfluidic device, the first reagent comprises at least one reagent selected from the group consisting of a polymerase, nucleotide, and a nucleotide analog. In some instances, the second reagent comprises a low-cost reagent, e.g., a solvent.

In some instances, the interior volume of the central region, e.g., a central capillary flow cell cartridge, or microfluidic device comprising one or more fluid channels or fluid chambers, can be adjusted based on the specific application to be performed, e.g., nucleic acid sequencing. In some embodiments, the central region comprises an interior volume suitable for sequencing a eukaryotic genome. In some embodiments, the central region comprises an interior volume suitable for sequencing a prokaryotic genome. In some embodiments, the central region comprises an interior volume suitable for sequencing a viral genome. In some embodiments, the central region comprises an interior volume suitable for sequencing a transcriptome. For example, in some embodiments, the interior volume of the central region may comprise a volume of less than 0.05 µl, between 0.05 µl and 0.1 µl, between 0.05 µl and 0.2 µl, between 0.05 µl and 0.5 µl, between 0.05 µl and 0.8 µl, between 0.05 µl and 1 µl, between 0.05 µl and 1.2 µl, between 0.05 µl and 1.5 µl, between 0.1 µl and 1.5 µl, between 0.2 µl and 1.5 µl, between 0.5 µl and 1.5 µl, between 0.8 µl and 1.5 µl, between 1 µl and 1.5 µl, between 1.2 µl and 1.5 µl, or greater than 1.5 µl, or a range defined by any two of the foregoing. In some embodiments, the interior volume of the central region may comprise a volume of less than 0.5 µl, between 0.5 µl and 1 µl, between 0.5 µl and 2 µl, between 0.5 µl and 5 µl, between 0.5 µl and 8 µl, between 0.5 µl and 10 µl, between 0.5 µl and 12 µl, between 0.5 µl and 15 µl, between 1 µl and 15 µl, between 2 µl and 15 µl, between 5 µl and 15 µl, between 8 µl and 15 µl, between 10 µl and 15 µl, between 12 µl and 15 µl, or greater than 15 µl, or a range defined by any two of the foregoing. In some embodiments, the interior volume of the central region may comprise a volume of less than 5 µl, between 5 µl and 10 µl, between 5 µl and 20 µl, between 5 µl and 500 µl, between 5 µl and 80 µl, between 5 µl and 100 µl, between 5 µl and 120 µl, between 5 µl and 150 µl, between 10 µl and 150 µl, between 20 µl and 150 µl, between 50 µl and 150 µl, between 80 µl and 150 µl, between 100 µl and 150 µl, between 120 µl and 150 µl, or greater than 150 µl, or a range defined by any two of the foregoing. In some embodiments, the interior volume of the central region may comprise a volume of less than 50 µl, between 50 µl and 100 µl, between 50 µl and 200 µl, between 50 µl and 500 µl, between 50 µl and 800 µl, between 50 µl and 1000 µl, between 50 µl and 1200 µl, between 50 µl and 1500 µl, between 100 µl and 1500 µl, between 200 µl and 1500 µl, between 500 µl and 1500 µl, between 800 µl and 1500 µl, between 1000 µl and 1500 µl, between 1200 µl and 1500 µl, or greater than 1500 µl, or a range defined by any two of the foregoing. In some embodiments, the interior volume of the central region may comprise a volume of less than 500 µl, between 500 µl and 1000 µl, between 500 µl and 2000 µl, between 500 µl and 5 ml, between 500 µl and 8 ml, between 500 µl and 10 ml, between 500 µl and 12 ml, between 500 µl and 15 ml, between 1 ml and 15 ml, between 2 ml and 15 ml, between 5 ml and 15 ml, between 8 ml and 15 ml, between 10 ml and 15 ml, between 12 ml and 15 ml, or greater than 15 ml, or a range defined by any two of the foregoing. In some embodiments, the interior volume of the central region may comprise a volume of less than 5 ml, between 5 ml and 10 ml, between 5 ml and 20 ml, between 5 ml and 50 ml, between 5 ml and 80 ml, between 5 ml and 100 ml, between 5 ml and 120 ml, between 5 ml and 150 ml, between 10 ml and 150 ml, between 20 ml and 150 ml, between 50 ml and 150 ml, between 80 ml and 150 ml, between 100 ml and 150 ml, between 120 ml and 150 ml, or greater than 150 ml, or a range defined by any two of the foregoing. In some embodiments, the systems described herein comprise an array or collection of flow cell devices or systems comprising multiple discrete capillaries, microfluidic channels, fluidic channels, chambers, or lumenal regions, wherein the combined interior volume is, comprises, or includes one or more of the values within a range disclosed herein.

In some instances, the ratio of volumetric flow rate for the delivery of the first reagent to the central capillary flow cell or microfluidic device to that for delivery of the second reagent to the central capillary flow cell or microfluidic device may be less than 1:20, less than 1:16, least than 1:12, less than 1:10, less than 1:8, less than 1:6, or less than 1:2. In some instances, the ratio of volumetric flow rate for the delivery of the first reagent to the central capillary flow cell or microfluidic device to that for delivery of the second reagent to the central capillary flow cell or microfluidic device may have any value with the range spanned by these values, e.g., less than 1:15.

As noted, the flow cell devices and/or fluidics systems disclosed herein may be configured to achieve a more efficient use of the reagents than that achieved by, e.g., other sequencing devices and systems, particularly for the costly reagents used in a variety of sequencing chemistry steps. In some instances, the first reagent comprises a reagent that is more expensive than the second reagent. In some instances, the first reagent comprises a reaction-specific reagent and the second reagent comprises a nonspecific reagent common to all reactions performed in the central capillary flow cell or microfluidic device region, and wherein the reaction specific reagent is more expensive than the nonspecific reagent.

In some instances, utilization of the flow cell devices and/or fluidic systems disclosed herein may convey advantages in terms of reduced consumption of costly reagents. In some instances, for example, utilization of the flow cell devices and/or fluidic systems disclosed herein may results in at least a 5%, at least a 7.5%, at least a 10%, at least a 12.5%, at least a 15%, at least a 17.5%, at least a 20%, at least a 22.5%, at least a 25%, at least a 30%, at least a 35%, at least a 40%, at least a 45%, or at least a 50% reduction in reagent consumption compared to the reagent consumption encountered when operating, e.g., current commercially-available nucleic acid sequencing systems.

Figure 26:
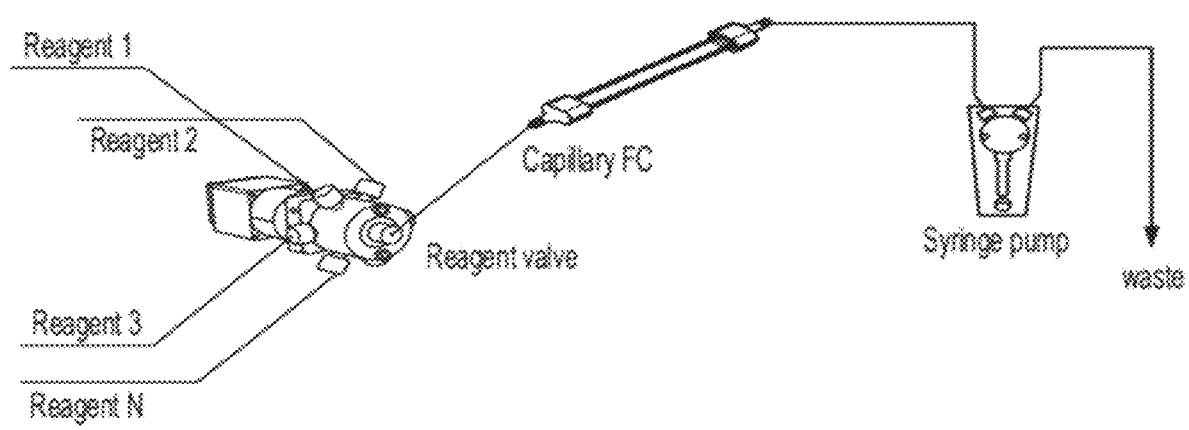
FIG. 26 illustrates one non-limiting example of a system comprising a single capillary flow cell connected to various fluid flow control components, where the single capillary is compatible with mounting on a microscope stage or in a custom imaging instrument for use in various imaging applications.

FIG. 26 illustrates a non-limiting example of a simple fluidics system comprising a single capillary flow cell connected to various fluid flow control components, where the single capillary is optically accessible and compatible with mounting on a microscope stage or in a custom imaging instrument for use in various imaging applications. A plurality of reagent reservoirs is fluidically-coupled with the inlet end of the single capillary flow cell device, where the reagent flowing through the capillary at any given point in time is controlled by means of a programmable rotary valve that allows the user to control the timing and duration of reagent flow. In this non-limiting example, fluid flow is controlled by means of a programmable syringe pump that provides precise control and timing of volumetric fluid flow and fluid flow velocity.

Temperature control modules: In some implementations the disclosed systems will include temperature control functionality for the purpose of facilitating the accuracy and reproducibility of assay or analysis results. Examples of temperature control components that may be incorporated into the instrument system (or capillary flow cell cartridge) design include, but are not limited to, resistive heating elements, infrared light sources, Peltier heating or cooling devices, heat sinks, thermistors, thermocouples, and the like. In some instances, the temperature control module (or "temperature controller") may provide for a programmable temperature change at a specified, adjustable time prior to performing specific assay or analysis steps. In some instances, the temperature controller may provide for programmable changes in temperature over specified time intervals. In some embodiments, the temperature controller may further provide for cycling of temperatures between two or more set temperatures with specified frequency and ramp rates so that thermal cycling for amplification reactions may be performed.

Fluid dispensing robotics: In some implementations, the disclosed systems may comprise an automated, programmable fluid-dispensing (or liquid-dispensing) system for use in dispensing reagents or other solutions into, e.g., microplates, capillary flow cell devices and cartridges, microfluidic devices and cartridges, etc. Suitable automated, programmable fluid-dispensing systems are commercially available from a number of vendors, e.g. Beckman Coulter, Perkin Elmer, Tecan, Velocity 11, and many others. In a preferred aspect of the disclosed systems, the fluid-dispensing system further comprises a multichannel dispense head, e.g. a 4 channel, 8 channel, 16 channel, 96 channel, or 384 channel dispense head, for simultaneous delivery of programmable volumes of liquid (e.g. ranging from about 1 microliter to several milliliters) to multiple wells or locations on a flow cell cartridge or microfluidic cartridge.

Cartridge- and or microplate-handling (pick-and-place) robotics: In some implementations, the disclosed system may comprise a cartridge- and/or microplate-handling robotic system for automated replacement and positioning of microplates, capillary flow cell cartridges, or microfluidic device cartridges in relation to the optical imaging system, or for optionally moving microplates, capillary flow cell cartridges, or microfluidic device cartridges between the optical imaging system and a fluid-dispensing system. Suitable automated, programmable microplate-handling robotic systems are commercially available from a number of vendors, including Beckman Coulter, Perkin Elemer, Tecan, Velocity 11, and many others. In a preferred aspect of the disclosed systems, an automated microplate-handling robotic system is configured to move collections of microwell plates comprising samples and/or reagents to and from, e.g., refrigerated storage units.

Spectroscopy or imaging modules: As indicated above, in some implementations the disclosed analysis systems will include optical imaging capabilities and may also include other spectroscopic measurement capabilities. For example, the disclosed imaging modules may be configured to operate in any of a variety of imaging modes known to those of skill in the art including, but not limited to, bright-field, dark-field, fluorescence, luminescence, or phosphorescence imaging. In some instances, the one or more capillary flow cells or microfluidic devices of a fluidics sub-system comprise a window that allows at least a section of one or more capillaries or one or more fluid channels in each flow cell or microfluidic device to be illuminated and imaged.

In some embodiments, single wavelength excitation and emission fluorescence imaging may be performed. In some embodiments, dual wavelength excitation and emission (or multi-wavelength excitation or emission) fluorescence imaging may be performed. In some instances, the imaging module is configured to acquire video images. The choice of imaging mode may impact the design of the flow cells devices or cartridges in that all or a portion of the capillaries or cartridge will necessarily need to be optically transparent over the spectral range of interest. In some instances, a plurality of capillaries within a capillary flow cell cartridge may be imaged in their entirety within a single image. In some instances, only a single capillary or a subset of capillaries within a capillary flow cell cartridge, or portions thereof, may be imaged within a single image. In some instances, a series of images may be "tiled" to create a single high-resolution image of one, two, several, or the entire plurality of capillaries within a cartridge. In some instances, a plurality of fluid channels within a microfluidic chip may be imaged in their entirety within a single image. In some instances, only a single fluid channel or a subset of fluid channels within a microfluidic chip, or portions thereof, may be imaged within a single image. In some instances, a series of images may be "tiled" to create a single high-resolution image of one, two, several, or the entire plurality of fluid channels within a cartridge.

A spectroscopy or imaging module may comprise, e.g., a microscope equipped with a CMOS of CCD camera. In some instances, the spectroscopy or imaging module may comprise, e.g., a custom instrument such as one of the imaging modules described herein that is configured to perform a specific spectroscopic or imaging technique of interest. In general, the hardware associated with the spectroscopy or imaging module may include light sources, detectors, and other optical components, as well as processors or computers.

Light sources: Any of a variety of light sources may be used to provide the imaging or excitation light, including but not limited to, tungsten lamps, tungsten-halogen lamps, arc lamps, lasers, light emitting diodes (LEDs), or laser diodes. In some instances, a combination of one or more light sources, and additional optical components, e.g. lenses, filters, apertures, diaphragms, mirrors, and the like, may be configured as an illumination system (or sub-system).

Detectors: Any of a variety of image sensors may be used for imaging purposes, including but not limited to, photodiode arrays, charge-coupled device (CCD) cameras, or complementary metal-oxide-semiconductor (CMOS) image sensors. As used herein, "imaging sensors" may be one-dimensional (linear) or two-dimensional array sensors. In many instances, a combination of one or more image sensors, and additional optical components, e.g. lenses, filters, apertures, diaphragms, mirrors, and the like, may be configured as an imaging system (or sub-system). In some instances, e.g., where spectroscopic measurements are performed by the system rather than imaging, suitable detectors may include, but are not limited to, photodiodes, avalanche photodiodes, and photomultipliers.

Other optical components: The hardware components of the spectroscopic measurement or imaging module may also include a variety of optical components for steering, shaping, filtering, or focusing light beams through the system. Examples of suitable optical components include, but are not limited to, lenses, mirrors, prisms, apertures, diffraction gratings, colored glass filters, long-pass filters, short-pass filters, bandpass filters, narrowband interference filters, broadband interference filters, dichroic reflectors, optical fibers, optical waveguides, and the like. In some instances, as noted above, the spectroscopic measurement or imaging module may further comprise one or more translation stages or other motion control mechanisms for the purpose of moving capillary flow cell devices and cartridges relative to the illumination and/or detection/imaging sub-systems, or vice versa.

Total internal reflection: In some instances, the optical module or sub-system may be designed to use all or a portion of an optically transparent wall of the capillaries or microfluidic channels in flow cell devices and cartridges as a waveguide for delivering excitation light to the capillary or channel lumen(s) via total internal reflection. When incident excitation light strikes the surface of the capillary or channel lumen at an angle with respect to a normal to the surface that is larger than the critical angle (determined by the relative refractive indices of the capillary or channel wall material and the aqueous buffer within the capillary or channel), total internal reflection occurs at the surface and the light propagates through the capillary or channel wall along the length of the capillary or channel. Total internal reflection generates an evanescent wave at the lumen surface which penetrates the lumen interior for extremely short distances, and which may be used to selectively excite fluorophores at the surface, e.g., labeled nucleotides that have been incorporated by a polymerase into a growing oligonucleotide through a solid-phase primer extension reaction.

Light-tight housings and environmental control chambers: In some implementations, the disclosed systems may comprise a light-tight housing to prevent stray ambient light from creating glare and obscuring, e.g., relatively faint fluorescence signals. In some implementations, the disclosed systems may comprise an environmental control chamber that enables the system to operate under a tightly controlled temperature, humidity level, etc.

Processors and computers: In some instances, the disclosed systems may comprise one or more processors or computers. The processor may be a hardware processor such as a central processing unit (CPU), a graphic processing unit (GPU), a general-purpose processing unit, or a computing platform. The processor may be comprised of any of a variety of suitable integrated circuits, microprocessors, logic devices, field-programmable gate arrays (FPGAs) and the like. In some instances, the processor may be a single core or multi core processor, or a plurality of processors may be configured for parallel processing. Although the disclosure is described with reference to a processor, other types of integrated circuits and logic devices are also applicable. The processor may have any suitable data operation capability. For example, the processor may perform 512 bit, 256 bit, 128 bit, 64 bit, 32 bit, or 16 bit data operations.

The processor or CPU can execute a sequence of machine-readable instructions, which can be embodied in a program or software. The instructions may be stored in a memory location. The instructions can be directed to the CPU, which can subsequently program or otherwise configure the CPU to implement, e.g., the system control methods of the present disclosure. Examples of operations performed by the CPU can include fetch, decode, execute, and write back.

Some processors may comprise a processing unit of a computer system. The computer system may enable cloud-based data storage and/or computing. In some instances, the computer system may be operatively coupled to a computer network ("network") with the aid of a communication interface. The network may be the internet, an intranet and/or extranet, an intranet and/or extranet that is in communication with the internet, or a local area network (LAN). The network in some cases is a telecommunication and/or data network. The network may include one or more computer servers, which may enable distributed computing, such as cloud-based computing.

The computer system may also include computer memory or memory locations (e.g., random-access memory, read-only memory, flash memory), electronic storage units (e.g., hard disk), communication interfaces (e.g., network adapters) for communicating with one or more other systems, and peripheral devices, such as cache, other memory units, data storage units and/or electronic display adapters. In some instances, the communication interface may allow the computer to be in communication with one or more additional devices. The computer may be able to receive input data from the coupled devices for analysis. Memory units, storage units, communication interfaces, and peripheral devices may be in communication with the processor or CPU through a communication bus (solid lines), such as may be incorporated into a motherboard. A memory or storage unit may be a data storage unit (or data repository) for storing data. The memory or storage units may store files, such as drivers, libraries and saved programs. The memory or storage units may store user data, e.g., user preferences and user programs.

The system control, image processing, and/or data analysis methods as described herein can be implemented by way of machine-executable code stored in an electronic storage location of the computer system, such as, for example, in the memory or electronic storage unit. The machine-executable or machine-readable code can be provided in the form of software. During use, the code can be executed by the processor. In some cases, the code can be retrieved from the storage unit and stored in memory for ready access by the processor. In some situations, the electronic storage unit can be precluded, and machine-executable instructions are stored in memory.

In some instances, the code may be pre-compiled and configured for use with a machine having a processor adapted to execute the code. In some instances, the code may be compiled during runtime. The code can be supplied in a programming language that can be selected to enable the code to execute in a pre-compiled or as-compiled fashion.

Some aspects of the systems and methods provided herein can be embodied in software. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

In some instances, the system control, image processing, and/or data analysis methods of the present disclosure may be implemented by way of one or more algorithms. An algorithm may be implemented by way of software upon execution by the central processing unit.

System control software: In some instances, the system may comprise a computer (or processor) and a computer-readable medium that includes code for providing a user interface as well as manual, semi-automated, or fully-automated control of all system functions, e.g., control of the fluid flow control module(s), the temperature control module (s), and/or the spectroscopy or imaging module(s), as well as other data analysis and display options. The system computer or processor may be an integrated component of the system (e.g. a microprocessor or mother board embedded within the instrument) or may be a stand-alone module, for example, a main frame computer, a personal computer, or a laptop computer. Examples of fluid flow control functions provided by the system control software include, but are not limited to, volumetric fluid flow rates, fluid flow velocities, the timing and duration for sample and reagent addition, buffer addition, and rinse steps. Examples of temperature control functions provided by the system control software include, but are not limited to, specifying temperature set point(s) and control of the timing, duration, and ramp rates for temperature changes. Examples of spectroscopic measurement or imaging control functions provided by the system control software include, but are not limited to, autofocus capability, control of illumination or excitation light exposure times and intensities, control of image acquisition rate, exposure time, and data storage options.

Image processing software: In some instances, the system may further comprise a computer (or processor) and computer-readable medium that includes code for providing image processing and analysis capability. Examples of image processing and analysis capability that may be provided by the software include, but are not limited to, manual, semi-automated, or fully-automated image exposure adjustment (e.g. white balance, contrast adjustment, signal-averaging and other noise reduction capability, etc.), automated edge detection and object identification (e.g., for identifying clonally-amplified clusters of fluorescently-labeled oligonucleotides on the lumen surface of capillary flow cell devices), automated statistical analysis (e.g., for determining the number of clonally-amplified clusters of oligonucleotides identified per unit area of the capillary lumen surface, or for automated nucleotide base-calling in nucleic acid sequencing applications), and manual measurement capabilities (e.g. for measuring distances between clusters or other objects, etc.). Optionally, instrument control and image processing/analysis software may be written as separate software modules. In some embodiments, instrument control and image processing/analysis software may be incorporated into an integrated package.

Any of a variety of image processing methods known to those of skill in the art may be used for image processing/pre-processing. Examples include, but are not limited to, Canny edge detection methods, Canny-Deriche edge detection methods, first-order gradient edge detection methods (e.g., the Sobel operator), second order differential edge detection methods, phase congruency (phase coherence) edge detection methods, other image segmentation algorithms (e.g., intensity thresholding, intensity clustering methods, intensity histogram-based methods, etc.), feature and pattern recognition algorithms (e.g., the generalized Hough transform for detecting arbitrary shapes, the circular Hough transform, etc.), and mathematical analysis algorithms (e.g., Fourier transform, fast Fourier transform, wavelet analysis, auto-correlation, etc.), or any combination thereof.

Nucleic acid sequencing systems & applications: Nucleic acid sequencing, e.g., cellularly-addressable nucleic acid sequencing, provides one non-limiting example of an application for the disclosed flow cell devices (e.g., capillary flow cell devices or cartridges, and microfluidic devices and cartridges) and imaging systems. The improvements in flow cell device design disclosed herein, e.g., comprising hydrophilic coated surfaces that maximize foreground signals for, e.g., fluorescently-labeled nucleic acid clusters disposed thereon, while minimizing background signal may give rise to improvements in CNR for images used for base-calling purposes, in combination with improvements in optical imaging system design for fast dual-surface flow cell imaging (comprising simultaneous or near-simultaneous imaging of the interior flow cell surfaces) achieved through improved objective lens and/or tube lens designs that provide for larger depth of field and larger fields-of-view, and reduced reagent consumption (achieved through improved flow cell design)

may give rise to dramatic improvements in base-calling accuracy, shortened imaging cycle times, shortened overall sequencing reaction cycle times, and higher throughput nucleic acid sequencing at reduced cost per base.

In some instances, the disclosed hydrophilic, polymer coated flow cell devices used in combination with the optical imaging systems disclosed herein may confer one or more of the following additional advantages for a nucleic acid sequencing system: (i) decreased fluidic wash times (due to reduced non-specific binding, and thus faster sequencing cycle times), (ii) decreased imaging times (and thus faster turnaround times for assay readout and sequencing cycles), (iii) decreased overall work flow time requirements (due to decreased cycle times), (iv) decreased detection instrumentation costs (due to the improvements in CNR), (v) improved readout (base-calling) accuracy (due to improvements in CNR), (vi) improved reagent stability and decreased reagent usage requirements (and thus reduced reagents costs), and (vii) fewer runtime failures due to nucleic acid amplification failures.

Flow cell devices con figured for sequencing: In some instances, one or more flow cell devices according to the present disclosure may be configured for nucleic acid sequencing applications, e.g., wherein two or more interior flow cell device surfaces comprise hydrophilic polymer coatings, as disclosed elsewhere herein, that further comprise one or more capture oligonucleotides, e.g., adapter/primer oligonucleotides, or any other oligonucleotides as disclosed elsewhere herein. In some instances, the hydrophilic, polymer-coated surfaces of the disclosed flow cell devices may comprise a plurality of oligonucleotides tethered thereto that have been selected for use in sequencing a eukaryotic genome. In some instances, the hydrophilic, polymer-coated surfaces of the disclosed flow cell devices may comprise a plurality of oligonucleotides tethered thereto that have been selected for use in sequencing a prokaryotic genome or portion thereof. In some instances, the hydrophilic, polymer-coated surfaces of the disclosed flow cell devices may comprise a plurality of oligonucleotides tethered thereto that have been selected for use in sequencing a viral genome or portion thereof. In some instances, the hydrophilic, polymer-coated surfaces of the disclosed flow cell devices may comprise a plurality of oligonucleotides tethered thereto that have been selected for use in sequencing a transcriptome.

In some instances, a flow cell device of the present disclosure may comprise a first surface in an orientation generally facing the interior of the flow channel, a second surface in an orientation generally facing the interior of the flow channel and further generally facing or parallel to the first surface, a third surface generally facing the interior of a second flow channel, and a fourth surface, generally facing the interior of the second flow channel and generally opposed to or parallel to the third surface; wherein said second and third surfaces may be located on or attached to opposite sides of a generally planar substrate which may be a reflective, transparent, or translucent substrate. In some instances, an imaging surface or imaging surfaces within a flow cell may be located within the center of a flow cell or within or as part of a division between two subunits or subdivisions of a flow cell, wherein said flow cell may comprise a top surface and a bottom surface, one or both of which may be transparent to such detection mode as may be utilized; and wherein a surface comprising oligonucleotides adapters/primers tethered to one or more polymer coatings may be placed or interposed within the lumen of the flow cell. In some instances, the top and/or bottom surfaces do not include attached oligonucleotide adapters/primers. In some instances, said top and/or bottom surfaces do comprise attached oligonucleotide adapters/primers. In some instances, either said top or said bottom surface may comprise attached oligonucleotide adapters/primers. A surface or surfaces placed or interposed within the lumen of a flow cell may be located on or attached to one side, to an opposite side, or to both sides of a generally planar substrate which may be a reflective, transparent, or translucent substrate.

Fluorescence imaging of hydrophilic, polymer-coated flow cell device surfaces: The disclosed hydrophilic, polymer-coated flow cell devices comprising, e.g., clonal clusters of labeled target nucleic acid molecules disposed thereon may be used in any of a variety of nucleic acid analysis applications, e.g., nucleic acid base discrimination, nucleic acid base classification, nucleic acid base calling, nucleic acid detection applications, nucleic acid sequencing applications, and nucleic acid-based (genetic and genomic) diagnostic applications. In many of these applications, fluorescence imaging techniques may be used to monitor hybridization, amplification, and/or sequencing reactions performed on the low-binding supports. Fluorescence imaging may be performed using any of the optical imaging modules disclosed herein, as well as a variety of fluorophores, fluorescence imaging techniques, and other fluorescence imaging instruments known to those of skill in the art.

Nucleic acid sequencing system performance: In some instances, the disclosed nucleic acid sequencing systems, comprising one or more of the disclosed flow cell devices used in combination with one or more of the disclosed optical imaging systems, and optionally utilizing one of the emerging sequencing biochemistries such as the "sequencing-by-nucleotide binding" approach described in U.S. Pat. No. 10,655,176 B2, and the "sequencing-by-avidity" approach described in U.S. Pat. No. 10,768,173 B2 instead of more conventional sequencing-by-nucleotide incorporation approaches, may provide improved nucleic acid sequencing performance in terms of, e.g., reduced sample input requirements, reduced image acquisition cycle time, reduced sequencing reaction cycle time, reduced sequencing run time, improved base-calling accuracy, reduced reagent consumption and cost, higher sequencing throughput, and reduced sequencing cost.

Nucleic acid sample input (pM): In some instances, the sample input requirements for the disclosed system may be significantly reduced due to the improved hybridization and amplification efficiencies that may be attained, and the high CNR images that may be acquired for base-calling, using the disclosed hydrophilic, polymer coated flow cell devices and imaging systems. In some instances, the nucleic acid sample input requirement for the disclosed systems may range from about 1 pM to about 10,000 pM. In some instances, the nucleic acid sample input requirement may be at least 1 pM, at least 2 pM, at least 5 pM, at least 10 pM, at least 20 pM, at least 50 pM, at least 100 pM, at least 200 pM, at least 500 pM, at least 1,000 pM, at least 2,000 pM, at least 5,000 pM, at least 10,000 pM. In some instances, the nucleic acid sample input requirement for the disclosed systems may be at most 10,000 pM, at most 5,000 pM, at most 2,000 pM, at most 1,000 pM, at most 500 pM, at most 200 pM, at most 100 pM, at most 50 pM, at most 20 pM, at most 10 pM, at most 5 pM, at most 2 pM, or at most 1 pM. Any of the lower and upper values described in this paragraph may be combined to form a range included within the present disclosure, for example, in some instances the nucleic acid sample input requirement for the disclosed systems may range from about 5 pM to about 500 pM. Those of skill in the art will recognize that the nucleic acid sample input requirement may have any value within this range, e.g., about 132 pM. In one exemplary instance, a nucleic acid sample input of about 100 pM is sufficient to generate signals for reliable base-calling.

Nucleic acid sample input (nanograms): In some instances, the nucleic acid sample input requirement for the disclosed systems may range from about 0.05 nanograms to about 1,000 nanograms. In some instances, the nucleic acid sample input requirement may be at least 0.05 nanograms, at least 0.1 nanograms, at least 0.2 nanograms, at least 0.4 nanograms, at least 0.6 nanograms, at least 0.8 nanograms, at least 1.0 nanograms, at least 2 nanograms, at least 4 nanograms, at least 6 nanograms, at least 8 nanograms, at least 10 nanograms, at least 20 nanograms, at least 40 nanograms, at least 60 nanograms, at least 80 nanograms, at least 100 nanograms, at least 200 nanograms, at least 400 nanograms, at least 600 nanograms, at least 800 nanograms, or at least 1,000 nanograms. In some instances, the nucleic acid sample input requirement may be at most 1,000 nanograms, at most 800 nanograms, at most 600 nanograms, at most 400 nanograms, at most 200 nanograms, at most 100 nanograms, at most 80 nanograms, at most 60 nanograms, at most 40 nanograms, at most 20 nanograms, at most 10 nanograms, at most 8 nanograms, at most 6 nanograms, at most 4 nanograms, at most 2 nanograms, at most 1 nanograms, at most 0.8 nanograms, at most 0.6 nanograms, at most 0.4 nanograms, at most 0.2 nanograms, at most 0.1 nanograms, or at most 0.05 nanograms. Any of the lower and upper values described in this paragraph may be combined to form a range included within the present disclosure, for example, in some instances the nucleic acid sample input requirement for the disclosed systems may range from about 0.6 nanograms to about 400 nanograms. Those of skill in the art will recognize that the nucleic acid sample input requirement may have any value within this range, e.g., about 2.65 nanograms.

FOV images required to tile flow cell: In some instances, the field-of-view (FOV) of the disclosed optical imaging module is sufficiently large that a multi-channel (or multi-lane) flow cell (i.e., the fluid channel portions thereof) of the present disclosure may be imaged by tiling from about 10 FOV images (or "frames") to about 1,000 FOV images (or "frames"). In some instances, an image of the entire multi-channel flow cell may require tiling at least 10, at least 20, at least 30, at least 40, at least 50, at least 60, at least 70, at least 80, at least 90, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1,000 FOV images (or "frames"). In some instances, an image of the entire multi-channel flow cell may require tiling at most 1,000, at most 950, at most 900, at most 850, at most 800, at most 750, at most 700, at most 650, at most 600, at most 550, at most 500, at most 450, at most 400, at most 350, at most 300, at most 250, at most 200, at most 150, at most 100, at most 90, at most 80, at most 70, at most 60, at most 50, at most 40, at most 30, at most 20, or at most 10 FOV images (or "frames"). Any of the lower and upper values described in this paragraph may be combined to form a range included within the present disclosure, for example, in some instances an image of the entire multi-channel flow cell may require tiling from about 30 to about 100 FOV images. Those of skill in the art will recognize that in some instances the number of required FOV images may have any value within this range, e.g., about 54 FOV images.

Imaging cycle time: In some instances, the combination of large FOV, image sensor response sensitivity, and/or fast FOV translation times enables shortened imaging cycle times (i.e., the time required to acquire a sufficient number of FOV images to tile the entire multichannel flow cell (or the fluid channel portions thereof). In some instances, the imaging cycle time may range from about 10 seconds to about 10 minutes. In some instances, the imaging cycle time may be at least 10 seconds at least 20 seconds, at least 30 seconds, at least 40 seconds, at least 50 seconds, at least 1 minute, at least 2 minutes, at least 3 minutes, at least 4 minutes, at least 5 minutes, at least 6 minutes, at least 7 minutes, at least 8 minutes, at least 9 minutes, or at least 10 minutes. In some instances, the imaging cycle time may be at most 10 minutes, at most 9 minutes, at most 8 minutes, at most 7 minutes, at most 6 minutes, at most 5 minutes, at most 4 minutes, at most 3 minutes, at most 2 minutes, at most 1 minute, at most 50 second, at most 40 second, at most 30 seconds, at most 20 seconds, or at most 10 seconds. Any of the lower and upper values described in this paragraph may be combined to form a range included within the present disclosure, for example, in some instances the imaging cycle time may range from about 20 seconds to about 1 minute. Those of skill in the art will recognize that in some instances the imaging cycle time may have any value within this range, e.g., about 57 seconds.

Sequencing cycle time: In some instances, shortened sequencing reaction steps, e.g., due to reduced wash time requirements for the disclosed hydrophilic, polymer-coated flow cells, may result in shortened overall sequencing cycle times. In some instances, the sequencing cycle times for the disclosed systems may range from about 1 minute to about 60 minutes. In some instances, the sequencing cycle time may be at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, or at least 60 minutes. In some instances, the sequencing reaction cycle time may be at most 60 minutes, at most 55 minutes, at most 50 minutes, at most 45 minutes, at most 40 minutes, at most 35 minutes, at most 30 minutes, at most 25 minutes, at most 20 minutes, at most 15 minutes, at most 10 minutes, at most 9 minutes, at most 8 minutes, at most 7 minutes, at most 6 minutes, at most 5 minutes, at most 4 minutes, at most 3 minutes, at most 2 minutes, or at most 1 minutes. Any of the lower and upper values described in this paragraph may be combined to form a range included within the present disclosure, for example, in some instances the sequencing cycle time may range from about 2 minutes to about 15 minutes. Those of skill in the art will recognize that in some instances the sequencing cycle time may have any value within this range, e.g., about 1 minute, 12 seconds.

Sequencing read length: In some instances, the enhanced CNR images that may be achieved using the disclosed hydrophilic, polymer-coated flow cell devices in combination with the disclosed imaging systems, and in some cases, the use of milder sequencing biochemistries, may enable longer sequencing read lengths for the disclosed systems. In some instances, the maximum (single read) read length may range from about 50 bp to about 500 bp. In some instances, the maximum (single read) read length may be at least 50 bp, at least 100 bp, at least 150 bp, at least 200 bp, at least 250 bp, at least 300 bp, at least 350 bp, at least 400 bp, at least 450 bp, or at least 500 bp. In some instances, the maximum (single read) read length is at most 500 bp, at most 450 bp, at most 400 bp, at most 350 bp, at most 300 bp, at most 250 bp, at most 200 bp, at most 150 bp, at most 100 bp, or at most 50 bp. Any of the lower and upper values described in this paragraph may be combined to form a range included within the present disclosure, for example, in some instances the maximum (single read) read length may range from about 100 bp to about 450 bp. Those of skill in the art will recognize that in some instances the maximum (single read) read length may have any value within this range, e.g., about 380 bp.

Sequencing run time: In some instances, the sequencing run time for the disclosed nucleic acid sequencing systems may range from about 8 hours to about 20 hours. In some instances, the sequencing run time is at least 8 hours, at least 9 hours, at least 10 hours, at least 12 hours, at least 14 hours, at least 16 hours, at least 18 hours, or at least 20 hours. In some instances, the sequencing run time is at most 20 hours, at most 18 hours, at most 16 hours, at most 14 hours, at most 12 hours, at most 10 hours, at most 9 hours, or at most 8 hours. Any of the lower and upper values described in this paragraph may be combined to form a range included within the present disclosure, for example, in some instances the sequencing run time may range from about 10 hours to about 16 hours. Those of skill in the art will recognize that in some instances the sequencing run time may have any value within this range, e.g., about 7 hours, 35 minutes.

Average base-calling accuracy: In some instances, the disclosed nucleic acid sequencing systems may provide an average base-calling accuracy of at least 80%, at least 85%, at least 90%, at least 92%, at least 94%, at least 96%, at least 98%, at least 99%, at least 99.5%, at least 99.8%, or at least 99.9% correct over the course of a sequencing run. In some instances, the disclosed nucleic acid sequencing systems may provide an average base-calling accuracy of at least 80%, at least 85%, at least 90%, at least 92%, at least 94%, at least 96%, at least 98%, at least 99%, at least 99.5%, at least 99.8%, or at least 99.9% correct per every 1,000 bases, 10,0000 bases, 25,000 bases, 50,000 bases, 75,000 bases, or 100,000 bases called.

Average Q-score: In some instances, the disclosed nucleic acid sequencing systems may provide a more accurate base readout. In some instances, for example, the disclosed nucleic acid sequencing systems may provide an average Q-score for base-calling accuracy over a sequencing run that ranges from about 20 to about 50. In some instances, the average Q-score may be at least 20, at least 25, at least 30, at least 35, at least 40, at least 45, or at least 50. Those of skill in the art will recognize that the average Q-score may have any value within this range, e.g., about 32.

Q-score vs. % nucleotides identified: In some instances, the disclosed nucleic acid sequencing systems may provide a Q-score of greater than 30 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 35 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 40 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 45 for at least 50%, at least 60%, at least 70%, at least 80%, at least 85%, at least 90%, at least 95%, at least 98%, or at least 99% of the terminal (or N+1) nucleotides identified. In some instances, the disclosed compositions and methods for nucleic acid sequencing may provide a Q-score of greater than 50 for at least 50%, at least 60%, at least 70%, at least 80%, at least 85%, at least 90%, at least 95%, at least 98%, or at least 99% of the terminal (or N+1) nucleotides identified.

Reagent consumption: In some instances, the disclosed nucleic acid sequencing systems may have lower reagent consumption rates and costs due to, e.g., the use of the disclosed flow cell devices and fluidic systems that minimize fluid channel volumes and dead volumes. In some instances, the disclosed nucleic acid sequencing systems may thus require an average of at least 5% less, at least 10% less, at least 15% less, at least 20% less, at least 25% less, at least 30% less, at least 35% less, at least 40% less, at least 45% less, or at least 50% less reagent by volume per Gbase sequenced that that consumed by an Illumina MiSeq sequencer.

Sequencing throughput: In some instances, the disclosed nucleic acid sequencing systems may provide a sequencing throughput ranging from about 50 Gbase/run to about 200 Gbase/run. In some instances, the sequencing throughput may be at least 50 Gbase/run, at least 75 Gbase/run, at least 100 Gbase/run, at least 125 Gbase/run, at least 150 Gbase/run, at least 175 Gbase/run, or at least 200 Gbase/run. In some instances, the sequencing throughput may be at most 200 Gbase/run, at most 175 Gbase/run, at most 150 Gbase/run, at most 125 Gbase/run, at most 100 Gbase/run, at most 75 Gbase/run, or at most 50 Gbase/run. Any of the lower and upper values described in this paragraph may be combined to form a range included within the present disclosure, for example, in some instances the sequencing throughput may range from about 75 Gbase/run to about 150 Gbase/run. Those of skill in the art will recognize that in some instances the sequencing throughput may have any value within this range, e.g., about 119 Gbase/run.

Sequencing cost: In some instances, the disclosed nucleic acid sequencing systems may provide nucleic acid sequencing at a cost ranging from about $5 per Gbase to about $30 per Gbase. In some instances, the sequencing cost may be at least $5 per Gbase, at least $10 per Gbase, at least $15 per Gbase, at least $20 per Gbase, at least $25 per Gbase, or at least $30 per Gbase. In some instances, the sequencing cost may be at most $30 per Gbase, at most $25 per Gbase, at most $20 per Gbase, at most $15 per Gbase, at most $10 per Gbase, or at most $30 per Gbase. Any of the lower and upper values described in this paragraph may be combined to form a range included within the present disclosure, for example, in some instances the sequencing cost may range from about $10 per Gbase to about $15 per Gbase. Those of skill in the art will recognize that in some instances the sequencing cost may have any value within this range, e.g., about $7.25 per Gbase.

Enablement of optical systems is further provided in U.S. patent application Ser. No. 16/363,842, hybridization methods as disclosed in U.S. patent application Ser. No. 17/016, 349, U.S. patent application Ser. No. 17/016,350, and U.S. patent application Ser. No. 17/016,353, the contents of which are hereby expressly incorporated by reference for all purposes.

I. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Generally, terminologies pertaining to techniques of molecular biology, nucleic acid chemistry, protein chemistry, genetics, microbiology, transgenic cell production, and hybridization described herein are those well-known and commonly used in the art. Techniques and procedures described herein are generally performed according to conventional methods well known in the art and as described in various general and more specific references that are cited and discussed throughout the instant specification. For example, see Sambrook et al., Molecular Cloning: A Laboratory Manual (Third ed., Cold Spring Harbor Laboratory Press, Cold Spring Harbor, N.Y. 2000). See also Ausubel et al., Current Protocols in Molecular Biology, Greene Publishing Associates (1992). The nomenclatures utilized in connection with, and the laboratory procedures and techniques described herein are those well-known and commonly used in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The term "and/or" used herein is to be taken mean specific disclosure of each of the specified features or components with or without the other. For example, the term "and/or" as used in a phrase such as "A and/or B" herein is intended to include: "A and B"; "A or B"; "A" (A alone); and "B" (B alone). In a similar manner, the term "and/or" as used in a phrase such as "A, B, and/or C" is intended to encompass each of the following aspects: "A, B, and C"; "A, B, or C"; "A or C"; "A or B"; "B or C"; "A and B"; "B and C"; "A and C"; "A" (A alone); "B" (B alone); and "C" (C alone).

As used herein and in the appended claims, terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising," otherwise analogous aspects described in terms of "consisting of" and/or "consisting essentially of" are also provided.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The term "in vivo" is used to describe an event that takes place in a subject's body.

The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

As used herein, the terms "about" and "approximately" refer to a value or composition that is within an acceptable error range for the particular value or composition as determined by one of ordinary skill in the art, which will depend in part on how the value or composition is measured or determined, e.g., the limitations of the measurement system. For example, "about" or "approximately" can mean within one or more than one standard deviation per the practice in the art. Alternatively, "about" or "approximately" can mean a range of up to 10% (i.e., ±10%) or more depending on the limitations of the measurement system. For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition. Also, where ranges and/or subranges of values are provided, the ranges and/or subranges can include the endpoints of the ranges and/or subranges.

The term "polymerase" and its variants, as used herein, comprises an enzyme comprising a domain that binds a nucleotide (or nucleoside) where the polymerase can form a complex having a template nucleic acid and a complementary nucleotide. The polymerase can have one or more activities including, but not limited to, base analog detection activities, DNA polymerization activity, reverse transcriptase activity, DNA binding, strand displacement activity, and nucleotide binding and recognition. A polymerase can be any enzyme that can catalyze polymerization of nucleotides (including analogs thereof) into a nucleic acid strand. Typically but not necessarily such nucleotide polymerization can occur in a template-dependent fashion. Typically, a polymerase comprises one or more active sites at which nucleotide binding and/or catalysis of nucleotide polymerization can occur. In some embodiments, a polymerase includes other enzymatic activities, such as for example, 3' to 5' exonuclease activity or 5' to 3' exonuclease activity. In some embodiments, a polymerase has strand displacing activity. A polymerase can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze nucleotide polymerization (e.g., catalytically active fragment). The polymerase includes catalytically inactive polymerases, catalytically active polymerases, reverse transcriptases, and other enzymes comprising a nucleotide binding domain. In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof. A polymerase can be derived from a prokaryote, eukaryote, virus or phage. A polymerase comprises DNA-directed DNA polymerase and RNA-directed DNA polymerase.

As used herein, the term "strand displacing" refers to the ability of a polymerase to locally separate strands of double-stranded nucleic acids and synthesize a new strand in a template-based manner. Strand displacing polymerases displace a complementary strand from a template strand and catalyze new strand synthesis. Strand displacing polymerases include mesophilic and thermophilic polymerases. Strand displacing polymerases include wild type enzymes, and variants including exonuclease minus mutants, mutant versions, chimeric enzymes and truncated enzymes. Examples of strand displacing polymerases include phi29 DNA polymerase, large fragment of Bst DNA polymerase, large fragment of Bsu DNA polymerase (exo-), Bca DNA polymerase (exo-), Klenow fragment of E. coli DNA polymerase, T5 polymerase, M-MuLV reverse transcriptase, HIV viral reverse transcriptase, Deep Vent DNA polymerase and KOD DNA polymerase. The phi29 DNA polymerase can be wild type phi29 DNA polymerase (e.g., MagniPhi from Expedeon), or variant EquiPhi29 DNA polymerase (e.g., from Thermo Fisher Scientific), or chimeric QualiPhi DNA polymerase (e.g., from 4basebio).

The terms "nucleic acid", "polynucleotide" and "oligonucleotide" and other related terms used herein are used interchangeably and refer to polymers of nucleotides and are not limited to any particular length. Nucleic acids include recombinant and chemically-synthesized forms. Nucleic acids can be isolated. Nucleic acids include DNA molecules (e.g., cDNA or genomic DNA), RNA molecules (e.g., mRNA), analogs of the DNA or RNA generated using nucleotide analogs (e.g., peptide nucleic acids (PNA) and non-naturally occurring nucleotide analogs), and chimeric forms containing DNA and RNA. Nucleic acids can be single-stranded or double-stranded. Nucleic acids comprise polymers of nucleotides, where the nucleotides include natural or non-natural bases and/or sugars. Nucleic acids comprise naturally-occurring internucleosidic linkages, for example phosphodiester linkages. Nucleic acids can lack a phosphate group. Nucleic acids comprise non-natural internucleoside linkages, including phosphorothioate, phosphorothiolate, or peptide nucleic acid (PNA) linkages. In some embodiments, nucleic acids comprise a one type of polynucleotides or a mixture of two or more different types of polynucleotides.

The term "primer" and related terms used herein refers to an oligonucleotide that is capable of hybridizing with a DNA and/or RNA polynucleotide template to form a duplex molecule. Primers comprise natural nucleotides and/or nucleotide analogs. Primers can be recombinant nucleic acid molecules. Primers may have any length, but typically range from 4-50 nucleotides. A typical primer comprises a 5' end and 3' end. The 3' end of the primer can include a 3' OH moiety which serves as a nucleotide polymerization initiation site in a polymerase-catalyzed primer extension reaction. Alternatively, the 3' end of the primer can lack a 3' OH moiety, or can include a terminal 3' blocking group that inhibits nucleotide polymerization in a polymerase-catalyzed reaction. Any one nucleotide, or more than one nucleotide, along the length of the primer can be labeled with a detectable reporter moiety. A primer can be in solution (e.g., a soluble primer) or can be immobilized to a support (e.g., a capture primer).

The nucleic acids of interest can be extracted from cells or biological sample s using any of a number of techniques known to those of skill in the art. For example, a typical DNA extraction procedure comprises (i) collection of the cell sample or tissue sample from which DNA is to be extracted, (ii) disruption of cell membranes (i.e., cell lysis) to release DNA and other cytoplasmic components, (iii) treatment of the lysed sample with a concentrated salt solution to precipitate proteins, lipids, and RNA, followed by centrifugation to separate out the precipitated proteins, lipids, and RNA, and (iv) purification of DNA from the supernatant to remove detergents, proteins, salts, or other reagents used during the cell membrane lysis. A variety of suitable commercial nucleic acid extraction and purification kits are consistent with the disclosure herein. Examples include, but are not limited to, the QIAamp kits (for isolation of genomic DNA from human samples) and DNAeasy kits (for isolation of genomic DNA from animal or plant samples) from Qiagen (Germantown, MD), or the Maxwell® and ReliaPrep™ series of kits from Promega (Madison, WI).

The term "template nucleic acid", "template polynucleotide", "target nucleic acid" "target polynucleotide", "template strand" and other variations refer to a nucleic acid strand that serves as the basis nucleic acid molecule for any of the analysis methods describe herein (e.g., amplifying and/or sequencing). The template nucleic acid can be single-stranded or double-stranded, or the template nucleic acid can have single-stranded or double-stranded portions. The template nucleic acid can be obtained from a naturally-occurring source, recombinant form, or chemically synthesized to include any type of nucleic acid analog. The template nucleic acid can be linear, circular, or other forms. The template nucleic acids can include an insert portion having an insert sequence. The template nucleic acids can also include at least one adaptor sequence. The insert portion can be isolated in any form, including chromosomal, genomic, organellar (e.g., mitochondrial, chloroplast or ribosomal), recombinant molecules, cloned, amplified, cDNA, RNA such as precursor mRNA or mRNA, oligonucleotides, whole genomic DNA, obtained from fresh frozen paraffin embedded tissue, needle biopsies, circulating tumor cells, cell free circulating DNA, or any type of nucleic acid library. The insert portion can be isolated from any source including from organisms such as prokaryotes, eukaryotes (e.g., humans, plants and animals), fungus, viruses cells, tissues, normal or diseased cells or tissues, body fluids including blood, urine, serum, lymph, tumor, saliva, anal and vaginal secretions, amniotic samples, perspiration, semen, environmental samples, culture samples, or synthesized nucleic acid molecules prepared using recombinant molecular biology or chemical synthesis methods. The insert portion can be isolated from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs. The template nucleic acid can be subjected to nucleic acid analysis, including sequencing and composition analysis.

The term "adaptor" and related terms refers to oligonucleotides that can be operably linked to a target polynucleotide, where the adaptor confers a function to the co-joined adaptor-target molecule. Adaptors comprise DNA, RNA, chimeric DNA/RNA, or analogs thereof. Adaptors can include at least one ribonucleoside residue. Adaptors can be single-stranded, double-stranded, or have single-stranded and/or double-stranded portions. Adaptors can be configured to be linear, stem-looped, hairpin, or Y-shaped forms. Adaptors can be any length, including 4-100 nucleotides or longer. Adaptors can have blunt ends, overhang ends, or a combination of both. Overhang ends include 5' overhang and 3' overhang ends. The 5' end of a single-stranded adaptor, or one strand of a double-stranded adaptor, can have a 5' phosphate group or lack a 5' phosphate group. Adaptors can include a 5' tail that does not hybridize to a target polynucleotide (e.g., tailed adaptor), or adaptors can be non-tailed. An adaptor can include a sequence that is complementary to at least a portion of a primer, such as an amplification primer, a sequencing primer, or a capture primer (e.g., soluble or immobilized capture primers). Adaptors can include a random sequence or degenerate sequence. Adaptors can include at least one inosine residue. Adaptors can include at least one phosphorothioate, phosphorothiolate and/or phosphoramidate linkage. Adaptors can include a barcode sequence which can be used to distinguish polynucleotides (e.g., insert sequences) from different sample sources in a multiplex assay. Adaptors can include a unique identification sequence (e.g., unique molecular index, UMI; or a unique molecular tag) that can be used to uniquely identify a nucleic acid molecule to which the adaptor is appended. In some embodiments, a unique identification sequence can be used to increase error correction and accuracy, reduce the rate of false-positive variant calls and/or increase sensitivity of variant detection. Adaptors can include at least one restriction enzyme recognition sequence, including any one or any combination of two or more selected from a group consisting of type I, type II, type III, type IV, type IIs or type IIB.

In some embodiments, any of the amplification primer sequences, sequencing primer sequences, capture primer sequences, target capture sequences, circularization anchor sequences, sample barcode sequences, spatial barcode sequences, or anchor region sequences can be about 3-50 nucleotides in length, or about 5-40 nucleotides in length, or about 5-25 nucleotides in length.

The term "universal sequence" and related terms refers to a sequence in a nucleic acid molecule that is common among two or more polynucleotide molecules. For example, an adaptor having a universal sequence can be operably joined to a plurality of polynucleotides so that the population of co-joined molecules carry the same universal adaptor sequence. Examples of universal adaptor sequences include an amplification primer sequence, a sequencing primer sequence or a capture primer sequence (e.g., soluble or immobilized capture primers).

When used in reference to nucleic acid molecules, the terms "hybridize" or "hybridizing" or "hybridization" or other related terms refers to hydrogen bonding between two different nucleic acids to form a duplex nucleic acid. Hybridization also includes hydrogen bonding between two different regions of a single nucleic acid molecule to form a self-hybridizing molecule having a duplex region. Hybridization can comprise Watson-Crick or Hoogstein binding to form a duplex double-stranded nucleic acid, or a double-stranded region within a nucleic acid molecule. The double-stranded nucleic acid, or the two different regions of a single nucleic acid, may be wholly complementary, or partially complementary. Complementary nucleic acid strands need not hybridize with each other across their entire length. The complementary base pairing can be the standard A-T or C-G base pairing, or can be other forms of base-pairing interactions. Duplex nucleic acids can include mismatched base-paired nucleotides.

When used in reference to nucleic acids, the terms "extend", "extending", "extension" and other variants, refers to incorporation of one or more nucleotides into a nucleic acid molecule. Nucleotide incorporation comprises polymerization of one or more nucleotides into the terminal 3' OH end of a nucleic acid strand, resulting in extension of the nucleic acid strand. Nucleotide incorporation can be conducted with natural nucleotides and/or nucleotide analogs. Typically, but not necessarily, nucleotide incorporation occurs in a template-dependent fashion. Any suitable method of extending a nucleic acid molecule may be used, including primer extension catalyzed by a DNA polymerase or RNA polymerase.

In some embodiments, any of the amplification primer sequences, sequencing primer sequences, capture primer sequences (capture oligonucleotides), target capture sequences, circularization anchor sequences, sample barcode sequences, spatial barcode sequences, or anchor region sequences can be about 3-50 nucleotides in length, or about 5-40 nucleotides in length, or about 5-25 nucleotides in length.

The term "nucleotides" or "nucleic acid" and related terms refers to a molecule comprising an aromatic base, a five carbon sugar (e.g., ribose or deoxyribose), and at least one phosphate group. Canonical or non-canonical nucleotides are consistent with use of the term. The phosphate in some embodiments comprises a monophosphate, diphosphate, or triphosphate, or corresponding phosphate analog. The term "nucleoside" refers to a molecule comprising an aromatic base and a sugar. Nucleotides and nucleosides can be non-labeled or labeled with a detectable reporter moiety. A "derivative" of a nucleic acid or nucleotide can be substantially similar nucleotide derived from the nucleotide, such as, for example, in an amplification reaction.

Nucleotides (and nucleosides) typically comprise a hetero cyclic base including substituted or unsubstituted nitrogen-containing parent heteroaromatic ring which are commonly found in nucleic acids, including naturally-occurring, substituted, modified, or engineered variants, or analogs of the same. The base of a nucleotide (or nucleoside) is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), etheno-adenine, $N^6$-$\Delta^2$-isopentenyladenine (6 iA), $N^6$-$\Delta^2$-isopentenyl-2-methylthioadenine (2 ms6 iA), $N^6$-methyladenine, guanine (G), isoguanine, $N^2$-dimethylguanine (dmG), 7-methylguanine (7 mG), 2-thiopyrimidine, 6-thioguanine (6 sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4 sT), 5,6-dihydrothymine, $O^4$-methylthymine, uracil (U), 4-thiouracil (4 sU) and 5,6-dihydrouracil (dihydrouracil; D); indoles such as nitroindole and 4-methylindole; pyrroles such as nitropyrrole; nebularine; inosines, hydroxymethylcytosines; 5-methylcytosines; base (Y); as well as methylated, glycosylated, and acylated base moieties; and the like. Additional exemplary bases can be found in Fasman, 1989, in "Practical Handbook of Biochemistry and Molecular Biology", pp. 385-394, CRC Press, Boca Raton, Fla.

Nucleotides (and nucleosides) typically comprise a sugar moiety, such as carbocyclic moiety (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other sugar moieties (Joeng, et al., 1993 J. Med. Chem. 36: 2627-2638; Kim, et al., 1993 J. Med. Chem. 36: 30-7; Eschenmosser 1999 Science 284:2118-2124; and U.S. Pat. No. 5,558,991). The sugar moiety comprises: ribosyl; 2'-deoxyribosyl; 3'-deoxyribosyl; 2',3'-dideoxyribosyl; 2',3'-didehydrodideoxyribosyl; 2'-alkoxyribosyl; 2'-azidoribosyl; 2'-aminoribosyl; 2'-fluororibosyl; 2'-mercaptoriboxyl; 2'-alkylthioribosyl; 3'-alkoxyribosyl; 3'-azidoribosyl; 3'-aminoribosyl; 3'-fluororibosyl; 3'-mercaptoriboxyl; 3'-alkylthioribosyl carbocyclic; acyclic or other modified sugars.

In some embodiments, nucleotides comprise a chain of one, two or three phosphorus atoms where the chain is typically attached to the 5' carbon of the sugar moiety via an ester or phosphoramide linkage. In some embodiments, the nucleotide is an analog having a phosphorus chain in which the phosphorus atoms are linked together with intervening O, S, NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphorodithioate, and O-methylphophoroamidite groups.

The term "reporter moiety", "reporter moieties" or related terms refers to a compound that generates, or causes to generate, a detectable signal. A reporter moiety is sometimes called a "label". Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. A reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other. It is well known to one skilled in the art to select reporter moieties so that each absorbs excitation radiation and/or emits fluorescence at a wavelength distinguishable from the other reporter moieties to permit monitoring the presence of different reporter moieties in the same reaction or in different reactions. Two or more different reporter moieties can be selected having spectrally distinct emission profiles, or having minimal overlapping spectral emission profiles. Reporter moieties can be linked (e.g., operably linked) to nucleotides, nucleosides, nucleic acids, enzymes (e.g., polymerases or reverse transcriptases), or support (e.g., surfaces).

A reporter moiety (or label) comprises a fluorescent label or a fluorophore. Exemplary fluorescent moieties which may serve as fluorescent labels or fluorophores include, but are not limited to fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10, NHS-rhodamine, TMR-iodoacetamide, lissamine rhodamine B sulfonyl chloride, lissamine rhodamine B sulfonyl hydrazine, Texas Red sulfonyl chloride, Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550 C3 hydrazide, BODIPY 493/503 C3 hydrazide, BODIPY FL C3 hydrazide, BODIPY FL IA, BODIPY 530/551 IA, Br-BODIPY 493/503, Cascade Blue and derivatives such as Cascade Blue acetyl azide, Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy 3, Cy5, lanthanide chelates and derivatives such as BCPDA, TBP, TMT, BHHCT, BCOT, Europium chelates, Terbium chelates, Alexa Fluor dyes, DyLight dyes, Atto dyes, LightCycler Red dyes, CAL Flour dyes, JOE and derivatives thereof, Oregon Green dyes, WellRED dyes, IRD dyes, phycoerythrin and phycobilin dyes, Malachite green, stilbene, DEG dyes, NR dyes, near-infrared dyes and others known in the art such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and consist of two indolenin, benzo-indolium, pyridium, thiozolium, and/or quinolinium groups separated by a polymethine bridge between two nitrogen atoms. Commercially available cyanine fluorophores include, for example, Cy3, (which may comprise 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-1,3-dihydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-5-sulfo-1,3-dihydro-2H-indol-2-ylidene}prop-1-en-1-yl)-3,3-dimethyl-3H-indolium-5-sulfonate), Cy5 (which may comprise 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-indolin-2-ylidene)penta-1,3-dien-1-yl)-3,3-dimethyl-3H-indol-1-ium or 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-sulfoindolin-2-ylidene)penta-1,3-dien-1-yl)-3,3-dimethyl-3H-indol-1-ium-5-sulfonate), and Cy7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1- ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy2 which is an oxazole derivative rather than indolenin, and the benzo-derivatized Cy3.5, Cy5.5 and Cy7.5 are exceptions to this rule.

In some embodiments, the reporter moiety can be a FRET pair, such that multiple classifications can be performed under a single excitation and imaging step. As used herein, FRET may comprise excitation exchange (Forster) transfers, or electron-exchange (Dexter) transfers.

The terms "linked", "joined", "attached", "appended" and variants thereof comprise any type of fusion, bond, adherence or association between any combination of compounds or molecules that is of sufficient stability to withstand use in the particular procedure. The procedure can include but are not limited to: nucleotide binding; nucleotide incorporation; de-blocking (e.g., removal of chain-terminating moiety); washing; removing; flowing; detecting; imaging and/or identifying. Such linkage can comprise, for example, covalent, ionic, hydrogen, dipole-dipole, hydrophilic, hydrophobic, or affinity bonding, bonds or associations involving van der Waals forces, mechanical bonding, and the like. In some embodiments, such linkage occurs intramolecularly, for example linking together the ends of a single-stranded or double-stranded linear nucleic acid molecule to form a circular molecule. In some embodiments, such linkage can occur between a combination of different molecules, or between a molecule and a non-molecule, including but not limited to: linkage between a nucleic acid molecule and a solid surface; linkage between a protein and a detectable reporter moiety; linkage between a nucleotide and detectable reporter moiety; and the like. Some examples of linkages can be found, for example, in Hermanson, G., "Bioconjugate Techniques", Second Edition (2008); Aslam, M., Dent, A., "Bioconjugation: Protein Coupling Techniques for the Biomedical Sciences", London: Macmillan (1998); Aslam, M., Dent, A., "Bioconjugation: Protein Coupling Techniques for the Biomedical Sciences", London: Macmillan (1998).

When used in reference to nucleic acids, the terms "amplify", "amplifying", "amplification", and other related terms include producing multiple copies of an original polynucleotide template molecule, where the copies comprise a sequence that is complementary to the template sequence, or the copies comprise a sequence that is the same as the template sequence. In some embodiments, the copies comprise a sequence that is substantially identical to a template sequence, or is substantially identical to a sequence that is complementary to the template sequence.

The term "support" as used herein refers to a substrate that is designed for deposition of biological molecules or biological samples for assays and/or analyses. Examples of biological molecules to be deposited onto a support include nucleic acids (e.g., DNA, RNA), polypeptides, saccharides, lipids, a single cell or multiple cells. Examples of biological samples include but are not limited to saliva, phlegm, mucus, blood, plasma, serum, urine, stool, sweat, tears and fluids from tissues or organs.

In some embodiments, the support is solid, semi-solid, or a combination of both. In some embodiments, the support is porous, semi-porous, non-porous, or any combination of porosity. In some embodiments, the support can be substantially planar, concave, convex, or any combination thereof. In some embodiments, the support can be cylindrical, for example comprising a capillary or interior surface of a capillary.

In some embodiments, the surface of the support can be substantially smooth. In some embodiments, the support can be regularly or irregularly textured, including bumps, etched, pores, three-dimensional scaffolds, or any combination thereof.

In some embodiments, the support comprises a bead having any shape, including spherical, hemi-spherical, cylindrical, barrel-shaped, toroidal, disc-shaped, rod-like, conical, triangular, cubical, polygonal, tubular or wire-like.

The support can be fabricated from any material, including but not limited to glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The support can have a plurality (e.g., two or more) of nucleic acid templates immobilized thereon. The plurality of immobilized nucleic acid templates have the same sequence or have different sequences. In some embodiments, individual nucleic acid template molecules in the plurality of nucleic acid templates are immobilized to a different site on the support. In some embodiments, two or more individual nucleic acid template molecules in the plurality of nucleic acid templates are immobilized to a site on the support.

When used in reference to support, the term "feature" refers to a region on a support. In some embodiments, the feature is a region on a coating which is layered on the support. In some embodiments, the feature is a region on a low non-specific binding coating which is layered on a support. A support or coating can have a plurality of regions (e.g., features) located at different pre-determined locations on the support or coating (FIG. 3, right). The different features on the support can be placed at non-overlapping positions or at overlapping positions on the support. The features can be configured to have any shape, for example circular, ovular, square, rectangular, or polygonal. The features can be arranged in a grid pattern having rows and columns, or can be arranged in a row or a column. In some embodiments, any given feature contains a plurality of capture oligonucleotides and/or a plurality of circularization oligonucleotides immobilized to the support or to the coating. The plurality of features includes at least a first and second feature.

The term "array" refers to a support comprising a plurality of sites located at pre-determined locations on the support to form an array of sites. The sites can be discrete and separated by interstitial regions. In some embodiments, the pre-determined sites on the support can be arranged in one dimension in a row or a column, or arranged in two dimensions in rows and columns. In some embodiments, the plurality of pre-determined sites is arranged on the support in an organized fashion. In some embodiments, the plurality of pre-determined sites is arranged in any organized pattern, including rectilinear, hexagonal patterns, grid patterns, patterns having reflective symmetry, patterns having rotational symmetry, or the like. The pitch between different pairs of sites can be that same or can vary. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are located at pre-determined locations on the support. In some embodiments, a plurality of pre-determined sites on the support (e.g., $10^2$-$10^{15}$ sites or more) are immobilized with nucleic acid templates to form a nucleic acid template array. In some embodiments, the nucleic acid templates that are immobilized at a plurality of pre-determined sites by hybridization to immobilized surface capture primers, or the nucleic acid templates are covalently attached to the surface capture primer. In some embodiments, the nucleic acid templates that are immobilized at a plurality of pre-determined sites, for example immobilized at $10^2$-$10^{15}$ sites or more. In some embodiments, the immobilized nucleic acid templates are clonally-amplified to generate immobilized nucleic acid clusters at the plurality of pre-determined sites. In some embodiments, individual immobilized nucleic acid clusters comprise linear clusters, or comprise single-stranded or double-stranded concatemers.

In some embodiments, a support comprising a plurality of sites located at random locations on the support is referred to herein as a support having randomly located sites thereon. The location of the randomly located sites on the support are not pre-determined. The plurality of randomly-located sites is arranged on the support in a disordered and/or unpredictable fashion. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are randomly located on the support. In some embodiments, a plurality of randomly located sites on the support (e.g., $10^2$-$10^{15}$ sites or more) are immobilized with nucleic acid templates to form a support immobilized with nucleic acid templates. In some embodiments, the nucleic acid templates that are immobilized at a plurality of randomly located sites by hybridization to immobilized surface capture primers, or the nucleic acid templates are covalently attached to the surface capture primer. In some embodiments, the nucleic acid templates that are immobilized at a plurality of randomly located sites, for example immobilized at $10^2$-$10^{15}$ sites or more. In some embodiments, the immobilized nucleic acid templates are clonally-amplified to generate immobilized nucleic acid clusters at the plurality of randomly located sites. In some embodiments, individual immobilized nucleic acid clusters comprise linear clusters, or comprise single-stranded or double-stranded concatemers.

In some embodiment, the plurality of immobilized surface capture primers on the support are in fluid communication with each other to permit flowing a solution of reagents (e.g., nucleic acid template molecules, soluble primers, enzymes, nucleotides, divalent cations, buffers, and the like) onto the support so that the plurality of immobilized surface capture primers on the support can be essentially simultaneously reacted with the reagents in a massively parallel manner. In some embodiments, the fluid communication of the plurality of immobilized surface capture primers can be used to conduct nucleic acid amplification reactions (e.g., RCA, MDA, PCR and bridge amplification) essentially simultaneously on the plurality of immobilized surface capture primers.

In some embodiment, the plurality of immobilized nucleic acid clusters on the support are in fluid communication with each other to permit flowing a solution of reagents (e.g., enzymes, nucleotides, divalent cations, and the like) onto the support so that the plurality of immobilized nucleic acid clusters on the support can be essentially simultaneously reacted with the reagents in a massively parallel manner. In some embodiments, the fluid communication of the plurality of immobilized nucleic acid clusters can be used to conduct nucleotide binding assays and/or conduct nucleotide polymerization reactions (e.g., primer extension or sequencing) essentially simultaneously on the plurality of immobilized nucleic acid clusters, and optionally to conduct detection and imaging for massively parallel sequencing.

When used in reference to immobilized enzymes, the term "immobilized" and related terms refer to enzymes (e.g., polymerases) that are attached to a support through covalent bond or non-covalent interaction, or attached to a coating on the support, or buried within a matrix formed by a coating on the support.

When used in reference to immobilized nucleic acids, the term "immobilized" and related terms refer to nucleic acid molecules that are attached to a support through covalent bond or non-covalent interaction, or attached to a coating on the support, or buried within a matrix formed by a coating on the support, where the nucleic acid molecules include surface capture primers, nucleic acid template molecules and extension products of capture primers. Extension products of capture primers includes nucleic acid concatemers (e.g., nucleic acid clusters).

In some embodiments, one or more nucleic acid templates are immobilized on the support, for example immobilized at the sites on the support. In some embodiments, the one or more nucleic acid templates are clonally-amplified. In some embodiments, the one or more nucleic acid templates are clonally-amplified off the support (e.g., in-solution) and then deposited onto the support and immobilized on the support. In some embodiments, the clonal amplification reaction of the one or more nucleic acid templates is conducted on the support resulting in immobilization on the support. In some embodiments, the one or more nucleic acid templates are clonally-amplified (e.g., in solution or on the support) using a nucleic acid amplification reaction, including any one or any combination of: polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification (RCA), circle-to-circle amplification, helicase-dependent amplification, recombinase-dependent amplification, and/or single-stranded binding (SSB) protein-dependent amplification.

The term "surface capture primer", "capture oligonucleotide" and related terms refers to single-stranded oligonucleotides that are immobilized to a support and comprise a sequence that can hybridize to at least a portion of a nucleic acid template molecule. Surface capture primers can be used to immobilize template molecules to a support via hybridization. Surface capture primers can be immobilized to a support in a manner that resists primer removal during flowing, washing, aspirating, and changes in temperature, pH, salts, chemical and/or enzymatic conditions. Typically, but not necessarily, the 5' end of a surface capture primer can be immobilized to a support. Alternatively, an interior portion or the 3' end of a surface capture primer can be immobilized to a support.

The sequence of surface capture primers can be wholly or partially complementary along their length to at least a portion of the nucleic acid template molecule. A support can include a plurality of immobilized surface capture primers having the same sequence, or having two or more different sequences. Surface capture primers can be any length, for example 4-50 nucleotides, or 50-100 nucleotides, or 100-150 nucleotides, or longer lengths.

A surface capture primer can have a terminal 3' nucleotide having a sugar 3' OH moiety which is extendible for nucleotide polymerization (e.g., polymerase catalyzed polymerization). A surface capture primer can have a terminal 3' nucleotide having the 3' sugar position linked to a chain-terminating moiety that inhibits nucleotide polymerization. The 3' chain-terminating moiety can be removed (e.g., de-blocked) to convert the 3' end to an extendible 3' OH end using a de-blocking agent. Examples of chain terminating moieties include alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. Azide type chain terminating moieties including azide, azido and azidomethyl groups. Examples of de-blocking agents include a phosphine compound, such as Tris(2-carboxyethyl)phosphine (TCEP) and bis-sulfo triphenyl phosphine (BS-TPP), for chain-terminating groups azide, azido and azidomethyl groups. Examples of de-blocking agents include tetrakis(triphenylphosphine)palladium(0) (Pd(PPh$_3$)$_4$) with piperidine, or with 2,3-Dichloro-5,6-dicyano-1,4-benzo-quinone (DDQ), for chain-terminating groups alkyl, alkenyl, alkynyl and allyl. Examples of a de-blocking agent includes Pd/C for chain-terminating groups aryl and benzyl. Examples of de-blocking agents include phosphine, beta-mercaptoethanol or dithiothritol (DTT), for chain-terminating groups amine, amide, keto, isocyanate, phosphate, thio and disulfide. Examples of de-blocking agents include potassium carbonate (K$_2$CO$_3$) in MeOH, triethylamine in pyridine, and Zn in acetic acid (AcOH), for carbonate chain-terminating groups. Examples of de-blocking agents include tetrabutylammonium fluoride, pyridine-HF, with ammonium fluoride, and triethylamine trihydrofluoride, for chain-terminating groups urea and silyl.

The term "branched polymer" and related terms refers to a polymer having a plurality of functional groups that help conjugate a biologically active molecule such as a nucleotide, and the functional group can be either on the side chain of the polymer or directly attaches to a central core or central backbone of the polymer. The branched polymer can have linear backbone with one or more functional groups coming off the backbone for conjugation. The branched polymer can also be a polymer having one or more sidechains, wherein the side chain has a site suitable for conjugation. Examples of the functional group include but are not limited to hydroxyl, ester, amine, carbonate, acetal, aldehyde, aldehyde hydrate, alkenyl, acrylate, methacrylate, acrylamide, active sulfone, hydrazide, thiol, alkanoic acid, acid halide, isocyanate, isothiocyanate, maleimide, vinylsulfone, dithiopyridine, vinylpyridine, iodoacetamide, epoxide, glyoxal, dione, mesylate, tosylate, and tresylate.

When used in reference to a low binding surface coating, one or more layers of a multi-layered surface coating may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some embodiments, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branched.

Linear, branched, or multi-branched polymers used to create one or more layers of any of the multi-layered surfaces disclosed herein may have a molecular weight of at least 500, at least 1,000, at least 2,000, at least 3,000, at least 4,000, at least 5,000, at least 10,000, at least 15,000, at least 20,000, at least 25,000, at least 30,000, at least 35,000, at least 40,000, at least 45,000, or at least 50,000 daltons.

In some embodiments, e.g., wherein at least one layer of a multi-layered surface comprises a branched polymer, the number of covalent bonds between a branched polymer molecule of the layer being deposited and molecules of the previous layer may range from about one covalent linkages per molecule and about 32 covalent linkages per molecule. In some embodiments, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32 covalent linkages per molecule.

Any reactive functional groups that remain following the coupling of a material layer to the surface may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

The number of layers of low non-specific binding material, e.g., a hydrophilic polymer material, deposited on the surface, may range from 1 to about 10. In some embodiments, the number of layers is at least 1, at least 2, at least 3, at least 4, at least 5, at least 6, at least 7, at least 8, at least 9, or at least 10. In some embodiments, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some embodiments the number of layers may range from about 2 to about 4. In some embodiments, all of the layers may comprise the same material. In some embodiments, each layer may comprise a different material. In some embodiments, the plurality of layers may comprise a plurality of materials. In some embodiments at least one layer may comprise a branched polymer. In some embodiment, all of the layers may comprise a branched polymer.

One or more layers of low non-specific binding material may in some cases be deposited on and/or conjugated to the substrate surface using a polar protic solvent, a polar or polar aprotic solvent, a nonpolar solvent, or any combination thereof. In some embodiments the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N- morpholino)propanesulfonic acid (MOPS), etc.), or any combination thereof. In some embodiments, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of water or an aqueous buffer solution. In some embodiments, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of an organic solvent. The pH of the solvent mixture used may be less than 6, about 6, 6.5, 7, 7.5, 8, 8.5, 9, or greater than pH 9.

The term "persistence time" and related terms refers to the length of time that a binding complex, which is formed between the target nucleic acid, a polymerase, a conjugated or unconjugated nucleotide, remains stable without any binding component dissociates from the binding complex. The persistence time is indicative of the stability of the binding complex and strength of the binding interactions. Persistence time can be measured by observing the onset and/or duration of a binding complex, such as by observing a signal from a labeled component of the binding complex. For example, a labeled nucleotide or a labeled reagent comprising one or more nucleotides may be present in a binding complex, thus allowing the signal from the label to be detected during the persistence time of the binding complex. One exemplary label is a fluorescent label.

The hybridization buffers described herein comprise a first and second polar aprotic solvent, a pH buffer system and a crowding agent. The polar solvent as included in the hybridization composition described herein is a solvent or solvent system comprising one or more molecules characterized by the presence of a permanent dipole moment, i.e., a molecule having a spatially unequal distribution of charge density. A polar solvent may be characterized by a dielectric constant of 20, 25, 30, 35, 40, 45, 50, 55, 60 or by a value or a range of values having any of the aforementioned values. A polar solvent as described herein may comprise a polar aprotic solvent. A polar aprotic solvent as described herein may further contain no ionizable hydrogen in the molecule. In addition, polar solvents or polar aprotic solvents may be preferably substituted in the context of the presently disclosed compositions with a strong polarizing functional groups such as nitrile, carbonyl, thiol, lactone, sulfone, sulfite, and carbonate groups so that the underlying solvent molecules have a dipole moment. Polar solvents and polar aprotic solvents can be present in both aliphatic and aromatic or cyclic form. In some embodiments, the polar solvent is acetonitrile.

The polar or polar aprotic solvent described herein can have a dielectric constant that is the same as or close to acetonitrile. The dielectric constant of the polar or polar aprotic solvent can be in the range of about 20-60, about 25-55, about 25-50, about 25-45, about 25-40, about 30-50, about 30-45, or about 30-40. The dielectric constant of the polar or polar aprotic solvent can be greater than 20, 25, 30, 35, or 40. The dielectric constant of the polar or polar aprotic solvent can be lower than 30, 40, 45, 50, 55, or 60. The dielectric constant of the polar or polar aprotic solvent can be about 35, 36, 37, 38, or 39.

The polar or polar aprotic solvent described herein can have a polarity index that is the same as or close to acetonitrile. The polarity index of the polar or polar aprotic solvent can be in the range of about 2-9, 2-8, 2-7, 2-6, 3-9, 3-8, 3-7, 3-6, 4-9, 4-8, 4-7, or 4-6. The polarity index of the polar or polar aprotic solvent can be greater than about 2, 3, 4, 4.5, 5, 5.5, or 6. The polarity index of the polar or polar aprotic solvent can be lower than about 4.5, 5, 5.5, 6, 6.5, 7, 7.5, 8, 8.5, 9, or 10. The polarity index of the polar or polar aprotic solvent can be about 5.5, 5.6, 5.7, or 5.8.

Some examples of the polar or polar aprotic solvent include but are not limited to acetonitrile, dimethylformamide (DMF), dimethylsulfoxide (DMSO), acetanilide, N-acetyl pyrrolidone, 4-amino pyridine, benzamide, benzimidazole, 1,2,3-benzotriazole, butadienedioxide, 2,3-butylene carbonate, γ-butyrolactone, caprolactone (epsilon), chloro maleic anhydride, 2-chlorocyclohexanone, chloroethylene carbonate, chloronitromethane, citraconic anhydride, crotonlactone, 5-cyano-2-thiouracil, cyclopropylnitrile, dimethyl sulfate, dimethyl sulfone, 1,3-dimethyl-5-tetrazole, 1,5-dimethyl tetrazole, 1,2-dinitrobenzene, 2,4-dinitrotoluene, diphenyl sulfone, 1,2-dinitrobenzene, 2,4-dinitrotoluene, diphenyl sulfone, epsilon-caprolactam, ethanesulfonylchloride, ethyl ethyl phosphinate, N-ethyl tetrazole, ethylene carbonate, ethylene trithiocarbonate, ethylene glycol sulfate, ethylene glycol sulfite, furfural, 2-furonitrile, 2-imidazole, isatin, isoxazole, malononitrile, 4-methoxy benzonitrile, 1-methoxy-2-nitrobenzene, methyl alpha bromo tetronate, 1-methyl imidazole, N-methyl imidazole, 3-methyl isoxazole, N-methyl morpholine-N-oxide, methyl phenyl sulfone, N-methyl pyrrolidinone, methyl sulfolane, methyl-4-toluenesulfonate, 3-nitroaniline, nitrobenzimidazole, 2-nitrofuran, 1-nitroso-2-pyrolidinone, 2-nitrothiophene, 2-oxazolidinone, 9,10-phenanthrenequinone, N-phenyl sydnone, phthalic anhydride, picolinonitrile (2-cyanopyridine), 1,3-propane sultone, β-propiolactone, propylene carbonate, 4H-pyran-4-thione, 4H-pyran-4-one (Y-pyrone), pyridazine, 2-pyrrolidone, saccharin, succinonitrile, sulfanilamide, sulfolane, 2,2,6,6-tetrachlorocyclohexanone, tetrahydrothiapyran oxide, tetramethylene sulfone (sulfolane), thiazole, 2-thiouracil, 3,3,3-trichloro propene, 1,1,2-trichloro propene, 1,2,3-trichloro propene, trimethylene sulfide-dioxide, and trimethylene sulfite.

The amount of the polar solvent or polar aprotic solvent is present in an amount effective to denature a double stranded nucleic acid. In some embodiments, the amount of the polar or polar aprotic solvent is greater than about 10% by volume based on the total volume of the formulation. The amount of the polar or polar aprotic solvent is about or more than about 5%, 10%, 15%, 20%, 25%, 30%, 35%, 40%, 50%, 60%, 70%, 80%, 90%, or higher, by volume based on the total volume of the formulation. The amount of the polar or polar aprotic solvent is lower than about 15%, 20%, 25%, 30%, 35%, 40%, 50%, 60%, 70%, 80%, 90%, or higher, by volume based on the total volume of the formulation. In some embodiments, the amount of the polar or polar aprotic solvent is in the range of about 10% to 90% by volume based on the total volume of the formulation. In some embodiments, the amount of the polar or polar aprotic solvent is in the range of about 25% to 75% by volume based on the total volume of the formulation. In some embodiments, the amount of the polar or polar aprotic solvent is in the range of about 10% to 95%, 10% to 85%, 20% to 90%, 20% to 80%, 20% to 75%, or 30% to 60% by volume based on the total volume of the formulation.

In some embodiments, the disclosed hybridization buffer formulations may include the addition of an organic solvent. Examples of suitable solvents include, but are not limited to, acetonitrile, ethanol, DMF, and methanol, or any combination thereof at varying percentages (typically >5%). In some embodiments, the percentage of organic solvent (by volume) included in the hybridization buffer may range from about 1% to about 20%. In some embodiments, the percentage by volume of organic solvent may be at least 1%, at least 2%, at least 3%, at least 4%, at least 5%, at least 6%, at least 7%, at least 8%, at least 9%, at least 10%, at least 15%, or at least 20%. In some embodiments, the percentage by volume of organic solvent may be at most 20%, at most 15%, at most 10%, at most 9%, at most 8%, at most 7%, at most 6%, at most 5%, at most 4%, at most 3%, at most 2%, or at most 1%. Any of the lower and upper values described in this paragraph may be combined to form a range included within the present disclosure, for example, the percentage by volume of organic solvent may range from about 4% to about 15%. Those of skill in the art will recognize that the percentage by volume of organic solvent may have any value within this range, e.g., about 7.5%.

Improvements in hybridization rate: In some embodiments, the use of optimized buffer formulations disclosed herein (optionally, used in combination with low non-specific binding surface) yield relative hybridization rates that range from about 2× to about 20× faster than that for a conventional hybridization protocol. In some embodiments, the relative hybridization rate may be at least 2×, at least 3×, at least 4×, at least 5×, at least 6×, at least 7×, at least 8×, at least 9×, at least 10×, at least 12×, at least 14×, at least 16×, at least 18×, or at least 20× that for a conventional hybridization protocol.

Improvements in hybridization efficiency (or yield) is a measure of the percentage of total available tethered adapter sequences on a solid surface, primer sequences, or oligonucleotide sequences in general that are hybridized to complementary sequences. In some embodiments, the use of optimized buffer formulations disclosed herein (optionally, used in combination with low non-specific binding surface) yield improved hybridization efficiency compared to that for a conventional hybridization protocol. In some embodiments, the hybridization efficiency that may be achieved is better than 80%, 85%, 90%, 95%, 98%, or 99% in any of the hybridization reaction times specified above.

Improvements in hybridization specificity is a measure of the ability of tethered adapter sequences, primer sequences, or oligonucleotide sequences in general to correctly hybridize only to completely complementary sequences. In some embodiments, the use of the optimized buffer formulations disclosed herein (optionally, used in combination with low non-specific binding surface) yield improved hybridization specificity compared to that for a conventional hybridization protocol. In some embodiments, the hybridization specificity that may be achieved is better than 1 base mismatch in 10 hybridization events, 1 base mismatch in 100 hybridization events, 1 base mismatch in 1,000 hybridization events, or 1 base mismatch in 10,000 hybridization events.

The term "polymer-nucleotide conjugate," or "multivalent molecule", and related terms refers generally to a molecule comprising (a) a core, and (b) a plurality of nucleotide arms where each nucleotide arm comprises (i) a core attachment moiety, (ii) a spacer comprising a PEG moiety, (iii) a linker, and (iv) a nucleotide unit. In some embodiments, the polymer-nucleotide conjugate comprises a core which is attached to the plurality of nucleotide arms. In some embodiments, the spacer is attached to the linker, wherein the linker is attached to the nucleotide unit. The multivalent comprise a polymer-nucleotide conjugate, comprising a plurality of copies of the same nucleotide attached to the particle, wherein the plurality of nucleotides are each part of a nucleotide arm. See for example FIGS. 5A-D and FIGS. 6A-C. When the nucleotide is complementary to the target nucleic acid, the polymer-nucleotide conjugate forms a binding complex with the polymerase and the target nucleic acid, and the binding complex exhibits increased stability and longer persistence time than the binding complex formed using a single unconjugated or untethered nucleotide. Compositions and methods for preparing and using the multivalent molecules are described in U.S. Ser. No. 16/579,794, filed on Sep. 23, 2019, the contents of which is hereby expressly incorporated by reference in its entirety.

The term "multivalent binding complex" and related terms refers generally to a complex formed between a polymer-nucleotide conjugate and two or more nucleotides in two or more copies of a target nucleic acid sequence at substantially the same time, such as, for example, in a single nucleotide binding reaction. The two or more copies of the target nucleic acid sequence may be on the same target nucleic acid molecule (e.g., concatemer) or a different target nucleic acid molecule.

The term "crowding agent" and related terms refers to a compound that alters the properties of other molecules in a solution. Crowding agents typically have high molecular weight and/or bulky structures. Crowding agents in solution can increase the concentration of other molecules in the solution. Crowding agents can reduce the volume of solvent that is available for other molecules in the solution which can create a molecular crowding environment. Crowding agents in a solution can generate a crowded environment for molecules in the solution. Crowding agents can alter the rates or equilibrium constants of a reaction. Examples of crowding agents include polyethylene glycol (e.g., PEG), ficoll, dextran, glycogen, polyvinyl alcohol, triblock polymers (e.g., Pluronics), polystyrene, polyvinylpyrrolidone (PVP), hydroxypropyl methyl cellulose (HPMC), hydroxyethyl methyl cellulose (HEMC), hydroxybutyl methyl cellulose, hydroxypropyl cellulose, methylcellulose, and hydroxyl methyl cellulose. In some embodiments, the crowding agent comprises linear or branched PEG. In some embodiments, the crowding agent comprise PEG 400, PEG 1500, PEG 2000, PEG 3400, PEG 3350, PEG 4000, PEG 6000 or PEG 8000. In some embodiments, a solution can include at least one crowding agent at about 1%, 2%, 3%, 5%, 10%, 15%, 20%, 25%, 30%, 35%, 40%, 50%, 60%, or higher percent based on volume of the solution. In some embodiments, the solution can be used for nucleic acid amplification including rolling circle amplification and/or multiple displacement amplification reactions.

A suitable amount of a crowding agent in the composition allows for, enhances, or facilitates molecular crowding. The amount of the crowding agent is about or more than about 1%, 2%, 3%, 5%, 10%, 15%, 20%, 25%, 30%, 35%, 40%, 50%, 60%, or higher, by volume based on the total volume of the formulation. In some cases, the amount of the molecular crowding agent is greater than 5% by volume based on the total volume of the formulation. The amount of the crowding agent is lower than about 3%, 5%, 10%, 12.5%, 15%, 20%, 25%, 30%, 35%, 40%, 50%, 60%, 70%, 80%, 90%, or higher, by volume based on the total volume of the formulation. In some cases, the amount of the molecular crowding agent can be less than 30% by volume based on the total volume of the formulation. In some embodiments, the amount of the polar or polar aprotic solvent is in the range of about 25% to 75% by volume based on the total volume of the formulation. In some embodiments, the amount of the polar or polar aprotic solvent is in the range of about 1% to 40%, 1% to 35%, 2% to 50%, 2% to 40%, 2% to 35%, 2% to 30%, 2% to 25%, 2% to 20%, 2% to 10%, 5% to 50%, 5% to 40%, 5% to 35%, 5% to 30%, 5% to 25%, 5% to 20%, by volume based on the total volume of the formulation. In some cases, the amount of the molecular crowding agent can be in the range of about 5% to about 20% by volume based on the total volume of the formulation. In some embodiments, the amount of the crowding agent is in the range of about 1% to 30% by volume based on the total volume of the formulation.

In some embodiments, the disclosed hybridization buffer formulations may include the addition of a molecular crowding or volume exclusion agent. Molecular crowding or volume exclusion agents are typically macromolecules (e.g., proteins) which, when added to a solution in high concentrations, may alter the properties of other molecules in solution by reducing the volume of solvent available to the other molecules. In some embodiments, the percentage by volume of molecular crowding or volume exclusion agent included in the hybridization buffer formulation may range from about 1% to about 50%. In some embodiments, the percentage by volume of molecular crowding or volume exclusion agent may be at least 1%, at least 5%, at least 10%, at least 15%, at least 20%, at least 25%, at least 30%, at least 35%, at least 40%, at least 45%, or at least 50%. In some embodiments, the percentage by volume of molecular crowding or volume exclusion agent may be at most 50%, at most 45%, at most 40%, at most 35%, at most 30%, at most 25%, at most 20%, at most 15%, at most 10%, at most 5%, or at most 1%. Any of the lower and upper values described in this paragraph may be combined to form a range included within the present disclosure, for example, the percentage by volume of molecular crowding or volume exclusion agent may range from about 5% to about 35%. Those of skill in the art will recognize that the percentage by volume of molecular crowding or volume exclusion agent may have any value within this range, e.g., about 12.5%.

The hybridization buffer described herein includes a pH buffer system that maintains the pH of the compositions in a range suitable for hybridization process. The pH buffer system can include one or more buffering agents selected from the group consisting of Tris, HEPES, TAPS, Tricine, Bicine, Bis-Tris, NaOH, KOH, TES, EPPS, MES, and MOPS. The pH buffer system can further include a solvent. A preferred pH buffer system includes MOPS, MES, TAPS, phosphate buffer combined with methanol, acetonitrile, ethanol, isopropanol, butanol, t-butyl alcohol, DMF, DMSO, or any combination therein.

The hybridization buffer includes an amount of the pH buffer system that is effective to maintain the pH of the formulation to be in a range suitable for the hybridization. In some embodiments, the pH may be at least 3, at least 4, at least 5, at least 6, at least 7, at least 8, at least 9, or at least 10. In some embodiments, the pH may be at most 10, at most 9, at most 8, at most 7, at most 6, at most 5, at most 4, or at most 3. Any of the lower and upper values described in this paragraph may be combined to form a range included within the present disclosure, for example, the pH of the hybridization buffer may range from about 4 to about 8. Those of skill in the art will recognize that the pH of the hybridization buffer may have any value within this range, e.g., about pH 7.8. In some cases, the pH range is about 3 to about 10. In some embodiments, the disclosed hybridization buffer formulations may include adjustment of pH over the range of about pH 3 to pH 10, with a preferred buffer range of 5-9.

The hybridization buffer described herein includes an additive (e.g., polar aprotic solvent) for controlling melting temperature of nucleic acid can vary depending on other agents used in the compositions. The amount of the additive for controlling melting temperature of the nucleic acid is about or more than about 1%, 2%, 3%, 5%, 10%, 15%, 20%, 25%, 30%, 35%, 40%, 50%, 60%, or higher, by volume based on the total volume of the formulation. In some cases, the amount of the additive for controlling melting temperature of the nucleic acid is greater than about 2% by volume based on the total volume of the formulation. In some cases, the amount of the additive for controlling melting temperature of the nucleic acid is greater than 5% by volume based on the total volume of the formulation. In some cases, the amount of the additive for controlling melting temperature of the nucleic acid is lower than about 3%, 5%, 10%, 12.5%, 15%, 20%, 25%, 30%, 35%, 40%, 50%, 60%, 70%, 80%, 90%, or higher, by volume based on the total volume of the formulation. In some embodiments, the amount of the additive for controlling melting temperature of the nucleic acid is in the range of about 1% to 40%, 1% to 35%, 2% to 50%, 2% to 40%, 2% to 35%, 2% to 30%, 2% to 25%, 2% to 20%, 2% to 10%, 5% to 50%, 5% to 40%, 5% to 35%, 5% to 30%, 5% to 25%, 5% to 20%, by volume based on the total volume of the formulation. In some embodiments, the amount of the additive for controlling melting temperature of the nucleic acid is in the range of about 2% to 20% by volume based on the total volume of the formulation. In some cases, the amount of the additive for controlling melting temperature of the nucleic acid is in the range of about 5% to 10% by volume based on the total volume of the formulation.

In some embodiments, the disclosed hybridization buffer formulations may include the addition of an additive that alters nucleic acid duplex melting temperature. Examples of suitable additives that may be used to alter nucleic acid melting temperature include, but are not limited to, Formamide. In some embodiments, the percentage by volume of a melting temperature additive included in the hybridization buffer formulation may range from about 1% to about 50%. In some embodiments, the percentage by volume of a melting temperature additive may be at least 1%, at least 5%, at least 10%, at least 15%, at least 20%, at least 25%, at least 30%, at least 35%, at least 40%, at least 45%, or at least 50%. In some embodiments, the percentage by volume of a melting temperature additive may be at most 50%, at most 45%, at most 40%, at most 35%, at most 30%, at most 25%, at most 20%, at most 15%, at most 10%, at most 5%, or at most 1%. Any of the lower and upper values described in this paragraph may be combined to form a range included within the present disclosure, for example, the percentage by volume of a melting temperature additive may range from about 10% to about 25%. Those of skill in the art will recognize that the percentage by volume of a melting temperature additive may have any value within this range, e.g., about 22.5%.

In some embodiments, the hybridization buffer described herein includes an additive that impacts DNA hydration: In some embodiments, the disclosed hybridization buffer formulations may include the addition of an additive that impacts nucleic acid hydration. Examples include, but are not limited to, betaine, urea, glycine betaine, or any combination thereof. In some embodiments, the percentage by volume of a hydration additive included in the hybridization buffer formulation may range from about 1% to about 50%. In some embodiments, the percentage by volume of a hydration additive may be at least 1%, at least 5%, at least 10%, at least 15%, at least 20%, at least 25%, at least 30%, at least 35%, at least 40%, at least 45%, or at least 50%. In some embodiments, the percentage by volume of a hydration additive may be at most 50%, at most 45%, at most 40%, at most 35%, at most 30%, at most 25%, at most 20%, at most 15%, at most 10%, at most 5%, or at most 1%. Any of the lower and upper values described in this paragraph may be combined to form a range included within the present disclosure, for example, the percentage by volume of a hydration additive may range from about 1% to about 30%. Those of skill in the art will recognize that the percentage by volume of a melting temperature additive may have any value within this range, e.g., about 6.5%.

The term "sequencing" and related terms refers to a method for obtaining nucleotide sequence information from a nucleic acid molecule, typically by determining the identity of at least some nucleotides (including their nucleobase components) within the nucleic acid molecule. In some embodiments, the sequence information of a given region of a nucleic acid molecule includes identifying each and every nucleotide within a region that is sequenced. In some embodiments, sequencing information determines only some of the nucleotides a region, while the identity of some nucleotides remains undetermined or incorrectly determined. Any suitable method of sequencing may be used. In an exemplary embodiment, sequencing can include label-free or ion based sequencing methods. In some embodiments, sequencing can include labeled or dye-containing nucleotide or fluorescent based nucleotide sequencing methods. In some embodiments, sequencing can include cluster-based sequencing or bridge sequencing methods.

In some embodiments, in any of the sequencing steps can be conducted using a sequence-by-synthesis, sequence-by-hybridization or sequence-by-binding procedure. Examples of massively parallel sequence-by-synthesis procedures include polony sequencing, pyrosequencing (e.g., from 454 Life Sciences; U.S. Pat. Nos. 7,211,390, 7,244,559 and 7,264,929), chain-terminator sequencing (e.g., from Illumina; U.S. Pat. No. 7,566,537; Bentley 2006 Current Opinion Genetics and Development 16:545-552; and Bentley, et al., 2008 Nature 456:53-59, ion-sensitive sequencing (e.g., from Ion Torrent), probe-anchor ligation sequencing (e.g., Complete Genomics), DNA nanoball sequencing, nanopore DNA sequencing. Examples of single molecule sequencing include Heliscope single molecule sequencing, and single molecule real time (SMRT) sequencing. An example of sequence-by-hybridization includes SOLiD sequencing (e.g., from Life Technologies; WO 2006/084132). An example of sequence-by-binding includes Omniome sequencing (e.g., U.S. Pat. No. 10,246,744).

As used herein, "paired end" information refers to genetic sequence information pertaining to both the forward and reverse strands of a double stranded nucleic acid molecule or nucleic acid segment. A paired-end read or paired-end sequencing thus refers to the determination of the sequence of both the forward and the reverse strand. This determination may be made directly and may in some embodiments be made without reference to the sequence of a known complementary strand.

As used herein, the phrases "imaging module", "imaging unit", "imaging system", "optical imaging module", "optical imaging unit", and "optical imaging system" are used interchangeably, and may comprise components or sub-systems of a larger system that may also include, e.g., fluidics modules, temperature control modules, translation stages, robotic fluid dispensing and/or microplate handling, processor or computers, instrument control software, data analysis and display software, etc.

As used herein, the term "detection channel" refers to an optical path (and/or the optical components therein) within an optical system that is configured to deliver an optical signal arising from a sample to a detector. In some instances, a detection channel may be configured for performing spectroscopic measurements, e.g., monitoring a fluorescence signal or other optical signal using a detector such as a photomultiplier. In some instances, a "detection channel" may be an "imaging channel", i.e., an optical path (and/or the optical components therein) within an optical system that is configured to capture and deliver an image to an image sensor.

As used herein, a "detectable label" may refer to any of a variety of detectable labels or tags known to those of skill in the art. Examples include, but are not limited to, chromophores, fluorophores, quantum dots, upconverting phosphors, luminescent or chemiluminescent molecules, radioisotopes, magnetic nanoparticles, mass tags, and the like. In some instances, a preferred label may comprise a fluorophore.

As used herein, the term "excitation wavelength" refers to the wavelength of light used to excite a fluorescent indicator (e.g., a fluorophore or dye molecule) and generate fluorescence. Although the excitation wavelength is typically specified as a single wavelength, e.g., 620 nm, it will be understood by those of skill in the art that this specification refers to a wavelength range or excitation filter bandpass that is centered on the specified wavelength. For example, in some instances, light of the specified excitation wavelength comprises light of the specified wavelength ±2 nm, ±5 nm, ±10 nm, ±20 nm, ±40 nm, ±80 nm, or more. In some instances, the excitation wavelength used may or may not coincide with the absorption peak maximum of the fluorescent indicator.

As used herein, the term "emission wavelength" refers to the wavelength of light emitted by a fluorescent indicator (e.g., a fluorophore or dye molecule) upon excitation by light of an appropriate wavelength. Although the emission wavelength is typically specified as a single wavelength, e.g., 670 nm, it will be understood by those of skill in the art that this specification refers to a wavelength range or emission filter bandpass that is centered on the specified wavelength. In some instances, light of the specified emission wavelength comprises light of the specified wavelength ±2 nm, ±5 nm, ±10 nm, ±20 nm, ±40 nm, ±80 nm, or more. In some instances, the emission wavelength used may or may not coincide with the emission peak maximum of the fluorescent indicator.

As used herein, fluorescence is 'specific' if it arises from fluorophores that are annealed or otherwise tethered to the surface, such as fluorescently labeled nucleic acid sequences having a region of reverse complementarity to a corresponding segment of an oligonucleotide adapter on the surface and annealed to said corresponding segment. This fluorescence is contrasted with fluorescence arising from fluorophores not tethered to the surface through such an annealing process, or in some cases to background florescence of the surface.

The term "simple cell media" or related terms refers to a cell media that typically lacks ingredients to support cell growth and/or proliferation in culture. Simple cell media can be used for example to wash, suspend, or dilute the cellular biological sample. Simple cell media can be mixed with certain ingredients to prepare a cell media that can support cell growth and/or proliferation in culture. A simple cell media comprises any one or any combination of two or more of a buffer, a phosphate compound, a sodium compound, a potassium compound, a calcium compound, a magnesium compound and/or glucose. In some embodiments, the simple cell media comprises PBS (phosphate buffered saline), DPBS (Dulbecco's phosphate-buffered saline), HBSS (Hank's balanced salt solution), DMEM (Dulbecco's Modified Eagle's Medium), EMEM (Eagle's Minimum Essential Medium), and/or EBSS. In some embodiments, the cellular biological sample or single cell can be placed in a simple cell media prior to or during the step of conducting any of the nucleic acid methods described herein.

The term "complex cell media" or related terms refers to a cell media that can be used to support cell growth and/or proliferation in culture without supplementation or additives. Complex cell media can include any combination of two or more of a buffering system (e.g., HEPES), inorganic salt(s), amino acid(s), protein(s), polypeptide(s), carbohydrate(s), fatty acid(s), lipid(s), purine(s) and their derivatives (e.g., hypoxanthine), pyrimidine(s) and their derivatives, and/or trace element(s). Complex cell media includes fluids obtained from a biological fluid or tissue extract. Complex cell media includes artificial cell media. In some embodiments, complex cell media can be a serum-containing media, for example complex cell media includes biological fluids such as fetal bovine serum, blood plasma, blood serum, lymph fluid, human placental cord serum and amniotic fluid. In some embodiments, complex cell media can be a serum-free media, which are typically (but not necessarily) defined cell culture media. In some embodiments, complex cell media can be a chemically-defined media which typically (but not necessarily) include recombinant polypeptides, and ultra-pure inorganic and/or organic compounds. In some embodiments, complex cell media can be a protein-free media which include for example MEM (minimal essential media) and RPMI-1640 (Roswell Park Memorial Institute). In some embodiments, the complex cell media comprises IMDM (Iscove's Modified Dulbecco's Medium. In some embodiments, the complex cell media comprises DMEM (Dulbecco's Modified Eagle's Medium). In some embodiments, the cellular biological sample or single cell can be placed in a complex cell media prior to or during the step of conducting any of the nucleic acid methods described herein.

The term "padlock probe" refers to a nucleic acid probe that typically comprises a linear single oligonucleotide strand that is designed to capture target nucleic acid molecules by hybridization. The hybridization complex can be circularized, and the circular molecule can be subjected to a rolling circle amplification reaction for single-plex or multi-plex molecular detection methods. The padlock probe includes target capture sequences at its 5'terminal-end and 3'terminal-end that are complementary to contiguous regions of the target nucleic acid molecule. The padlock probe can also include any one or any combination of two or more adaptor sequences including an amplification primer binding sequence, a sequencing primer binding sequence, an immobilization sequence and/or a sample index sequence. The various adaptor sequences can be located in any region, for example the internal portion of the padlock probe. The 5' and 3' ends of the padlock probe can hybridize to adjacent positions on the target nucleic acid molecule to form an open circularized molecule with a nick between the hybridized 5' and 3' ends. The nick can be ligated to generate a covalently close circular molecule. Alternatively, the 5' and 3' ends of the padlock probe can hybridize to adjacent positions on the target nucleic acid molecule to form an open circularized molecule with a gap between the hybridized 5' and 3' ends. The gap can be subject to a polymerase-mediated filled-in reaction to form a nick, and the nick can be ligated to generate a covalently close circular molecule. The covalently closed circular molecule can be subjected to a rolling circle amplification reaction to generate a concatemer having tandem repeat regions containing the target sequence. The specificity for capturing the target molecule in a mixture of target and non-target molecules is afforded by the requirement for specific hybridization of the 5' and 3' ends to adjacent positions of the target molecule of interest to form a nick, and enzymatically closing the nick which is only possible when the 5' and 3' ends of the padlock probe have the correct base complementarity with the target molecule. A ligase enzyme that discriminates between matched and mis-matched ends can be used to ensure sequence-specific hybridization. Thus, the covalently closed circular molecule is formed if the target nucleic acid is present in the sample being tested.

Compositions and methods using the compositions for padlock-probe based rolling circle amplification reactions are described in U.S. 63/059,723, filed on Jul. 31, 2020, the contents of which is hereby expressly incorporated by reference in its entirety.

The term rolling circle amplification generally refers to an amplification method that employs a circularized nucleic acid template molecule containing a target sequence of interest, an amplification primer binding sequence, and optionally one or more adaptor sequences such as a sequencing primer binding sequence and/or a barcode. The rolling circle amplification reaction can be conducted under isothermal amplification conditions, and includes the circularized nucleic acid template molecule, an amplification primer, a strand-displacing polymerase and a plurality of nucleotides, to generate a concatemer containing tandem repeat sequences of the circular template molecule and any adaptor sequences present in the original circularized nucleic acid template molecule. The concatemer can self-collapse to form a nucleic acid nanoball. The shape and size of the nanoball can be further compacted by including a pair of inverted repeat sequences in the circular template molecule, or by conducting the rolling circle amplification reaction with one or more compaction oligonucleotides. One of the advantages of using rolling circle amplification to generate clonal amplicons for a sequencing workflow, is that the repeat copies of the target sequence in the nanoball can be simultaneously sequenced to increase signal intensity.

Kits. Provided here are kits useful for carrying out the methods disclosed herein using the systems and compositions disclosed herein. A kit may comprise a detectable polymer-nucleotide conjugate comprising: (i) a polymer core: and (ii) two or more nucleotide moieties attached to said polymer core. The kits described herein may have at least one, two, three, or four different types of detectable polymer-nucleotide conjugate, for example, in which each type of detectable polymer-nucleotide conjugate has a different nucleotide moiety. The kit may have a substrate comprising a surface having coupled thereto a polymer layer suitable to immobilize a biological sample or derivative thereof to said surface. In some kits, the biological sample (e.g., cell or tissue) is included in the kit. In some kits, the biological sample is not included in the kit. The kit may comprise a hybridization buffer disclosed herein, for example, comprising (i) a first polar aprotic solvent having a dielectric constant that is no greater than 40 and having a polarity index of 4-9; and/or (ii) a second polar aprotic solvent having a dielectric constant that is less than or equal to 115. Optionally, capture oligonucleotides or components thereof, in situ amplification reagents (e.g., buffers, primers, detectable labels), or combinations thereof are included in the kit.

Instructions may be provided in the kits described herein, including instructions for hybridizing at least a portion of said target nucleic acid sequence to at least a portion of a capture oligonucleotide coupled to said surface. The kit may also comprise instructions for identifying at least a portion of the target nucleic acid sequence within the biological sample or derivative thereof by contacting said detectable polymer-nucleotide conjugate with said biological sample or derivative thereof (e.g., containing the target nucleic acid molecule) under conditions sufficient to form a multivalent binding complex between said two or more nucleotide moieties and said target nucleic acid sequence.

The kit may also comprise instructions for identifying at least a portion of a sub-cellular component within a cell or tissue in situ by contacting said detectable polymer-nucleotide conjugate with said sub-cellular component under conditions sufficient to form a multivalent binding complex between said two or more nucleotide moieties and said sub-cellular component.

Optionally, the kit also contains other useful components, such as, diluents, buffers, pharmaceutically acceptable carriers, syringes, catheters, applicators, pipetting or measuring tools, bandaging materials or other useful paraphernalia. The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as compositions and the like. The packaging material is constructed by well-known methods, preferably to provide a sterile, contaminant-free environment. The packaging materials employed in the kit are those customarily utilized in gene expression assays and in the administration of treatments. As used herein, the term "package" refers to a suitable solid matrix or material such as glass, plastic, paper, foil, and the like, capable of holding the individual kit components. Thus, for example, a package can be a glass vial or prefilled syringes used to contain suitable quantities of the pharmaceutical composition. The packaging material has an external label which indicates the contents and/or purpose of the kit and its components.

The section headings used herein are for organizational purposes only and are not to be construed as limiting the subject matter described.

II. Exemplary Embodiments

Among the exemplary embodiments are:

1. A support comprising:
    (a) a substrate coated with at least one hydrophilic polymer coating having a water contact angle of no more than 45 degrees;
    (b) a first feature comprising a first region of the hydrophilic coating having immobilized thereon (1) a first plurality of capture oligonucleotides which can hybridize to a plurality of a first target nucleic acid molecules, and optionally, (2) a first plurality of circularization oligonucleotides which can circularize a captured first target nucleic acid molecule; and optionally, (c) a second feature comprising a second region of the hydrophilic coating having immobilized thereon (1) a second plurality of capture oligonucleotides which can hybridize to a plurality of a second target nucleic acid molecules, and (2) a second plurality of circularization oligonucleotides which can circularize a captured second target nucleic acid molecule.

2. The support of embodiment 1, wherein the support further comprises a biological sample placed in contact with the first and second features, wherein the biological sample comprises a tissue, a plurality of cells or a single cell.

3. The support of embodiment 2, wherein the single cell, cells in the tissue or the plurality of cells can be intact or permeabilized or lysed.

4. The support of embodiments 1-2, wherein the support further comprises a first target nucleic acid molecule hybridized to the first target capture region in the first feature, and a second target nucleic acid molecule hybridized to the second target capture region in the second feature.

5. The support of embodiment 4, wherein the first and second target nucleic acid molecules comprise DNA or RNA.

6. The support of embodiments 1-5, wherein a fluorescent image of the support exhibits a contrast to noise ratio (CNR) of at least 20.

7. The support of embodiments 1-6, wherein the hydrophilic polymer coating can comprise at least one hydrophilic polymer coating comprising a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, and dextran.

8. The support of embodiment 7, wherein at least one layer of the hydrophilic polymer coating comprises polyethylene glycol (PEG).

9. The support of embodiments 1-8, wherein the substrate is coated with a second hydrophilic polymer coating.

10. The support of embodiments 1-9, wherein the at least one hydrophilic polymer coating comprises a polymer having a molecular weight of at least 1,000 Daltons.

11. The support of embodiments 1-10, wherein the at least one hydrophilic polymer coating comprises a branched hydrophilic polymer having at least 4 branches.

12. The support of embodiments 1-11, wherein the at least one hydrophilic polymer coating comprises: (a) a first layer comprising a first monolayer of polymer molecules tethered to the surface; (b) a second layer comprising a second monolayer of polymer molecules tethered to the first monolayer of polymer molecules; and (c) a third layer comprising a third monolayer of polymer molecules tethered to the second monolayer of polymer molecules, wherein the polymer molecules of the first layer, the second layer or the third layer comprises branched polymer molecules.

13. The support of embodiments 1-12, wherein the support can be glass or plastic.

14. The support of embodiments 1-13, wherein the support can be a planar support or a bead.

15. The support of embodiments 1-14, wherein the first plurality of capture oligonucleotides and the first plurality of circularization oligonucleotides in the first feature, and the second plurality of capture oligonucleotides and the second plurality of circularization oligonucleotides in the second feature, are in fluid communication with each other so that the first and second capture oligonucleotides and the first and second circularization oligonucleotide react with reagents (e.g., enzymes including polymerases, polymer-nucleotide conjugates, nucleotides and/or divalent cations) in a massively parallel manner.

16. The support of embodiments 1-15, wherein the support further comprises a hybridization buffer comprising:

(i) a first polar aprotic solvent having a dielectric constant that is no greater than 40 and having a polarity index of 4-9;
(ii) a second polar aprotic solvent having a dielectric constant that is no greater than 115 and is present in the hybridization buffer formulation in an amount effective to denature double-stranded nucleic acids;
(iii) a pH buffer system that maintains the pH of the hybridization buffer formulation in a range of about 4-8; and
(iv) a crowding agent in an amount sufficient to enhance or facilitate molecular crowding.

17. The support of embodiment 16, wherein the first polar aprotic solvent comprises acetonitrile at 25-50% by volume of the hybridization buffer.

18. The support of embodiments 16-17, wherein the second polar aprotic solvent comprises formamide at 5-10% by volume of the hybridization buffer.

19. The support of embodiments 16-18, wherein the pH buffer system comprises 2-(N-morpholino)ethanesulfonic acid (MES) at a pH of 5-6.5.

20. The support of embodiments 16-19, wherein the crowding agent comprises polyethylene glycol (PEG) at 5-35% by volume of the hybridization buffer.

21. The support of embodiments 16-20, wherein the hybridization buffer further comprises betaine.

22. The support of embodiments 1-21, wherein the support further comprises at least one polymer-nucleotide conjugate comprising two or more duplicates of a nucleotide moiety that are connected to a core via a linker.

23. The support of embodiment 22, wherein the polymer-nucleotide conjugate comprises:
(a) a core; and
(b) a plurality of nucleotide arms which comprise:
(i) a core attachment moiety;
(ii) a spacer comprising a PEG moiety;
(iii) a linker; and
(iv) a nucleotide unit.

24. The support of embodiments 1-23, wherein the first plurality of capture oligonucleotides comprises:
(a) a first target capture region that hybridizes to at least a portion of a first target nucleic acid molecule;
(b) a first universal sequence region comprising a first spatial barcode sequence and, optionally, a first sample barcode sequence;
(c) a first circularization anchor sequence; or
(d) a first cleavable region, and the first feature having immobilized thereon, or any combination thereof.

25. The support of embodiments 1-24, wherein the second plurality of capture oligonucleotides comprises:
(a) a second target capture region that hybridizes to at least a portion of a second target nucleic acid molecule;
(b) a second universal sequence region comprising a second spatial barcode sequence, and optionally, a second sample barcode sequence, and a second circularization anchor sequence; and
(c) a second cleavable region, and the second feature having immobilized thereon.

26. The support of embodiments 1-25, wherein the second plurality of circularization oligonucleotides comprise:
(a) a second homopolymer region, and
(b) a second universal sequence region comprising a second sequencing primer binding sequence and a second circularization anchor binding sequence.

27. The support of embodiments 1-26, wherein the first plurality of circularization oligonucleotides comprise:
(a) a first homopolymer region, and
(b) a first universal sequence region comprising a first sequencing primer binding sequence and a first circularization anchor binding sequence.

28. The support of embodiments 24-27, wherein the first and second target capture regions of the first and second capture oligonucleotides each comprise a random nucleotide sequence or a target-specific nucleotide sequence.

29. The support of embodiments 24-28, wherein the first target capture region in the first feature has the same sequence as the second target capture region in the second feature.

30. The support of embodiments 24-29, wherein the first spatial barcode sequence in the first feature has a different sequence compared to the second spatial barcode sequence in the second feature.

31. The support of embodiments 24-30, wherein the first sample barcode sequence in the first feature has the same sequence as the second sample barcode sequence in the second feature.

32. The support of embodiments 24-30, wherein the first circularization anchor sequence in the first feature has the same nucleotide sequence as the second circularization anchor sequence in the second feature.

33. The support of embodiments 24-32, wherein the first cleavable region in the first feature is cleavable with an enzyme, a chemical compound, light or heat.

34. The support of embodiments 24-33, wherein the first cleavable region is cleavable with the same condition as the second cleavable region in the second feature.

35. The support of embodiments 24-34, wherein the first homopolymer region of the first circularization oligonucleotide in the first feature has the same sequence as the second homopolymer region of the second circularization oligonucleotide in the second feature.

36. The support of embodiments 24-35, wherein the first sequencing primer binding sequence in the first feature has the same sequence as the second sequencing primer binding sequence in the second feature.

37. The support of embodiments 24-36, the first circularization anchor binding sequence in the first feature has the same sequence as the second circularization anchor binding sequence in the second feature.

38. The support of embodiments 24-37, further comprising a first primer extension product extended from the first target capture region, wherein the first extension product comprises a complementary sequence of at least a portion of the first target nucleic acid molecule.

39. The support of embodiments 24-37, further comprising a second primer extension product extended from the second target capture region where the second extension product comprises a complementary sequence of at least a portion of the second target nucleic acid molecule.

40. The support of embodiments 23-39, wherein the core is attached to the plurality of nucleotide arms.

41. The support of embodiments 23-40, wherein the spacer is attached to the linker.

42. The support of embodiments 23-41, wherein the linker is attached to the nucleotide unit.

43. The support of embodiments 23-42, wherein the nucleotide unit comprises a base, sugar and at least one phosphate group.

44. The support of embodiments 23-43, wherein the linker is attached to the nucleotide unit through the base.

45. The support of embodiments 23-44, wherein the linker comprises an aliphatic chain or an oligo ethylene glycol chain where both linker chains having 2-6 subunits and, optionally, the linker includes an aromatic moiety.

46. The support of embodiments 23-45, wherein the plurality of nucleotide arms have the same type of nucleotide unit which is selected from a group consisting of dATP, dGTP, dCTP, dTTP and dUTP.

47. The support of embodiments 23-45, wherein the plurality of nucleotide arms have two or more different types of nucleotides selected from a group consisting of dATP, dGTP, dCTP, dTTP and dUTP.

48. The support of embodiments 23-47, wherein the nucleotide unit has a chain terminating moiety (e.g., blocking moiety) at the sugar 2' position, at the sugar 3' position, or at the sugar 2' and 3' position.

49. The support of embodiment 48, wherein the chain terminating moiety is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

50. The support of embodiment 49, wherein the chain terminating moiety is cleavable/removable from the nucleotide arm.

51. The support of embodiments 23-50, wherein the core is labeled with detectable reporter moiety.

52. The support of embodiment 51, wherein the detectable reporter moiety comprises a fluorophore.

53. The support of embodiments 23-52, wherein the core comprises an avidin-like moiety and the core attachment moiety comprises biotin.

54. A method for conducting cellularly addressable sequencing and for analyzing nucleic acids from a biological sample, comprising:
    (a) providing a support comprising a low non-specific binding coating to which an oligonucleotide suitable for capturing/hybridizing a target nucleic acid molecule is attached;
    (b) contacting a target nucleic acid molecule with the oligonucleotide under a buffer condition suitable to allow the oligonucleotide to capture the target nucleic acid molecule;
    (c) optionally, amplifying the target nucleic acid molecule to form an amplified nucleic acid product comprising a linear single-stranded nucleic acid molecule comprising two or more copies of the target nucleic acid sequence;
    (d) contacting the amplified nucleic acid product with two or more polymerases, and two or more sequencing primers that hybridize to one or more regions of the amplified nucleic acid product;
    (e) contacting the amplified nucleic acid product with a polymer-nucleotide conjugate comprising a polymer-nucleotide conjugate under a condition suitable for forming a binding complex between the amplified nucleic acid product and the polymer-nucleotide conjugate, wherein the polymer-nucleotide conjugate comprises two or more copies of a nucleotide and (optionally) one or more detectable reporter moieties; and
    (f) detecting the binding complex thereby identifying the nucleotide base in the target nucleic acid molecule, wherein the target nucleic acid molecule originates from a biological tissue, and wherein the target nucleic acid molecule is captured on the support in a manner so as to preserve information related to the location of the cellular origin of the target nucleic acid molecule.

55. The method of embodiment 54, wherein the oligonucleotide comprises a capture oligonucleotide comprising:
    (a) a target capture region that hybridizes to at least a portion of a target nucleic acid molecule;
    (b) a universal sequence region comprising a spatial barcode sequence;
    (c) a circularization anchor sequence configured to bind to a circularization oligonucleotide; and
    (d) a cleavable region.

56. The method of embodiment 55, wherein the circularization oligonucleotide comprises:
    (a) a homopolymer region;
    (b) a universal sequence region comprising a sequencing primer binding sequence; and
    (c) a circularization anchor binding sequence; and 57. The method of embodiments 54-56, wherein the low non-specific binding coating comprises at least one hydrophilic polymer coating having a water contact angle of no more than 45 degrees.

58. The method of embodiments 54-57, wherein contacting in (b) comprises hybridizing at least a portion of the target nucleic acid molecule to the target capture region of the immobilized capture oligonucleotide thereby forming an immobilized nucleic acid duplex.

59. The method of embodiments 54-58, wherein optionally amplifying in (c) comprises:
    (a) conducting a primer extension reaction on the immobilized nucleic acid duplex using the hybridized target nucleic acid molecule as a template thereby forming an immobilized target extension product;
    (b) conducting a non-template tailing reaction on the immobilized target extension product under conditions suitable for appending a homopolymer tail to the target extension product thereby forming an immobilized tailed target extension product;
    (c) cleaving the immobilized tailed target extension product to release the immobilized tailed target extension product from the low binding coating thereby forming a soluble tailed target extension product;
    (d) binding the soluble tailed target extension product to one of a circularization oligonucleotide immobilized to the low binding coating under a condition suitable to hybridize the appended homopolymer tail of the soluble tailed target extension product to the homopolymer region of the immobilized circularization oligonucleotide, and suitable to hybridize the circularization anchor sequence of the soluble tailed target extension product to the circularization anchor binding sequence of the immobilized circularization oligonucleotide thereby forming an open circularized target extension product with a gap;
    (e) conducting a gap-filling primer extension reaction and a ligation reaction on the open circularized target extension product thereby forming a closed circular target extension product which is hybridized to the immobilized circularization oligonucleotide having a homopolymer region with a 3' extendible end; and
    (f) conducting a rolling circle amplification reaction using the 3' extendible end of the homopolymer region under a condition suitable to form an immobilized concatemer molecule having tandem repeat regions comprising the sequencing primer binding sequence, the target sequence, and the spatial barcode sequence.

60. The method of embodiment 62, wherein determining the sequence of the immobilized concatemer molecule comprises sequencing the target sequence and the spatial barcode sequence.

61. The method of embodiments 54-60, wherein the target nucleic acid molecule is RNA.

62. The method of embodiments 54-60, wherein the target nucleic acid molecule is DNA.

63. A method for analyzing nucleic acids from a biological sample, comprising:
(a) providing a support comprising a low non-specific binding coating to which a plurality of capture oligonucleotides are immobilized, wherein the plurality of capture oligonucleotides comprise (i) a target capture region (e.g., having a homopolymer sequence e.g., poly-T) that hybridizes to at least a portion of a target RNA molecule, (ii) a universal sequence region comprising a spatial barcode sequence, and (iii) a cleavable region, and wherein the low non-specific binding coating comprises at least one hydrophilic polymer coating having a water contact angle of no more than 45 degrees,
(b) contacting the low non-specific binding coating with a target nucleic acid molecule under a condition (e.g., a hybridization buffer) suitable for hybridizing at least a portion of the target nucleic acid molecule to the target capture region of one of the immobilized capture oligonucleotides thereby forming an immobilized nucleic acid duplex;
(c) conducting a primer extension reaction (e.g., reverse transcription) on the immobilized nucleic acid duplex using the hybridized target nucleic acid molecule as a template thereby forming an immobilized target extension product;
(d) appending a nucleic acid adaptor to the immobilized target extension product thereby forming an immobilized adaptor-target extension product, wherein the nucleic acid adaptor comprises a sequencing primer binding sequence;
(e) contacting the low non-specific binding coating with a plurality of soluble circularization oligonucleotides under a condition suitable for immobilizing at least one of soluble circularization oligonucleotides to the low non-specific binding coating in proximity to the immobilized adaptor-target extension product, wherein the each of the soluble circularization oligonucleotides in the plurality comprises (i) an adaptor binding region (e.g., having a sequencing primer binding sequence and optionally an amplification primer binding sequence), (ii) a homopolymer region, (iii) an anchor region, and (iv) an anchor moiety;
(f) hybridizing the target capture region (e.g., homopolymer poly-T) of the immobilized adaptor-target extension product to the homopolymer region of the immobilized circularization oligonucleotide thereby forming a homopolymer duplex region, and hybridizing the appended adaptor sequence of the immobilized adaptor-target extension product to the adaptor binding region of the immobilized circularization oligonucleotide, thereby forming an immobilized looped target extension product;
(g) cleaving the immobilized looped target extension product (e.g., at the cleavable region) under a condition suitable to release the homopolymer duplex region while retaining the adaptor-hybridized region of the immobilized circularization oligonucleotide;
(h) hybridizing the homopolymer region of the adaptor-target extension product to the homopolymer region of the immobilized circularization oligonucleotide thereby forming an open circularized adaptor-target extension product with a nick or gap;
(i) closing the gap and/or nick by conducting a gap-filling primer extension reaction and/or a ligation reaction on the open circularized adaptor-target extension product thereby forming a closed circular target extension product which is hybridized to the immobilized circularization oligonucleotide having an adaptor binding region with a 3' extendible end; and
(j) conducting a rolling circle amplification reaction using the 3' extendible end of the adaptor binding region under a condition suitable to form an immobilized concatemer molecule having tandem repeat regions comprising the sequencing primer binding sequence, the target sequence, and the spatial barcode sequence.

64. The method of embodiments 54-63, wherein a fluorescent image of the support exhibits a contrast to noise ratio (CNR) of at least 20.

65. The method of embodiments 54-64 wherein the at least one hydrophilic polymer coating comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, and dextran.

66. The method of embodiment 65, wherein the least one hydrophilic polymer coating comprises polyethylene glycol (PEG).

67. The method of embodiments 54-66, wherein the substrate is coated with a second hydrophilic polymer coating.

68. The method of embodiments 54-67, the at least one hydrophilic polymer coating comprises a polymer having a molecular weight of at least 1,000 Daltons.

69. The method of embodiments 54-68, wherein the at least one hydrophilic polymer coating comprises a branched hydrophilic polymer having at least 4 branches.

70. The method of embodiments 54-69, wherein the at least one hydrophilic polymer coating comprises: (a) a first layer comprising a first monolayer of polymer molecules tethered to the surface; (b) a second layer comprising a second monolayer of polymer molecules tethered to the first monolayer of polymer molecules; and (c) a third layer comprising a third monolayer of polymer molecules tethered to the second monolayer of polymer molecules, wherein the polymer molecules of the first layer, the second layer or the third layer comprises branched polymer molecules.

71. The method of embodiments 54-70, wherein the support comprises glass or plastic.

72. The method of embodiments 54-71, wherein the support comprises a planar support or a bead.

73. The method of embodiments 54-72, wherein the target nucleic acid molecule is derived from a biological sample that is placed onto the plurality of capture oligonucleotides that are immobilized on the low binding coating on the support.

74. The method of embodiments 54-73, wherein the target nucleic acid molecule is hybridized (captured) on the support in a manner that preserves spatial location information of the target nucleic acid molecule in the biological sample.

75. The method of embodiments 54-74, wherein the condition which is suitable for hybridizing at least a portion of the target nucleic acid molecule to the target capture region of one of the immobilized capture oligonucleotides comprises contacting the low non-specific binding coating with a target nucleic acid molecule and a hybridization buffer comprising:
   (i) a first polar aprotic solvent having a dielectric constant that is no greater than 40 and having a polarity index of 4-9;
   (ii) a second polar aprotic solvent having a dielectric constant that is no greater than 115 and is present in the hybridization buffer formulation in an amount effective to denature double-stranded nucleic acids;
   (iii) a pH buffer system that maintains the pH of the hybridization buffer formulation in a range of about 4-8; and
   (iv) a crowding agent in an amount sufficient to enhance or facilitate molecular crowding.

76. The method of embodiments 54-75, wherein the hybridization buffer comprises the first polar aprotic solvent comprises acetonitrile at 25-50% by volume of the hybridization buffer.

77. The method of embodiments 54-76, wherein the second polar aprotic solvent comprises formamide at 5-10% by volume of the hybridization buffer.

78. The method of embodiments 54-77, wherein the pH buffer system comprises 2-(N-morpholino)ethanesulfonic acid (MES) at a pH of 5-6.5

79. The method of embodiments 54-78, wherein the crowding agent comprises polyethylene glycol (PEG) at 5-35% by volume of the hybridization buffer.

80. The method of embodiments 54-79, wherein the hybridization buffer further comprises betaine.

81. The method of embodiments 63-80, further comprising: determining the sequence of the immobilized concatemer molecule by:
   (a) contacting the immobilized concatemer molecule with (i) a plurality of polymerases, (ii) at least one polymer-nucleotide conjugate comprising two or more duplicates of a nucleotide moiety that are connected to a core via a linker, and (iii) a plurality of sequencing primers that hybridize with the sequencing primer binding sequence, under a condition suitable for binding at least one polymerase and at least one sequencing primer to a portion of the immobilized concatemer molecule, and suitable for binding at least one of the nucleotide moieties of the polymer-nucleotide conjugate to the 3' end of the sequencing primer at a position that is opposite a complementary nucleotide in the immobilized concatemer molecule wherein the bound nucleotide moiety does not incorporate into the sequencing primer;
   (b) detecting and identifying the bound nucleotide moiety of the polymer-nucleotide conjugate thereby determining the sequence of the immobilized concatemer molecule;
   (c) optionally repeating steps (a) and (b) at least once;
   (d) contacting the immobilized concatemer molecule with (i) a plurality of polymerases, and (ii) a plurality of nucleotides, under a condition suitable binding at least one polymerase to at least a portion of the immobilized concatemer molecule and suitable for binding at least one of the nucleotides from the plurality to the 3' ends of the hybridized sequencing primers at a position that is opposite a complementary nucleotide in the immobilized concatemer molecule wherein the bound nucleotides incorporate into the hybridized sequencing primers; (e) optionally detecting the incorporated nucleotides;
   (f) optionally identifying the incorporation nucleotides thereby determining or confirming the sequence of the immobilized concatemer; and
   (g) repeating steps (a)-(f) at least once. In some embodiments, the determining the sequence of the immobilized concatemer molecule comprises sequencing the target sequence and the spatial barcode sequence.

82. The method of embodiments 63-80, further comprising: determining the sequence of the immobilized concatemer molecule by:
   (a) contacting the immobilized concatemer molecule with (i) a plurality of polymerases, (ii) a plurality of nucleotides, and (iii) a plurality of sequencing primers that hybridize with the sequencing primer binding sequence, under a condition suitable for binding at least one polymerase and at least one sequencing primer to a portion of the immobilized concatemer molecule, and suitable for binding at least one of the nucleotides to the 3' end of the sequencing primer at a position that is opposite a complementary nucleotide in the immobilized concatemer molecule wherein the bound nucleotide incorporates into the 3' end of the sequencing primer;
   (b) detecting and identifying the incorporated nucleotide thereby determining the sequence of the immobilized concatemer molecule; and
   (c) optionally repeating steps (a) and (b) at least once. In some embodiments, the determining the sequence of the immobilized concatemer molecule comprises sequencing the target sequence and the spatial barcode sequence.

83. A method for nucleic acid sequence determination comprising:
   (a) fixing a biological sample comprising a target nucleic acid molecule to a surface of a substrate; and
   (b) contacting said surface with a nucleotide moiety comprising a detectable label under conditions sufficient to allow a complex to be formed between said nucleotide moiety and said target nucleic acid molecule, wherein an image of said surface exhibits a contrast-to-noise ratio of greater than or equal to about 5 when said image of said surface is obtained using an inverted microscope and a camera under non-signal saturating conditions while said surface is immersed in a buffer and wherein said detectable label is a fluorescent dye.

84. A method for nucleic acid sequence determination comprising:
   (a) fixing a biological sample comprising a target nucleic acid molecule to a surface of a substrate;
   (b) contacting said surface with a polymer nucleotide conjugate under conditions sufficient to allow a multivalent binding complex to be formed between said polymer-nucleotide conjugate and said target nucleic acid molecule, wherein said polymer-nucleotide conjugate comprises a nucleotide and a detectable label; and
   (c) detecting said multivalent binding complex in the presence of the biological sample fixed to said surface, thereby determining an identity of said nucleotide in the target nucleic acid molecule.

Further embodiments of the present disclosure are provided:

1. A method for analyzing biological molecules from a cellular biological sample, wherein the cells of the cellular biological sample comprise cellular nucleic acids and polypeptides, and wherein at least one cell in the sample includes a target nucleic acid that encodes a target polypeptide, the method comprising the general step of:
  a) providing a support comprising a low non-specific binding coating to which a plurality of capture oligonucleotides and optionally a plurality of circularization oligonucleotides are immobilized, wherein the plurality of immobilized capture oligonucleotides comprise (i) a target capture region that hybridizes to at least a portion of a target nucleic acid molecule, and (ii) a spatial barcode sequence, wherein the low non-specific binding coating comprises at least one hydrophilic polymer layer having a water contact angle of no more than 45 degrees;
  b) contacting the low non-specific binding coating with the cellular biological sample in the presence of a high efficiency hybridization buffer under conditions suitable to promote migration of the target nucleic acid molecule from the cellular biological sample to one of the immobilized capture oligonucleotides thereby forming an immobilized target nucleic acid duplex, wherein the target nucleic acid molecule is immobilized to the low non-specific binding coating in a manner that preserves spatial location information of the target nucleic acid molecule in the cellular biological sample;
  c) conducting a primer extension reaction on the immobilized target nucleic acid duplex thereby forming an immobilized target extension product;
  d) forming an open circular target molecule using the immobilized circularization oligonucleotide, or if the low non-specific binding coating does not already include an immobilized circularization oligonucleotide then immobilizing a soluble circularization oligonucleotide to the low non-specific binding coating in proximity to the immobilized target extension product and forming an open circular target molecule using the now-immobilized circularization oligonucleotide;
  e) forming a covalently closed circular target molecule which is immobilized to the low non-specific binding coating;
  f) conducting a rolling circle amplification reaction on the immobilized covalently closed circular target molecule to form an immobilized nucleic acid concatemer molecule having tandem repeat regions comprising the target sequence and the spatial barcode sequence; and
  g) sequencing at least a portion of the nucleic acid concatemer, including sequencing the target sequence and the spatial barcode sequence, to determine the spatial location of the target nucleic acid in the cellular biological sample.

2. The method of embodiment 1, wherein step (g) comprises: sequencing at least a portion of the nucleic acid concatemers using an optical imaging system comprising a field-of-view (FOV) greater than 1.0 mm$^2$.

3. The method of embodiment 1, wherein the target nucleic acid comprises RNA.

4. The method of embodiment 3, wherein the spatial location of the target RNA in the cellular biological sample corresponds to the spatial location of at least one cell in the cellular biological sample that expresses the target RNA which encodes the target polypeptide.

5. The method of embodiment 1, wherein the primer extension reaction of step (c) comprises a reverse transcription reaction.

6. The method of embodiment 1, wherein the high efficiency hybridization buffer comprises:
  (i) a first polar aprotic solvent having a dielectric constant that is no greater than 40 and having a polarity index of 4-9;
  (ii) a second polar aprotic solvent having a dielectric constant that is no greater than 115 and is present in the high efficiency hybridization buffer formulation in an amount effective to denature double-stranded nucleic acids;
  (iii) a pH buffer system that maintains the pH of the high efficiency hybridization buffer formulation in a range of about 4-8; and
  (iv) a crowding agent in an amount sufficient to enhance or facilitate molecular crowding.

7. The method of embodiment 6, wherein the high efficiency hybridization buffer further comprises betaine.

8. The method of embodiment 1, wherein the rolling circle amplification reaction of step (g) comprises contacting the covalently closed circularized target molecule (e.g., circularized nucleic acid template molecule(s)) with a DNA polymerase, a plurality of nucleotides, and at least one catalytic divalent cation, under a condition suitable for generating at least one nucleic acid concatemer, wherein the at least one catalytic divalent cation comprises magnesium or manganese.

9. The method of embodiment 1, wherein the rolling circle amplification reaction of step (g) comprises:
  a) contacting the covalently closed circularized target molecule (e.g., circularized nucleic acid template molecule(s)) with a DNA polymerase, a plurality of nucleotides, and at least one non-catalytic divalent cation that does not promote polymerase-catalyzed nucleotide incorporation into the 3' extendible end, wherein the non-catalytic divalent cation comprises strontium or barium; and
  b) contacting the covalently closed circularized target molecule with at least one catalytic divalent cation, under a condition suitable for generating at least one nucleic acid concatemer, wherein the at least one catalytic divalent cation comprises magnesium or manganese.

10. The method of embodiment 1, wherein the rolling circle amplification reaction of step (f) can be conducted at a constant temperature (e.g., isothermal) ranging from room temperature to about 70° C.

11. The method of embodiment 1, further comprising: conducting a multiple displacement amplification (MDA) reaction prior to step (g), wherein the MDA reaction comprises (1) contacting at least one nucleic acid concatemer with at least one amplification primer comprising a random sequence, a DNA polymerase having strand displacement activity, a plurality of nucleotides, and a catalytic divalent cation comprising magnesium or manganese, or wherein the MDA reaction comprises (2) contacting at least one nucleic acid concatemer with a DNA primase-polymerase enzyme, a DNA polymerase having strand displacement activity, a plurality of nucleotides, and a catalytic divalent cation comprising magnesium or manganese.

12. The method of embodiment 9, further comprising, conducting the following steps after the rolling circle amplification of step (f) and prior to step (g):
  a) forming a nucleic acid relaxant reaction mixture by contacting the nucleic acid concatemer with one or a combination of two or more compounds selected from a group consisting of formamide, acetonitrile, ethanol, guanidine hydrochloride, urea, potassium iodide and/or polyamines, to generate a relaxed nucleic acid concatemer, wherein the forming a nucleic acid relaxant reaction mixture is conducted with a temperature ramp-up, a relaxant incubation temperature, and a temperature ramp-down;

b) washing the relaxed concatemer;

c) forming a flexing amplification reaction mixture by contacting the relaxed concatemer with a strand-displacing DNA polymerase, a plurality of nucleotides, a catalytic divalent cation, (in the absence of added amplification primers), to generate double-stranded concatemers, wherein the forming a flexing amplification reaction mixture is conducted with a temperature ramp-up, a flexing incubation temperature, and a temperature ramp-down;

d) washing the double-stranded concatemer; and e) repeating steps (a)-(d) at least once.

13. The method of embodiment 1, wherein the sequencing of step (g) comprises monitoring the sequential binding of labeled nucleotides in a template strand of the concatemer (e.g., sequencing by binding).

14. The method of embodiment 13, wherein the sequencing of step (g) further comprises monitoring the incorporation of the labeled nucleotides in a template strand of the concatemer (e.g., sequencing by synthesis).

15. The method of embodiment 1, wherein the sequencing of step (g) comprises detecting a complex formed between a polymerase and a primed template strand of the concatemer, wherein the polymerase is optionally labeled.

16. The method of embodiment 1, wherein the sequencing of step (g) comprises: contacting the plurality of nucleic acid concatemers with a plurality of sequencing primers, a plurality of polymerases, and a plurality of multivalent molecules, wherein each of the multivalent molecules comprise two or more duplicates of a nucleotide moiety that are connected to a core via a linker.

17. The method of embodiment 16, wherein the multivalent molecule comprises:
a) a core, and
b) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit, wherein the nucleotide unit comprises a base, sugar and at least one phosphate group, and wherein the linker is attached to the nucleotide unit through the base, wherein the linker comprises an aliphatic chain or an oligo ethylene glycol chain where both linker chains having 2-6 subunits and optionally the linker includes an aromatic moiety.

18. The method of embodiment 16, wherein the multivalent molecule comprises a core attached to multiple nucleotide arms, and wherein the multiple nucleotide arms have the same type of nucleotide unit which is selected from a group consisting of dATP, dGTP, dCTP, dTTP and dUTP.

19. The method of embodiment 16, wherein the multivalent molecule further comprises a plurality of multivalent molecules which includes a mixture of multivalent molecules having two or more different types of nucleotides selected from a group consisting of dATP, dGTP, dCTP, dTTP and dUTP.

20. The method of embodiment 16, wherein the multivalent molecule comprises a core attached to multiple nucleotide arms, wherein the core is labeled with detectable reporter moiety.

21. The method of embodiment 16, wherein the detectable reporter moiety comprises a fluorophore.

22. The method of embodiment 16, wherein the core comprises an avidin-like moiety and the core attachment moiety comprises biotin.

23. The method of embodiment 1, wherein the sequencing of step (h) comprises:

a) contacting the plurality of nucleic acid concatemers with (i) a plurality of polymerases, (ii) at least one multivalent molecule comprising two or more duplicates of a nucleotide moiety that are connected to a core via a linker, and (iii) a plurality of sequencing primers that hybridize with a portion of the concatemers, under a condition suitable for binding at least one polymerase and at least one sequencing primer to a portion of one of the nucleic acid concatemer molecules, and suitable for binding at least one of the nucleotide moieties of the multivalent molecule to the 3' end of the sequencing primer at a position that is opposite a complementary nucleotide in the concatemer molecule wherein the bound nucleotide moiety does not incorporate into the sequencing primer;

b) detecting and identifying the bound nucleotide moiety of the multivalent molecule thereby determining the sequence of the concatemer molecule;

c) optionally repeating steps (a) and (b) at least once;

d) contacting the concatemer molecule with (i) a plurality of polymerases, and (ii) a plurality of nucleotides, under a condition suitable binding at least one polymerase to at least a portion of the concatemer molecule and suitable for binding at least one of the nucleotides from the plurality to the 3' ends of the hybridized sequencing primers at a position that is opposite a complementary nucleotide in the concatemer molecule wherein the bound nucleotides incorporate into the hybridized sequencing primers;

e) optionally detecting the incorporated nucleotides;

f) optionally identifying the incorporation nucleotides thereby determining or confirming the sequence of the concatemer; and g) repeating steps (a)-(f) at least once.

III. Examples

The following examples are included for illustrative purposes only and are not intended to limit the scope of the invention.

Example 1: In Situ Sequencing

A. Preparing Tissue Samples

Fresh frozen tissue samples from an animal or human subject is embedded in paraffin or OCT (Optimal Cutting Temperature) and cryo-sectioned at approximately 10 micron thickness. The embedded tissue slices are positioned on a support that lacks capture oligonucleotides. For example, the tissue slices are positioned on a slide (e.g., SuperFrost Plus microscope slide, e.g., from Fisher Scientific catalog No. 12-550-15) and stored at −80° C. until ready for use.

The slides are removed from −80° C. and thawed to room temperature. The tissue sample is fixed by applying to the tissue slices 3% (w/v) paraformaldehyde in DEPC-PBS and incubated for approximately 5 minutes at room temperature. The tissue sections are rinsed at least twice with DEPC-PBS. The tissue is permeabilized with acidic condition by dipping the slide into a solution of 0.1 M HCl at room temperature for approximately 5 minutes. The slides are washed with DEPC-PBS at room temperature for at least 1 minute. The slides are dehydrated in an ethanol series: (1) 70% ethanol at room temperature for approximately 1 minute; (2) 100% ethanol at room temperature for approximately 1 minute. The slides are air-dried. Hybridization chambers are mounted over the tissue slices on the slide with SECURE-SEAL hybridization chambers (e.g., from Grace Bio-Labs). The tissue sections are rehydrated with DEPC-PBS-T and then with DEPC-PBS.

B. In Situ Reverse Transcriptase Reaction

A reverse transcriptase reaction is prepared by adding to the chamber: a reverse transcriptase enzyme (e.g., TranscriptME Reverse Transcriptase which is an M-MuLV reverse transcriptase from CytoGen), reverse transcriptase buffer, dNTPs (500 uM), random primers (e.g., decamers, 5 uM), RNase inhibitor (1 U/uL), BSA (0.2 ug/uL), and DEPC-water. An exemplary reverse transcriptase buffer can include: 50 mM Tris-HCl (pH 8.3); 75 mM KCl; 3 mM $MgCl_2$; and 10 mM DTT. The chamber is sealed, and the slide is placed in a humidity chamber, and incubated at 37° C. for at least 6 hours. The reverse transcriptase reagents are removed. The tissue slices are fixed with 3% (w/v) paraformaldehyde at room temperature for approximately 30 minutes. The tissue slices are washed several times with DPEC-PBS-T.

C. Rolling Circle Amplification

The padlock probes are 70-100 nucleotides in length and are phosphorylated at their 5' ends, and include: terminal target regions (5' arm and 3' arm) that hybridize to the target sequence each 15 nucleotides in length, backbone region that includes an ID sequence (about 6-20 nucleotides in length) and optionally an anchor binding sequence (about 6-20 nucleotides in length). In some embodiments, the terminal target regions of the padlock probes comprise random sequences. Padlock probe hybridization and ligation is conducted in situ by adding to the tissue slices: the padlock probe (e.g., approximately 10 nM of each type of padlock probe), 1× Tth ligase buffer, KCl (0.05 M), formamide (20%), BSA (0.2 ug/uL), Tth ligase enzyme (0.5 U/uL) and RNaseH (0.4 U/uL). An exemplary ligase buffer includes 20 mM Tris-HCl (pH 8.3), 25 mM KCl, 10 mM $MgCl_2$, 0.5 mM NAD, and 0.01% Triton X-100. The padlock probe hybridization reaction was conducted at about 37° C. for approximately 30 minutes, then at about 45° C. for about 1½ to 2 hours. The slide is washed several times with DEPC-PBS-T.

A two-step rolling circle amplification is conducted to generate concatemers in the cells of the tissue slices.

Step One: add to the tissue slices a non-catalytic solution: 10 mM ACES pH 7.4, dNTPs (10 uM), 1 mM strontium acetate, 0.01% Tween-20, 50 mM ammonium sulfate, and 10 mM DTT. The chamber is sealed and incubated in a humidity chamber at room temperature or 35° C. for 15 minutes. The non-catalytic solution is removed from the chamber.

Step Two: add to the tissue slices a catalytic solution: 50 mM ACES pH 7.4, 100 mM potassium acetate, 10 mM $MgSO_4$, dNTPs (2 mM), 10 mM DTT, 0.01% Tween-20, 50 mM ammonium sulfate, and 10 mM DTT. Optionally, compaction oligonucleotides are included in 10-200 nM. The chamber is sealed and placed in a humidity chamber. Rolling circle amplification reaction is conducted at room temperature or 35° C. for different time ranges from 5 minutes up to 2 hours. The tissue slices are washed with a buffer containing 50 mM Tris-HCl pH 8, 750 mM NaCl, 0.1 mM EDTA and 0.02% Tween-20.

D1. Multiple Displacement Amplification with Soluble Random Primers

Multiple displacement amplification (MDA) is conducted following the rolling circle amplification reaction to generate branched concatemers. The MDA reaction is conducted by adding to the tissue slices: 50 mM Tris pH7.5, 75 mM NaCl, 10 mM $MgCl_2$, 1 mM DTT, 2.5% glycerol, 0.1 mg/mL BSA, 1.5-2 mM dNTPs, 1-10 uM random-sequence hexamers (exonuclease resistant), and a strand displacing DNA polymerase. The strand displacing DNA polymerase that are tested include phi29 (wild type), EquiPhi29 (e.g., Thermo Fisher Scientific, catalog No. A39390), QualiPhi (e.g., from 4basebio, catalog No. 510025), large fragment of Bst DNA polymerase exonuclease minus (e.g., Lucigen, catalog NO. 30027-1), and large fragment of Bsu DNA polymerase exonuclease minus (e.g., New England Biolabs, catalog No. MS330S). The DNA polymerases are typically added at 150 nM. Alternative MDA formulas can include: commercially-available buffers including: phi29 10× reaction buffer (Thermo Fisher, catalog No. B62) supplemented with 1-20 mM DTT and 0.5-4 mM dNTPs; EquiPhi29 10× reaction buffer (Thermo Fisher Scientific, catalog No. B39) supplemented with 1-20 mM DTT and 0.5-4 mM dNTPs; and TruePrime Kit buffer (e.g., Lucigen, catalog No. SYG370025) supplemented with 0.5-4 mM dNTPs. The chamber is place in a humidity chamber to conduct the multiple displacement amplification reaction. Different incubation conditions are tested including: temperatures ranging from 30-45° C., for 30-90 minutes. The chamber is washed with a buffer containing either (1) 50 mM Tris-HCl pH 8, 750 mM NaCl, 0.1 mM EDTA, 0.02% Tween-20; or (2) 3×SSC buffer, followed by a buffer containing 50 mM Tris pH 8, 100 mM NaCl, 0.1 mM EDTA, and 0.01% Tween-20.

D2. Multiple Displacement Amplification with DNA Primase-Polymerase

Following the rolling circle amplification reaction, an alternative MDA reaction is conducted using DNA primase-polymerase and lacking any primers to generate branched concatemers. Different MDA formulas are tested. One of the MDA formulas contains 50 mM Tris pH7.5, 75 mM NaCl, 10 mM $MgCl_2$, 1 mM DTT, 2.5% glycerol, 0.1 mg/mL BSA, 1.5-2 mM dNTPs, a strand displacing DNA polymerase, and DNA primase-polymerase. Other MDA formulas can include commercially-available buffers including: phi29 10× reaction buffer (Thermo Fisher, catalog No. B62) supplemented with 1-20 mM DTT and 0.5-4 mM dNTPs; EquiPhi29 10× reaction buffer (Thermo Fisher Scientific, catalog No. B39) supplemented with 1-20 mM DTT and 0.5-4 mM dNTPs; and TruePrime Kit buffer (e.g., Lucigen, catalog No. SYG370025) supplemented with 0.5-4 mM dNTPs. The strand displacing DNA polymerase that are tested include phi29 (wild type), EquiPhi29 (e.g., Thermo Fisher Scientific, catalog No. A39390), QualiPhi (e.g., from 4basebio, catalog No. 510025), large fragment of Bst DNA polymerase exonuclease minus (e.g., Lucigen, catalog NO. 30027-1), and large fragment of Bsu DNA polymerase exonuclease minus (e.g., New England Biolabs, catalog No. MS330S). The DNA polymerases were typically added at 150 nM. The DNA primase-polymerase enzyme was Tth PrimPol (4basebio, catalog No. 390100). The chamber is place in a humidity chamber to conduct the multiple displacement amplification reaction. Different incubation conditions are tested including: temperatures ranging from 30-45° C., for 30-90 minutes. The chamber is washed with a buffer containing either (1) 50 mM Tris-HCl pH 8, 750 mM NaCl, 0.1 mM EDTA, 0.02% Tween-20; or (2) 3×SSC buffer, followed by a buffer containing 50 mM Tris pH 8, 100 mM NaCl, 0.1 mM EDTA, and 0.01% Tween-20.

D3. Relaxant Conditions and Flexing Amplification

Instead of conducting a multiple displacement amplification reaction following rolling circle amplification, the tissue slices are subject to a relaxant condition followed by a flexing amplification reaction to generate highly compact concatemers.

A buffer containing nucleic acid relaxing agents is deposited onto the tissue slices with (1) a temperature ramp-up, incubation, and temperature ramp-down profile, followed by (2) a flexing amplification reaction using a strand-displacing DNA polymerase. Multiple cycles of stages (1) and (2) were tested.

Relaxant Conditions:

Different relaxing buffer formulas are tested. Exemplary relaxing agents can include nucleic acid denaturants, chaotropic compounds, amide compounds, aprotic compounds, primary alcohols and ethylene glycol derivatives. Chaotropic compounds comprise urea, guanidine hydrochloride or guanidine thiocyanate. Amide compounds comprise formamide, acetamide or NN-dimethylformamide (DMF). Aprotic compounds comprise acetonitrile, DMSO (dimethyl sulfoxide), 1,4-dioxane or tetrahydrofuran. Primary alcohols comprise 1-propanol, ethanol or methanol. Ethylene glycol derivatives comprise 1,3-propanediol, ethylene glycol, glycerol, 1,2-dimethyoxyethane or 2-methoxyethanol. Other relaxing agents can include sodium iodide, potassium iodide and polyamines The relaxant reaction mixture can contain any one or a combination of two or more of a group selected from urea, guanidine hydrochloride, guanidine thiocyanate, formamide, acetamide, NN-dimethylformamide (DMF), acetonitrile, DMSO (dimethyl sulfoxide), 1,4-dioxane, tetrahydrofuran, 1-propanol, ethanol, methanol, 1,3-propanediol, ethylene glycol, glycerol, 1,2-dimethyoxyethane, 2-methoxyethanol, sodium iodide, potassium iodide and/or polyamines.

Different nucleic acid relaxing temperature profiles are tested in a humidity chamber. Typically, a nucleic acid relaxing temperature profile can include: T1 initial temperature; T2 temperature ramp-up; incubate for the nucleic acid relaxing reaction; and T3 temperature ramp-down.

An exemplary nucleic acid relaxing temperature cycle profile can include: T1 initial temperature is 25° C.; T2 ramp-up to 55° C. with a temperature gradient of +1° C./second; incubate at 55° C. for 30 seconds; T3 ramp-down to 25° C. with a temperature gradient of −1° C./second.

After the T3 ramp-down, the chamber is washed to remove the relaxing buffer. The Wash buffer contained 1×SSC and 0.1 mM cobalt hexamine.

Flexing Amplification:

A buffer containing a strand-displacing DNA polymerase is deposited onto the tissue slices to conduct flexing amplification with amplification temperature cycling.

Any strand-displacing DNA polymerase can be used, including large fragment of Bst DNA polymerase (e.g., exonuclease minus), phi29 DNA polymerase, large fragment of Bsu DNA polymerase, and Bca (exo-) DNA polymerase, Klenow fragment of E. coli DNA polymerase, T5 polymerase, M-MuLV reverse transcriptase, HIV viral reverse transcriptase, or Deep Vent DNA polymerase. The phi29 DNA polymerase can be wild type phi29 DNA polymerase (e.g., MagniPhi from Expedeon), or variant EquiPhi29 DNA polymerase (e.g., from Thermo Fisher Scientific), or chimeric QualiPhi DNA polymerase (e.g., from 4basebio).

For example, large fragment of Bst DNA polymerase is tested. A flexing amplification reaction buffer is deposited onto the tissue slices: Bst DNA polymerase (400 nM), 20 mM Tris pH 8.5, 50 mM KCl, 5 mM MgSO$_4$, 0.1% Tween-20, 1.5 M Betaine, and 0.25 mM dNTP (total).

Different flexing amplification temperature cycle profiles can be tested in a humidity chamber. For example, a single flexing amplification temperature cycle profile can include: T1 initial temperature, T2 temperature ramp-up, incubate for the flexing amplification reaction, T3 temperature ramp-down. The temperature cycles can be repeated 2-50 times or more.

An exemplary flexing amplification temperature cycle profile can include: T1 initial temperature is 25° C.; T2 ramp-up to 63° C. with a temperature gradient of +1° C./second; incubate at 63° C. for 55 seconds; T3 ramp-down to 25° C. with a temperature gradient of −1° C./second. The relaxing stage and flexing amplification stage represent a cycle. The cycles can be repeated 5-15 times.

After the last flexing T3 ramp-down, the chamber is washed to remove the relaxing buffer. The Wash buffer can contain 1×SSC and 0.1 mM cobalt hexamine.

E. Sequencing with Multivalent Molecules

Multivalent molecules comprising a fluorescently-labeled streptavidin core attached to multiple nucleotide arms (see FIGS. 5A, 5B and 5D) are used to sequence the concatemers in the cells of the tissue slices. A non-catalytic buffer can be flowed onto the tissue slices, where the non-catalytic buffer includes 20 nM Klenow polymerase (or other suitable polymerase), sequencing primers, 2.5 mM strontium and labeled multivalent molecules (e.g., at 2.5 uM). A fluorescent image of the polymerase bound to the labeled multivalent molecule (ternary complex where the multivalent molecule is not incorporated) can be obtained. The multivalent molecule can be dissociated by adding a wash buffer having 10 mM Tris pH 8.0, 0.5 mM EDTA, 50 mM NaCl, 0.016% Triton X100 (but lacking strontium). A catalytic buffer can be flowed onto the tissue slices, where the catalytic buffer can include 20 nM Klenow polymerase (or other suitable polymerase), magnesium, optionally sequencing primers, and labeled or non-labeled nucleotides. The nucleotides can have 2' or 3' chain terminating moiety, such as for example an azide, azido or azido-methyl group. The nucleotides can incorporate into the sequencing primers to extend the primers. If the incorporated nucleotide is labeled, an image can be obtained. The chain-terminating moiety in the incorporated nucleotides can be removed using an appropriate reagent (e.g., phosphine compound). Repeat cycles can be conducted, which include non-catalytic binding with the multivalent molecules, imaging the bound multivalent molecules, catalytic incorporation of nucleotides, and optional imaging the incorporated nucleotides.

Example 2: In Situ Single Cell Sequencing

A single cell can be obtained from an animal or human and can be placed in simple or complex cell media for at least 15 minutes. The simple cell media can be PBS (phosphate buffered saline), DPBS (Dulbecco's phosphate-buffered saline), HBSS (Hank's balanced salt solution), DMEM (Dulbecco's Modified Eagle's Medium), EMEM (Eagle's Minimum Essential Medium), and/or EBSS. The complex cell media can be fetal bovine serum, blood plasma or blood serum.

The single cell can be embedded in paraffin or OCT (Optimal Cutting Temperature) and cryo-sectioned as described in Example 1-A above. The sections can be fixed as described in Example 1-A above. The sections of the single cell can be positioned on a glass support that is passivated with a low non-specific binding coating and lacks immobilized capture oligonucleotides. The sectioned single cell, while being positioned on the passivated support, can be permeabilized, dehydrated and rehydrated as described in Example 1-A above.

The sections of the single cell can be subjected to reverse transcriptase as described in Example 1-B above.

The sections of the single cell can be subject to rolling circle amplification, to generate concatemers, as described in Example 1-C above.

Following rolling circle amplification, the sections of the single cell can be subjected to multiple displacement amplification using random primers, to generate branched concatemers, as described in Example 1-D1 above, or can be subjected to multiple displacement amplification using DNA primase-polymerase to generate branched concatemers, as described in Example 1-D2 above. Alternatively, following rolling circle amplification, the sections of the single cell can be subjected to a relaxant condition and flexing amplification, to generate highly compact concatemers, as described in Example 1-D3 above.

The concatemers can be sequenced using multivalent molecules as described in Example 1-E above.

Example 3: Biological Molecule Capture on a Low Non-Specific Binding Coating A. Preparing Tissue Samples Fresh frozen tissue samples from an animal or human subject is embedded in paraffin or OCT (Optimal Cutting Temperature) and cryo-sectioned at approximately 10 micron thickness. The tissue slices are positioned on a support which is passivated with a low non-specific binding coating which includes capture oligonucleotides immobilized to the coating. The coating optionally also includes immobilized circularization oligonucleotides (FIG. 2). The tissue slices on the support can be stored at −80° C. until ready for use.

The low non-specific binding coating can have an array of surface features (e.g., shaped as spots, FIG. 3), where the features each have immobilized thereon approximately 100,000 or more capture oligonucleotides. The capture oligonucleotides include a target capture region, a spatial barcode sequence (e.g., FIG. 2) and optionally a sequencing primer binding sequence. Different features contain capture oligonucleotides with different spatial barcode sequences. Different features contain capture oligonucleotides with the same or different target capture region sequences.

The slides are removed from −80° C. and thawed to room temperature. The tissue sample is fixed by applying to the tissue slices 3% (w/v) paraformaldehyde in DEPC-PBS and incubated for approximately 5 minutes at room temperature.

B. Surface Capture of Target Nucleic Acids

The tissue sections are rinsed at least twice with DEPC-PBS. The cells in the tissue slices are permeabilized by flowing an acidic solution of 0.1 M HCl on the tissue slices at room temperature. A high efficiency hybridization solution is flowed onto the tissue slices to allow the nucleic acids from the tissue to migrate from the tissue to the capture oligonucleotides on the passivated support. The high efficiency hybridization solution includes: (i) acetonitrile at 25-50% by volume of the high efficiency high efficiency hybridization buffer; (ii) formamide at 5-10% by volume of the high efficiency high efficiency hybridization buffer; (iii) 2-(N-morpholino)ethanesulfonic acid (MES) at a pH of 5-6.5; and (iv) polyethylene glycol (PEG) (e.g., PEG 4000) at 5-35% by volume of the high efficiency high efficiency hybridization buffer. The tissue slices are incubated at approximately 55° C. for about 3 minutes, and then at 37° C. for about 3 minutes, then at room temperature for about 3 minutes. The tissue slices are washed with DEPC-PBS at room temperature.

C. Reverse Transcriptase Reaction

A reverse transcriptase reaction was prepared by adding to the tissue slices: a reverse transcriptase enzyme (e.g., TranscriptME Reverse Transcriptase which is an M-MuLV reverse transcriptase from CytoGen), reverse transcriptase buffer, dNTPs (500 uM), 5 uM reverse transcription primers (e.g., target-specific primers or random-sequence decamers), RNase inhibitor (1 U/uL), BSA (0.2 ug/uL), and DEPC-water. An exemplary reverse transcriptase buffer can include: 50 mM Tris-HCl (pH 8.3); 75 mM KCl; 3 mM MgCl$_2$; and 10 mM DTT. The tissue slices are placed in a humidity chamber, and incubated at 37° C. for at least 6 hours or overnight. The reverse transcriptase reagents are removed by washing with DEPC-PBS at room temperature. The tissue slices are fixed with 3% (w/v) paraformaldehyde at room temperature for approximately 30 minutes. The tissue slices are washed several times with DPEC-PBS-T.

The cells of the tissue slices are enzymatically removed with collagenase, neutral dispase protease and/or thermolysin (e.g., LIBERASE) enzymes.

D. Rolling Circle Amplification

A two-step rolling circle amplification is conducted to generate concatemers in the cells of the tissue slices.

Step One: add to the tissue slices a non-catalytic solution: 10 mM ACES pH 7.4, dNTPs (10 uM), 1 mM strontium acetate, 0.01% Tween-20, 50 mM ammonium sulfate, and 10 mM DTT. The chamber is sealed and incubated in a humidity chamber at room temperature or 35° C. for 15 minutes. The non-catalytic solution is removed from the chamber.

Step Two: add to the tissue slices a catalytic solution: 50 mM ACES pH 7.4, 100 mM potassium acetate, 10 mM MgSO$_4$, dNTPs (2 mM), 10 mM DTT, 0.01% Tween-20, 50 mM ammonium sulfate, and 10 mM DTT. Optionally, compaction oligonucleotides are included at 10-200 nM. The chamber is sealed and placed in a humidity chamber. Rolling circle amplification reaction is conducted at room temperature or 35° C. for different time ranges from 5 minutes up to 2 hours. The tissue slices are washed with a buffer containing 50 mM Tris-HCl pH 8, 750 mM NaCl, 0.1 mM EDTA and 0.02% Tween-20.

E1. Multiple Displacement Amplification with Soluble Random Primers

Multiple displacement amplification (MDA) is conducted following the rolling circle amplification reaction to generate branched concatemers using the protocol described in Example 1-D1 above.

E2. Multiple Displacement Amplification with DNA Primase-Polymerase

Following the rolling circle amplification reaction, an alternative MDA reaction is conducted using DNA primase-polymerase and lacking any primers to generate branched concatemers, using the protocol described in Example 1-D2 above.

E3. Relaxant Conditions and Flexing Amplification

Instead of conducting a multiple displacement amplification reaction following rolling circle amplification, the tissue slices are subject to a relaxant condition followed by a flexing amplification reaction to generate highly compact concatemers, using the protocol described in Example 1-D3 above.

F. Sequencing with Multivalent Molecules

The concatemers were sequenced using multivalent molecules and nucleotides as described in Example 1-E above.

Example 4: Capturing Nucleic Acids from a Single Cell onto a on a Low Non-Specific Binding Coating A single cell can be obtained from an animal or human and can be placed in simple or complex cell media for at least 15 minutes. The simple cell media can be PBS (phosphate buffered saline), DPBS (Dulbecco's phosphate-buffered saline), HBSS (Hank's balanced salt solution), DMEM (Dulbecco's Modified Eagle's Medium), EMEM (Eagle's Minimum Essential Medium), and/or EBSS. The complex cell media can be fetal bovine serum, blood plasma or blood serum.

The single cell can be embedded in paraffin or OCT (Optimal Cutting Temperature) and cryo-sectioned as described in Example 1-A above. The sections can be fixed as described in Example 1-A above.

The tissue slices are positioned on a support which is passivated with a low non-specific binding coating which includes capture oligonucleotides immobilized to the coating. The coating optionally also includes immobilized circularization oligonucleotides (FIG. 2). The tissue slices on the support can be stored at −80° C. until ready for use.

The low non-specific binding coating can have an array of surface features (e.g., shaped as spots, FIG. 3), where the features each have immobilized thereon approximately 100,000 or more capture oligonucleotides. The capture oligonucleotides include a target capture region, a spatial barcode sequence (e.g., FIG. 2) and optionally a sequencing primer binding sequence. Different features contain capture oligonucleotides with different spatial barcode sequences. Different features contain capture oligonucleotides with the same or different target capture region sequences.

The slides are removed from −80° C. and thawed to room temperature. The tissue sample is fixed by applying to the tissue slices 3% (w/v) paraformaldehyde in DEPC-PBS and incubated for approximately 5 minutes at room temperature.

The nucleic acids (e.g., RNA) from the embedded single cell can be captured by the immobilized capture oligonucleotides on the coating, using the high efficiency hybridization solution as described in Example 3-B above.

The captured RNA can be subjected to a reverse transcription reaction to generate cDNA, followed by fixation and enzymatic cell removal, as described in Example 3-C above.

The cDNA can be subjected to the two-step rolling circle amplification reaction as described in Example 3-D above.

Following rolling circle amplification, the sections of the single cell can be subjected to multiple displacement amplification using random primers, to generate branched concatemers, as described in Example 3-E1 above, or can be subjected to multiple displacement amplification using DNA primase-polymerase to generate branched concatemers, as described in Example 3-E2 above. Alternatively, following rolling circle amplification, the sections of the single cell can be subjected to a relaxant condition and flexing amplification, to generate highly compact concatemers, as described in Example 3-E3 above.

The concatemers can be sequenced using multivalent molecules as described in Example 3-F above.

Example 5: Design Specifications for a Fluorescence Imaging Module for Genomics Applications A non-limiting example of design specifications for a fluorescence imaging module of the present disclosure is provided in Table 1.

| Design Parameter | Specification |
| --- | --- |
| Numerical aperture | ≥0.3 |
| Image quality | Diffraction limited |
| Field-of-view (FOV) | >2.0 mm$^2$ |
| Image plane curvature | Best focal plane within 100 nm for >90% of the FOV, within 150 nm for 99% of the FOV, and within 200 nm for the entire FOV |
| Image distortion | <0.5% across the FOV |
| Magnification | 2× to 20× |
| Camera pixel size at sample plane | ≥2 × optical system modulation transfer function (MTF) limit |
| Coverslip thickness | >700 μm |
| Number of fluorescence imaging channels | ≥3 |
| Chromatic focal plane difference at camera between all imaging channels | ≤100 nm equivalent at sample plane |
| Number of AF channels | 1 |
| Imaging time | ≤2 seconds per FOV |
| Autofocus | Single step autofocus with error correction |
| Autofocus accuracy | <100 nm |
| Scanning stage step and settle time | <0.4 seconds |
| Channel-specific optimized tube lens | 1 per imaging channel |
| Illumination optical path | Liquid light guide with underfilled entrance aperture |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A method for identifying at least a portion of a sub-cellular component within a cell or tissue in situ, the method comprising:
    (a) detecting a signal from a binding complex between said sub-cellular component and a detectable polymer-nucleotide conjugate within said cell or said tissue, wherein said detectable polymer-nucleotide conjugate comprises at least two nucleotides that are transiently interacting with at least two of said sub-cellular components; and
    (b) processing at least said signal detected in (a) to identify said at least said portion of said sub-cellular component.

2. The method of claim 1, wherein said sub-cellular component is a protein.

3. The method of claim 1, further comprising: (c) immobilizing said cell or said tissue on a surface of a substrate.

4. The method of claim 3, further comprising: (d) coupling at least a portion of said sub-cellular component to a capture molecule coupled to said surface.

5. The method of claim 1, further comprising permeabilizing said tissue or lysing said cell prior to said detecting in (a).

6. The method of claim 3, wherein said surface has a water contact angle of less than or equal to 45 degrees.

7. The method of claim 4, wherein said coupling in (d) comprises hybridizing said capture molecule with said at least said portion of said sub-cellular component in a presence of a hybridization buffer comprising:
    (a) a first polar aprotic solvent having a dielectric constant that is no greater than 40 and having a polarity index of 4-9; and
    (b) a second polar aprotic solvent having a dielectric constant that is less than or equal to 115.

8. The method of claim 3, wherein an image of said surface exhibits a contrast-to-noise ratio of greater than or equal to 5 as measured by:
    (a) contacting said surface with a fluorescently labeled nucleotide molecule comprising a nucleic acid sequence that is complementary to at least a portion of a capture oligonucleotide immobilized to said surface; and
    (b) following (a), imaging said surface with an inverted microscope and a camera under non-signal saturating conditions while said surface is immersed in a buffer.

9. The method of claim 1, wherein detecting said signal from said binding complex in (a) comprises: performing a nucleotide binding reaction between a nucleotide moiety coupled to said detectable polymer-nucleotide conjugate and said sub-cellular component, wherein said detectable polymer-nucleotide conjugate comprises one or more detectable moieties.

10. The method of claim 1, wherein said detectable polymer-nucleotide conjugate comprises: two or more nucleotide moieties attached to a polymer core, wherein said detectable polymer-nucleotide conjugate is configured to form said binding complex between said two or more nucleotide moieties and said sub-cellular component.

11. The method of claim 3, further comprising: (d) determining an origin of said at least said portion of said sub-cellular component in said cell or said tissue, wherein said origin comprises a cell type or a tissue type.

12. The method of claim 1, wherein (a) and (b) are performed with accuracy of base-calling that is characterized by a Q-score of greater than 25 for at least 80% of nucleotides identified.

13. The method of claim 1, wherein said sub-cellular component is a nucleic acid sequence.

14. The method of claim 13, wherein said nucleic acid sequence is a deoxyribonucleic acid (DNA) sequence.

15. The method of claim 13, wherein said signal detected in (a) is from a detectable moiety coupled to said binding complex, and wherein said signal is indicative of an identity of a nucleotide in said nucleic acid sequence.

16. The method of claim 11, wherein said determining in (d) is performed, at least in part, by analyzing a relative three-dimensional relationship between said sub-cellular component and a point of reference of said cell or said tissue.

17. The method of claim 16, wherein said immobilizing in (c) comprises immobilizing said cell or said tissue on said surface in a manner that is sufficient to fix said relative three-dimensional relationship.

18. The method of claim 4, wherein said sub-cellular component is a nucleic acid sequence.

19. The method of claim 18, further comprising amplifying said nucleic acid sequence on said surface of said substrate, wherein said amplifying comprises performing a rolling circle amplification reaction.

20. The method of claim 19, wherein said signal detected in (a) is from a detectable moiety coupled to said binding complex, and wherein said signal is indicative of an identity of a nucleotide in said nucleic acid sequence.

* * * * *